(12) United States Patent
Perlroth et al.

(10) Patent No.: US 10,363,290 B2
(45) Date of Patent: Jul. 30, 2019

(54) BUTYRYLCHOLINESTERASE ZWITTERIONIC POLYMER CONJUGATES

(71) Applicant: Kodiak Sciences Inc., Palo Alto, CA (US)

(72) Inventors: D. Victor Perlroth, Palo Alto, CA (US); Stephen A. Charles, Ravenna, OH (US); Wayne To, San Mateo, CA (US); Xiaojian Huang, Mountain View, CA (US); Martin Linsell, San Mateo, CA (US); Didier Benoit, San Jose, CA (US)

(73) Assignee: KODIAK SCIENCES INC., Palo Alto, CA (US)

( * ) Notice: Subject to any disclaimer, the term of this patent is extended or adjusted under 35 U.S.C. 154(b) by 0 days.

(21) Appl. No.: 14/932,913

(22) Filed: Nov. 4, 2015

(65) Prior Publication Data
US 2016/0184445 A1 Jun. 30, 2016

Related U.S. Application Data

(63) Continuation of application No. PCT/US2015/056112, filed on Oct. 16, 2015.

(60) Provisional application No. 62/065,471, filed on Oct. 17, 2014.

(51) Int. Cl.
| | |
|---|---|
| *C12N 9/18* | (2006.01) |
| *A61K 38/46* | (2006.01) |
| *C08L 33/24* | (2006.01) |
| *C07K 7/08* | (2006.01) |
| *C12N 9/96* | (2006.01) |
| *A61K 47/60* | (2017.01) |

(52) U.S. Cl.
CPC ............ *A61K 38/465* (2013.01); *A61K 47/60* (2017.08); *C07K 7/08* (2013.01); *C08L 33/24* (2013.01); *C12N 9/18* (2013.01); *C12N 9/96* (2013.01); *C07K 2319/30* (2013.01); *C12Y 301/01008* (2013.01)

(58) Field of Classification Search
CPC ................. C12N 9/18; C07K 2319/30; C12Y 301/01008
See application file for complete search history.

(56) References Cited

U.S. PATENT DOCUMENTS

| | | | |
|---|---|---|---|
| 4,634,664 A | 1/1987 | Oestberg | |
| 4,634,666 A | 1/1987 | Engleman et al. | |
| 4,892,538 A | 1/1990 | Aebischer et al. | |
| 5,225,539 A | 7/1993 | Winter | |
| 5,283,187 A | 2/1994 | Aebischer et al. | |
| 5,336,603 A | 8/1994 | Capon et al. | |
| 5,530,101 A | 6/1996 | Queen et al. | |
| 5,545,806 A | 8/1996 | Lonberg et al. | |
| 5,565,332 A | 10/1996 | Hoogenboom et al. | |
| 5,569,825 A | 10/1996 | Lonberg et al. | |
| 5,585,089 A | 12/1996 | Queen et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,681,746 A | 10/1997 | Bodner et al. | |
| 5,733,743 A | 3/1998 | Johnson et al. | |
| 5,741,923 A | 4/1998 | Driver et al. | |
| 5,763,548 A | 6/1998 | Matyjaszewski et al. | |
| 5,770,429 A | 6/1998 | Lonberg et al. | |
| 5,789,487 A | 8/1998 | Matyjaszewski et al. | |
| 5,789,650 A | 8/1998 | Lonberg et al. | |
| 5,807,937 A | 9/1998 | Matyjaszewski et al. | |
| 5,814,318 A | 9/1998 | Lonberg et al. | |
| 5,834,597 A | 11/1998 | Tso et al. | |
| 5,837,242 A | 11/1998 | Holliger et al. | |
| 5,858,657 A | 1/1999 | Winter et al. | |
| 5,859,205 A | 1/1999 | Adair et al. | |
| 5,871,907 A | 2/1999 | Winter et al. | |
| 5,872,218 A | 2/1999 | Wolf et al. | |
| 5,874,299 A | 2/1999 | Lonberg et al. | |
| 5,877,218 A | 3/1999 | Herzig et al. | |
| 5,877,397 A | 3/1999 | Lonberg et al. | |
| 5,882,644 A | 3/1999 | Chang et al. | |
| 5,945,491 A | 8/1999 | Matyjaszewski et al. | |
| 5,981,786 A | 11/1999 | Kitano et al. | |
| 6,111,022 A | 8/2000 | Matyjaszewski et al. | |
| 6,121,371 A | 9/2000 | Matyjaszewski et al. | |
| 6,124,411 A | 9/2000 | Matyjaszewski et al. | |
| 6,162,882 A | 12/2000 | Matyjaszewski et al. | |
| 6,407,187 B1 | 6/2002 | Matyjaszewski et al. | |
| 6,407,213 B1 | 6/2002 | Carter et al. | |

(Continued)

FOREIGN PATENT DOCUMENTS

| | | |
|---|---|---|
| AU | 2010330727 | 12/2010 |
| AU | 2011239434 | 8/2015 |

(Continued)

OTHER PUBLICATIONS

IMGT Scientific Chart. 2001; www.imgt.org/IMGTScientificChart/Numbering/Hu_IGHGnber.html.*
PCT/US2015/056112 Invitation to Pay Additional Fees and, Where Applicable, Protest Fee dated Feb. 3, 2016.
PCT/US2015/056112 International Search Report and Written Opinion of the International Searching Authority dated Apr. 1, 2016.
UniProtKB—G3R0B5, retrieved on Mar. 19, 2016 from <http://www.uniprot.org/uniprot/G3R0B5> Nov. 16, 2011 (date sequence last modification).
Alconcel, S.N.S. et al., "FDA-approved poly(ethylene glycol)-protein conjugate drugs," Polymer Chemistry, vol. 2, Issue 7, pp. 1442, 2011.

(Continued)

*Primary Examiner* — Karen Cochrane Carlson
(74) *Attorney, Agent, or Firm* — Knobbe, Martens, Olson & Bear, LLP

(57) ABSTRACT

The present invention provides recombinant butyrylcholinesterase fusion proteins, including Fc fusion proteins and multi-armed high MW polymers containing hydrophilic groups conjugated to the fusion proteins, and methods of preparing such polymers.

19 Claims, 5 Drawing Sheets
Specification includes a Sequence Listing.

(56) References Cited

U.S. PATENT DOCUMENTS

| | | |
|---|---|---|
| 6,512,060 B1 | 1/2003 | Matyjaszewski et al. |
| 6,538,091 B1 | 3/2003 | Matyjaszewski et al. |
| 6,541,580 B1 | 4/2003 | Matyjaszewski et al. |
| 6,555,593 B1 | 4/2003 | Hoyle et al. |
| 6,583,272 B1 | 6/2003 | Bailon |
| 6,624,262 B2 | 9/2003 | Matyjaszewski et al. |
| 6,627,314 B2 | 9/2003 | Matyjaszewski et al. |
| 6,759,491 B2 | 7/2004 | Matyjaszewski et al. |
| 6,790,919 B2 | 9/2004 | Matyjaszewski et al. |
| 6,852,816 B2 | 2/2005 | Lewis et al. |
| 6,881,557 B2 | 4/2005 | Foote |
| 6,887,962 B2 | 5/2005 | Matyjaszewski et al. |
| 6,979,556 B2 | 12/2005 | Simmons et al. |
| 7,019,082 B2 | 3/2006 | Matyjaszewski et al. |
| 7,049,373 B2 | 5/2006 | Matyjaszewski et al. |
| 7,056,455 B2 | 6/2006 | Matyjaszewski et al. |
| 7,060,271 B2 | 6/2006 | Ramakrishnan et al. |
| 7,064,166 B2 | 6/2006 | Matyjaszewski et al. |
| 7,125,938 B2 | 10/2006 | Matyjaszewski et al. |
| 7,157,530 B2 | 1/2007 | Matyjaszewski et al. |
| 7,169,901 B2 | 1/2007 | Baca et al. |
| 7,300,990 B2 | 11/2007 | Lewis et al. |
| 7,306,799 B2 | 12/2007 | Wiegand et al. |
| 7,348,424 B2 | 3/2008 | Miyazawa et al. |
| 7,374,757 B2 | 5/2008 | Papadopoulos et al. |
| 7,375,193 B2 | 5/2008 | Baca et al. |
| 7,521,541 B2 | 4/2009 | Eigenbrot et al. |
| 7,569,655 B2 | 8/2009 | Pacetti et al. |
| 7,740,850 B2 | 6/2010 | Zhu et al. |
| 7,754,208 B2 * | 7/2010 | Ledbetter ............ C07K 16/2809 424/133.1 |
| 7,754,855 B1 | 7/2010 | Cox, III et al. |
| 7,759,472 B2 | 7/2010 | Shima et al. |
| 7,855,178 B2 | 12/2010 | Alitalo et al. |
| 7,893,173 B2 | 2/2011 | Matyjaszewski et al. |
| 8,008,453 B2 | 8/2011 | Gegg et al. |
| 8,063,097 B2 | 8/2011 | Schroeter et al. |
| 8,187,597 B2 | 5/2012 | Shima et al. |
| 8,206,707 B2 | 6/2012 | Shima et al. |
| 8,273,353 B2 | 9/2012 | Davis-Smyth et al. |
| 8,455,622 B2 | 6/2013 | McDonagh et al. |
| 8,486,397 B2 | 7/2013 | Bagri et al. |
| 8,492,527 B2 | 7/2013 | Fuh et al. |
| 8,512,699 B2 | 8/2013 | Fuh et al. |
| 8,765,432 B2 | 7/2014 | Charles et al. |
| 8,815,236 B2 | 8/2014 | Burke et al. |
| 8,846,021 B2 | 9/2014 | Charles et al. |
| 9,079,953 B2 | 7/2015 | Harding et al. |
| 9,416,210 B2 | 8/2016 | Emrick et al. |
| 9,840,553 B2 | 12/2017 | Perlroth et al. |
| 2003/0143596 A1 | 7/2003 | Bentley et al. |
| 2003/0235536 A1 | 12/2003 | Blumberg et al. |
| 2004/0063881 A1 | 4/2004 | Lewis et al. |
| 2004/0253596 A1 | 12/2004 | Pawlak et al. |
| 2005/0041080 A1 | 2/2005 | Hall et al. |
| 2005/0112088 A1 | 5/2005 | Zhao et al. |
| 2005/0118651 A1 | 6/2005 | Wyeth Corp |
| 2005/0123501 A1 | 6/2005 | Lews |
| 2005/0136049 A1 | 6/2005 | Ledbetter et al. |
| 2005/0159556 A1 | 7/2005 | Lewis et al. |
| 2005/0180945 A1 | 8/2005 | Chaikof et al. |
| 2005/0220880 A1 | 10/2005 | Lewis et al. |
| 2005/0276796 A1 | 12/2005 | Tomatsu et al. |
| 2006/0135714 A1 | 6/2006 | Lewis et al. |
| 2006/0165804 A1 | 7/2006 | Lewis et al. |
| 2006/0167230 A1 | 7/2006 | Koga et al. |
| 2006/0217285 A1 | 9/2006 | Destarac |
| 2006/0234437 A1 | 10/2006 | Harding et al. |
| 2007/0041967 A1 | 2/2007 | Jung et al. |
| 2007/0111279 A1 | 5/2007 | Rosenberg |
| 2007/0141104 A1 | 6/2007 | Hauenstein |
| 2008/0008736 A1 | 1/2008 | Glauser |
| 2008/0124450 A1 | 5/2008 | Pacetti |
| 2008/0147178 A1 | 6/2008 | Pacetti et al. |
| 2008/0199464 A1 | 8/2008 | Plowman et al. |
| 2008/0249503 A1 | 10/2008 | Fields et al. |
| 2009/0053137 A1 | 2/2009 | Moore |
| 2009/0060906 A1 | 3/2009 | Barry et al. |
| 2009/0061533 A1 | 3/2009 | Minami |
| 2009/0117103 A1 | 7/2009 | Devalaraja et al. |
| 2009/0249503 A1 * | 10/2009 | Rosendahl ............... C12N 9/18 800/13 |
| 2009/0324679 A1 | 12/2009 | Ippoliti et al. |
| 2010/0111942 A1 | 5/2010 | Shima et al. |
| 2010/0158850 A1 | 6/2010 | Baker, Jr. et al. |
| 2010/0166700 A1 | 7/2010 | Charles |
| 2010/0291065 A1 | 11/2010 | Kabanov et al. |
| 2010/0322931 A1 | 12/2010 | Harding et al. |
| 2011/0033378 A1 | 2/2011 | Dimasi et al. |
| 2011/0165648 A1 | 7/2011 | Campange et al. |
| 2012/0100136 A1 | 4/2012 | Patel et al. |
| 2012/0213705 A1 | 8/2012 | Dimasi et al. |
| 2012/0282211 A1 | 11/2012 | Washburn et al. |
| 2012/0322738 A1 | 12/2012 | Behrens et al. |
| 2013/0034517 A1 | 2/2013 | Charles et al. |
| 2013/0040889 A1 | 2/2013 | Bolt et al. |
| 2013/0045522 A1 | 2/2013 | Charles et al. |
| 2013/0071394 A1 | 3/2013 | Troyer et al. |
| 2013/0259881 A1 | 10/2013 | Fandl et al. |
| 2013/0337534 A1 | 12/2013 | Charles |
| 2014/0024776 A1 | 1/2014 | Charles et al. |
| 2014/0170140 A1 | 2/2014 | Bennett et al. |
| 2014/0242082 A1 | 8/2014 | Shima et al. |
| 2015/0004128 A1 | 1/2015 | Charles et al. |
| 2015/0050714 A1 | 2/2015 | Charles |
| 2015/0071861 A1 | 3/2015 | Kondo et al. |
| 2015/0093390 A1 | 4/2015 | Bansal |
| 2015/0158952 A1 | 6/2015 | Mao et al. |
| 2015/0376271 A1 | 12/2015 | Perlroth et al. |
| 2016/0008485 A1 | 1/2016 | Marquette et al. |
| 2016/0199501 A1 | 7/2016 | Charles et al. |
| 2016/0287715 A1 | 10/2016 | Charles et al. |
| 2016/0346400 A1 | 12/2016 | Emrick et al. |
| 2016/0369005 A1 | 12/2016 | Lippincott et al. |
| 2017/0007710 A1 | 1/2017 | Charles et al. |
| 2017/0143841 A1 | 5/2017 | Charles et al. |
| 2017/0190766 A1 | 7/2017 | Perlroth et al. |
| 2018/0244762 A1 | 8/2018 | Perlroth et al. |
| 2018/0334496 A1 | 11/2018 | Perlroth et al. |

FOREIGN PATENT DOCUMENTS

| | | |
|---|---|---|
| AU | 2015207898 | 8/2015 |
| AU | 2017201930 | 4/2017 |
| BR | 11 2012 0145568 | 3/2017 |
| BR | 11 2012 0261185 | 8/2017 |
| CA | 2783615 | 6/2011 |
| CA | 2795667 | 10/2011 |
| CL | 02881/2012 | 7/2013 |
| CN | 101389690 | 3/2009 |
| CN | 102811713 | 12/2012 |
| CN | 103193819 | 7/2013 |
| CN | 103421039 | 12/2013 |
| CN | 103492489 | 1/2014 |
| CN | 103898101 A | 7/2014 |
| CN | 106075466 | 11/2016 |
| CN | 106432557 | 2/2017 |
| CN | 107208076 | 9/2017 |
| CN | 107428824 | 12/2017 |
| CO | 12119310 | 12/2012 |
| CO | 12203725 | 2/2013 |
| EP | 1465933 | 10/2004 |
| EP | 1592719 | 11/2005 |
| EP | 1732621 | 12/2006 |
| EP | 1988910 | 11/2008 |
| EP | 2260873 | 12/2010 |
| EP | 2512462 | 10/2012 |
| EP | 2203180 | 11/2012 |
| EP | 2558538 | 2/2013 |
| EP | 3041513 | 7/2016 |
| EP | 3222142 | 9/2017 |
| EP | 3254678 | 12/2017 |
| IL | 260323 | 8/2018 |
| IN | 6116/CHENP/2012 | 12/2015 |

(56) References Cited

FOREIGN PATENT DOCUMENTS

| | | |
|---|---|---|
| IN | 9473CHENP/2015 | 12/2015 |
| JP | H04-502850 | 5/1992 |
| JP | H10 139832 | 5/1998 |
| JP | H11 217588 | 8/1999 |
| JP | 2003-064132 | 3/2003 |
| JP | 2005-239989 | 9/2005 |
| JP | 2005-255969 | 9/2005 |
| JP | 2006-503549 | 2/2006 |
| JP | 2007-263935 | 10/2007 |
| JP | 2007-531513 | 11/2007 |
| JP | 2008-133434 | 6/2008 |
| JP | 2008-524247 | 7/2008 |
| JP | 2009-042617 | 2/2009 |
| JP | 2013-515099 | 5/2009 |
| JP | 2009-532330 | 9/2009 |
| JP | 2009-533519 | 9/2009 |
| JP | 2009-542862 | 12/2009 |
| JP | 2009-543895 | 12/2009 |
| JP | 2010-117189 | 5/2010 |
| JP | 2010-279389 | 12/2010 |
| JP | 2011-50073 | 1/2011 |
| JP | 2012-025820 | 2/2012 |
| JP | 2013-519699 | 5/2013 |
| JP | 2013-534931 | 9/2013 |
| JP | 2014-043456 | 3/2014 |
| JP | 5528710 | 6/2014 |
| JP | 5760007 | 6/2015 |
| JP | 5745009 | 7/2015 |
| JP | 2016-14015 | 1/2016 |
| JP | 5846044 | 1/2016 |
| JP | 2016-040371 | 3/2016 |
| JP | 5990629 | 8/2016 |
| JP | 2016-530302 | 9/2016 |
| JP | 2017-31410 | 2/2017 |
| JP | 2018-087339 | 6/2018 |
| JP | 6416832 | 10/2018 |
| KR | 10-0808116 | 3/2008 |
| KR | 20120123340 | 11/2012 |
| KR | 2013-0097636 | 9/2013 |
| KR | 10-1852044 | 4/2018 |
| MX | 2012006970 | 10/2012 |
| MX | 2012011876 | 11/2012 |
| MX | 346423 | 3/2017 |
| MX | 2016017290 | 8/2017 |
| WO | WO 91/10741 | 7/1991 |
| WO | WO 91/17271 | 11/1991 |
| WO | WO 92/01047 | 1/1992 |
| WO | WO 93/12227 | 6/1993 |
| WO | WO 93/25673 | 12/1993 |
| WO | WO 1994/016748 | 8/1994 |
| WO | WO 97/14702 | 4/1997 |
| WO | WO 97/14703 | 4/1997 |
| WO | WO 98/45331 | 10/1998 |
| WO | WO 2000/059968 | 10/2000 |
| WO | WO 01/41827 | 6/2001 |
| WO | WO 2002/028929 | 4/2002 |
| WO | WO 2003/062290 | 7/2003 |
| WO | WO 2003/074026 | 9/2003 |
| WO | WO 2003/074090 | 9/2003 |
| WO | WO 2004/020405 | 3/2004 |
| WO | WO 2004/063237 | 7/2004 |
| WO | WO 2004/091494 | 10/2004 |
| WO | WO 2004/113394 | 12/2004 |
| WO | WO 2005/028539 | 3/2005 |
| WO | WO 2005/047334 | 5/2005 |
| WO | WO 2005/058367 | 6/2005 |
| WO | WO 2006/063055 | 6/2006 |
| WO | WO 2006/118547 | 11/2006 |
| WO | WO 2007/005253 | 1/2007 |
| WO | WO 2007/075534 | 7/2007 |
| WO | WO 2007/100902 | 9/2007 |
| WO | WO 2007/100902 A2 | 9/2007 |
| WO | WO 2008/020827 | 2/2008 |
| WO | WO 2008/025856 | 3/2008 |
| WO | WO 2008/098930 | 8/2008 |
| WO | WO 2008/112257 | 9/2008 |
| WO | WO 2008/112289 | 9/2008 |
| WO | WO 2008/144248 | 11/2008 |
| WO | WO 2008/155134 | 12/2008 |
| WO | WO 2009/052249 | 4/2009 |
| WO | WO 2009/138473 | 11/2009 |
| WO | WO 2010/040508 | 4/2010 |
| WO | WO 2010/068862 | 6/2010 |
| WO | WO 2010/068864 | 6/2010 |
| WO | WO 2010/111625 | 9/2010 |
| WO | WO 01/18080 | 3/2011 |
| WO | WO 2011/075185 | 6/2011 |
| WO | WO 2011/075736 | 6/2011 |
| WO | WO 2011/130694 | 10/2011 |
| WO | WO 2011/130694 A2 | 10/2011 |
| WO | WO 2013/059137 | 4/2013 |
| WO | WO 2013/093809 | 6/2013 |
| WO | WO 2014/060401 | 4/2014 |
| WO | WO 2014/160507 | 10/2014 |
| WO | WO 2015/035342 | 3/2015 |
| WO | WO 2015/200905 | 12/2015 |
| WO | WO 2016/061562 A2 | 4/2016 |
| WO | WO 2017/117464 | 7/2017 |
| WO | WO 2018/191548 | 10/2018 |

OTHER PUBLICATIONS

Alley, S. et al., "Contribution of linker stability to the activities of anticancer immunoconjugates," Bioconjugate Chem., vol. 19, No. 3, pp. 759-765, 2008.

Altamirano, C.V. et al., "Association of tetramers of human butyrylcholinesterase is mediated by conserved aromatic residues of the carboxy terminus," Chemico-Biological Interactions, vols. 119-120, pp. 53-60, May 14, 1999.

Baldwin, A. et al. "Reversible maleimide-thiol adducts yield glutathione-sensitive poly(ethylene glycol)-heparin hydrogels," Polymer Chemistry, vol. 4, Issue 1, pp. 133-143, Jan. 7, 2013.

Baldwin, A. et al. "Tunable degradation of maleimide-thiol adducts in reducing environments," Bioconjug Chem, vol. 22, No. 10, pp. 1946-1953, Oct. 19, 2011.

Blong, M. Renee et al., "Tetramerization domain of human butyrylcholinesterase is at the C-terminus," Biochemical Journal, vol. 327, No. 3, pp. 747-757, Nov. 1, 1997.

Cannard, K., "The acute treatment of nerve agent exposure," Journal of the Neurological Sciences, vol. 249, Issue 1, pp. 86-94, Nov. 1, 2006.

Cascio, C. et al., "Use of serum cholinesterases in severe organophosphorus poisoning," Minerva Anestesiologica, vol. 54, pp. 337-345, 1988.

Edelman, et al. "The Covalent Structure of an Entire gammaG Immunoglobulin Molecule," Proc Natl Acad Sci U S A, 63(1), pp. 78-85, (1969).

Ellman, G. et al., "A new and rapid colorimetric determination of acetylcholinesterase activity," Biochemical Pharmacology, vol. 7, Issue 2, pp. 88-95, Jul. 1961.

Foster, Graham R., "Pegylated Interferons for the treatment of chronic Hepatitis C," Drugs, vol. 70, Issue 2, pp. 147-165, Jan. 2010.

Goel, N. et al., "Certolizumab pegol," mAbs, vol. 2, No. 2, pp. 137-147, Mar./Apr. 2010.

Goodson, R.J. et al., "Site-directed pegylation of recombinant interleukin-2 at its glycosylation site," Nature Biotechnology, vol. 8, pp. 343-346, 1990.

Gordon, M. et al., "Determinatino of the normality of cholinesterase solutions," Analytical Biochemistry, vol. 85, Issue 2, pp. 519-527, Apr. 1978.

Gorun, V. et al., "Modified Ellman procedure for assay of cholinesterases in crude enzymatic preparations," Analytical Biochemistry, vol. 86, Issue 1, pp. 324-326, May 1978.

Greene T.W. et al., "Protective Groups in Organic Synthesis," 3rd Edition, John Wiley and Sons, Inc., New York, 1999.

Gualberto, Antonio, "Brentuximab Vedotin (SGN-35), an antibody-drug conjugate for the treatment of CD30-positive malignancies," Expert Opinion on Investigational Drugs, vol. 21, Issue 2, pp. 205-216, 2012.

(56) References Cited

OTHER PUBLICATIONS

Haupt, H. et al., "Isolierung und physikallsch-chemische Charakterisierung der Cholinesterase aus Humanserum," Blut, vol. 14, Issue 2, pp. 65-75, Nov. 1966.

Holliger, P. et al., "'Diabodies'; small bivalent and bispecific antibody fragments," Proc. Natl. Acad. Sci. USA, vol. 90, No. 14, pp. 6444-6448, Jul. 15, 1993.

Huang, Y.J. et al., "Recombinant human butyrylcholinesterase from milk of transgenic animals to protect against organophosphate poisoning," PNAS, vol. 104, No. 34, pp. 13603-13608, Aug. 21, 2007.

Kallis, G.B. et al., "Differential reactivity of the functional sulfhydryl groups of cysteine-32 and cysteine-35 present in the reduced form of thioredoxin from *Escherichia coli.*," The Journal of Biological Chemistry, vol. 255, No. 21, pp. 10261-10266, Nov. 10, 1980.

Lee, Ernes C., "Clinical manifestations of sarin nerve gas exposure," J. AM. Med. Assoc., vol. 290, No. 5, pp. 659-662, Aug. 6, 2003.

Lindley, H., "A study of the kinetics of the reaction between thiol compounds and chloroacetamide," Biochem J., vol. 74, pp. 577-584, Mar. 1960.

Lockridge, O. et al., "Complete amino acid sequence of human serum cholinesterase," The Journal of Biological Chemistry, vol. 262, pp. 549-557, Jan. 15, 1987.

Lockridge, O. et al., "Large scale purification of butyrylcholinesterase from human plasma suitable for injection into monkeys; A potential new therapeutic for protection against cocaine and nerve agent toxicity," The Journal of Medical, Chemical, Biological, and Radiological Defense, 3:nimhs5095, doi: 10.1901/jaba.2005.3-nihms5095, 2005.

Luxon, B. et al, "Pegylated interferons for the treatment of chronic hepatitis C infection," Clinical Therapeutics, vol. 24, Issue 9, pp. 1363-1383, Sep. 2002.

Masson, P. et al., "Multidisciplinary approaches to cholinesterase functions. expression and refoldin of functional human butyrylcholinesterase in." *E. coli.*, pp. 49-52, 1992.

Millard, C.B. et al., "Design and expression of organophosphorus acid anhydride hydrolase activity in human butyrylcholinesterase," Biochemistry, vol. 34, No. 49, pp. 15925-15933, 1995.

Piedmonte, D. et al., "Formulation of Neulasta® (pegfilgrastim)," Advanced Drug Delivery Reviews, vol. 60, Issue 3, pp. 50-58, Jan. 3, 2008.

Poljak, R. "Production and structure of diabodies," Structure, vol. 2, Issue 12, pp. 1121-1123, Dec. 1994.

Roberts, M.J. et al., "Chemistry for peptide and protein PEGylation," Advanced Drug Delivery Reviews, vol. 54, pp. 459-576, 2002.

Shen, B.Q. et al., "Conjugation site modulates the in vivo stability and therapeutic activity of antibody-drug conjugates," Nature Biotechnology, vol. 30, pp. 184-189, 2012.

Stenzel, Martina H., "Bioconjugation using thiols: Old chemistry rediscovered to connect polymers with nature's building blocks," ACS Macro letters, vol. 2, No. 1, pp. 14-18, 2013.

Veronese, Francesco M., "Peptide and protein PEGylation: a review of problems and solutions," Biomaterials, vol. 22, Issue 5, pp. 405-417, Mar. 1, 2001.

Wang, X. et al., "Disulfide scrambling in IgG2 monoclonal antibodies: Insights from molecular dynamics simulations," Pharmaceutical Research, vol. 28, Issue 12, pp. 3128-3144, Dec. 2011.

Wolfe, A. et al., "Use of cholinesterases as pretreatment drugs for the protection of rhesus monkeys against soman toxicity," Toxicology and Applied Pharmacology, vol. 117, Issue 2, pp. 189-193, Dec. 1992.

Notice of Allowance, issued in U.S. Appl. No. 14/753,824, dated Aug. 9, 2017.

Ambati et al., "Mechanisms of age-related macular degeneration," Neuron, vol. 75, No. 1, pp. 26-39, 2012.

Andrae et al., "Role of platelet-derived growth factors in physiology and medicine," Genes & Development, vol. 22, pp. 1276-1312, 2008.

Armulik, A. et al., "Endothelial/Pericyte Interactions," Circulation Research, vol. 97, Issue 6, pp. 512-523, Sep. 16, 2005.

Baluk, P. et al., "Cellular abnormalities of blood vessels as targets in cancer," Current Opinion in Genetics & Development, vol. 15, Issue 1, pp. 102-111, Feb. 2005.

Bates, D.O., et al., "Vascular endothelial growth factor increases microvascular permeability via a Ca(2+)-dependent pathway," American Journal of Physiology, vol. 273, No. 2, pp. H687-H694, Aug. 1, 1997.

Berthold, W. et al., "Protein Purification: Aspects of Processes for Pharmaceutical Products," Biologicals, vol. 22, Issue 2, pp. 135-150, Jun. 1994.

Bowen-Pope et al., "History of Discovery: Platelet-derived Growth Factor," Arterioscler Thromb Vasc Biol., vol. 31, No. 11, pp. 2397-2401, Nov. 2011.

Bontempo, et al., "Cysteine-Reactive Polymers Synthesized by Atom Transfer Radical Polymerization for Conjugation to Proteins," J. Am. Chem. Soc. (2004), 126, pp. 15372-15373.

Brown, D. et al., "Ranibizumab versus Verteporfin for Neovascular Age-Related Macular Degeneration," The New England Journal of Medicine, vol. 355, No. 14, pp. 1432-1444, Oct. 5, 2006.

Carmeliet, P., "Angiogenesis in healt and disease," Nature Medicine, vol. 9, pp. 653-660, (2003).

Carmeliet, P., "Synergism between vascular endothelial growth factor and placental growth factor contributes to angiogenesis and plasma extravasation in pathological conditions," Nature Medicine, vol. 7, No. 5, pp. 575-583, May 2001.

Carmeliet, "Mechanisms of angiogenesis and arteriogenesis," Nature Medicine, vol. 6, No. 3, pp. 389-395, 2000.

Chen et al., "Factors affecting endotoxin removal from recombinant therapeutic proteins by anion exchange chromatography," Protein Expression and Purification, vol. 64, pp. 76-81, 2009.

Chen, et al., "Polymeric Phosphorylcholine-Camptothecin Conjugates Prepared by Controlled Free Radical Polymerizationand Click Chemistry," Bioconjugate Chem., (2009), 20:12, pp. 2331-2341.

Chothia, C. et al., "Canonical structures for the hypervariable regions of immunoglobulins," Journal of Molecular Biology, vol. 196, Issue 4, pp. 901-917, Aug. 20, 1989.

Chothia, C. et al., "Conformations of immunoglobulin hypervariable regions," Nature, vol. 342, pp. 877-883, Dec. 1989.

Christy, N.E. et al., "Antibiotic prophylaxis of postoperative endophthalmitis," Annals of Ophthalmology, vol. 11, No. 8, pp. 1261-1265, Aug. 1, 1979.

Crowe, et al., "Recombinant human respiratory syncytial virus (RSV) monoclonal antibody Fab is effective therapeutically when introduced directly into the lungs of RSV-infected mice," Proc. Natl. Acad. Sci. USA, (1994) 91 pp. 1386-1390.

Da Pieve, et al., "Modification of Thiol Functionalized Aptamers by Conjugation of Synthetic Polymers," Bioconjugate Chem., (2010), 21:1, pp. 169-174.

Daneshian, M. et al., "In vitro pyrogen test for toxic or immunomodulatory drugs," Journal of Immunological Methods, vol. 313, Issues 1-2, pp. 169-175, Jun. 30, 2006.

De Pascalis, R. et al., "Grafting of "abbreviated" complementarity-determining regions containing specificity-determining residues essential for ligand contact to engineer a less immunogenic humanized monoclonal antibody," J. Immunol., vol. 169, No. 6, pp. 3076-3084, Sep. 15, 2002.

Declaration of Harvey N. Masonson, M.D., Jul. 6, 2011.

Dillon et al., "Structural and functional characterization of disulfide isoforms of the human IgG2 subclass," The Journal of Biological Chemistry, vol. 283, No. 23, pp. 16206-16215, 2008.

Dong, et al., "ARGET ATRP of 2-(Dimethylamino)ethyl Methacrylate as an Intrinsic Reducing Agent," Macromolecules, (2008), 41:19 pp. 6868-6870.

Dong, et al., "Well-Defined High-Molecular-Weight Polyacrylonitrile via Activators Regenerated by Electron Transfer ATRP," Macromolecules, (2007), 40:9, pp. 2974-2977.

Edelman et al., "The covalent structure of an entire yG immunoglobulin molecule," Proceedings of the National Academy of Sciences, vol. 63, pp. 78-85, May 1, 1969.

Engelgau, M et al. Evolving Diabetes Burden in the United States. Ann of Int Med. 140 (11): 945-951, 2004.

(56) References Cited

OTHER PUBLICATIONS

Extended European Search Report received in European Patent Application No. 17165316.5 dated Aug. 2, 2017.

Extended European Search Report received in European Patent Application No. 17181272.0 dated Feb. 23, 2018 in.

Extended European Search Report dated Mar. 21, 2016 in EP Application No. 11769715.1, dated Jul. 18, 2016.

Extended Search Report received in European Patent Application No. 14841835.3 dated Mar. 14, 2017.

Extended Search Report received in European Patent Application No. 15851363.0 dated Jan. 30, 2 2018.

Fares, F.A, et al., "Design of a long-acting follitropin agonist by fusing the C-terminal sequence of the chorionic gonadotropin beta subunit to the follitropin beta subunit," Proc Natl Acad Sci USA, vol. 89, No. 10, pp. 4304-4308, May 15, 1992.

Ferrara, N. et al., "Discovery and development of bevacizumab, an anti-VEGF antibody for treating cancer," Nature Reviews Drug Discovery, vol. 3, pp. 391-400, May 2004.

Ferrara, N. et al., "The biology of vascular endothelial growth factor," Endocrine Reviews, vol. 18, No. 1, pp. 4-25, (1997).

First Examination Report in NZ Application No. 6009449, dated Mar. 14, 2013.

First Examination Report in NZ Application No. 603048, dated Jun. 13, 2013 i.

Fiske, M. et al., "Method for reducing endotoxin in Moraxella catarrhalis UspA2 protein preparations," Journal of Chromatography B: Biomedical Sciences and Applications, vol. 753, Issue 2, pp. 269-278, Apr. 5, 2001.

Folkman, J., "Angiogenesis: an organizing principle for drug discover?" Nature Reviews, Drug Discovery, vol. 6, pp. 273-286, Apr. 2007.

Fontaine et al., "Long-Term Stabilization of Maleimide-Thiol Conjugates," Bioconjugate Chem., vol. 26, pp. 145-152, 2015.

Friedman, D.S. et al., "Prevalence of age-related macular degeneration in the United States," Arch. Ophthalmol., vol. 122, No. 4, pp. 564-572, Apr. 2004.

Greene et al., "Protective Groups in Organic Synthesis," 3rd Edition, John Wiley and Sons, Inc., New York, (1999).

Gillies, et al., "Dendrimers and Dedritic Polymers in Drug Delivery," Drug Delivery today, Jan. 2005, vol. 10, No. 1, pp. 35-43.

Haddleton, et al., "Phenolic Ester-Based Initiators for Transition Metal Mediated Living Polymerization," Macromolecules, (1999), 32, pp. 8732-8739.

Haishima, Y et al. Estimation of uncertainty in kinetic-colorimetric assay of bacterial endotoxins, J Pharm Biomed Analysis, 32: 1, pp. 495-503, (2003).

Heise, et al., "Investigation of the Initiation Behavior of a Dendritic 12-Arm Initiator in Atom Transfer Radical Polymerization," Macromolecules, (2001), 34:11, pp. 3798-3801.

Heise et al. Macromolecules 2000 33:2346-2354.

Heredia, et al., "In Situ Preparation of Protein-'Smart' Polymer Conjugates with Retention of Bioactivity," J. Am. Chem. Soc., (2005), 127, pp. 16955-16960.

Hirayama, C. et al., "Chromatographic removal of endotoxin from protein solutions by polymer particles," Journal of Chromatography B, vol. 781, Issues 1-2, pp. 419-432, Dec. 5, 2002.

Hong, et al., "Preparation of Segmented Copolymers in the Presence of an Immobilized/Soluble Hybrid ATRP Catalyst System," Macromolecules, (2003), 36:1, pp. 27-35.

Humphreys et al., "Alternative antibody FAB' fragment PEGylation strategies: combination of strong reducing agents, disruption of the interchain disulphide bond and disulphide engineering," Protein Engineering, Design & Selection, vol. 20, No. 5, pp. 227-234, 2007.

Huston, James S., "Protein engineering of single-chain Fv analogs and fusion proteins," Methods of Enzymology, vol. 203, pp. 46-96, 1991.

International Search Report in PCT Application No. PCT/US2007/005372, dated Aug. 8, 2008 in 4 pages.

International Search Report and Written Opinion dated Sep. 9, 2010 in PCT Application No. PCT/US2010/034252.

International Search Report and Written Opinion dated May 9, 2011 in PCT Application No. PCT/US2010/61358.

International Search Report and Written Opinion dated Dec. 16, 2011 in PCT Application No. PCT/US2011/32768.

International Search Report dated Jun. 4, 2013, in International Application No. PCT/IB2012/057491, 9 pages.

International Search Report and Written Opinion dated Feb. 27, 2013 in Internatnional Application No. PCT/US2012/060301.

International Search Report in PCT Application No. PCT/US2014/054622, dated Feb. 27, 2015.

International Search Report and Written Opinion for PCT/US2015/038203, dated Dec. 8, 2015.

International Preliminary Report on Patentability (IPRP) dated Jun. 24, 2014, in International Application No. PCT/IB2012/057491, 10 pages.

International Preliminary Report on Patentability (IPRP) dated Jul. 5, 2016, in International Application No. PCT/US2015/038203.

International Preliminary Report on Patentability dated Apr. 18, 2017 in International Application No. PCT/US2015/056112.

International Search Report and Written Opinion dated Mar. 30, 2017 for International Patent Application No. PCT/US2016/069336 filed Dec. 29, 2016, 22 pages.

IUPAC Gold Book, Random copolymer, available at https://goldbook.iupac.org/html/R/R05126.html, accessed Nov. 21, 2017; However, as this item is accessible on the world wide web, it may have been available in some form at an earlier point in time.

IUPAC Gold Book, Random Copolymerization, available at https://goldbook.iupac.org/html/R/R05126.html, accessed Nov. 21, 2017; However, as this item is accessible on the world wide web, it may have been available in some form at an earlier point in time.

Ishikawa, K. et al., "Molecular mechanisms of subretinal fibrosis in age-related macular degeneration," Experimental Eye Research, vol. 142, pp. 19-25, Jan. 2016.

Iwasaki, et al., "Platelet compatible blood filtration fabrics using a phosphorylcholine polymer having high surface mobility," Biomaterials, (2003), 24 pp. 3599-3604.

Jakubowski, et al., "Activators Regenerated by Electron Transfer for Atom Transfer Radical Polymerization of Styrene," Macromolecules, (2006), 39:1, pp. 39-45.

Jankova, et al., "Star Polymers by ATRP of Styrene and Acrylates Employing Multifunctional Initiators," Journal of Polymer Science Part A: Polymer Chemistry, Mar. 30, 2005, vol. 43, pp. 3748-3759.

Jo, N. et al., "Inhibition of platelet-derived growth factor B signaling enhances the efficacy of anti-vascular endothelial growth factor therapy in multiple models of ocular neovascularization," American Journal of Pathology, vol. 168, No. 6, pp. 2036-2053, Jun. 2006.

Junghans, R.P., "Anti-Tac-H, a humanized antibody to the interleukin 2 receptor with new features for immunotherapyin malignant and immune disorders," Cancer Research, vol. 50, pp. 1495-1502, Mar. 1, 1990.

Kizhakkedathu, et al., "Synthesis of Well-Defined Environmentally Responsive Polymer Brushes by Aqueous ATRP," Macromolecules, (2004), 37:3, pp. 734-743.

Kwiatdowski, et al., "High Molecular Weight Polymethacrylates by AGET ATRP under High Pressure," Macromolecules, (2008), 41:4, pp. 1067-1069.

Kostelny, S.A. et al., "Formation of a bispecific antibody by the use of leucine zippers," J. Immunol., vol. 148, No. 5, pp. 1547-1553, Mar. 1, 1992.

Kuhnert, F. et al. "Soluble receptor-mediated selective inhibition of VEGFR and PDGFR_ signaling during physiologic and tumor angiogenesis", PNAS, vol. 105, No. 29, pp. 10185-10190, (2008).

Kumar et al., "PDGF-DD targeting arrests pathological angiogenesis by modulating GSK3β phosphorylation," JBC Papers in Press, published on Mar. 15, 2010 as Manuscript M110.113787, retrieved on Jun. 18, 2015 from http://www.jbc.org; However, as this item is accessible on the world wide web, it may have been available in some form at an earlier point in time.

Kumar, A. et al., "Platelet-derived growth factor-DD targeting arrests pathological angiogenesis by modulating glycogen synthase kinase-3β phosphorylation," The Journal of Biological Chemistry, vol. 285, No. 20, pp. 15500-15510, May 14, 2010.

(56) References Cited

OTHER PUBLICATIONS

Lacciardi, et al., "Synthesis of Novel Folic Acid-Functionalized Biocompatible Block Copolymers by Atom Transfer Radical Polymerization for Gene Delivery and Encapsulation of Hydrophobic Drugs," Biomacromolecules, (2005), 6:2, pp. 1085-1096.
Lafaut et al., "Clinicopathological correlation in exudative age related macular degeneration: histological differentiation between classic and occult choroidal neovascularisation," Br J Ophthalmol, vol. 84, pp. 239-243, 2000.
Lena, et al., "Investigation of metal ligand affinities of atom transfer radical polymerization catalysts with a quadrupole ion trap," Dalton Transactions, (2009), 41, pp. 8884-8889.
Lewis, et al., "Crosslinkable coatings from phosphorylcholine-based polymers," Biomaterials, (2001), 22, pp. 99-111.
Lin, Weifeng et al., "A novel zwitterionic copolymer with a short poly(methyl acrylic acid) block for improving both conjugation and separation efficiency of a protein without losing its bioactivity". Journal of Materialos Chemistry B. May 21, 2013, vol. 1, No. 19, pp. 2482-2488, See abstract; and p. 2487.
Liu, et al., "Syntheses and Micellar Properties of Well-Defined Amphiphilic $AB_2$ and $A_2B$ Y-Shaped Miltoarm Star Copolymers of ε-Caprolactone 2-(Dimethylamino) ethyl Methacdrylate," *Journal Polymer Science: Part A: Polymer Chemistry*, DOI 10.1002/pola, published online in Wiley InterSciences (www.interscience.wiley.com), Sep. 22, 2006; accepted Nov. 23, 2006.
Lucentis ramibizumab (reb) Product Information Sheet most recent amendment Oct. 23, 2013.
Lutz, et al., "Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate," Macromolecules, (2006), 39:2, pp. 893-896.
Ma, et al., "Synthesis of Biocompatible Polymers. 1. Homopolymerization of 2-Methacryloyloxyethyl Phosphorylcholine via ATRP in Protic Solvents: An Optimization Study," Macromolecules, (2002), 35:25, pp. 9306-9314.
Ma, et al., "Well-Defined Biocompatible Block Copolymers via Atom Transfer Radical Polymerization of 2-Methacryloyloxyethyl Phosphorylcholine in Protic Media," Macromolecules, (2003), 36:10, pp. 3475-3484.
Mabry, R. et al., "A dual-targeting PDGFRβ/VEGF—A molecule assembled from stable antibody fragments demonstrates anti-angiogenic activity in vitro and in vivo", Landes Bioscience, vol. 2, Issue 2, pp. 20-34 (2010).
Magalhaes et al., "Methods of Endotoxin Removal from Biological Preparations: a Review," J. Pharm Pharmaceut Sci., vol. 10, No. 3, pp. 388-404, 2007.
Mantovani, et al., "Design and Synthesis of N-Maleimido-Functionalized Hydrophilic Polymers via Copper-Mediated Living Radical Polymerization: A Suitable Alternative to PEGylation," J. Am. Chem. Soc., (2005), 127, pp. 2966-2973.
Marticorena, J. et al., "Sterile endophthalmitis after intravitreal injections," Mediators of Inflammation, vol. 2012, Article ID 928123, 6 pages, 2012.
Matyjaszewski, et al., "Diminishing catalyst concentration in atom transfer radical polymerization with reducing agents," PNAS, (Oct. 17, 2006), 103:42, pp. 15309-15314.
Meng, X. et al. New Generation Recombinant hBuChe-FC Fusion with In-Vivo Performance Equivilanet to Gold Standard Plasma-Derive hbuChe—A First-in-Class Broad Spectrum Bioscanvenger that is Sustainable, Scalable, and Highly Cost-Effective on a Troop-Equivalent-Dose (TED) Basis.
McRae, et al. "Pentafluorophenyl Ester-Functionalized Phosphorylcholine Polymers: Preparation of Linear, Two-Arm, and Grafted Polymer-Protein Conjugates," Biomacromolecules, 13, 2099-2109 (2012).
Min, et al., "Use of Ascorbic Acid as Reducing Agent for Synthesis of Well-Defined Polymers by ARGET ATRP," Macromolecules, (2007), 40:6, pp. 1789-1791.
Miyamoto, et al., "Effect of water-soluble Phospholipid polymers conjugated with papain on the enzymatic stability," Biomaterials, (2004), 25, pp. 71-76.
Mones, "Inhibiting VEGF and PDGF to Treat AMD," Review of Ophthalmology, retrieved from <http://www.reviewofophthalmology.com/content/d/retinal_insider/c/29979/#>, Sep. 9, 2011; However, as this item is accessible on the world wide web, it may have been available in some form at an earlier point in time.
Morris, G.E., "Epitope mapping protocols in methods in molecular biology," vol. 66, 1996.
Neuberger, M., "Generating high-avidity human Mabs in mice," Nature Biotechnology, vol. 14, pp. 826, 1996.
Notice of Allowance dated Jan. 28, 2014 in U.S. Appl. No. 13/515,913.
Notice of Allowance dated Jul. 31, 2014 in U.S. Appl. No. 13/959,563.
Notice of Allowance dated Aug. 9, 2017 in U.S. Appl. No. 14/753,824.
Notice of Final Rejection received in Korean Patent Application No. 10-2012-7029878 dated Aug. 28, 2017.
Notice of Final Rejection received in Korean Patent Application No. 10-2012-7029878 dated Oct. 27, 2017.
Office Action in U.S. Appl. No. 13/959,563, dated Oct. 10, 2013 in 15 pages.
Office Action in U.S. Appl. No. 13/959,563, dated Feb. 20, 2014 in 17 pages.
Office Action dated Feb. 7, 2012 in U.S. Appl. No. 12/281,071.
Office Action in U.S. Appl. No. 14/456,875, dated Apr. 20, 2017.
Office Action in U.S. Appl. No. 14/456,875, dated Jun. 9, 2015.
Office Action in U.S. Appl. No. 14/456,875, dated Oct. 5, 2016.
Office Action in JP Patent Application No. 2008-557399, dated May 25, 2013.
Office Action in CA Application No. 2795667, dated Apr. 6, 2017.
Office Action in CN Application No. 201180028682.1, dated Aug. 11, 2015.
Office Action in CN Application No. 201180028682.1, dated Aug. 21, 2014.
Office Action in CN Application No. 201180028682.1, dated Jan. 26, 2015.
Office Action in JP Application No. 2013-505799, dated Feb. 19, 2015.
Office Action in JP Application No. 2015-165282, dated Aug. 1, 2017.
Office Action in JP Application No. 2015-165282, dated Aug. 15, 2016.
Office Action in KR Application No. 10-2012-7029878, dated Mar. 8, 2017.
Office Action dated Jul. 2, 2014 in U.S. Appl. No. 13/516,173.
Office Action dated Dec. 16, 2014 in U.S. Appl. No. 13/516,173.
Office Action dated Oct. 14, 2015 U.S. Appl. No. 13/516,173.
Office Action dated Dec. 31, 2013 in U.S. Appl. No. 13/516,173.
Office Action dated Dec. 14, 2015 in U.S. Appl. No. 14/265,174.
Office Action in CA Application No. 2783615, dated Sep. 16, 2016.
Office Action in CA Application No. 2783615, dated Jan. 9, 2018.
Office Action in CA Application No. 2795667, dated Dec. 29, 2017.
Office Action in EP Application No. 10838353.0, dated Oct. 4, 2016.
Office Action in JP Application No. 2012-544945, dated Jul. 9, 2014.
Office Action in JP Application No. 2016-159104, dated Jun. 27, 2017.
Office Action dated May 30, 2017 U.S. Appl. No. 15/099,234.
Office Action dated Nov. 27, 2017 U.S. Appl. No. 15/099,234.
Office Action dated Jun. 2, 2016 U.S. Appl. No. 13/901,483.
Office Action dated Feb. 27, 2017 in U.S. Appl. No. 14/753,824.
Office Action dated Oct. 10, 2013 in U.S. Appl. No. 13/959,563.
Office Action dated Jan. 24, 2018 in U.S. Appl. No. 14/916,180.
Oh, et al., "Preparation of Poly(oligo(ethylene glycol) monomethyl ether methacrylate) by Homogeneous Aqueous AGET ATRP," Macromolecules, (2006), 39:9, pp. 3161-3167.
Ong, K. et al., "A rapid highly-sensitive endotoxin detection system," Biosensors and Bioelectronics, vol. 21, Issue 12, pp. 2270-2274, Jun. 15, 2006.
Ostberg, L. et al., "Human X (mouse X human) hybridomas stably producing human antibodies," Hybridoma, vol. 2, No. 4, pp. 361-367, 1983.

(56) References Cited

OTHER PUBLICATIONS

Padlan, Eduardo A., "A possible procedure for reducing the immunogenicity of antibody variable domains while preserving their ligand-binding properties," Molecular Immunology, vol. 28, Issues 4-5, pp. 489-498, Apr.-May 1991.
Palma, et al., "A new bispphosphonate-containing $^{99}$mTc(I) tricarbonyl complex potentially useful as bone-seeking agent: synthesis and biological evaluation," J Biol Inorg Chem, 12:667-679, (2007).
Papadopoulos et al., "Binding and neutralization of vascular endothelial growth factor (VEGF) and related ligands by VEGF Trap, ranibizumab and bevacizumab," Angiogenesis, vol. 15, pp. 171-185, 2012.
Partial Search Report dated Dec. 21, 2017 in European Patent Application No. 15812238.2.
Pasut, et al., "Protein peptide and non-peptide drug PEGylation for therapeutic application," Expert Opin. Ther. Patents, 14(6) 859-894 (2004)\.
Patent Examination Report No. 1 in AU Application No. 2010330727, dated Nov. 19, 2014.
Patent Examination Report in AU Application No. 2011239434, dated Mar. 19, 2014.
Patent Examination Report in AU Application No. 2015207898, dated Mar. 23, 2016 in 3 pages.
Patent Examination Report in AU Application No. 2015207898, dated May 27, 2016 in 6 pages.
Paul, W., Fundamental Immunology, 2nd ed. Raven Press, N.Y., (1989).
Petsch, D. et al., "Endotoxin removal from protein solutions," Journal of Biotechnology, vol. 76, Issues 2-3, pp. 97-119, Jan. 21, 2000.
Pietrasik, et al., "Synthesis of High Molecular Weight Poly(styrene-co-acrylonitrile) Copolymers with Controlled Architecture," Macromolecules, (2006), 39:19, pp. 6384-6390.
Pratt, et al. End-Functionalized Phosphorycholine Methacrylate and Their Use in Protein Conjugation, Biomacromlecules, vol. 9, pp. 2891-2897, (2008).
Presta et al., "Humanization of an Anti-Vascular Endothelial Growth Factor Monoclonal Antibody for the Therapy of Solid Tumors and Other Disorders," Cancer Research, vol. 57, pp. 4593-4599, 1997.
Raetz, C.R. et al., "Gram-negative endotoxin: an extraordinary lipid with profound effects on eukaryotic signal transduction," The FASEB Journal, vol. 5, No. 12, pp. 2652-2660, Sep. 1991.
Raica, M. et al., "Platelet-derived growth factor (PDGF)/PDGF receptors (PDGFR) axis as target for antitumor and antiangiogenic therapy," Pharmaceuticals, vol. 3, No. 3, pp. 572-599, (2010).
Ranganathan, et al., "Synthesis of Thermoresponsive Mixed Arm Star Polymers by Combination of RAFT and ATRP from a Multifunctional Core and Its Self-Assembly in Water," Macromolecules, (2008), 41:12, pp. 4226-4234.
*Regeneron Pharmaceuticals Inc.* vs. *Bayer Pharma AG* Approved Judgment dated Feb. 21, 2013.
Regillo, C. et al., "Randomized, double-masked, sham-controlled trial of ranibizumab for neovascular age-related macular degeneration: PIER Study Year 1," American Journal of Ophthalmology, vol. 145, Issue 2, pp. 239-248, Feb. 2008.
Restriction Requirement dated Mar. 7, 2018 in U.S. Appl. No. 15/394,500.
Restriction Requirement dated Jun. 20, 2011 in U.S. Appl. No. 12/28107.
Restriction Requirement dated Jul. 15, 2015 in U.S. Appl. No. 14/265,174.
Restriction Requirement dated Aug. 14, 2013 in U.S. Appl. No. 13/515,913.
Restriction Requirement dated Sep. 3, 2013 in U.S. Appl. No. 13/516,173.
Restriction Requirement dated Feb. 9, 2017 U.S. Appl. No. 15/099,234.
Restriction Requirement dated Nov. 3. 2015 U.S. Appl. No. 13/901,483.
Restriction Requirement dated Aug. 21, 2017 in U.S. Appl. No. 15/368,376.
Restriction Requirement dated Jan. 31, 2017 in U.S. Appl. No. 14/916,180.
Restriction Requirement dated Aug. 16, 2017 in U.S. Appl. No. 14/916,180.
Roberts et al., "Chemistry for Peptide and Protein PEGylation," Advanced Drug Delivery Reviews 2002 54:459-476.
Roberts, W.G. et al., "Increased microvascular permeability and endothelial fenestration induced by vascular endothelial growth factor," Journal of Cell Science, vol. 108, pp. 2369-2379, (1995).
Rosenfeld, P. et al., "Ranibizumab for neovascular age-related macular degeneration," The New England Journal of Medicine, vol. 355, No. 14, pp. 1419-1431, Oct. 5, 2006.
Ruiz, et al., "Synthesis structure and surface dynamics of phosphorylcholine functional biomimicking polymers," Biomaterials, (1998), 19, pp. 987-998.
Ryan, et al., "Conjugation of salmon calcitonin to a combed-shaped end functionalized poly(poly(ethylene glycol) methyl ether methacrylate) yields a bioactive stable conjugate," Journal of Controlled Release, (2009), 135 pp. 51-59.
Rycroft, B.W., "Penicillin and the control of deep intra-ocular infection," British J. Ophthalmol, vol. 29, No. 2, pp. 57-87, Feb. 1945.
Sakaki, et al., "Stabilization of an antibody conjugated with enzyme by 2-methacryloyloxyethyl phosphorylcholine copolymer in enzyme-linked immunosorbent assay," J Biomed Mater Res, (1999), 47, pp. 523-528.
Samanta, et al., "End-Functionalized Phosphorylcholine Methacrylates and their Use in Protein Conjugation," Biomacromolecules, (2008), 9:(10), pp. 2891-2897.
Sayers, et al., "The Reduced Viscosity of PolyPEG® Compared with Linear PEG," Poster, Warwick Effect Polymers Ltd, retrieved from <http:www.wep-ltd.co.uk> on Feb. 11, 2009; However, as this item is accessible on the world wide web, it may have been available in some form at an earlier point in time.
Schellenberger, V. et al., "A recombinant polypeptide extends the in vivo half-life of peptides and proteins in a tunable manner," Nature Biotechnology, vol. 27, pp. 1186-1190, 2009.
Schlapschy, M. et al., "Fusion of a recombinant antibody fragment with a homo-amino-acid polymer: effects on biophysical properties and prolonged plasma half-life," Protein Eng Des Sel, vol. 20, Issue 6, pp. 273-284, Jun. 1, 2007.
Seo et al., "Conformational Recovery and Preservation of Protein Nature from Heat-Induced Debaturation by Water-Soluble Phospholipid Plymer Conjugation," Biomaterials, vol. 30, 2009, pp. 4859-4867.
Shim et al., "Structures of a platelet-derived growth factor/propeptide complex and a platelet-derived growth factor/receptor complex," PNAS, vol. 107, No. 25, pp. 11307-11312, 2010.
Songsivilai, S. et al., "Bispecific antibody: a tool for diagnosis and treatment of disease," Clin Exp. Immunol., vol. 79, No. 3, pp. 315-321, Mar. 1990.
Stuttfeld et al., "Structure and function of VEGF receptors," Life, vol. 61, No. 9, pp. 915-922, 2009.
Supplemental European Search Report received in European Patent Application No. EP 07752096.3 dated Feb. 19, 2013.
Supplemental European Search Report dated Feb. 2, 2015 in European Patent Application No. EP 10838353.0 dated Feb. 2, 2015.
Tamura, M. et al., "Structural correlates of an anticarcinoma antibody: Identification of specificity-determining residues (SDRs) and development of a minimally immunogenic antibody variant by retention of SDRs only," The Journal of Immunology, vol. 164, No. 3, pp. 1432-1441, Feb. 1, 2000.
Tao, et al., "α-Aldehyde Terminally Functional Methacrylic Polymers from Living Radical Polymerization: Application in Protein Conjugation 'Pegylation'," J. Am. Chem. Soc., (2004), 126:41, pp. 13220-13221.
Tao, Lei et al., "Branched polymer-protein conjugates made from mid-chain-functional P (HPMA)", Biomacromolecules, 2009, vol. 10, No. 10, pp. 2487-2851. See abstract; pp. 2847 and 2850; and scheme 2.
Ueda, et al., "Preparation of 2-Methacryloyloxyethyl Phosphocrycholine Copolymers with Alkyl Methacrylates and their Blood Campatability," Polymer Journal, vol. 24, No. 11, pp. 1259-1269 (1992).

(56) References Cited

OTHER PUBLICATIONS

Uutela et al., "PDFG-D induces macrophage recruitment, increased intersitial pressure, and blood vessel maturation during angiogenesis," Blood, vol. 104, No. 10, pp. 3198-3204, Nov. 15, 2004.
Vajdos, F. et al., "Comprehensive functional maps of the antigen-binding site of an anti-ErbB2 antibody obtained with shotgun scanning mutagenesis," Journal of Molecular Biology, vol. 320, Issue 2, pp. 415-428, Jul. 5, 2002.
Venditto, et al., "Cancer Therapies Utilizing the Camtothecins: A Review of the Vivo Literature," Molecular Pharmaceutics, vol. 7, No. 2, pp. 307-349 (2010).
Wagner, E. et al., "Transferrin-polycation conjugates as carriers for DNA uptake into cells," Proc. Natl. Acad. Sci. USA, vol. 87, No. 9, pp. 3410-3414, May 1, 1990.
Wang, et al., "Controlled/'Living' Radical Polymerization. Atom Transfer Radical Polymerization in the Presence of Transition-Metal Complexes," J. Am. Chem. Soc., (1995), 117:20, pp. 5614-5615\.
Warwick Effect Polymers, PowerPoint presentation, "Polymers for the Healthcare and Specialty Materials Industries," Jan. 2009, pp. 1-29.
Wu, G.Y. et al., "Receptor-mediated in vitro gene transformation by a soluble DNA carrier system," Journal of Biological Chemistry, vol. 262, pp. 4429-4432, Apr. 5, 1987.
Yaseen, et al., "The Structure of Zwitterionic Phosphoacholine Surfactant Monolayers," Langmuir, (2006), 22:13, pp. 5825-5832.
Yeh, P. et al., "Design of yeast-secreted albumin derivatives for human therapy: biological and antiviral properties of a serum albumin-CD4 genetic conjugate," Proc Natl Acad Sci USA, vol. 89, No. 5, pp. 1904-1908, Mar. 1, 1992.
Yusa, et al., "Synthesis of Well-Defined Amphiphilic Block Copolymers Having Phospholipid Polymer Sequences as a Novel biocompatible Polymer Micelle Reagents," Biomacromolecules, 6, 663-670 (2005).
Zebrowski, B. et al., "Vascular endothelial growth factor levels and induction of permeability in malignant pleural effusions," Clinical Cancer Research, vol. 5, pp. 3364-3368, Nov. 1999.
Zetter, "Angiogenesis and Tumor Metastasis," Annu. Rev. Med., vol. 49, pp. 407-424, 1998.
Zhang, X et al., Prevalence of Diabetic Retinopathy in the United States, 2005-2008, JAMA. vol. 304, No. 6, pp. 649-656, (2010).
Anderson, W.F., "Human gene therapy," Science, vol. 256, No. 5058, pp. 808-813, May 8, 1992.
Capon, D. et al., "Designing CD4 immunoadhesins for AIDS therapy," Nature, vol. 337, pp. 525-531, 1989.
Chen, et al., "Lubrication at Physiological Pressures by Polyzwitterionic Brushes," Science, 323 pp. 1698-1701, (2009).
Cohen, S.Y. et al., "Causes of unsuccessful ranibizumab treatment in exudative age-related macular degeneration in clinical settings," Retina, vol. 32, Issue 8, pp. 1480-1485, Sep. 2012.
Dapieve, et al., "Conjugation of PolyPEG® Linear PEG and, Branched PEG to a Thiol-Modified Aptamer," Poster, Warwick Effect Polymers Ltd, retrieved from <http:www.wep-ltd.co.uk> (2010).
Ding, J.L. et al., "A new era of pyrogen testing," Trends in Biotechnology, vol. 19, Issue 8, pp. 277-281, Aug. 1, 2001.
Du, J. et al. "pH-Sensitive Vesicles based on a Biocompatible Zwitterionic Diblock Copolymer" J. Am. Chem. Soc., 127, 17982-17983; (2005).
Facts About Diabetic Eye Disease, National Eye Institute, National Institute of Health <https://nei.nih.gov/health/diabetic/retinopathy> accessed Mar. 27, 2018; However, as this item is accessible on the world wide web, it may have been available in some form at an earlier point in time.
Hoffmann, S. et al., "International validation of novel pyrogen tests based on human monocytoid cells," Journal of Immunological Methods, vol. 298, Issues 1-2, pp. 161-173, Mar. 2005.
Holash, J et al. VEGF-TRAP: A VEGF Blocker with Potent Antitumor Effects, PNAS, vol. 9, No. 17, pp. 11393-11398, (2002).

Huang, Y-S. et al., "Engineering a pharmacologically superior form of granulocyte-colony-stimulating factor by fusion with gelatin-like-protein polymer," European Journal of Pharmaceutics and Biopharmaceutics, vol. 74, Issue 3, pp. 435-441, Mar. 2010.
Iwahashi, M. et al., "CDR substitutions of a humanized monoclonal antibody (CC49): contributions of individual CDRs to antigen binding and immunogenicity," Molecular Immunology, vol. 36, Issues 15-16, pp. 1079-1091, Oct.-Nov. 1999.
Iwasaki, Yasuhiko et al., "Synthesis and Characterization of Amphiphilic Polyphosphates with hydrophilic graft chains and Cholesteryl Groups as Nanocarriers", Biomacromolecules, 2006, 7, 1433-1438.
Jaffe, G. et al., "Intraocular drug delivery," CRC Press, Mar. 2006.
Jeon, et al., "Synthesis of High Molecular Weight 3-Arm Star PMMA by ARGET ATRP," Macromolecular, 17:4 pp. 240-244, (2009).
Jones, A., Analysis of Polypeptides and Proteins, Adv. Drug Delivery Rev. 10:, pp. 29-90, (1993).
Kabat, E.A. et al., "Sequences of proteins of immunological interest," DIANE publishing, 1992.
Kempen, J, et al. The Prevalence of Diabetic Retinopathy Among Adults in the United States, Arch Opthalmol., vol. 122, pp. 532-563, (2004).
Lee, Vincent H.L., "Peptide and Protein Drug Delivery," CRC Press, 1990.
Lewis, et al., "Poly(2-methacryloyloxyethyl phosphorylcholine) for Protein Conjugation," Bioconjugate Chem. 19:11 pp. 2144-2155, (2008).
McPherson, D. et al., "Production and Purification of a Recombinant Elastomeric Polypeptide, G-(VPGVG)19-VPGV, from *Escherichia coli*," Biotechnology Process, vol. 8, Issue 4, pp. 347-352, Jul./Aug. 1992.
Ng, et al., "Successful Cu-Mediated Atom Transfer Radical Polymerization in the Absence of Conventional Chelating Nitrogen Ligands," Macromolecules, 43:2 pp. 592-594, (2010).
Office Action in U.S. Appl. No. 14/456,875, dated Dec. 14, 2017.
Office Action dated Feb. 9, 2018 in U.S. Appl. No. 15/368,376.
Office Action dated Feb. 8, 2018 in Indian Patent Application No. 6116/CHENP/2012.
Ogikubo, Y. et al., "Evaluation of the bacterial endotoxin test for quantification of endotoxin contamination of porcine vaccines," Biologicals, vol. 32, Issue 2, pp. 88-93, Jun. 2004.
Petsch, D. et al., "Endotoxin removal from protein solutions," Journal of Biotechnology, vol. 76, Issued 2-3, pp. 97-119, Jan. 21, 2000.
Pennock, S. et al Vascular Endothelial Growth Factor A Competitively Inhibits Platelet-Derived Growth Factor (PDGF)-Dependent Activation of PDGF Receptor and Subsequent Signaling Events and Cellar Responses, Molecular and Cell Biology, vol. 32, No. 2, pp. 1955-1966, (2012).
Tonkinson, J. et al., "New Drugs: Antisense Oligodeoxynucleotides as Clinical Therapeutic Agents," Cancer Investigation, vol. 14, No. 1, pp. 54-65, 1996.
Voynov et al., "Design and application of antibody cysteine variants," Bioconjugate Chemistry, vol. 21, pp. 385-392, Jan. 21, 2010.
International Preliminary Report on Patentability dated Feb. 11, 2014 in PCT Application Np. PCT/US2011/32768.
File History of U.S. Appl. No. 15/394,500, filed Dec. 29, 2016.
File History of U.S. Appl. No. 13/959,563, filed Aug. 5, 2013.
File History of U.S. Appl. No. 14/456,875, filed Aug. 11, 2014.
File History of U.S. Appl. No. 12/281,071, filed Aug. 28, 2008.
File History of U.S. Appl. No. 14/265,174, filed Apr. 29, 2014.
File History of U.S. Appl. No. 15/182,278, filed Jun. 14, 2016.
File History of U.S. Appl. No. 13/515,913, filed Aug. 27, 2012.
File History of U.S. Appl. No. 13/516,173, filed Aug. 27, 2012.
File History of U.S. Appl. No. 15/099,234, filed Apr. 14, 2016.
File History of U.S. Appl. No. 13/901,483, filed May 23, 2013.
File History of U.S. Appl. No. 15/368,376, filed Dec. 2, 2016.
File History of U.S. Appl. No. 14/916,180, filed Mar. 2, 2016.
File History of U.S. Appl. No. 14/753,824, filed Jun. 29, 2015.
File History of U.S. Appl. No. 15/820,325, filed Nov. 21, 2017.
Ferrara, et al. Development of Ranibizumab, An Anti-Vascular Endothelial Growth, as Therapy for Neovascular Age-Related Macular

(56) References Cited

OTHER PUBLICATIONS

Degeneration, Retina, The Journal of Retinal and Vitreous Diseas, vol. 26, Issue No. 8, pp. 859-870, (2006).
Ferrara, et al The Biology of VEGF and its Receptors, Nature Medicine, vol. 9 No. 6, pp. 669-676, (2003).
Wang, et al., "Synthesis and Evaluation of Water-Soluble Polymers Bone-Targeted Drug Delivery Systems," Bioconjugate Chem., 14, 853-859 (2003).
Yu, L et al. Internaction Between Bevacizumab and Murie VEGF-A: A Reassessment, Investigative Opthalmology & Visual Science, vol. 49, No. 2, pp. 522-527, (2008).
Advisory Action dated Jun. 12, 2014 in U.S. Appl. No. 13/959,563.
International Preliminary Report on Patentability dated Jul. 3, 2018 for International Patent Application No. PCT/US2016/069336 filed Dec. 29, 2016.
Notice of Rejection received in Japanese Patent Application No. 2016-159104 dated Feb. 26, 2018.
Notice to File a Response received in Korean Patent Application No. 10-2012-7018788 dated Sep. 13, 2017.
Office Action dated Jun. 21, 2018 in U.S. Appl. No. 15/394,500.
Office Action dated Apr. 12, 2018 in Australian Patent Application Np. 2017201930.
Office Action received in European Patent Application No. 11769715.1 dated Nov. 9, 2017.
Office Action dated Mar. 9, 2018 in KR Application No. 10-217-703456.
Office Action dated May 8, 2018 in Japanese Patent Application No. 2017-520515.
Office Action dated Jun. 27, 2018 in Indian Patent Application No. 9476/CHENP/2012 in 5 pages.
Adviosry Action dated Nov. 29. 2018 in U.S. Appl. No. 14/916,180.
International Search Report and Written Opinion for PCT/US2018/027378 dated Sep. 27, 2018.
Notice of Allowance dated Sep. 26, 2018 in Canadian Patent Application No. 2,783,615.
Office Action in U.S. Appl. No. 14/456,875, dated Aug. 28, 2018.
Office Action in European Patent Application No. 17181272.0 dated Oct. 31, 2018.
Office Action Dated Oct. 19, 2018 U.S. Appl. No. 15/099,234.
Office Action dated Sep. 10, 2018 in U.S. Appl. No. 15/368,376.
Office Action in JP Application No. 2015-165282, dated Sep. 27, 2018.
Office Action dated Aug. 28, 2018 in KR Application No. 10-217-703456.
Office Action Dated Jul. 13, 2018 in Japanese Patent Application No. 2016-540916.
Office Action dated Aug. 10. 2018 in U.S. Appl. No. 14/916,180.
File History of U.S. Appl. No. 15/952,092, filed Apr. 12, 2018.
Casset, F. et al. A Peptide Mimetic of an Anti0CD4 Monoclonal Antibody by Rational Design, Biochemical and Biophysical Research Communications, vol. 307, pp. 198-205, (2003).
Chen, Y et al. Selection and Analysisi an Optimized Anti-VEGF Antibody: Crystal Structure of an Affinity-Matured Complex with Antigen, J. Mol. Biol,, vol. 293, pp. 865-881, (1999).
Janssen, Alzheimer Immunotherapy Research & Development, LLC, AAB-001 in Patients With Mild to Moderate Alzheimer's Diesear, Clinical Trials, gov, NIH, 2005, [retrieved on Jun. 19, 2012]. Retreived from the Internet: <http://clinicaltrials.gov/ct2/show/NCT00112073?term=aab-001&rank=3>.
Maccallum, R. et al., Antibody-Antigen Interactions: Contact Analysis and Binding Site Toopgraphy, J/. Mol Biol., vol. 262, pp. 732-745, (1996).
Rudikoff, S. et al, Single Amino Acid Substituon Altering Antigen-Bidning Specificity, Proc Natl. Acad. Sci. USA, vol. 79, pp. 1979-1983, (1982).
Wu, H et al., Humanization of a Murine Monoclonal Antibody by Simultaneous Optimization of Frameork and CDR Resiudes, J. Mol. Biol., vol. 294, pp. 151-162, (1999).
Adviosry Action dated Dec. 11. 2018 in U.S. Appl. No. 14/916,180.
Office Action dated Jan. 7, 2019 in U.S. Appl. No. 15/394,500.
Office Action dated Nov. 27, 2018 in Japanese Patent Application No. JP 2017-231724.
Office Action dated Jan. 9, 2019 in U.S. Appl. No. 15/820,325.
Office Action dated Dec. 18, 2018 in Japanese Patent Application No. 2017-520515.
Office Action dated Feb. 21, 2019 in European Patent Application No. 15851363.0.
Office Action in U.S. Appl. No. 14/456,875, dated Mar. 8, 2019.
Office Action dated Mar. 11, 2019 in U.S. Appl. No. 15/368,376.
Office Action dated Mar. 8, 2019 in U.S. Appl. No. 14/916,180.
Office Action dated Jan. 23, 2019 in European Patent Application No. EP 14841835.3.
Vafa, O. et al. An Engineered FC Variant of an IG Elimaties All Immune Effecotr Functions via Structural Pertubations, Methods, vol. 65, pp. 114-126, (2014).
Office Action dated Apr. 23, 2019 in Korean Patent Application No. KR 10-2017-7013268.
Office Action dated May 14, 2019 U.S. Appl. No. 15/099,234.

\* cited by examiner

SEQUENCE LISTING

<160> NUMBER OF SEQ ID NOS: 28

<210> SEQ ID NO 1
<211> LENGTH: 602
<212> TYPE: PRT
<213> ORGANISM: Homo sapiens

<400> SEQUENCE: 1

```
Met His Ser Lys Val Thr Ile Ile Cys Ile Arg Phe Leu Phe Trp Phe
 1               5                  10                  15
Leu Leu Leu Cys Met Leu Ile Gly Lys Ser His Thr Glu Asp Asp Ile
             20                  25                  30
Ile Ile Ala Thr Lys Asn Gly Lys Val Arg Gly Met Asn Leu Thr Val
         35                  40                  45
Phe Gly Gly Thr Val Thr Ala Phe Leu Gly Ile Pro Tyr Ala Gln Pro
     50                  55                  60
Pro Leu Gly Arg Leu Arg Phe Lys Lys Pro Gln Ser Leu Thr Lys Trp
 65                  70                  75                  80
Ser Asp Ile Trp Asn Ala Thr Lys Tyr Ala Asn Ser Cys Cys Gln Asn
                 85                  90                  95
Ile Asp Gln Ser Phe Pro Gly Phe His Gly Ser Glu Met Trp Asn Pro
            100                 105                 110
Asn Thr Asp Leu Ser Glu Asp Cys Leu Tyr Leu Asn Val Trp Ile Pro
        115                 120                 125
Ala Pro Lys Pro Lys Asn Ala Thr Val Leu Ile Trp Ile Tyr Gly Gly
    130                 135                 140
Gly Phe Gln Thr Gly Thr Ser Ser Leu His Val Tyr Asp Gly Lys Phe
145                 150                 155                 160
Leu Ala Arg Val Glu Arg Val Ile Val Val Ser Met Asn Tyr Arg Val
                165                 170                 175
Gly Ala Leu Gly Phe Leu Ala Leu Pro Gly Asn Pro Glu Ala Pro Gly
            180                 185                 190
Asn Met Gly Leu Phe Asp Gln Gln Leu Ala Leu Gln Trp Val Gln Lys
        195                 200                 205
Asn Ile Ala Ala Phe Gly Gly Asn Pro Lys Ser Val Thr Leu Phe Gly
    210                 215                 220
Glu Ser Ala Gly Ala Ala Ser Val Ser Leu His Leu Leu Ser Pro Gly
225                 230                 235                 240
Ser His Ser Leu Phe Thr Arg Ala Ile Leu Gln Ser Gly Ser Phe Asn
                245                 250                 255
Ala Pro Trp Ala Val Thr Ser Leu Tyr Glu Ala Arg Asn Arg Thr Leu
            260                 265                 270
Asn Leu Ala Lys Leu Thr Gly Cys Ser Arg Glu Asn Glu Thr Glu Ile
        275                 280                 285
Ile Lys Cys Leu Arg Asn Lys Asp Pro Gln Glu Ile Leu Leu Asn Glu
    290                 295                 300
Ala Phe Val Val Pro Tyr Gly Thr Pro Leu Ser Val Asn Phe Gly Pro
305                 310                 315                 320
Thr Val Asp Gly Asp Phe Leu Thr Asp Met Pro Asp Ile Leu Leu Glu
                325                 330                 335
Leu Gly Gln Phe Lys Lys Thr Gln Ile Leu Val Gly Val Asn Lys Asp
            340                 345                 350
Glu Gly Thr Ala Phe Leu Val Tyr Gly Ala Pro Gly Phe Ser Lys Asp
        355                 360                 365
Asn Asn Ser Ile Ile Thr Arg Lys Glu Phe Gln Glu Gly Leu Lys Ile
    370                 375                 380
Phe Phe Pro Gly Val Ser Glu Phe Gly Lys Glu Ser Ile Leu Phe His
385                 390                 395                 400
Tyr Thr Asp Trp Val Asp Asp Gln Arg Pro Glu Asn Tyr Arg Glu Ala
                405                 410                 415
```

```
Leu Gly Asp Val Val Gly Asp Tyr Asn Phe Ile Cys Pro Ala Leu Glu
            420                 425                 430

Phe Thr Lys Lys Phe Ser Glu Trp Gly Asn Asn Ala Phe Phe Tyr Tyr
        435                 440                 445

Phe Glu His Arg Ser Ser Lys Leu Pro Trp Pro Glu Trp Met Gly Val
450                 455                 460

Met His Gly Tyr Glu Ile Glu Phe Val Phe Gly Leu Pro Leu Glu Arg
465                 470                 475                 480

Arg Asp Asn Tyr Thr Lys Ala Glu Glu Ile Leu Ser Arg Ser Ile Val
                485                 490                 495

Lys Arg Trp Ala Asn Phe Ala Lys Tyr Gly Asn Pro Asn Glu Thr Gln
            500                 505                 510

Asn Asn Ser Thr Ser Trp Pro Val Phe Lys Ser Thr Glu Gln Lys Tyr
        515                 520                 525

Leu Thr Leu Asn Thr Glu Ser Thr Arg Ile Met Thr Lys Leu Arg Ala
    530                 535                 540

Gln Gln Cys Arg Phe Trp Thr Ser Phe Phe Pro Lys Val Leu Glu Met
545                 550                 555                 560

Thr Gly Asn Ile Asp Glu Ala Glu Trp Glu Trp Lys Ala Gly Phe His
                565                 570                 575

Arg Trp Asn Asn Tyr Met Met Asp Trp Lys Asn Gln Phe Asn Asp Tyr
            580                 585                 590

Thr Ser Lys Lys Glu Ser Cys Val Gly Leu
        595                 600

<210> SEQ ID NO 2
<211> LENGTH: 772
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Tyr Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
```

-continued

```
                165                 170                 175
Trp Val Gln Lys Asn Ile Ala Ala Phe Gly Gly Asn Pro Lys Ser Val
            180                 185                 190

Thr Leu Phe Gly Glu Ser Ala Gly Ala Ala Ser Val Ser Leu His Leu
            195                 200                 205

Leu Ser Pro Gly Ser His Ser Leu Phe Thr Arg Ala Ile Leu Gln Ser
            210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
            245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Ser Val
            275                 280                 285

Asn Phe Gly Pro Thr Val Asp Gly Asp Phe Leu Thr Asp Met Pro Asp
            290                 295                 300

Ile Leu Leu Glu Leu Gly Gln Phe Lys Lys Thr Gln Ile Leu Val Gly
305                 310                 315                 320

Val Asn Lys Asp Glu Gly Thr Ala Phe Leu Val Tyr Gly Ala Pro Gly
            325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
            355                 360                 365

Ile Leu Phe His Tyr Thr Asp Trp Val Asp Asp Gln Arg Pro Glu Asn
370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
            405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
            435                 440                 445

Pro Leu Glu Arg Arg Asp Asn Tyr Thr Lys Ala Glu Glu Ile Leu Ser
            450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
            485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
            515                 520                 525

Val Leu Glu Met Thr Gly Gly Ser Gly Gly Gly Ser Gly Gly Gly
            530                 535                 540

Ser Asp Lys Thr His Thr Cys Pro Pro Cys Pro Ala Pro Glu Ala Glu
545                 550                 555                 560

Gly Ala Pro Ser Val Phe Leu Phe Pro Pro Lys Pro Lys Asp Thr Leu
            565                 570                 575

Met Ile Ser Arg Thr Pro Glu Val Thr Cys Val Val Val Asp Val Ser
            580                 585                 590
```

```
His Glu Asp Pro Glu Val Lys Phe Asn Trp Tyr Val Asp Gly Val Glu
            595                 600                 605

Val His Asn Ala Lys Thr Lys Pro Arg Glu Glu Gln Tyr Asn Ser Thr
    610                 615                 620

Tyr Arg Val Val Ser Val Leu Thr Val Leu His Gln Asp Trp Leu Asn
625                 630                 635                 640

Gly Lys Glu Tyr Lys Cys Lys Val Ser Asn Lys Ala Leu Pro Ser Ser
                645                 650                 655

Ile Glu Lys Thr Ile Ser Lys Ala Lys Gly Gln Pro Arg Glu Pro Cys
            660                 665                 670

Val Tyr Thr Leu Pro Pro Ser Arg Asp Glu Leu Thr Lys Asn Gln Val
    675                 680                 685

Ser Leu Thr Cys Leu Val Lys Gly Phe Tyr Pro Ser Asp Ile Ala Val
    690                 695                 700

Glu Trp Glu Ser Asn Gly Gln Pro Glu Asn Asn Tyr Lys Thr Thr Pro
705                 710                 715                 720

Pro Val Leu Asp Ser Asp Gly Ser Phe Phe Leu Tyr Ser Lys Leu Thr
                725                 730                 735

Val Asp Lys Ser Arg Trp Gln Gln Gly Asn Val Phe Ser Cys Ser Val
            740                 745                 750

Met His Glu Ala Leu His Asn His Tyr Thr Gln Lys Ser Leu Ser Leu
    755                 760                 765

Ser Pro Gly Lys
    770

<210> SEQ ID NO 3
<211> LENGTH: 614
<212> TYPE: PRT
<213> ORGANISM: Homo sapiens

<400> SEQUENCE: 3

Met Arg Pro Pro Gln Cys Leu Leu His Thr Pro Ser Leu Ala Ser Pro
1               5                   10                  15

Leu Leu Leu Leu Leu Leu Trp Leu Leu Gly Gly Gly Val Gly Ala Glu
            20                  25                  30

Gly Arg Glu Asp Ala Glu Leu Leu Val Thr Val Arg Gly Gly Arg Leu
        35                  40                  45

Arg Gly Ile Arg Leu Lys Thr Pro Gly Gly Pro Val Ser Ala Phe Leu
    50                  55                  60

Gly Ile Pro Phe Ala Glu Pro Pro Met Gly Pro Arg Arg Phe Leu Pro
65                  70                  75                  80

Pro Glu Pro Lys Gln Pro Trp Ser Gly Val Val Asp Ala Thr Thr Phe
                85                  90                  95

Gln Ser Val Cys Tyr Gln Tyr Val Asp Thr Leu Tyr Pro Gly Phe Glu
            100                 105                 110

Gly Thr Glu Met Trp Asn Pro Asn Arg Glu Leu Ser Glu Asp Cys Leu
        115                 120                 125

Tyr Leu Asn Val Trp Thr Pro Tyr Pro Arg Pro Thr Ser Pro Thr Pro
    130                 135                 140

Val Leu Val Trp Ile Tyr Gly Gly Gly Phe Tyr Ser Gly Ala Ser Ser
145                 150                 155                 160

Leu Asp Val Tyr Asp Gly Arg Phe Leu Val Gln Ala Glu Arg Thr Val
                165                 170                 175

Leu Val Ser Met Asn Tyr Arg Val Gly Ala Phe Gly Phe Leu Ala Leu
```

```
                180             185             190
Pro Gly Ser Arg Glu Ala Pro Gly Asn Val Gly Leu Leu Asp Gln Arg
            195                 200                 205
Leu Ala Leu Gln Trp Val Gln Glu Asn Val Ala Ala Phe Gly Gly Asp
        210                 215                 220
Pro Thr Ser Val Thr Leu Phe Gly Glu Ser Ala Gly Ala Ala Ser Val
225                 230                 235                 240
Gly Met His Leu Leu Ser Pro Pro Ser Arg Gly Leu Phe His Arg Ala
                245                 250                 255
Val Leu Gln Ser Gly Ala Pro Asn Gly Pro Trp Ala Thr Val Gly Met
            260                 265                 270
Gly Glu Ala Arg Arg Arg Ala Thr Gln Leu Ala His Leu Val Gly Cys
        275                 280                 285
Pro Pro Gly Gly Thr Gly Gly Asn Asp Thr Glu Leu Val Ala Cys Leu
        290                 295                 300
Arg Thr Arg Pro Ala Gln Val Leu Val Asn His Glu Trp His Val Leu
305                 310                 315                 320
Pro Gln Glu Ser Val Phe Arg Phe Ser Phe Val Pro Val Val Asp Gly
                325                 330                 335
Asp Phe Leu Ser Asp Thr Pro Glu Ala Leu Ile Asn Ala Gly Asp Phe
            340                 345                 350
His Gly Leu Gln Val Leu Val Gly Val Val Lys Asp Glu Gly Ser Tyr
        355                 360                 365
Phe Leu Val Tyr Gly Ala Pro Gly Phe Ser Lys Asp Asn Glu Ser Leu
        370                 375                 380
Ile Ser Arg Ala Glu Phe Leu Ala Gly Val Arg Val Gly Val Pro Gln
385                 390                 395                 400
Val Ser Asp Leu Ala Ala Glu Ala Val Val Leu His Tyr Thr Asp Trp
                405                 410                 415
Leu His Pro Glu Asp Pro Ala Arg Leu Arg Glu Ala Leu Ser Asp Val
            420                 425                 430
Val Gly Asp His Asn Val Val Cys Pro Val Ala Gln Leu Ala Gly Arg
        435                 440                 445
Leu Ala Ala Gln Gly Ala Arg Val Tyr Ala Tyr Val Phe Glu His Arg
        450                 455                 460
Ala Ser Thr Leu Ser Trp Pro Leu Trp Met Gly Val Pro His Gly Tyr
465                 470                 475                 480
Glu Ile Glu Phe Ile Phe Gly Ile Pro Leu Asp Pro Ser Arg Asn Tyr
                485                 490                 495
Thr Ala Glu Glu Lys Ile Phe Ala Gln Arg Leu Met Arg Tyr Trp Ala
            500                 505                 510
Asn Phe Ala Arg Thr Gly Asp Pro Asn Glu Pro Arg Asp Pro Lys Ala
        515                 520                 525
Pro Gln Trp Pro Pro Tyr Thr Ala Gly Ala Gln Gln Tyr Val Ser Leu
        530                 535                 540
Asp Leu Arg Pro Leu Glu Val Arg Arg Gly Leu Arg Ala Gln Ala Cys
545                 550                 555                 560
Ala Phe Trp Asn Arg Phe Leu Pro Lys Leu Leu Ser Ala Thr Asp Thr
                565                 570                 575
Leu Asp Glu Ala Glu Arg Gln Trp Lys Ala Glu Phe His Arg Trp Ser
            580                 585                 590
Ser Tyr Met Val His Trp Lys Asn Gln Phe Asp His Tyr Ser Lys Gln
        595                 600                 605
```

Asp Arg Cys Ser Asp Leu
    610

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Gly Gly Ser Gly Gly Gly Gly Ser
1               5                   10

<210> SEQ ID NO 5
<211> LENGTH: 329
<212> TYPE: PRT
<213> ORGANISM: Desulfarculus baarsii

<400> SEQUENCE: 5

Met Ala Ala Lys Met Val Asn Thr Val Ala Gly Pro Val Ser Ala Asp
1               5                   10                  15

Glu Leu Gly Leu Thr Leu Met His Glu His Ile Val Phe Gly Tyr Pro
                20                  25                  30

Gly Trp Asn Gly Asp Val Thr Leu Gly Ala Phe Asp Arg Pro Ala Ala
            35                  40                  45

Val Lys Gln Ala Val Glu Thr Leu Ser Ala Leu Lys Gln Ala Phe Gly
        50                  55                  60

Leu Gly Thr Leu Val Asp Ala Thr Pro Asn Glu Thr Gly Arg Asp Pro
65                  70                  75                  80

Leu Leu Leu Lys Glu Val Ser Glu Lys Ser Gly Val Asn Ile Val Cys
                85                  90                  95

Ser Thr Gly Tyr Tyr Ser Gln Ala Glu Gly Gly Ala Ala Tyr Phe Ala
                100                 105                 110

Phe Arg Ala Ser Leu Gly Asp Ala Val Ala Glu Ile Arg Glu Met Phe
            115                 120                 125

Leu Thr Glu Leu Thr Lys Gly Val Ala Asp Thr Gly Val Arg Pro Gly
        130                 135                 140

Val Ile Lys Leu Ala Ser Ser Gln Gly Gln Ile Thr Asp Tyr Glu Lys
145                 150                 155                 160

Met Phe Phe Thr Ala Ala Val Ala Ala Gln Lys Glu Thr Gly Ala Pro
                165                 170                 175

Ile Ile Thr His Thr Glu His Gly Thr Met Gly Pro Glu Gln Ala Lys
            180                 185                 190

Phe Leu Leu Glu Leu Gly Ala Asp Pro Lys Arg Thr Met Ile Gly His
        195                 200                 205

Met Cys Asp Asn Leu Asp Leu Asp Tyr Gln Glu Ala Val Leu Arg Gln
    210                 215                 220

Gly Val Tyr Val Ser Trp Asp Arg Met Gly Leu Gln Gly Leu Ala Gly
225                 230                 235                 240

Cys Pro Met Glu Ala Thr Arg Tyr Pro Val Leu Asn Glu Leu Ile Gln
                245                 250                 255

Arg Gly Trp Ala Lys Gln Leu Met Leu Ser His Asp Ser Ile Asn Thr
            260                 265                 270

Trp Leu Gly Arg Pro Leu Ser Ile Pro Glu Ala Ala Leu Pro Met Val
        275                 280                 285

-continued

```
Ile Asp Trp Arg Pro Asp His Ile Phe Asn Lys Val Ala Pro Ala Leu
290                 295                 300
Leu Ala Gly Gly Ala Thr Gln Ala Asp Leu Asp Val Ile Leu Lys Asp
305                 310                 315                 320
Asn Pro Arg Arg Leu Phe Ala Gly Val
                325

<210> SEQ ID NO 6
<211> LENGTH: 355
<212> TYPE: PRT
<213> ORGANISM: Homo sapiens

<400> SEQUENCE: 6

Met Ala Lys Leu Ile Ala Leu Thr Leu Leu Gly Met Gly Leu Ala Leu
1               5                   10                  15
Phe Arg Asn His Gln Ser Ser Tyr Gln Thr Arg Leu Asn Ala Leu Arg
                20                  25                  30
Glu Val Gln Pro Val Glu Leu Pro Asn Cys Asn Leu Val Lys Gly Ile
            35                  40                  45
Glu Thr Gly Ser Glu Asp Leu Glu Ile Leu Pro Asn Gly Leu Ala Phe
        50                  55                  60
Ile Ser Ser Gly Leu Lys Tyr Pro Gly Ile Lys Ser Phe Asn Pro Asn
65                  70                  75                  80
Ser Pro Gly Lys Ile Leu Leu Met Asp Leu Asn Glu Glu Asp Pro Thr
                85                  90                  95
Val Leu Glu Leu Gly Ile Thr Gly Ser Lys Phe Asp Val Ser Ser Phe
            100                 105                 110
Asn Pro His Gly Ile Ser Thr Phe Thr Asp Glu Asp Asn Ala Met Tyr
        115                 120                 125
Leu Leu Val Val Asn His Pro Asp Ala Lys Ser Thr Val Glu Leu Phe
130                 135                 140
Lys Phe Gln Glu Glu Glu Lys Ser Leu Leu His Leu Lys Thr Ile Arg
145                 150                 155                 160
His Lys Leu Leu Pro Asn Leu Asn Asp Ile Val Ala Val Gly Pro Glu
                165                 170                 175
His Phe Tyr Gly Thr Asn Asp His Tyr Phe Leu Asp Pro Tyr Leu Gln
            180                 185                 190
Ser Trp Glu Met Tyr Leu Gly Leu Ala Trp Ser Tyr Val Val Tyr Tyr
        195                 200                 205
Ser Pro Ser Glu Val Arg Val Val Ala Glu Gly Phe Asp Phe Ala Asn
    210                 215                 220
Gly Ile Asn Ile Ser Pro Asp Gly Lys Tyr Val Tyr Ile Ala Glu Leu
225                 230                 235                 240
Leu Ala His Lys Ile His Val Tyr Glu Lys His Ala Asn Trp Thr Leu
                245                 250                 255
Thr Pro Leu Lys Ser Leu Asp Phe Asn Thr Leu Val Asp Asn Ile Ser
            260                 265                 270
Val Asp Pro Glu Thr Gly Asp Leu Trp Val Gly Cys His Pro Asn Gly
        275                 280                 285
Met Lys Ile Phe Phe Tyr Asp Ser Glu Asn Pro Ala Ser Glu Val
    290                 295                 300
Leu Arg Ile Gln Asn Ile Leu Thr Glu Glu Pro Lys Val Thr Gln Val
305                 310                 315                 320
Tyr Ala Glu Asn Gly Thr Val Leu Gln Gly Ser Thr Val Ala Ser Val
```

```
                       325                 330                 335
Tyr Lys Gly Lys Leu Leu Ile Gly Thr Val Phe His Lys Ala Leu Tyr
                   340                 345                 350

Cys Glu Leu
        355

<210> SEQ ID NO 7
<211> LENGTH: 314
<212> TYPE: PRT
<213> ORGANISM: Loligo vulgaris

<400> SEQUENCE: 7

Met Glu Ile Pro Val Ile Glu Pro Leu Phe Thr Lys Val Thr Glu Asp
1               5                   10                  15

Ile Pro Gly Ala Glu Gly Pro Val Phe Asp Lys Asn Gly Asp Phe Tyr
            20                  25                  30

Ile Val Ala Pro Glu Val Glu Val Asn Gly Lys Pro Ala Gly Glu Ile
        35                  40                  45

Leu Arg Ile Asp Leu Lys Thr Gly Lys Lys Thr Val Ile Cys Lys Pro
    50                  55                  60

Glu Val Asn Gly Tyr Gly Gly Ile Pro Ala Gly Cys Gln Cys Asp Arg
65                  70                  75                  80

Asp Ala Asn Gln Leu Phe Val Ala Asp Met Arg Leu Gly Leu Leu Val
                85                  90                  95

Val Gln Thr Asp Gly Thr Phe Glu Glu Ile Ala Lys Lys Asp Ser Glu
            100                 105                 110

Gly Arg Arg Met Gln Gly Cys Asn Asp Cys Ala Phe Asp Tyr Glu Gly
        115                 120                 125

Asn Leu Trp Ile Thr Ala Pro Ala Gly Glu Val Ala Pro Ala Asp Tyr
    130                 135                 140

Thr Arg Ser Met Gln Glu Lys Phe Gly Ser Ile Tyr Cys Phe Thr Thr
145                 150                 155                 160

Asp Gly Gln Met Ile Gln Val Asp Thr Ala Phe Gln Phe Pro Asn Gly
                165                 170                 175

Ile Ala Val Arg His Met Asn Asp Gly Arg Pro Tyr Gln Leu Ile Val
            180                 185                 190

Ala Glu Thr Pro Thr Lys Lys Leu Trp Ser Tyr Asp Ile Lys Gly Pro
        195                 200                 205

Ala Lys Ile Glu Asn Lys Lys Val Trp Gly His Ile Pro Gly Thr His
    210                 215                 220

Glu Gly Gly Ala Asp Gly Met Asp Phe Asp Glu Asp Asn Asn Leu Leu
225                 230                 235                 240

Val Ala Asn Trp Gly Ser Ser His Ile Glu Val Phe Gly Pro Asp Gly
                245                 250                 255

Gly Gln Pro Lys Met Arg Ile Arg Cys Pro Phe Glu Lys Pro Ser Asn
            260                 265                 270

Leu His Phe Lys Pro Gln Thr Lys Thr Ile Phe Val Thr Glu His Glu
        275                 280                 285

Asn Asn Ala Val Trp Lys Phe Glu Trp Gln Arg Asn Gly Lys Lys Gln
    290                 295                 300

Tyr Cys Glu Thr Leu Lys Phe Gly Ile Phe
305                 310

<210> SEQ ID NO 8
<211> LENGTH: 227
```

<212> TYPE: PRT
<213> ORGANISM: Homo sapiens

<400> SEQUENCE: 8

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 9
<211> LENGTH: 2460
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gctagcgccg ccaccatggc atgcctcgga tttcaaagac ataaagccca gttgaacctc      60
gccactagaa cctggccttg caccctgctg ttcttcctcc tgttcattcc ggtgttctgc     120
aaggctgagg acgacatcat catcgctacc aagaatggaa aggtccgcgg tatgaacctt     180
acggtgttcg gcggaactgt cactgccttc ttggggatcc atacgcaca accccccactt     240 ggcagactgc gctttaagaa acctcaatcg ctcacgaagt ggagcgatat ctggaacgcg     300
accaagtacg caaatagctg ctaccagaat atcgatcaga gcttccccgg attccacggc     360
tcggaaatgt ggaacccgaa caccgatctg tcggaggatt gcctgtacct gaacgtctgg     420
atcccggccc ctaagccgaa aaatgctacc gtgttgatct ggatctacgg ggaggattc     480 caaaccggaa cttccagcct gcacgtctac gacggaaagt ttttggcgcg cgtggagcgg     540

```
gtcattgtgg tgtccatgaa ttacagagtg ggggctctcg gattcctggc actgccaggt    600
aacccagagg ccccgggaaa catgggcctg ttcgaccagc agctcgcgct tcagtgggtg    660
cagaagaata tcgccgcctt tggcggtaac ccgaagtcgg tgactctctt tggcgaatca    720
gccggagctg catcagtctc ccttcatctg ttgtcccccg gaagccactc gctgttcacc    780
agggcgatcc tgcaatccgg atccttcaac gccccatggg cggttacttc actttacgag    840
gcccgtaacc ggacccttaa cctggcaaag ctcaccggat gtagccgcga gaacgaaacc    900
gaaatcataa agtgcctgcg aaacaaagac ccacaagaaa tcctcctgaa tgaggcattc    960
gtggtcccat acgtacccc gctctcagtg aacttcggcc ccactgtgga cggagacttc   1020
ctgaccgaca tgccggacat tttgctggag ctgggccagt tcaagaaaac gcagatcctg   1080
gtgggcgtca acaaagatga aggaactgcg ttcctcgtgt acggcgcccc gggcttctca   1140
aaggacaaca attccatcat tacgcggaag gagttccaag aagggctgaa aatcttcttc   1200
cctggagtgt cggaatttgg aaaggaaagc atcctgttcc actacaccga ctgggtggac   1260
gatcagcggc cggaaaacta ccgggaggcg ctgggtgatg tggtcggaga ctataacttc   1320
atctgcccgg ccctggagtt taccaaaaag ttttccgaat ggggaataa tgctttcttt   1380
tactacttcg aacatagaag ctcgaagctc ccttggccgg aatggatggg agttatgcac   1440
gggtatgaaa tcgagtttgt ctttgggctc cctctggagc gcagggataa ctacactaaa   1500
gccgaagaga tcctgtcacg ctcgatcgtg aagcggtggg cgaatttcgc gaagtacgga   1560
aatccaaacg aaactcagaa caactcgacc tcgtggccgg tgttcaagtc taccgagcag   1620
aaatacctca ctctgaatac tgaatcaacc cgcattatga ctaagctcag ggcccagcaa   1680
tgtcggttct ggacttcctt cttcccgaaa gtgctcgaaa tgactggcgg tggatccgga   1740
ggcggatcgg gtgaggctc cgacaagacg cacacctgtc cgccctgccc tgcccctgaa   1800
gccgagggag caccgtcggt gtttctcttc ccgccaaagc caaggacac tctgatgatc   1860
tcgcgcactc cagaggtgac ttgcgtcgtc gtggatgtca gccacgagga cccagaagtg   1920
aagtttaact ggtacgtgga tggggtggaa gtccacaacg ctaagaccaa gccaagggaa   1980
gaacaataca attcaaccta ccgcgtcgtg tccgtcctga ccgtgctgca ccaagattgg   2040
ctgaacggaa aggagtacaa gtgtaaagtg tcaaacaaag ccctcccgtc atccattgaa   2100
aagactatct cgaaggcgaa aggtcagcct agagagccgt gcgtgtatac tctcccaccg   2160
tcgcgcgatg aactgaccaa aaaccaggtg tcccttacgt gtctcgtgaa ggggttctac   2220
ccgtccgaca tcgcagtgga gtgggagtca aatggccaac cggaaaacaa ttacaagact   2280
accccgcctg tgctggacag cgatggatcc tttttcttgt acagcaagct gaccgtcgac   2340
aagagccggt ggcagcaggg gaacgtgttt agctgcagcg tgatgcatga agctctgcat   2400
aatcattaca ctcagaaaag cctgtcgctc tcgcccggaa agtaataata cgtagaattc   2460
```

<210> SEQ ID NO 10
<211> LENGTH: 534
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro

```
                20                  25                  30
Tyr Ala Gln Pro Pro Leu Gly Arg Leu Arg Phe Lys Lys Pro Gln Ser
            35                  40                  45
Leu Thr Lys Trp Ser Asp Ile Trp Asn Ala Thr Lys Tyr Ala Asn Ser
        50                  55                  60
Cys Tyr Gln Asn Ile Asp Gln Ser Phe Pro Phe His Gly Ser Glu
65                  70                  75                  80
Met Trp Asn Pro Asn Thr Asp Leu Ser Glu Asp Cys Leu Tyr Leu Asn
                85                  90                  95
Val Trp Ile Pro Ala Pro Lys Pro Lys Asn Ala Thr Val Leu Ile Trp
            100                 105                 110
Ile Tyr Gly Gly Gly Phe Gln Thr Gly Thr Ser Ser Leu His Val Tyr
        115                 120                 125
Asp Gly Lys Phe Leu Ala Arg Val Glu Arg Val Ile Val Val Ser Met
    130                 135                 140
Asn Tyr Arg Val Gly Ala Leu Gly Phe Leu Ala Leu Pro Gly Asn Pro
145                 150                 155                 160
Glu Ala Pro Gly Asn Met Gly Leu Phe Asp Gln Gln Leu Ala Leu Gln
                165                 170                 175
Trp Val Gln Lys Asn Ile Ala Ala Phe Gly Gly Asn Pro Lys Ser Val
            180                 185                 190
Thr Leu Phe Gly Glu Ser Ala Gly Ala Ala Ser Val Ser Leu His Leu
        195                 200                 205
Leu Ser Pro Gly Ser His Ser Leu Phe Thr Arg Ala Ile Leu Gln Ser
    210                 215                 220
Gly Ser Phe Asn Ala Pro Trp Ala Val Thr Ser Leu Tyr Glu Ala Arg
225                 230                 235                 240
Asn Arg Thr Leu Asn Leu Ala Lys Leu Thr Gly Cys Ser Arg Glu Asn
                245                 250                 255
Glu Thr Glu Ile Ile Lys Cys Leu Arg Asn Lys Asp Pro Gln Glu Ile
            260                 265                 270
Leu Leu Asn Glu Ala Phe Val Val Pro Tyr Gly Thr Pro Leu Ser Val
        275                 280                 285
Asn Phe Gly Pro Thr Val Asp Gly Asp Phe Leu Thr Asp Met Pro Asp
    290                 295                 300
Ile Leu Leu Glu Leu Gly Gln Phe Lys Lys Thr Gln Ile Leu Val Gly
305                 310                 315                 320
Val Asn Lys Asp Glu Gly Thr Ala Phe Leu Val Tyr Gly Ala Pro Gly
                325                 330                 335
Phe Ser Lys Asp Asn Asn Ser Ile Ile Thr Arg Lys Glu Phe Gln Glu
            340                 345                 350
Gly Leu Lys Ile Phe Phe Pro Gly Val Ser Glu Phe Gly Lys Glu Ser
        355                 360                 365
Ile Leu Phe His Tyr Thr Asp Trp Val Asp Asp Gln Arg Pro Glu Asn
    370                 375                 380
Tyr Arg Glu Ala Leu Gly Asp Val Val Gly Asp Tyr Asn Phe Ile Cys
385                 390                 395                 400
Pro Ala Leu Glu Phe Thr Lys Lys Phe Ser Glu Trp Gly Asn Asn Ala
                405                 410                 415
Phe Phe Tyr Tyr Phe Glu His Arg Ser Ser Lys Leu Pro Trp Pro Glu
            420                 425                 430
Trp Met Gly Val Met His Gly Tyr Glu Ile Glu Phe Val Phe Gly Leu
        435                 440                 445
```

```
Pro Leu Glu Arg Arg Asp Asn Tyr Thr Lys Ala Glu Ile Leu Ser
    450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly
    530

<210> SEQ ID NO 11
<211> LENGTH: 524
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Tyr Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ala Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
```

```
            260                 265                 270
Leu Leu Asn Glu Ala Phe Val Val Pro Tyr Gly Thr Pro Leu Ser Val
        275                 280                 285

Asn Phe Gly Pro Thr Val Asp Gly Asp Phe Leu Thr Asp Met Pro Asp
        290                 295                 300

Ile Leu Leu Glu Leu Gly Gln Phe Lys Lys Thr Gln Ile Leu Val Gly
305                 310                 315                 320

Val Asn Lys Asp Glu Gly Thr Ala Phe Leu Val Tyr Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Gln Arg Pro Glu Asn
        370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
        435                 440                 445

Pro Leu Glu Arg Arg Asp Asn Tyr Thr Lys Ala Glu Glu Ile Leu Ser
450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser
        515                 520

<210> SEQ ID NO 12
<211> LENGTH: 528
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Tyr Gln Asn Ile Asp Gln Ser Phe Pro Gly Phe His Gly Ser Glu
65              70                  75                  80

Met Trp Asn Pro Asn Thr Asp Leu Ser Glu Asp Cys Leu Tyr Leu Asn
                85                  90                  95
```

-continued

```
Val Trp Ile Pro Ala Pro Lys Pro Lys Asn Ala Thr Val Leu Ile Trp
            100                 105                 110
Ile Tyr Gly Gly Gly Phe Gln Thr Gly Thr Ser Ser Leu His Val Tyr
        115                 120                 125
Asp Gly Lys Phe Leu Ala Arg Val Glu Arg Val Ile Val Val Ser Met
    130                 135                 140
Asn Tyr Arg Val Gly Ala Leu Gly Phe Leu Ala Leu Pro Gly Asn Pro
145                 150                 155                 160
Glu Ala Pro Gly Asn Met Gly Leu Phe Asp Gln Gln Leu Ala Leu Gln
                165                 170                 175
Trp Val Gln Lys Asn Ile Ala Ala Phe Gly Gly Asn Pro Lys Ser Val
            180                 185                 190
Thr Leu Phe Gly Glu Ser Ala Gly Ala Ala Ser Val Ser Leu His Leu
        195                 200                 205
Leu Ser Pro Gly Ser His Ser Leu Phe Thr Arg Ala Ile Leu Gln Ser
    210                 215                 220
Gly Ser Phe Asn Ala Pro Trp Ala Val Thr Ser Leu Tyr Glu Ala Arg
225                 230                 235                 240
Asn Arg Thr Leu Asn Leu Ala Lys Leu Thr Gly Cys Ser Arg Glu Asn
                245                 250                 255
Glu Thr Glu Ile Ile Lys Cys Leu Arg Asn Lys Asp Pro Gln Glu Ile
            260                 265                 270
Leu Leu Asn Glu Ala Phe Val Val Pro Tyr Gly Thr Pro Leu Ser Val
        275                 280                 285
Asn Phe Gly Pro Thr Val Asp Gly Asp Phe Leu Thr Asp Met Pro Asp
    290                 295                 300
Ile Leu Leu Glu Leu Gly Gln Phe Lys Lys Thr Gln Ile Leu Val Gly
305                 310                 315                 320
Val Asn Lys Asp Glu Gly Thr Ala Phe Leu Val Tyr Gly Ala Pro Gly
                325                 330                 335
Phe Ser Lys Asp Asn Asn Ser Ile Ile Thr Arg Lys Glu Phe Gln Glu
            340                 345                 350
Gly Leu Lys Ile Phe Phe Pro Gly Val Ser Glu Phe Gly Lys Glu Ser
        355                 360                 365
Ile Leu Phe His Tyr Thr Asp Trp Val Asp Asp Gln Arg Pro Glu Asn
    370                 375                 380
Tyr Arg Glu Ala Leu Gly Asp Val Val Gly Asp Tyr Asn Phe Ile Cys
385                 390                 395                 400
Pro Ala Leu Glu Phe Thr Lys Lys Phe Ser Glu Trp Gly Asn Asn Ala
                405                 410                 415
Phe Phe Tyr Tyr Phe Glu His Arg Ser Ser Lys Leu Pro Trp Pro Glu
            420                 425                 430
Trp Met Gly Val Met His Gly Tyr Glu Ile Glu Phe Val Phe Gly Leu
        435                 440                 445
Pro Leu Glu Arg Arg Asp Asn Tyr Thr Lys Ala Glu Glu Ile Leu Ser
    450                 455                 460
Arg Ser Ile Val Lys Arg Trp Ala Asn Phe Ala Lys Tyr Gly Asn Pro
465                 470                 475                 480
Asn Glu Thr Gln Asn Asn Ser Thr Ser Trp Pro Val Phe Lys Ser Thr
                485                 490                 495
Glu Gln Lys Tyr Leu Thr Leu Asn Thr Glu Ser Thr Arg Ile Met Thr
            500                 505                 510
Lys Leu Arg Ala Gln Gln Cys Arg Phe Trp Thr Ser Gly Gly Gly Cys
```

515                 520                 525

<210> SEQ ID NO 13
<211> LENGTH: 537
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Tyr Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ala Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Ser Val
        275                 280                 285

Asn Phe Gly Pro Thr Val Asp Gly Asp Phe Leu Thr Asp Met Pro Asp
    290                 295                 300

Ile Leu Leu Glu Leu Gly Gln Phe Lys Lys Thr Gln Ile Leu Val Gly
305                 310                 315                 320

Val Asn Lys Asp Glu Gly Thr Ala Phe Leu Val Tyr Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Phe Gly Lys Glu Ser
            355                 360                 365

Ile Leu Phe His Tyr Thr Asp Trp Val Asp Asp Gln Arg Pro Glu Asn
370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
            405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
            435                 440                 445

Pro Leu Glu Arg Arg Asp Asn Tyr Thr Lys Ala Glu Glu Ile Leu Ser
            450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
            485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
            515                 520                 525

Val Leu Glu Met Thr Gly Gly Gly Cys
            530                 535

<210> SEQ ID NO 14
<211> LENGTH: 772
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Tyr Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

```
Trp Val Gln Lys Asn Ile Ala Ala Phe Gly Asn Pro Lys Ser Val
            180                 185                 190

Thr Leu Phe Gly Glu Ser Ala Gly Ala Ala Ser Val Ser Leu His Leu
            195                 200                 205

Leu Ser Pro Gly Ser His Ser Leu Phe Thr Arg Ala Ile Leu Gln Ser
210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
                260                 265                 270

Leu Leu Asn Glu Ala Phe Val Val Pro Tyr Gly Thr Pro Leu Ser Val
                275                 280                 285

Asn Phe Gly Pro Thr Val Asp Gly Asp Phe Leu Thr Asp Met Pro Asp
                290                 295                 300

Ile Leu Leu Glu Leu Gly Gln Phe Lys Lys Thr Gln Ile Leu Val Gly
305                 310                 315                 320

Val Asn Lys Asp Glu Gly Thr Ala Phe Leu Val Tyr Gly Ala Pro Gly
                325                 330                 335

Phe Ser Lys Asp Asn Asn Ser Ile Ile Thr Arg Lys Glu Phe Gln Glu
                340                 345                 350

Gly Leu Lys Ile Phe Phe Pro Gly Val Ser Glu Phe Gly Lys Glu Ser
                355                 360                 365

Ile Leu Phe His Tyr Thr Asp Trp Val Asp Asp Gln Arg Pro Glu Asn
                370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
                420                 425                 430

Trp Met Gly Val Met His Gly Tyr Glu Ile Glu Phe Val Phe Gly Leu
                435                 440                 445

Pro Leu Glu Arg Arg Asp Asn Tyr Thr Lys Ala Glu Glu Ile Leu Ser
                450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
                500                 505                 510

Lys Leu Arg Ala Gln Gln Cys Arg Phe Trp Thr Ser Phe Phe Pro Lys
                515                 520                 525

Val Leu Glu Met Thr Gly Gly Gly Ser Gly Gly Ser Gly Gly Gly
                530                 535                 540

Ser Asp Lys Thr His Thr Cys Pro Pro Cys Pro Ala Pro Glu Leu Leu
545                 550                 555                 560

Gly Gly Pro Ser Val Phe Leu Phe Pro Pro Lys Pro Lys Asp Thr Leu
                565                 570                 575

Met Ile Ser Arg Thr Pro Glu Val Thr Cys Val Val Val Asp Val Ser
                580                 585                 590
```

His Glu Asp Pro Glu Val Lys Phe Asn Trp Tyr Val Asp Gly Val Glu
            595                 600                 605

Val His Asn Ala Lys Thr Lys Pro Arg Glu Glu Gln Tyr Asn Ser Thr
        610                 615                 620

Tyr Arg Val Val Ser Val Leu Thr Val Leu His Gln Asp Trp Leu Asn
625                 630                 635                 640

Gly Lys Glu Tyr Lys Cys Lys Val Ser Asn Lys Ala Leu Pro Ala Pro
                645                 650                 655

Ile Glu Lys Thr Ile Ser Lys Ala Lys Gly Gln Pro Arg Glu Pro Gln
            660                 665                 670

Val Tyr Thr Leu Pro Pro Ser Arg Asp Glu Leu Thr Lys Asn Gln Val
        675                 680                 685

Ser Leu Thr Cys Leu Val Lys Gly Phe Tyr Pro Ser Asp Ile Ala Val
690                 695                 700

Glu Trp Glu Ser Asn Gly Gln Pro Glu Asn Asn Tyr Lys Thr Thr Pro
705                 710                 715                 720

Pro Val Leu Asp Ser Asp Gly Ser Phe Phe Leu Tyr Ser Lys Leu Thr
                725                 730                 735

Val Asp Lys Ser Arg Trp Gln Gln Gly Asn Val Phe Ser Cys Ser Val
            740                 745                 750

Met His Glu Ala Leu His Asn His Tyr Thr Gln Lys Ser Leu Ser Leu
        755                 760                 765

Ser Pro Gly Lys
    770

<210> SEQ ID NO 15
<211> LENGTH: 772
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Tyr Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

```
Trp Val Gln Lys Asn Ile Ala Ala Phe Gly Asn Pro Lys Ser Val
            180                 185                 190

Thr Leu Phe Gly Glu Ser Ala Gly Ala Ala Ser Val Ser Leu His Leu
        195                 200                 205

Leu Ser Pro Gly Ser His Ser Leu Phe Thr Arg Ala Ile Leu Gln Ser
210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
            245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Ser Val
        275                 280                 285

Asn Phe Gly Pro Thr Val Asp Gly Asp Phe Leu Thr Asp Met Pro Asp
        290                 295                 300

Ile Leu Leu Glu Leu Gly Gln Phe Lys Lys Thr Gln Ile Leu Val Gly
305                 310                 315                 320

Val Asn Lys Asp Glu Gly Thr Ala Phe Leu Val Tyr Gly Ala Pro Gly
            325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
            355                 360                 365

Ile Leu Phe His Tyr Thr Asp Trp Val Asp Asp Gln Arg Pro Glu Asn
            370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
            405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
            435                 440                 445

Pro Leu Glu Arg Arg Asp Asn Tyr Thr Lys Ala Glu Glu Ile Leu Ser
        450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
            485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Gly Gly Ser Gly Gly Gly Ser Gly Gly Gly
        530                 535                 540

Ser Asp Lys Thr His Thr Cys Pro Pro Cys Pro Ala Pro Glu Ala Glu
545                 550                 555                 560

Gly Ala Pro Ser Val Phe Leu Phe Pro Pro Lys Pro Lys Asp Thr Leu
            565                 570                 575

Met Ile Ser Arg Thr Pro Glu Val Thr Cys Val Val Val Asp Val Ser
            580                 585                 590
```

His Glu Asp Pro Glu Val Lys Phe Asn Trp Tyr Val Asp Gly Val Glu
            595                 600                 605

Val His Asn Ala Lys Thr Lys Pro Arg Glu Glu Gln Tyr Asn Ser Thr
610                 615                 620

Tyr Arg Val Val Ser Val Leu Thr Val Leu His Gln Asp Trp Leu Asn
625                 630                 635                 640

Gly Lys Glu Tyr Lys Cys Lys Val Ser Asn Lys Ala Leu Pro Ser Ser
            645                 650                 655

Ile Glu Lys Thr Ile Ser Lys Ala Lys Gly Gln Pro Arg Glu Pro Gln
            660                 665                 670

Val Tyr Thr Leu Pro Pro Ser Arg Asp Glu Leu Thr Lys Asn Gln Val
            675                 680                 685

Ser Leu Thr Cys Leu Val Lys Gly Phe Tyr Pro Ser Asp Ile Ala Val
            690                 695                 700

Glu Trp Glu Ser Asn Gly Gln Pro Glu Asn Asn Tyr Lys Thr Thr Pro
705                 710                 715                 720

Pro Val Leu Asp Ser Asp Gly Ser Phe Phe Leu Tyr Ser Lys Leu Thr
            725                 730                 735

Val Asp Lys Ser Arg Trp Gln Gln Gly Asn Val Phe Ser Cys Ser Val
            740                 745                 750

Met His Glu Ala Leu His Asn His Tyr Thr Gln Lys Ser Leu Ser Leu
            755                 760                 765

Ser Pro Gly Lys
            770

<210> SEQ ID NO 16
<211> LENGTH: 772
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

```
Trp Val Gln Lys Asn Ile Ala Ala Phe Gly Asn Pro Lys Ser Val
            180                 185                 190

Thr Leu Phe Gly Glu Ser Ala Gly Ala Ala Ser Val Ser Leu His Leu
        195                 200                 205

Leu Ser Pro Gly Ser His Ser Leu Phe Thr Arg Ala Ile Leu Gln Ser
210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Ser Val
        275                 280                 285

Asn Phe Gly Pro Thr Val Asp Gly Asp Phe Leu Thr Asp Met Pro Asp
290                 295                 300

Ile Leu Leu Glu Leu Gly Gln Phe Lys Lys Thr Gln Ile Leu Val Gly
305                 310                 315                 320

Val Asn Lys Asp Glu Gly Thr Ala Phe Leu Val Tyr Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
        435                 440                 445

Pro Leu Glu Arg Arg Asp Asn Tyr Thr Lys Ala Glu Glu Ile Leu Ser
450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Gly Gly Ser Gly Gly Ser Gly Gly Gly
530                 535                 540

Ser Asp Lys Thr His Thr Cys Pro Pro Cys Pro Ala Pro Glu Leu Leu
545                 550                 555                 560

Gly Gly Pro Ser Val Phe Leu Phe Pro Pro Lys Pro Lys Asp Thr Leu
                565                 570                 575

Met Ile Ser Arg Thr Pro Glu Val Thr Cys Val Val Val Asp Val Ser
            580                 585                 590
```

```
His Glu Asp Pro Glu Val Lys Phe Asn Trp Tyr Val Asp Gly Val Glu
            595                 600                 605

Val His Asn Ala Lys Thr Lys Pro Arg Glu Glu Gln Tyr Asn Ser Thr
        610                 615                 620

Tyr Arg Val Val Ser Val Leu Thr Val Leu His Gln Asp Trp Leu Asn
625                 630                 635                 640

Gly Lys Glu Tyr Lys Cys Lys Val Ser Asn Lys Ala Leu Pro Ala Pro
                645                 650                 655

Ile Glu Lys Thr Ile Ser Lys Ala Lys Gly Gln Pro Arg Glu Pro Gln
            660                 665                 670

Val Tyr Thr Leu Pro Pro Ser Arg Asp Glu Leu Thr Lys Asn Gln Val
        675                 680                 685

Ser Leu Thr Cys Leu Val Lys Gly Phe Tyr Pro Ser Asp Ile Ala Val
        690                 695                 700

Glu Trp Glu Ser Asn Gly Gln Pro Glu Asn Asn Tyr Lys Thr Thr Pro
705                 710                 715                 720

Pro Val Leu Asp Ser Asp Gly Ser Phe Phe Leu Tyr Ser Lys Leu Thr
                725                 730                 735

Val Asp Lys Ser Arg Trp Gln Gln Gly Asn Val Phe Ser Cys Ser Val
            740                 745                 750

Met His Glu Ala Leu His Asn His Tyr Thr Gln Lys Ser Leu Ser Leu
        755                 760                 765

Ser Pro Gly Lys
    770

<210> SEQ ID NO 17
<211> LENGTH: 772
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Tyr Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175
```

```
Trp Val Gln Lys Asn Ile Ala Ala Phe Gly Gly Asn Pro Lys Ser Val
            180                 185                 190

Thr Leu Phe Gly Glu Ser Ala Gly Ala Ala Ser Val Ser Leu His Leu
            195                 200                 205

Leu Ser Pro Gly Ser His Ser Leu Phe Thr Arg Ala Ile Leu Gln Ser
210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
            245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Ser Val
            275                 280                 285

Asn Phe Gly Pro Thr Val Asp Gly Asp Phe Leu Thr Asp Met Pro Asp
            290                 295                 300

Ile Leu Leu Glu Leu Gly Gln Phe Lys Lys Thr Gln Ile Leu Val Gly
305                 310                 315                 320

Val Asn Lys Asp Glu Gly Thr Ala Phe Leu Val Tyr Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
            355                 360                 365

Ile Leu Phe His Tyr Thr Asp Trp Val Asp Asp Gln Arg Pro Glu Asn
            370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
            435                 440                 445

Pro Leu Glu Arg Arg Asp Asn Tyr Thr Lys Ala Glu Glu Ile Leu Ser
450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
            515                 520                 525

Val Leu Glu Met Thr Gly Gly Ser Gly Gly Ser Gly Gly Gly Gly Gly
            530                 535                 540

Ser Asp Lys Thr His Thr Cys Pro Pro Cys Pro Ala Pro Glu Leu Leu
545                 550                 555                 560

Gly Gly Pro Ser Val Phe Leu Phe Pro Pro Lys Pro Lys Asp Thr Leu
                565                 570                 575

Met Ile Ser Arg Thr Pro Glu Val Thr Cys Val Val Val Asp Val Ser
            580                 585                 590
```

His Glu Asp Pro Glu Val Lys Phe Asn Trp Tyr Val Asp Gly Val Glu
            595                 600                 605

Val His Asn Ala Lys Thr Lys Pro Arg Glu Glu Gln Tyr Asn Ser Thr
610                 615                 620

Tyr Arg Val Val Ser Val Leu Thr Val Leu His Gln Asp Trp Leu Asn
625                 630                 635                 640

Gly Lys Glu Tyr Lys Cys Lys Val Ser Asn Lys Ala Leu Pro Ala Pro
            645                 650                 655

Ile Glu Lys Thr Ile Ser Lys Ala Lys Gly Gln Pro Arg Glu Pro Gln
            660                 665                 670

Val Tyr Thr Leu Pro Pro Ser Arg Asp Glu Leu Thr Lys Asn Gln Val
            675                 680                 685

Ser Leu Thr Cys Leu Val Lys Gly Phe Tyr Pro Ser Asp Ile Ala Val
            690                 695                 700

Glu Trp Glu Ser Asn Gly Gln Pro Glu Asn Asn Tyr Lys Thr Thr Pro
705                 710                 715                 720

Pro Val Leu Asp Ser Asp Gly Ser Phe Phe Leu Tyr Ser Lys Leu Thr
            725                 730                 735

Val Asp Lys Ser Arg Trp Gln Gln Gly Asn Val Phe Ser Cys Ser Val
            740                 745                 750

Met His Glu Ala Leu His Asn His Tyr Thr Gln Lys Ser Leu Ser Leu
            755                 760                 765

Ser Pro Gly Lys
    770

<210> SEQ ID NO 18
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala
            35

<210> SEQ ID NO 19
<211> LENGTH: 574
<212> TYPE: PRT
<213> ORGANISM: Homo sapiens

<400> SEQUENCE: 19

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
            35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

```
Met Trp Asn Pro Asn Thr Asp Leu Ser Glu Asp Cys Leu Tyr Leu Asn
                 85                  90                  95
Val Trp Ile Pro Ala Pro Lys Pro Lys Asn Ala Thr Val Leu Ile Trp
            100                 105                 110
Ile Tyr Gly Gly Gly Phe Gln Thr Gly Thr Ser Ser Leu His Val Tyr
            115                 120                 125
Asp Gly Lys Phe Leu Ala Arg Val Glu Arg Val Ile Val Val Ser Met
            130                 135                 140
Asn Tyr Arg Val Gly Ala Leu Gly Phe Leu Ala Leu Pro Gly Asn Pro
145                 150                 155                 160
Glu Ala Pro Gly Asn Met Gly Leu Phe Asp Gln Gln Leu Ala Leu Gln
                165                 170                 175
Trp Val Gln Lys Asn Ile Ala Ala Phe Gly Gly Asn Pro Lys Ser Val
            180                 185                 190
Thr Leu Phe Gly Glu Ser Ala Gly Ala Ala Ser Val Ser Leu His Leu
            195                 200                 205
Leu Ser Pro Gly Ser His Ser Leu Phe Thr Arg Ala Ile Leu Gln Ser
    210                 215                 220
Gly Ser Phe Asn Ala Pro Trp Ala Val Thr Ser Leu Tyr Glu Ala Arg
225                 230                 235                 240
Asn Arg Thr Leu Asn Leu Ala Lys Leu Thr Gly Cys Ser Arg Glu Asn
                245                 250                 255
Glu Thr Glu Ile Ile Lys Cys Leu Arg Asn Lys Asp Pro Gln Glu Ile
                260                 265                 270
Leu Leu Asn Glu Ala Phe Val Val Pro Tyr Gly Thr Pro Leu Ser Val
            275                 280                 285
Asn Phe Gly Pro Thr Val Asp Gly Asp Phe Leu Thr Asp Met Pro Asp
            290                 295                 300
Ile Leu Leu Glu Leu Gly Gln Phe Lys Lys Thr Gln Ile Leu Val Gly
305                 310                 315                 320
Val Asn Lys Asp Glu Gly Thr Ala Phe Leu Val Tyr Gly Ala Pro Gly
                325                 330                 335
Phe Ser Lys Asp Asn Asn Ser Ile Ile Thr Arg Lys Glu Phe Gln Glu
                340                 345                 350
Gly Leu Lys Ile Phe Phe Pro Gly Val Ser Glu Phe Gly Lys Glu Ser
            355                 360                 365
Ile Leu Phe His Tyr Thr Asp Trp Val Asp Asp Gln Arg Pro Glu Asn
            370                 375                 380
Tyr Arg Glu Ala Leu Gly Asp Val Val Gly Asp Tyr Asn Phe Ile Cys
385                 390                 395                 400
Pro Ala Leu Glu Phe Thr Lys Lys Phe Ser Glu Trp Gly Asn Asn Ala
                405                 410                 415
Phe Phe Tyr Tyr Phe Glu His Arg Ser Ser Lys Leu Pro Trp Pro Glu
                420                 425                 430
Trp Met Gly Val Met His Gly Tyr Glu Ile Glu Phe Val Phe Gly Leu
            435                 440                 445
Pro Leu Glu Arg Arg Asp Asn Tyr Thr Lys Ala Glu Glu Ile Leu Ser
    450                 455                 460
Arg Ser Ile Val Lys Arg Trp Ala Asn Phe Ala Lys Tyr Gly Asn Pro
465                 470                 475                 480
Asn Glu Thr Gln Asn Asn Ser Thr Ser Trp Pro Val Phe Lys Ser Thr
                485                 490                 495
Glu Gln Lys Tyr Leu Thr Leu Asn Thr Glu Ser Thr Arg Ile Met Thr
```

```
                    500                 505                 510
Lys Leu Arg Ala Gln Gln Cys Arg Phe Trp Thr Ser Phe Phe Pro Lys
            515                 520                 525

Val Leu Glu Met Thr Gly Asn Ile Asp Glu Ala Glu Trp Glu Trp Lys
        530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Gly Gly Cys
1

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gly Gly Ser Gly Gly Gly Ser Gly Gly Gly Ser
1               5                   10

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Gly Gly Gly Ser
1               5

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Gly Ser
1

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 24

Gly Gly Gly Glu Ser
1               5

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Gly Ser Gly Gly Gly Ser Gly Gly Gly Ser
1               5                   10

<210> SEQ ID NO 26
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Gly Gly Gly Ser Gly Gly Gly Ser Gly Gly Gly Ser Gly
1               5                   10                  15

Gly Gly Ser Gly
            20

<210> SEQ ID NO 27
<211> LENGTH: 28
<212> TYPE: PRT
<213> ORGANISM: Homo sapiens

<400> SEQUENCE: 27

Met His Ser Lys Val Thr Ile Ile Cys Ile Arg Phe Leu Phe Trp Phe
1               5                   10                  15

Leu Leu Leu Cys Met Leu Ile Gly Lys Ser His Thr
            20                  25

<210> SEQ ID NO 28
<211> LENGTH: 6
<212> TYPE: PRT
<213> ORGANISM: Homo sapiens

<400> SEQUENCE: 28

Glu Asp Asp Ile Ile Ile
1               5
```

BUTYRYLCHOLINESTERASE ZWITTERIONIC POLYMER CONJUGATES

CROSS REFERENCE TO RELATED APPLICATIONS

The present application is a continuation of PCT PCT/US2015/056112 filed Oct. 16, 2015, which is a nonprovisional of 62/065,471 filed Oct. 17, 2014, each incorporated by reference in its entirety for all purposes.

STATEMENT OF GOVERNMENTAL SUPPORT

The invention was made with government support under the Chemical Biological Medical Systems (CBMS) contract number W911QY-12-1-0007 through the U.S. Army Medical Department. The government has certain rights in the invention.

REFERENCE TO A SEQUENCE LISTING

Sequences are provided in an ASCII txt filed designated 470678_SEQLST.TXT, of 84,727 bytes, created Oct. 16, 2015, incorporated by reference.

BACKGROUND

1. Bioscavengers

Organophosphorus compounds (OPs) are highly toxic to humans. First developed in the 1930s as insecticides, the extreme toxicity of OPs to humans eventually led to their development as nerve agents for warfare. Today, although generally banned by international law, OPs are considered an ever increasing military and civilian threat. In 1995, the Tokyo subway system was the subject of a sarin attack, killing over a dozen passengers and injuring scores of others. Sarin gas has also been reported to have been recently used on surface to surface missiles in conflicts in Syria with lethal effect.

OP nerve agents such as sarin are potent inhibitors of acetylcholinesterase. In vertebrates, acetylcholine is the neurotransmitter used to transmit signals from the nervous system to muscle fibers. Normally, acetylcholine is released from a neuron to stimulate a muscle. After stimulation, acetylcholinesterase metabolizes acetylcholine, allowing the muscle to relax. OPs such as sarin, however, irreversibly inhibit acetylcholinesterase, inhibiting degradation of acetylcholine. OP nerve agents are generally lethal at very small doses with subjects generally succumbing to some type of asphyxia. Subjects receiving less than lethal doses of OPs may develop permanent neurological damage. In addition, OP pesticides are still in wide use. Although OP pesticides are far less toxic than nerve agents, OP pesticide toxicity to humans is still of great concern.

Antidotes and treatment for OP poising are extremely limited. There are small molecule treatments for OP poisoning symptoms (e.g. tremors). Overall, however, these therapies are of very limited benefit. Atropine may be administered for muscarinic ACh receptor blockade and diazepam for symptomatic management of convulsions. Lee E. C. (2003) Clinical manifestations of sarin nerve gas exposure. J. Am. Med. Assoc. 290:659-662. Additionally, oxime therapy with 2-pralidoxime (2-PAM) can effectively reactivate some but not all OP-AChE adducts. Cannard, K. (2006) The acute treatment of nerve agent exposure. J Neurol Sci 249:86-94. Although these therapies can reduce mortality in cases of less toxic OPs such as insecticides or very low doses of nerve agents, they are generally seen by clinicians as highly ineffective with regard to possible battlefield levels of exposure to OP nerve agents.

For prophylactic anti-OP therapy, it has been found that certain enzymes will detoxify OPs such as sarin by acting as bioscavengers. Acetylcholinesterase (AChE) (fetal bovine serum-derived), the same enzyme which OPs irreversibly inactivate, when administered prophylactically was able to protect rhesus monkeys against a challenge of two to five times the LD50 of 3,3-Dimethylbutan-2-yl methylphosphonofluoridate (soman) a highly toxic OP nerve agent designed for chemical warfare. Wolfe, A. D., et al., (1992) Use of cholinesterases as pretreatment drugs for the protection of rhesus monkeys against soman toxicity. Toxicol. Appl Pharmacol. 117:189-193.

AChE is a member of the carboxyl/cholinesterases (CE/ChEs), a multi-gene family of enzymes that hydrolyze a diverse range of carboxylesters. Members of the family include AChE, human carboxylesterase 1 (hCE1) and 2 (hCE2) and butyrylcholinesterase (BuChE). Of these, BChE has generated the greatest interest as a bioscavenger. BuChE is the major cholinesterase in human serum. Although the closely related enzyme AChE is well described as the primary synaptic regulator of cholinergic transmission, a definitive physiological role for BChE has not yet been demonstrated.

BuChE is catalytically promiscuous and hydrolyzes not only acetylcholine (ACh), but also longer-chain choline esters (e.g., butyrylcholine, its preferred substrate, and succinylcholine) and a variety of non-choline esters, such as acetylsalicylic acid (aspirin) and cocaine. Moreover, BuChE binds most environmentally occurring ChE inhibitors as well as man-made OP pesticides and nerve agents. However, the physiologically available levels of natural BuChE are too low to give any meaningful protection with regard to OPs.

BuChE purified from human serum has been used to treat humans Patients successfully received a partially purified human BuChE to counteract the effects of muscle relaxants and for OP pesticide poisoning. Cascio, C., et al. (1988) The use of serum cholinesterase in severe phosphorous poisoning. Minerva Anestesiol (Italian) 54:337-345. However, products purified from human serum are highly undesirable due to the threat of contamination by unknown blood borne pathogens which of course cannot be tested for. In this regard, for example, FVIII for treatment of hemophilia is produced today by recombinant DNA technology and is no longer purified from human serum after thousands of patients became infected with the HIV virus in the late 70s and early 80s. In addition, production of serum purified BuChE is severely limited by the volume of serum available. Lockridge, O., et al. (2005) J. Med. Chem. Biol. Radiol. Def. 3:nimhs5095.

To avoid using blood serum purified BuChE, recombinant BuChE (rBuChE) was produced in *Escherichia coli*. Masson, P. (1992) in Multidisciplinary Approaches to Cholinesterase Functions, eds Shafferman, A., Velan, B. (Plenum, N.Y.) pp 49-52. The produced protein, however, was nonfunctional. rBuChE was also produced in mammalian 293T (Altamirano, C. V. and Lockridge, O. (1999) Chem. Biol. Interact. 119-120:53-60) and CHO (Millard, C. B., Lockridge, O., and Broomfield, C. A. (1995) Biochemistry 34:15925-15933). The mammalian expression systems, however, failed to produce sufficient quantities of protein such that the need for plasma purified BuChE could be eliminated. Given the difficulties experienced with mammalian cellular expression systems, transgenic goats were created having the human BuChE gene under the control of the goat β-casein promoter, allowing the produced rBuChE to be purified from goat milk. Huang, Y. J. et al (2007) Recombinant human butyrylcholinesterase from milk of transgenic animals to protect against organophosphate poisoning. Proc. Nat. Acad. Sci. 104(34):13603-13608. However, when the transgenic goat rBuChE was tested in animals, the PK and bioavailability results were very disappointing for the enzyme both itself and the enzyme conjugated to PEG. rBuChE produced in transgenic goats did not apparently have a residence time similar to native human BuChE purified from plasma to allow it to be developed as an agent for the prophylaxis of OP poisoning.

Thus there remains a need for recombinant versions of BuChE and related bioscavengers which can be produced in large quantities and have good PK properties.

2. Iodoacetamide Conjugation

Since the first recombinant insulin product was approved in 1982, protein and peptide therapeutics have been successfully used as very efficient drugs for the treatment of a wide variety of pathophysiological diseases. Development of these drugs was spurred by advances in recombinant DNA technology over the past decades. Protein therapeutics generally fall into one of two categories: (1) biopharmaceuticals that mimic native protein and serve as a replacement, e.g., insulin and (2) monoclonal antibodies that serve as agonists or antagonists of various pathways, e.g., AVASTIN®. While protein therapeutics enjoy great success both in terms of disease amelioration and sales, it has been observed that many have suboptimal physiochemical and pharmacokinetic properties. The main drawbacks seen with protein therapeutics are physicochemical instability, limited solubility, proteolytic instability, short elimination half-life, immunogenicity and toxicity.

One approach to improving the pharmacokinetic properties of protein therapeutics is conjugation of the protein to a biopolymer. In this regard, a dozen or so polyethylene glycol (PEG) conjugates have been approved as of the present date, e.g., Neulasta®. Various benefits have been observed with protein PEGylation, including: improved drug solubility, reduced dosage frequency without diminished efficacy and with potentially reduced toxicity, extended circulating life, increased drug stability and greater resistance to proteolytic degradation. Commercial benefits of PEGylation have also been observed, including opportunities for new delivery formats and dosing regimens. Also, since PEGylation produces a new chemical entity there are opportunities for more patent protection.

Historically, most PEGylation reagents have been developed to take advantage of the accessible amine functionalities on proteins Amine groups are present by definition in all proteins (i.e. the amino terminus) and in the great majority of proteins there is more than one amino group, e.g., as contributed by Lys Amine conjugated PEG proteins have received regulatory approval. Alconel, S. N. S., Baas, A. S. and Maynard, H. D. (2011) FDA-approved poly(ethylene glycol)-protein conjugate drugs. Polym. Chem. 2 (7), 1442. At least two amine PEG protein conjugates are first line therapies. Foster, G. R. (2010) Pegylated Interferons for the Treatment of Chronic Hepatitis C: Pharmacological and Clinical Differences between Peginterferon-2a and Peginterferon-2b. Drugs 70 (2), 147-165; Piedmonte, D. M. and Treuheit, M. J. (2008) Formulation of Neulasta (pegfilgrastim). Adv. Drug Delivery Rev. 60, 50-58.

However, there are a number of problems associated with amine conjugation. Reagents specific for amine conjugation are often inefficient due to competitive hydrolysis reactions of the reagent (e.g., PEG-N-hydroxysuccinimide ester) or unfavorable equilibria during imine formation, which is necessary for reductive animation conjugation. Wang, X., Kumar, S., and Singh, S. (2011) Disulfide Scrambling in IgG2 Monoclonal Antibodies: Insights from Molecular Dynamics Simulations. Pharm. Res. 28, 3128-3143. Moreover, most proteins have several amine residues available for reaction. Hence, amine PEG conjugates tend not to be site specific, resulting in heterogeneous mixtures of different PEG-protein conjugates in the final product. Veronese, F. (2001) Peptide and protein PEGylation a review of problems and solutions. Biomaterials 22 (5), 405-17; Luxon, B. A., Grace, M., Brassard, D., and Bordens, R. (2002) Pegylated interferons for the treatment of chronic hepatitis C infection. Clin. Ther. 24 (9) 1363-1383.

The various drawbacks associated with conjugation of PEG via protein amine groups have led to the development of methods to PEGylate proteins via cysteine. Indeed, polymer conjugation via Cys is one of the main approaches taken by researchers today. Roberts, M. J. and Harris, B. J. M. (2002) Chemistry for peptide and protein PEGylation. Adv. Drug Del. Rev. 54, 459-576; Stenzel, M. H. (2012) Bioconjugation Using Thiols: Old Chemistry Rediscovered to Connect Polymers with Nature's Building Blocks. ACS Macro Letters 2, 14-18. The number of free cysteines on the surface of a protein is much less than that of lysine. If a free cysteine is lacking, one or more free cysteines can be added by genetic engineering. Goodson, R. J. and Katre, N. V. (1990) Site-directed pegylation of recombinant interleukin-2 at its glycosylation site. Biotechnology 8, 343-46.

Various chemistries have been developed for conjugating polymer to proteins via cysteine, including alkyl halides, ester acrylates and vinyl sulfone reagents. But the most prevalent conjugation group is maleimide. Roberts, M. J., Bentley, M. D., and Harris, J. M. (2002) Chemistry for peptide and protein PEGylation. Adv. Drug Del. Rev. 54, 459-76. Maleimide reagents react efficiently with thiol groups to provide conjugates at neutral pH, reducing risks associated with protein denaturation. Maleimide conjugation has been used in a clinically approved PEG drug. Goel, N. and Stephens, S. (2010) Certolizumab pegol. mAbs 2 (2), 137-47. Maleimide has also been used in some approved non-PEG conjugates. See, e.g., Gualberto, A. (2012) Brentuximab Vedotin (SGN-35), an antibody-drug conjugate for the treatment of CD30-positive malignancies. Expert Opin. Invest. Drugs 21 (2), 205-16.

Although several maleimide based products have been approved, some maleimide-thiol conjugates are known to be unstable. In this regard, it has been observed the maleimide based conjugates can undergo exchange reactions. Baldwin, A. D. and Kiick, K. L. (2011) Tunable Degradation of Maleimide-Thiol Adducts in Reducing Environments. Bioconjugate Chem. 22 (10), 1946-53; Baldwin, A. D. and Kiick, K. L. (2012) Reversible maleimide-thiol adducts yield glutathione-sensitive poly(ethylene glycol)-heparin hydrogels. Polym. Chem. 4 (1), 133. Moreover, exchange products have been detected with regard to endogenous proteins. Alley, S. C., Benjamin, D. R., Jeffrey, S. C., Okeley, N. M., Meyer, D. L., Sanderson, R. J. and Senter, P. D. (2008) Contribution of linker stability to the activities of anticancer immunoconjugates. Bioconjugate Chem. 19, 759-65; Shen, B. Q., et al. (2012) Conjugation site modulates the in vivo stability and therapeutic activity of antibody-drug conjugates. Nature Biotechnol. 30 (2), 184-89.

As maleimide conjugates are known to be unstable under some circumstances, alternative conjugation strategies have been employed. Roberts, M. J. and Harris, B. J. M. (2002) Chemistry for peptide and protein PEGylation. Adv. Drug Del. Rev. 54, 459-576. One of these alternative approaches is the use of iodoacetamide based conjugation agents as shown below:

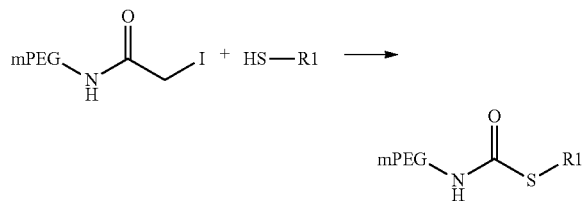

The PEG-iodoacetamide reacts with free thiols by nucleophilic substitution, creating a stable thioether bond. The thioether link is much more stable than the corresponding structure made using maleimide chemistry. The reaction of iodoacetamide with thiol is pH dependent. Thiols are generally only alkylated in the thiolate anionic form. Lindley, H. (1960) A study of the kinetics of the reaction between thiol compounds and chloroacetamide. Biochem. J. 74, 577-84. The pK value of the thiol in Cys is generally around 8.5+/−0.5, but it depends on the environment of the Cys in the native protein when it is being conjugated to the iodoacetamide moiety. Kallis, G. and Holmgren, A. (1980) Differential reactivity of the functional sulfhydryl groups of cysteine-32 and cysteine-35 present in the reduced form of thioredoxin from *Escherichia coli*. J. Bio. Chem. 255 (21) 10261-10266.

Kallis and Holmgren observed that Cys residues having the normal pK of around 8.5 are not readily acylated with iodoacetamide or alkylated with iodoacetic acid at neutral pHs. Rapid reaction of these normal thiols was only observed with elevated pHs. It is well known in the art the exposure of proteins to high pHs often leads to protein denaturation. Denaturation of proteins exposed to basic or high pHs is highly protein dependent. A few proteins can survive exposure to high pH. However, many are permanently denatured resulting in loss of activity and/or binding capacity.

There thus remains a need for methods for conjugating polymers to proteins using iodoacetamide conjugation at physiological pHs.

SUMMARY OF THE CLAIMED INVENTION

The invention provides a conjugate comprising an organophosphorus (OP) bioscavenger selected from the group consisting of a stoichiometric OP bioscavenger and a catalytic OP bioscavenger covalenily bound to a zwitterionic polymer wherein the polymer comprises one or more types of monomer units and wherein at least one type of monomer unit comprises a zwitterionic group. Optionally, the OP bioscavenger is a catalytic bioscavenger selected from the group consisting of aryldialkylphosphatases, organophosphate hydrolases (OPH), carboxylesterases, triesterases, phosphotriesterases, arylesterases, paraoxonases (PON), organophosphate acid anhydrases and diisopropylfluorophosphatases (DFPases). Optionally, the OP bioscavenger is a stoichiometric OP bioscavenger comprising a cholinesterase selected from the group consisting of acetylcholinesterase (ACNE) and butyrylcholinesterase (BChE). Optionally, the cholinesterase is purified from blood plasma. Optionally, the cholinesterase is produced by recombinant DNA technology. Optionally, the cholinesterase is a butyrylcholinesterase. Optionally, the butyrylcholinesterase is fused to a non-butyrylcholinesterase protein as fusion protein. Optionally, the non-butyrylcholinesterase protein comprises an immunoglobulin (Ig) domain. Optionally, the Ig domain is selected from the group consisting of IgG-Fc, IgG-CH and IgG-CL. Optionally, the IgG is IgGI. Optionally, the Ig domain is IgG-Fc (SEQ ID NO: 8). Optionally, the Fc domain has amino acid substitutions in one or more of the positions selected from the group consisting of E233, L234, L235, G236, S237, A327, A330 and P331 (EU numbering). These amino acid positions correspond to amino acid positions E13, L14. L15, G16, G17, Ala107, Ala110, and Pro111 in SEQ ID NO: 8. Optionally, the Fc domain has the following substitutions L234A, L235E, G237A, A330S and P331S. Optionally, the Fc domain further has one of the following substitutions 03470 or L443C (EU numbering). These amino acid positions correspond to amino acid positions Q127 and L223 in SEQ ID NO: 8. Optionally, the substitution is Q347C. Optionally, the fusion protein further comprises a linker between the butyrylcholinesterase enzyme and the non-butyrylcholinesterase protein. Optionally, the linker is selected from the group consisting of G, GG, GGGGS (SEQ ID NO: 22), GGGS (SEQ ID NO: 23), and GGGES (SEQ ID NO: 24), and oligomers of the foregoing. Optionally, the linker is selected From the group consisting of GGGSGGGSGGGS (SEQ ID NO: 21) and GGSGGGSGGGS (SEQ ID NO: 25). Optionally the butyrylcholinesterase enzyme is a carboxyl truncate. Optionally the butyrylcholinesterase enzyme comprises or consists of amino acids 29-561 of SEQ ID NO: 1. Optionally the butyrylcholinesterase enzyme comprises or consists of amino acids 29-562 of SEQ ID NO: 1. Optionally, the butyrylcholinesterase enzyme has a mutation wherein the C al residue 94 of SEQ ID NO: 1 is Y. Optionally, the butyrylcholinesterase fusion has the amino acid sequence set forth in SEC) ID NO. 2.

In any of the above conjugates, the zwitterionic group can comprise phosphorylcholine. Optionally, the at least one type of monomer unit comprises 2-(acryloyloxyethyl)-2'-(trimethylammoniumethyl) phosphate. Optionally, at least one type of monomer unit comprises 2-(methacryloyloxyethyl)-2'-(trimethylammoniumethyl) phosphate (HEMA-PC). Optionally, the polymer has 3 or more arms. Optionally, the polymer has 2, 3, 4, 5, 6, 7, 8, 9, 10, 11 or 12 arms. Optionally, the polymer has 3, 6 or 9 arms. Optionally, the polymer portion of the conjugate has a peak molecular weight of between 300,000 and 1,750,000 Daltons. Optionally, the polymer portion of the conjugate has a peak molecular weight between 500,000 and 1,000,000 Daltons. Optionally, the polymer portion of the conjugate has a peak molecular weight between 600,000 to 800,000 Daltons. Optionally, the polymer is covalently bonded to at least one of an amino group, a hydroxyl group, a sulfhydryl group and a carboxyl group of the cholinesterase. Optionally, the sulfhydryl group is from a cysteine residue in the cholinesterase. Optionally, the cysteine residue is at a position at which cysteine is not naturally present in the cholinesterase.

Optionally, the cholinesterase is a butyrylcholinesterase fusion corresponding to that of SEQ ID NO. 2 and the cysteine residue is that at amino acid 672. Optionally, the butyrylcholinesterase enzyme comprising or consists of amino acids 29 to 562 of SEQ ID NO: 1. Optionally, residue 94 is tyrosine. Optionally, the butyrylcholinesterase enzyme further comprises a cysteine residue introduced via recombinant DNA engineering. Optionally, the butyrylcholinesterase enzyme according to claim 41 comprising SEQ ID NO: 13.

The invention further provides a butyrylcholinesterase enzyme fusion protein comprising a butyrylcholinesterase enzyme and a non-butyrylcholinesterase protein. Optionally the non-butyrylcholinesterase protein comprises an immunoglobulin (Ig) domain. Optionally, the Ig domain is selected from the group consisting of IgG-Fc, IgG-CH and IgG-CL. Optionally, the IgG is IgG1. Optionally, the IgG1 domain is IgG1-Fc (SEQ ID NO: 8). Optionally, the Fc domain has amino acid substitutions in one or more of the positions selected from the group consisting of E233, L234, L235, G236, G237, A327, A330 and P331 (EU numbering). Optionally, the Fc domain has the following substitutions L234A, L235E, G237A, A330S and P331S. Optionally, the Fc domain further has one of the following substitutions Q347C or L443C (EU numbering). Optionally, the substitution is Q347C. Optionally, the fusion protein requires a linker between the butyrylcholinesterase enzyme and the non-butyrylcholinesterase protein. Optionally, the linker is selected from the group consisting of G, GG, GGGGS (SEQ ID NO: 22), GGGS (SEQ ID NO: 23), and GGGES (SEQ ID NO: 24), and oligomers of the foregoing. Optionally, the linker is selected from the group consisting of GGGSGGGSGGGS (SEQ ID NO: 21) and GGGSGGGSGGGS (SEQ ID NO: 25). Optionally, the butyrylcholinesterase enzyme is a carboxyl truncate. Optionally, the butyrylcholinesterase enzyme comprises or consists of amino acids 29-561 of SEQ ID NO: 1. Optionally, the butyrylcholinesterase enzyme comprises or consists of amino acids 29-562 of SEQ ID NO: 1. Optionally, the butyrylcholinesterase enzyme has a mutation wherein the C at residue 94 of SEQ ID NO: 1 is Y. Optionally, the fusion protein has the amino acid sequence set forth in SEQ ID NO: 2.

The invention further provides a method for treatment or prophylaxis of OP poisoning comprising administering to a patient an effective amount of any of the conjugates or fusion proteins in any preceding claim. Optionally, the conjugate is administered by intravenous administration, subcutaneous administration, intramuscular administration, intralesional administration or intradermal administration. Optionally, the conjugate is administered by intramuscular administration.

The invention further provides a method for effecting a long term prophylaxis against OP poisoning comprising administering a conjugate comprising an OP bioscavenger selected from the group consisting of a stoichiometric OP bioscavenger and a catalytic OP bioscavenger covalently bound to a zwitterionic polymer wherein the polymer comprises one or more types of monomer units and wherein at least one type of monomer unit comprises a zwitterionic group at least 7 days prior to expected exposure to an OP compound. Optionally, the OP compound is an OP pesticide or an OP nerve agent. Optionally, the conjugate is administered at least 14 days prior to expected exposure to the OP nerve agent. Optionally, the conjugate is administered at least 21 days prior to expected exposure to the OP nerve agent. Optionally, the conjugate is administered at least 30 days prior to expected exposure to the OP nerve agent.

The invention further provides a method for effecting rapid prophylaxis against OP poisoning comprising administering a conjugate comprising an OP bioscavenger selected from the group consisting of a stoichiometric OP bioscavenger and a catalytic OP bioscavenger covalently bound to a zwitterionic polymer wherein the polymer comprises one or more types of monomer units and wherein at least one type of monomer unit comprises a zwitterionic group at least 12 hours prior to expected exposure to an OP compound. Optionally, the OP compound is an OP pesticide or an OP nerve agent. Optionally, the conjugate is administered at least 24 hours prior to expected exposure to the OP nerve agent.

Any of the above methods can include administering another pharmaceutical agent selected from among carbamates, anti-muscarinics, cholinesterase reactivators and anti-convulsives.

The invention further provides an initiator for polymer synthesis comprising wherein L1 is a first linker, L2 is a second linker and L3 is a third linker, wherein L1, L2 and L3 are the same or different and are each selected from the group consisting of —C1-C12 alkyl-, —C3-C12 cycloalkyl-, (—(CH2)1-6-O—(CH2)1-6-)1-12-, (—(CH2)1-4-NH—(CH2)1-4)1-12-, —(CH2)1-12O—, (—(CH2)1-4-O—(CH2)1-4)1-12-O—, —(CH2)1-12-(CO)—O—, —(CH2)1-12-(CO)—NH—, —(CH2)1-12-O—(CO)—, —(CH2)1-12-NH—(CO)—, (—(CH2)1-4-O—(CH2)1-4)1-12-O—(CH2)1-12-, —(CH2)1-12-(CO)—O—(CH2)1-12-, —(CH2)1-12-(CO)—NH—(CH2)1-12-, —(CH2)1-12-O—(CO)—(CH2)1-12-, —(CH2)1-12-NH—(CO)—(CH2)1-12-, —(C3-C12 cycloalkyl)-, —(C1-C8alkyl)-(C3-C12 cycloalkyl)-, —(C3-C12 cycloalkyl)-(C1-8alkyl)-, —(C1-8alkyl)-(C3-C12 cycloalkyl)-(C1-8alkyl)-, —NH—(CH2CH2-O—)1-20-NH—(CH2CH2-O-)1-20- and —(CH2)0-3-aryl-(CH2)0-3-, a bond and any combination of the above; R1 and R2 are the same or different and are selected from the group consisting of H, provided that not both R1 and R2 are H, and one or more basic groups wherein a basic group is selected from the group consisting of wherein R6, R7, R8, R9 and R10 are the same or different and are selected from the group consisting of a bond, H, amino, aryl6-12 and alkyl1-6;

wherein R11 and R12 are the same or different and are selected from the group consisting of a bond, H, aryl6-12 and alkyl1-6;

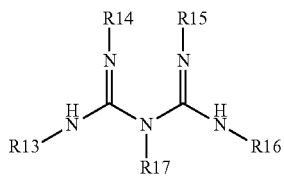

wherein R13, R14, R15, R16 and R17 are the same or different and are selected from the group consisting of a bond, H, amino, aryl6-12 and alkyl1-6 and one or more arginine residues; and R3, R4 and R5 are the same or different and are selected from the group consisting of

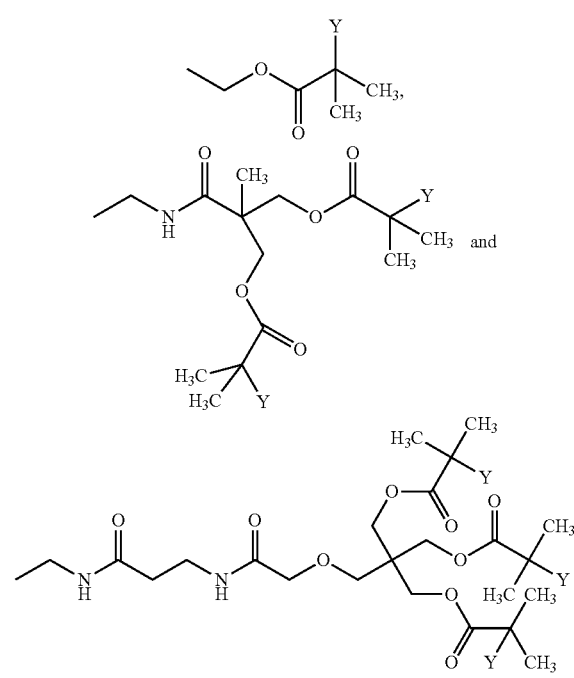

wherein Y is NCS, F, Cl, Br or I.
Optionally, Y is Br. Optionally, R3, R4 and R5 are each

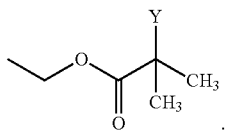

Optionally R3, R4 and R5 are each

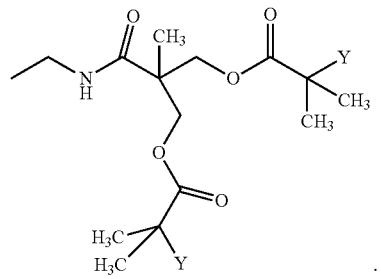

Optionally, R4, R5 and R6 are each

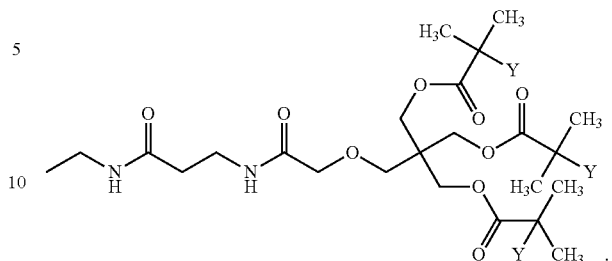

Optionally L3 is a bond and R2 is H and R1 is

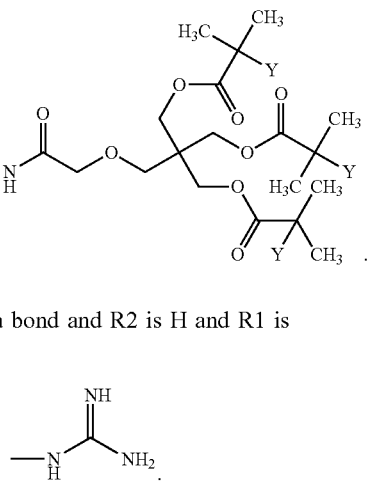

Optionally, L2 is —(CH2)1-6-. Optionally, L2 is —(CH2)3-.

The invention further provides a polymerization process, comprising:
polymerizing one or more radically polymerizable monomers in the presence of: an initiator comprising a homolytically cleavable bond with a radically transferable atom or group; a transition metal compound; and a ligand selected from the group consisting of

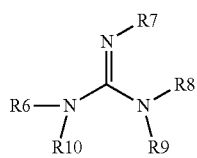

wherein R6, R7, R8, R9 and R10 are the same or different and are selected from the group consisting of a bond, H, amino, aryl6-12 and alkyl1-6;

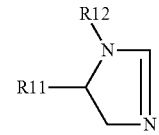

wherein R11 and R12 are the same or different and are selected from the group consisting of
a bond, H, aryl6-12 and alkyl1-6;

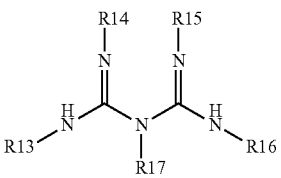

wherein R13, R14, R15, R16 and R17 are the same or different and are selected from the group consisting of a bond, H, amino, aryl6-12 and alkyl1-6 and one or more arginine residues; wherein the ligand is coordinated to the transition metal compound, and wherein the transition metal compound and the ligand are matched to initiate and propagate polymerization of the monomers. Optionally the ligand is covalently linked to the initiator to form a unimolecular initiator ligand.

Optionally, the unimolecular initiator ligand has the structure:

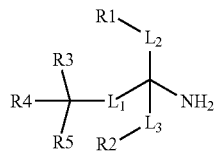

wherein L1 is a first linker, L2 is a second linker and L3 is a third linker, wherein L1, L2 and L3 are the same or different and are each selected from the group consisting of —C1-C12 alkyl-, —C3-C12 cycloalkyl-, (—(CH2)1-6-O—(CH2)1-6-)1-12-, (—(CH2)1-4-NH—(CH2)1-4)1-12-, —(CH2)1-12O—, (—(CH2)1-4-O—(CH2)1-4)1-12-O—, —(CH2)1-12-(CO)—O—, —(CH2)1-12-(CO)—NH—, —(CH2)1-12-O—(CO)—, —(CH2)1-12-NH—(CO)—, (—(CH2)1-4-O—(CH2)1-4)1-12-O—(CH2)1-12-, —(CH2)1-12-(CO)—O—(CH2)1-12-, —(CH2)1-12-(CO)—NH—(CH2)1-12-, —(CH2)1-12-O—(CO)—(CH2)1-12-, —(CH2)1-12-NH—(CO)—(CH2)1-12-, —(C3-C12 cycloalkyl)-, —(C1-C8alkyl)-(C3-C12 cycloalkyl)-, —(C3-C12 cycloalkyl)-(C1-8alkyl)-, —(C1-8alkyl)-(C3-C12 cycloalkyl)-(C1-8alkyl)-, —NH—(CH2CH2-O-)1-20-NH—(CH2CH2-O-)1-20- and —(CH2)0-3-aryl-(CH2)0-3-, a bond and any combination of the above; R1 and R2 are the same or different and are selected from the group consisting of H, provided that not both R1 and R2 are H, and one or more basic groups wherein a basic group is selected from the group consisting of

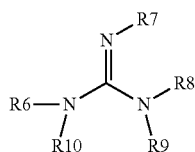

wherein R6, R7, R8, R9 and R10 are the same or different and are selected from the group consisting of a bond, H, amino, aryl6-12 and alkyl1-6;

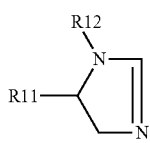

wherein R11 and R12 are the same or different and are selected from the group consisting of a bond, H, aryl6-12 and alkyl1-6;

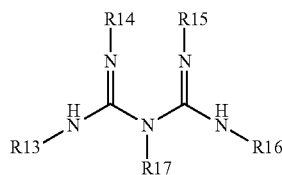

wherein R13, R14, R15, R16 and R17 are the same or different and are selected from the group consisting of a bond, H, amino, aryl6-12 and alkyl1-6 and one or more arginine residues; and R3, R4 and R5 are the same or different and are selected from the group consisting of

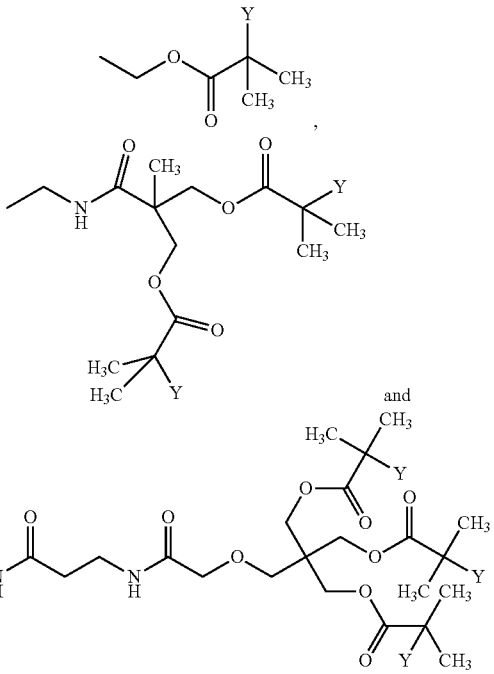

wherein Y is NCS, F, Cl, Br or I.

Optionally Y is Br. Optionally, R3, R4 and R5 are each

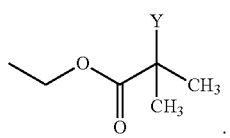

Optionally R3, R4 and R5 are each

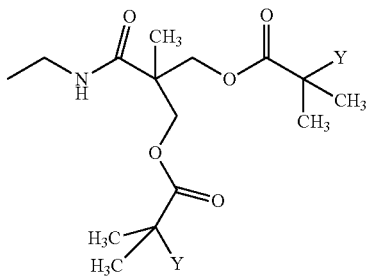

Optionally R4, R5 and R6 are each

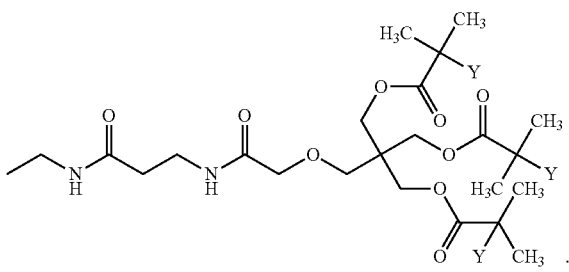

Optionally, L3 is a bond and R2 is H and R1 is

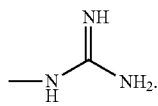

Optionally, L2 is —(CH2)1-6- or —(CH2)3-. Optionally, the radically polymerizable monomers are olefinically unsaturated monomers. Optionally, the unsaturated monomers comprise HEMA-PC. Optionally, the transition metal is one of a transition metal in a low valence state or a transition metal coordinated to at least one coordinating non-charged ligand and wherein the transition metal comprises a counterion. Optionally, the transition metal is selected from the group consisting of copper, iron, nickel or ruthenium.

DETAILED DESCRIPTION

I. General

Figure 1:
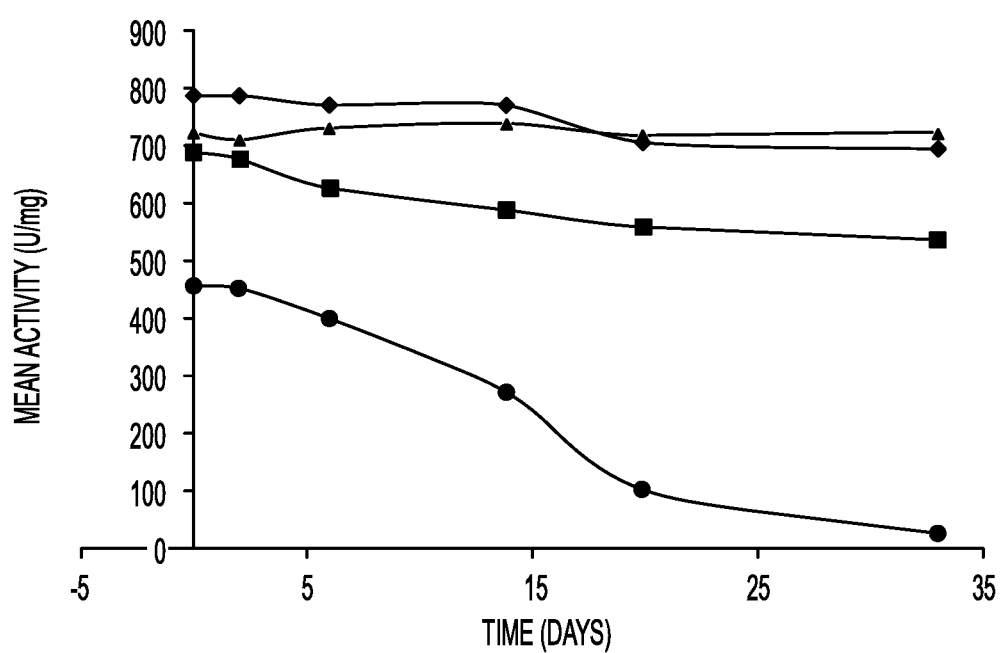
FIG. 1 shows the activity over time of plasma derived hBuChE versus full length rhBuChE from the milk of transgenic goats, rBuChE534GGC (C66Y) and rhBuChE534 (C66Y)-Fc (L234A, L235E, G237A, A330S, P331S and Q347C, EU numbering) stored in cyanomologus monkey plasma over time.
Figure 2:
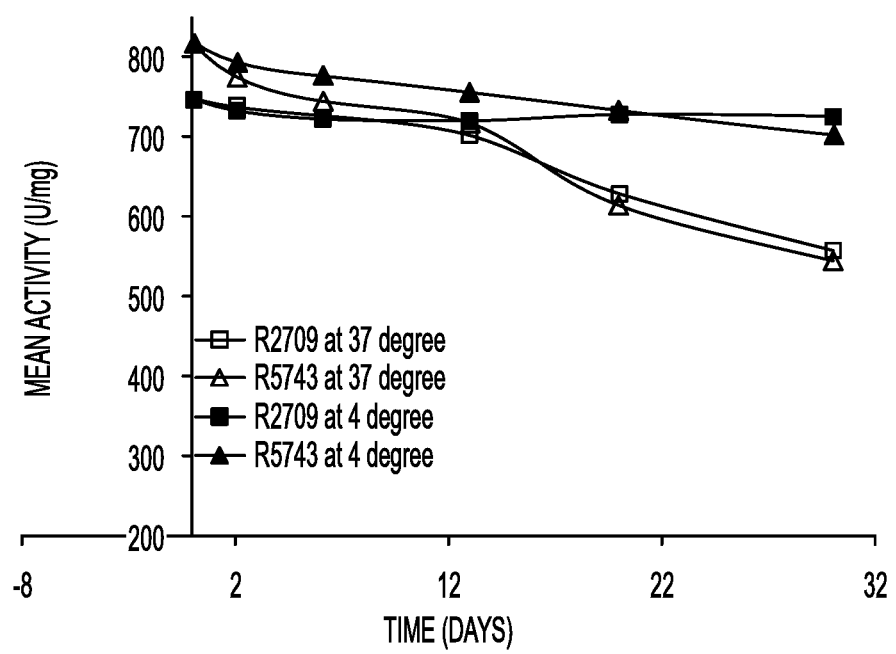
FIG. 2 depicts a plot of activity vs. time for rhBuChE534 (C66Y)-Fc (L234A, L235E, G237A, A330S, P331S and Q347C, EU numbering) conjugated to 9 arm 750 kDa HEMA-PC polymer compared with human plasma derived BuChE at 4° C. and 37° C. in cyanomologus monkey plasma.

The present invention provides high molecular weight (MW) polymers having hydrophilic groups or zwitterions, such as phosphorylcholine. Also provided in accordance with the present invention are methods and novel starting materials for making the high MW polymers. Also provided in accordance with the present invention are conjugates of the high MW polymers and cholinesterases. WO2011/130694 and WO/2007/100902 are hereby incorporated by reference for all purposes.

II. Definitions

"Cholinesterase" (ChE) refers to a family of enzymes involved in nerve impulse transmissions. Cholinesterases catalyze the hydrolysis of acetylcholine at cholinergic synapses. Cholinesterases include but are not limited to acetylcholinesterases and butyrylcholinesterases.

Reference to cholinesterases, including acetylcholinesterases and butyrylcholinesterases, includes precursor cholinesterases and mature cholinesterases (such as those in which a signal sequence has been removed), truncated forms thereof that have activity, and includes allelic variants and species variants, variants encoded by splice variants, and other variants, including polypeptides that have at least 85%, 90%, 95%, 96%, 97%, 98%, 99% or more sequence identity to the polypeptides set forth in the referenced SEQ ID NOs. Variants exhibit OP inactivating activity. Cholinesterases also include those that contain chemical or posttranslational modifications and those that do not contain chemical or posttranslational modifications. Such modifications include, but are not limited to, PEGylation, addition of poly(HEMA-PC), albumination, glycosylation, farnesylation, carboxylation, hydroxylation, phosphorylation, and other polypeptide modifications known in the art. A truncated cholinesterase is any N- or C-terminal shortened form thereof, particularly forms that are truncated and have OP inactivating activity.

"Acetylcholinesterase" (AChE) refers to enzymes or polypeptides capable of hydrolyzing acetyl esters, including acetylcholine, and whose catalytic activity is inhibited by the chemical inhibitor BW 284C51. Acetylcholinesterases include, but are not limited to, plasma derived or recombinant acetylcholinesterase. Acetylcholinesterases include human and any of non-human origin including, but not limited to, rat, mouse, cat, chicken, rabbit, and cow acetylcholinesterases. Exemplary human acetylcholinesterases include human AChE set forth in SEQ ID NO: 3. Acetylcholinesterases can be in any form, including, but not limited to, monomer, dimer and tetramer forms.

"Butyrylcholinesterase" (BuChE) refers to enzymes or polypeptides capable of hydrolyzing acetylcholine and butyrylcholine, and whose catalytic activity is inhibited by the chemical inhibitor tetraisopropyl-pyrophosphoramide (iso-OMPA). Butyrylcholinesterases include, but are not limited to, plasma derived or recombinant butyrylcholinesterases. Butyrylcholinesterases include any of nonhuman origin including, but not limited to, rat, mouse, cat, horse, chicken, pig, rabbit, and cow. Butyrylcholinesterases also include butyrylcholinesterases of human origin. Exemplary human butyrylcholinesterases include human BuChE set forth in SEQ ID NO: 1. Butyrylcholinesterases can be in any form, including, but not limited to, monomer, dimer and tetramer forms.

"Organophosphorus compound," "organophosphate compound," "OP compound," and "OP," which are used interchangeably herein, refer to chemical compounds that contain a phosphoryl center, and further contain one or more ester linkages. In some aspects, the type of phosphoester bond and/or additional covalent bond at the phosphoryl center classifies an organophosphorus compound. Organophosphorus compounds include organophosphorus pesticides and organophosphorus nerve agents.

"Organophosphorus nerve agent," "organophosphate nerve agent," or "OP nerve agent" refers to a chemical compound that disrupts the functioning of the nervous system of an organism, such as by inhibiting the actions of the enzyme acetylcholinesterase. Nerve agents are generally prepared by chemical synthesis and are highly toxic if inhaled, absorbed, ingested, or otherwise encountered. A nerve agent can be any organophosphorus compound, including, but not limited to G-type nerve agents and V-type nerve agents. Exemplary organophosphorus nerve agents include tabun (GA), sarin (GB), soman (GD), cyclosarin (GF), VX, Russian VX (VR), and classified non-traditional nerve agents (NTAs).

"Organophosphorus pesticide," "organophosphate pesticide" or "OP pesticide" refers to an organophosphorus compound that can be used a pesticide or insecticide to destroy pests and insects. An organophosphorus pesticide can be any organophosphorus pesticide, including, but not limited to, acephate, azinphos-methyl, bensulide, cadusafos, chlorethoxyfos, chlorpyrifos, chlorpyrifosmethyl, chlorthiophos, coumaphos, dialiflor, diazinon, diehlorvos (DDVP), dierotophos, dimethoate, dioxathion, disulfoton, ethion, ethoprop, ethyl parathion, fenamiphos, fenitrothion, fenthion, fonofos, isazophos methyl, isofenphos, malathion, methamidophos, methidathion, methyl parathion, mevinphos, monocrotophos, naled, oxydemeton methyl, phorate, phosalone, phosmet, phosphamidon, phostebupirim, pirimiphos methyl, profenofos, propetamphos, sulfotepp, sulprofos, temephos, terbufos, tetraehlorvinphos, tribufos (JDEF) and trichlorfon.

"Organophosphorus poisoning" or "OP poisoning" refers to deleterious or undesirable effects to a living creature exposed to an organophosphorus compound such as an organophosphorus nerve agent or an organophosphorus pesticide.

"Cholinergic toxicity" refers to toxicity achieved by nerve agent inhibition of acetylcholinesterase, accumulation of the neurotransmitter acetylcholine, and concomitant effects on the parasympathetic, sympathetic, motor, and central nervous systems. Cholinergic toxicity can result in myopathy, psychosis, general paralysis and death. Symptoms of exposure include twitching, trembling, hypersecretion, paralyzed breathing, convulsions, and ultimately death. Cholinergic toxicity can be monitored by measuring circulating (active) cholinesterase levels in the plasma. Generally lethality occurs only when cholinesterase activity falls below 20% of normal levels due to binding by nerve agents.

"Organophosphorus exposure associated damage" refers to short term (e.g., minutes to several hours post-exposure) and long term (e.g., one week up to several years post-exposure) damage, for example, due to cholinergic toxicity, to physiological function (e.g., motor and cognitive functions). Organophosphorus exposure associated damage can be manifested by the following clinical symptoms including, but not limited to, headache, diffuse muscle cramping, weakness, excessive secretions, nausea, vomiting, and diarrhea. The condition can progress to seizure, coma, paralysis, respiratory failure, delayed neuropathy, muscle weakness, tremor, convulsions, permanent brain dismorphology, social/behavioral deficits and general cholinergic crisis (which can be manifested for instance by exacerbated inflammation and low blood count). Extreme cases can lead to death of the poisoned subjects.

"Organophosphorus bioscavenger" or "organophosphate bioscavenger" or "OP bioscavenger" is an enzyme capable of binding to or hydrolyzing an organophosphorus compound, including organophosphorus pesticides and organophosphorus nerve agents. Organophosphorus bioscavengers include, but are not limited to, cholinesterases, aryldialkylphosphatases, organophosphate hydrolases (OPH), carboxylesterases, triesterases, phosphotriesterases, arylesterases, paraoxonases (PON), organophosphate acid anhydrases, and diisopropylfluorophosphatases (DFPases). Organophosphorus bioscavengers can be stoichiometric organophosphorus bioscavengers or catalytic organophosphorus bioscavengers.

"Stoichiometric organophosphorus bioscavenger" or "stoichiometric OP bioscavenger" refers to an enzyme where each active site of the enzyme binds to an organophosphorus compound in a stoichiometric 1:1 ratio. Stoichiometric OP bioscavengers include, but are not limited to, cholinesterases, such as acetylcholinesterases and butyrylcholinesterases.

"Catalytic organophosphorus bioscavenger" or "catalytic OP bioscavenger" refers to an enzyme that hydrolyzes an organophosphorus compound. Catalytic OP bisocavengers include, but are not limited to, aryldialkylphosphatases, organophosphate hydrolases (OPH), carboxylesterases, triesterases, phosphotriesterases, arylesterases, paraoxonases (PON), organophosphate acid anhydrylases and diisopropylfluorophosphatases (DFPases) including recombinant mutations introduced into such enzymes to increase their ability to hydrolyze OP compounds.

"Aryldialkylphosphatase" refers to naturally occurring or recombinant enzymes that inactivate or hydrolyze organophosphorus compounds. Aryldialkylphosphatases (EC 3.1.8.1) are a class of metal-dependent OP-hydrolases that are capable of hydrolyzing a broad range of organophosphorus compounds. Aryldialkylphosphatases require a divalent metal ion, such as $Zn^{2+}$, $Mn^{2+}$, $Co^{2+}$, or $Cd^{2+}$, for enzymatic activity. Aryldialkylphosphatases include, but are not limited to, phosphotriesterases or OP hydxolases (PTE or OPH), paraoxon hydrolases or paraoxonases, parathion hydrolases (PH), OpdA, carboxylesterases, triesterases, phosphotriesterases and arylesterases. Aryldialkylphosphatases include, but are not limited to, organophosphorus hydrolases from *Pseudomonas diminuata* MG, *Flavobacterium* sp., *Plesiomonas* sp. strain M6, *Streptomyces lividans* and *Agrobacterium radiobacter*; parathion hydrolases from *Burkholderia* sp. JBA3, *Pseudomonas diminuta* MG, *Brevundiomonas diminuta, Flavobacterium* sp. strain ATCC 27552, and *Sulfolobus acidocaldarius*; and methyl parathion hydrolases (MPH) from *Bacillus subtilis* WB800 and *Plesiomonas* sp. strain M6. Exemplary aryldiakylphosphatases include, but are not limited to the aryldialkylphosphatases set forth in SEQ ID NO: 5.

Reference to aryldialkylphosphatases includes truncated forms thereof that have activity, and includes allelic variants and species variants, variants encoded by splice variants, and other variants, including polypeptides that have at least 40%, 45%, 50%, 55%, 60%, 65%, 70%, 75%, 80%, 85%, 90%, 95%, 96%, 97%, 98%, 99% or more sequence identity to the polypeptides set forth above and in SEQ ID NO: 5. Variants exhibit OP inactivating activity.

"Paraoxonase" refers to naturally occurring or recombinant enzymes that inactivate or hydrolyze organophosphorus compounds. Paraoxonases include, but are not limited to, native or recombinant paraoxonases. Non-human paraoxonases include, but are not limited to, paraoxonases from rabbit, mouse, rat, pig, cow, chicken, turkey and dog. Exemplary paraoxonases include, but are not limited to, human paraoxonases, including PON1 (SEQ ID NO: 6).

Reference to paraoxonases includes truncated forms thereof that have activity, and includes allelic variants and species variants, variants encoded by splice variants, and other variants, including polypeptides that have at least 85%, 90%, 95%, 96%, 97%, 98%, 99% or more sequence identity to the polypeptide set forth in SEQ ID NO: 6. Variants exhibit OP inactivating activity. Paraoxonases also include those that contain chemical or posttranslational modifications and those that do not contain chemical or posttranslational modifications. Such modifications include, but are not limited to, PEGylation, albumination, glycosylation, farnesylation, carboxylation, hydroxylation, phosphorylation, and other polypeptide modifications known in the art.

"Diisopropylfluorophosphatase" refers to naturally occurring or recombinant enzymes that inactivate or hydrolyze organophosphorus compounds. Diisopropylfluorophosphatases include, but are not limited to, diisopropylfluorophosphatases from *Loligo vulgaris, Alteromonas* sp., *Pseudoalteromonas haloplanktis, Marinomonas mediterranea, Aplysia californica,* Octopus vulgaris and rat senescence marker protein 30; and organophosphate acid anhydrolases from *Mycobacterium* sp, *Amycolatopsis mediterranei, Streptomyces coelicolor, Streptomyces* spAA4, *Streptomyces lividans* TK24, *Streptomyces sviceus,* and *Streptomyces griseoaurantiacus* M045. Exemplary diisopropylfluorophosphatases and organophosphate acid anhydrolases include, but are not limited to, diisopropylfluorophosphatase from *Loligo vulgaris* set forth in any of SEQ ID NO. 7.

Reference to diisopropylfluorophosphatases includes truncated forms thereof that have activity, and includes allelic variants and species variants, variants encoded by splice variants, and other variants, including polypeptides that have at least 85%, 90%, 95%, 96%, 97%, 98%, 99% or more sequence identity to the polypeptide set forth in SEQ ID NO: 7. Variants exhibit OP inactivating activity.

"Carbamate" refers to any compound that is a carbamate inhibitor of cholinesterase. An exemplary carbamate is pyridostigmine bromide.

"Anti-muscarinic" refers to any compound that is a competitive antagonist to muscarinic receptors, including muscarinic acetylcholine receptors. An exemplary anti-muscarinic is atropine.

"Cholinesterase reactivator" refers to any compound that releases a bound organophosphorus compound from a cholinesterase. Cholinesterase reactivators include choline-re-activating oximes, including pyridinium and bispyridinium aldoximes, including, but not limited to, pralidoxime, trimedoxime, obidoxime and HI-6, methoxime, and diazepam.

"Anti-convulsive" refers to any compound that protects against or reverses seizures.

"Conjugate" refers to a polypeptide linked directly or indirectly to one or more chemical moieties such as polymers.

"Fusion protein" refers to a polypeptide encoded by a nucleic acid sequence containing a coding sequence from one nucleic acid molecule and the coding sequence from another nucleic acid molecule in which the coding sequences are in the same reading frame such that when the fusion construct is transcribed and translated in a host cell, the protein is produced containing the two proteins. The two molecules can be adjacent in the construct or separated by a linker polypeptide that contains, 1, 2, 3, or more, but typically fewer than 25, 20, 15, 10, 9, 8, 7, or 6 amino acids. The protein product encoded by a fusion construct is referred to as a fusion polypeptide or protein. Fusion proteins may have a peptide or protein linked between the two proteins.

"Half-life" or "half-life of elimination" or "t½" refers to the time required for any specified property or activity to decrease by half. For example, half-life refers to the time it takes a substance (e.g. an organophosphorous bioscavenger) to lose half of its activity of its original level. Hence, half-life can be determined by measuring the activity of a substance in plasma, or it can be determined by measuring the plasma level of the substance in the plasma. For example, half-life can be determined as the time necessary for the drug to be reduced to half of its original level in the body through various bodily processes. The longer the half-life, the longer it will take the substance or drug to be purged from the body. Units for half-life are generally units of time such as hour, minute or day.

"Absorption" refers to the movement of a drug into the bloodstream.

"Bioavailability" refers to the fraction of an administered dose of drug that reaches the systemic circulation. Bioavailability is a function of the absorption of a drug into the bloodstream.

"Dose" refers to the quantity or amount of drug that is administered to a subject for therapeutic or prophylactic purposes.

"Nucleic acids" include DNA, RNA and analogs thereof, including peptide nucleic acids (PNA) and mixtures thereof. Nucleic acids can be single or double stranded. When referring to probes or primers, which are optionally labeled, such as with a detectable label, such as a fluorescent or radiolabel, single-stranded molecules are contemplated. Such molecules are typically of a length such that their target is statistically unique or of low copy number (typically less than 5, generally less than 3) for probing or priming a library. Generally a probe or primer contains at least 14, 16 or 30 contiguous nucleotides of sequence complementary to or identical to a gene of interest. Probes and primers can be 10, 20, 30, 50, 100 or more nucleic acids long.

A "polypeptide linker" or "linker" is a polypeptide comprising two or more amino acid residues joined by peptide bonds that are used to link two polypeptides (e.g., a VH and VL domain or a VH domain and an extracellular trap segment). Examples of such linker polypeptides are well known in the art (see, e.g., Holliger et al. (1993) Proc. Natl. Acad. Sci. USA 90:6444-6448; Poljak et al. (1994) Structure 2:1121-1123). Exemplary linkers include G, GG, GGGGS (SEQ ID NO: 22), GGGS (SEQ ID NO: 23), and GGGES (SEQ ID NO: 24), and oligomers of such linkers (e.g., GGGGSGGGGS (SEQ ID NO: 4) and GGGGSGGGGSGGGGSGGGGSG (SEQ ID NO: 26)).

"Polymer" refers to a series of monomer groups linked together. The high MW polymers are prepared from monomers that include, but are not limited to, acrylates, methacrylates, acrylamides, methacrylamides, styrenes, vinyl-pyridine, vinyl-pyrrolidone, and vinyl esters such as vinyl acetate. Additional monomers are useful in the high MW polymers of the present invention. When two different monomer types are used, the two monomer types are called "comonomers," meaning that the different monomers types are copolymerized to form a single polymer. The polymer can be linear or branched. When the polymer is branched, each polymer chain is referred to as a "polymer arm." The end of the polymer arm linked to the initiator moiety is the proximal end, and the growing-chain end of the polymer arm is the distal end. On the growing chain-end of the polymer arm, the polymer arm end group can be the radical scavenger, or another group.

"Initiator" refers to a compound capable of initiating a polymerization using monomers or comonomers. The polymerization can be a conventional free radical polymerization or preferably a controlled/"living" radical polymerization, such as Atom Transfer Radical Polymerization (ATRP), Reversible Addition Fragmentation Termination (RAFT) polymerization or nitroxide mediated polymerization (NMP). The polymerization can be a "pseudo" controlled polymerization, such as degenerative transfer. When the initiator is suitable for ATRP, it contains a labile bond which can be homolytically cleaved to form an initiator fragment, I, being a radical capable of initiating a radical polymerization, and a radical scavenger, I', which reacts with the radical of the growing polymer chain to reversibly terminate the polymerization. The radical scavenger I' is typically a halogen, but can also be an organic moiety, such as a nitrile.

"Linker" refers to a chemical moiety that links two groups together. The linker can be cleavable or non-cleavable. Cleavable linkers can be hydrolysable, enzymatically cleavable, pH sensitive, photolabile, or disulfide linkers, among others. Other linkers include homobifunctional and heterobifunctional linkers. A "linking group" is a functional group capable of forming a covalent linkage consisting of one or more bonds to a bioactive agent. Nonlimiting examples include those illustrated in Table 1.

The term "reactive group" as used herein refers to a group that is capable of reacting with another chemical group to form a covalent bond, i.e. is covalently reactive under suitable reaction conditions, and generally represents a point of attachment for another substance. The reactive group is a moiety, such as maleimide or succinimidyl ester, on the compounds of the present invention that is capable of chemically reacting with a functional group on a different compound to form a covalent linkage. Reactive groups generally include nucleophiles, electrophiles, and photoactivatable groups.

"Functional agent" is defined to include a bioactive agent or a diagnostic agent. A "bioactive agent" is defined to include any agent, drug, compound, or mixture thereof that targets a specific biological location (targeting agent) and/or provides some local or systemic physiological or pharmacologic effect that can be demonstrated in vivo or in vitro. Non-limiting examples include drugs, vaccines, antibodies, antibody fragments, scFvs, diabodies, avimers, vitamins and cofactors, polysaccharides, carbohydrates, steroids, lipids, fats, proteins, peptides, polypeptides, nucleotides, oligonucleotides, polynucleotides, and nucleic acids (e.g., mRNA, tRNA, snRNA, RNAi, DNA, cDNA, antisense constructs, ribozymes, etc.). A "diagnostic agent" is defined to include any agent that enables the detection or imaging of a tissue or disease. Examples of diagnostic agents include, but are not limited to, radiolabels, fluorophores, and dyes.

"Therapeutic protein" refers to peptides or proteins regardless of length that include an amino acid sequence which in whole or in part makes up a drug and can be used in human or animal pharmaceutical applications. Numerous therapeutic proteins are known including, without limitation, those disclosed herein.

"Phosphorylcholine," also denoted as "PC," refers to the following:

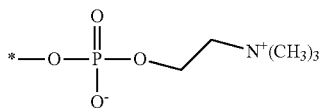

where * denotes the point of attachment.

"Phosphorylcholine containing polymer" is a polymer that contains phosphorylcholine. "Zwitterion containing polymer" refers to a polymer that contains a zwitterion.

Poly(acryloyloxyethyl phosphorylcholine) containing polymer refers to a polymer containing 2-(acryloyloxy)ethyl-2-(trimethylammonium)ethyl phosphate as monomer.

Poly(methacryloyloxyethyl phosphorylcholine) containing polymer refers to a polymer containing 2-(methacryloyloxy)ethyl-2-(trimethylammonium)ethyl phosphate as monomer.

Polymers defined by reference to a specified monomer type can be a homopolymer, i.e., only monomers of the specified type are present, or a copolymer in which case monomers of the specified type are present with other monomer type(s). If a co-polymer preferably, at least 50, 75 or 90% of monomer molecules are of the specified type.

"Molecular weight" in the context of the polymer can be expressed as either a number average molecular weight, or a weight average molecular weight, or a peak molecular weight. Unless otherwise indicated, all references to molecular weight herein refer to the peak molecular weight. These molecular weight determinations, number average (Mn), weight average (Mw), and peak (Mp), can be measured using size exclusion chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number average molecular weight, or the use of light scattering techniques, ultracentrifugation, or viscometry to determine weight average molecular weight. In a preferred embodiment of the present invention, the molecular weight is measured by SEC-MALS (size exclusion chromatography-multi angle light scattering). The polymeric reagents of the invention are typically polydisperse (i.e., number average molecular weight and weight average molecular weight of the polymers are not equal), preferably possessing a low polydispersity index (PDI) values of, for example, less than about 1.5, as judged by gel permeation chromatography. In other embodiments, the polydispersities are more preferably in the range of about 1.4 to about 1.2, still more preferably less than about 1.15, and still more preferably less than about 1.10, yet still more preferably less than about 1.05, and most preferably less than about 1.03.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

"About" as used herein means variation one might see in measurements taken among different instruments, samples, and sample preparations.

"Protected," "protected form," "protecting group," and "protective group" refer to the presence of a group (i.e., the protecting group) that prevents or blocks reaction of a particular chemically reactive functional group in a molecule under certain reaction conditions. Protecting groups vary depending on the type of chemically reactive group being protected as well as the reaction conditions to be employed and the presence of additional reactive or protecting groups in the molecule, if any. Suitable protecting groups include those such as found in the treatise by Greene et al., "Protective Groups In Organic Synthesis," 3rd Edition, John Wiley and Sons, Inc., New York, 1999.

"Alkyl" refers to a straight or branched, saturated, aliphatic radical having the number of carbon atoms indicated. For example, C1-C6 alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together.

The term "lower" referred to above and hereinafter in connection with organic radicals or compounds respectively defines a compound or radical which can be branched or unbranched with up to and including 7, preferably up to and including 4 and (as unbranched) one or two carbon atoms.

"Alkylene" refers to an alkyl group, as defined above, linking at least two other groups, i.e., a divalent hydrocarbon radical. The two moieties linked to the alkylene can be linked to the same atom or different atoms of the alkylene. For instance, a straight chain alkylene can be the bivalent radical of —(CH2)n, where n is 1, 2, 3, 4, 5 or 6. Alkylene groups include, but are not limited to, methylene, ethylene, propylene, isopropylene, butylene, isobutylene, sec-butylene, pentylene and hexylene.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —CO2R', —CONR'R", —OC(O)NR'R", —NR"C(O)R', —NR'—C(O)NR"R'", —NR"C(O)2R', —NH—C(NH2)=NH, —NR' C(NH2)=NH, —NH—C(NH2)=NR', —S(O)R', —S(O)2R', —S(O)2NR'R", —CN and —NO2 in a number ranging from zero to (2m'+1), where m' is the total number of carbon atoms in such radical. R', R" and R'" each independently refer to hydrogen, unsubstituted (C1-C8)alkyl and heteroalkyl, unsubstituted aryl, aryl substituted with 1-3 halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. The term "alkyl" includes groups such as haloalkyl (e.g., —CF3 and —CH2CF3) and acyl (e.g., —C(O)CH3, —C(O)CF3, —C(O)CH2OCH3, and the like). Preferably, the substituted alkyl and heteroalkyl groups have from 1 to 4 substituents, more preferably 1, 2 or 3 substituents. Exceptions are those perhalo alkyl groups (e.g., pentafluoroethyl and the like) which are also preferred and contemplated by the present invention.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO2R', —CONR'R", —OC(O)NR'R", —NR"C(O)R', —NR'—C(O)NR"R'", —NR"C(O)2R', —NR—C(NR'R"R'")=NR"", —NR—C(NR'R")=NR'", —S(O)R', —S(O)2R', —S(O)2NR'R", —NRSO2R', —CN and —NO2 in a number ranging from zero to (2m'+1), where m' is the total number of carbon atoms in such radical. R', R", R'" and R'" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R'" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. The term "alkyl" includes groups including carbon atoms bound to groups other than hydrogen groups, such as haloalkyl (e.g., —CF3 and —CH2CF3) and acyl (e.g., —C(O)CH3, —C(O)CF3, —C(O)CH2OCH3, and the like).

"Alkoxy" refers to alkyl group having an oxygen atom that either connects the alkoxy group to the point of attachment or is linked to two carbons of the alkoxy group. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "halo-alkoxy" group.

"Carboxyalkyl" means an alkyl group (as defined herein) substituted with a carboxy group. The term "carboxycycloalkyl" means an cycloalkyl group (as defined herein) substituted with a carboxy group. The term alkoxyalkyl means an alkyl group (as defined herein) substituted with an alkoxy group. The term "carboxy" employed herein refers to carboxylic acids and their esters.

"Haloalkyl" refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, fluoromethyl, 1,2,3,4,5-pentafluoro-phenyl, etc. The term "perfluoro" defines a compound or radical which has all available hydrogens that are replaced with fluorine. For example, perfluorophenyl refers to 1,2,3,4,5-pentafluorophenyl, perfluoromethyl refers to 1,1,1-trifluoromethyl, and perfluoromethoxy refers to 1,1,1-trifluoromethoxy.

"Fluoro-substituted alkyl" refers to an alkyl group where one, some, or all hydrogen atoms have been replaced by fluorine.

"Cycloalkyl" refers to a cyclic hydrocarbon group that contains from about 3 to 12, from 3 to 10, or from 3 to 7 endocyclic carbon atoms. Cycloalkyl groups include fused, bridged and spiro ring structures.

"Endocyclic" refers to an atom or group of atoms which comprise part of a cyclic ring structure.

"Exocyclic" refers to an atom or group of atoms which are attached but do not define the cyclic ring structure.

"Cyclic alkyl ether" refers to a 4 or 5 member cyclic alkyl group having 3 or 4 endocyclic carbon atoms and 1 endocyclic oxygen or sulfur atom (e.g., oxetane, thietane, tetrahydrofuran, tetrahydrothiophene); or a 6 to 7 member cyclic alkyl group having 1 or 2 endocyclic oxygen or sulfur atoms (e.g., tetrahydropyran, 1,3-dioxane, 1,4-dioxane, tetrahydrothiopyran, 1,3-dithiane, 1,4-dithiane, 1,4-oxathiane).

"Alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5- hexadienyl, 2,4-hexadienyl, or 1,3,5-hexatrienyl. Alkenyl groups can also have from 2 to 3, 2 to 4, 2 to 5, 3 to 4, 3 to 5, 3 to 6, 4 to 5, 4 to 6 and 5 to 6 carbons. The alkenyl group is typically monovalent, but can be divalent, such as when the alkenyl group links two moieties together.

"Alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene.

"Alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can also have from 2 to 3, 2 to 4, 2 to 5, 3 to 4, 3 to 5, 3 to 6, 4 to 5, 4 to 6 and 5 to 6 carbons. The alkynyl group is typically monovalent, but can be divalent, such as when the alkynyl group links two moieties together.

"Alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, butynylene, sec-butynylene, pentynylene and hexynylene.

"Cycloalkyl" refers to a saturated or partially unsaturated, monocyclic, fused bicyclic or bridged polycyclic ring assembly containing from 3 to 12 ring atoms, or the number of atoms indicated. Monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, C3-8cycloalkyl includes cyclopropyl, cyclobutyl, cyclopentyl, cyclohexyl, cyclooctyl, and norbornane.

"Cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Cycloalkylene groups include, but are not limited to, cyclopropylene, cyclobutylene, cyclopentylene, cyclohexylene, and cyclooctylene.

"Heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)2-. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

"Heterocycloalkylene" refers to a heterocyclalkyl group, as defined above, linking at least two other groups. The two moieties linked to the heterocycloalkylene can be linked to the same atom or different atoms of the heterocycloalkylene.

"Aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-C2-C3-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-C2-C3-alkylene is also a divalent substituent attached to two adjacent carbon atoms of phenyl, e.g. oxyethylene or oxypropylene. An example for oxy-C2-C3-alkylene-phenyl is 2,3-dihydrobenzofuran-5-yl.

Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phenyl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

"Arylene" refers to an aryl group, as defined above, linking at least two other groups. The two moieties linked to the arylene are linked to different atoms of the arylene. Arylene groups include, but are not limited to, phenylene.

"Arylene-oxy" refers to an arylene group, as defined above, where one of the moieties linked to the arylene is linked through an oxygen atom. Arylene-oxy groups include, but are not limited to, phenylene-oxy.

Similarly, substituents for the aryl and heteroaryl groups are varied and are selected from: -halogen, —OR', —OC(O)R', —NR'R", —SR', —R', —CN, —NO2, —CO2R', —CONR'R", —C(O)R', —OC(O)NR'R", —NR"C(O)R', —NR"C(O)2R', —NR'—C(O)NR"R''', —NH—C(NH2)=NH, —NR' C(NH2)=NH, —NH—C(NH2)=NR', —S(O)R', —S(O)2R', —S(O)2NR'R", —N3, —CH(Ph)2, perfluoro(C1-C4)alkoxy, and perfluoro(C1-C4)alkyl, in a number ranging from zero to the total number of open valences on the aromatic ring system; and where R', R" and R''' are independently selected from hydrogen, (C1-C8)alkyl and heteroalkyl, unsubstituted aryl and heteroaryl, (unsubstituted aryl)-(C1-C4)alkyl, and (unsubstituted aryl)oxy-(C1-C4)alkyl.

Two of the substituents on adjacent atoms of the aryl or heteroaryl ring may optionally be replaced with a substituent of the formula -T-C(O)—(CH2)q-U—, wherein T and U are independently —NH—, —O—, —CH2- or a single bond, and q is an integer of from 0 to 2. Alternatively, two of the substituents on adjacent atoms of the aryl or heteroaryl ring may optionally be replaced with a substituent of the formula -A-(CH2)r-B—, wherein A and B are independently —CH2-, —O—, —NH—, —S—, —S(O)—, —S(O)2-, —S(O)2NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH2)s-X—(CH2)t-, where s and t are independently integers of from 0 to 3, and X is —O—, —NR'—, —S—, —S(O)—, —S(O)2-, or —S(O)2NR'—. The substituent R' in —NR'— and —S(O)2NR'— is selected from hydrogen or unsubstituted (C1-C6)alkyl.

"Heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

As used herein, the term "heteroalkyl" refers to an alkyl group having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)2-. For example, heteroalkyl can include ethers, thioethers, alkyl-amines and alkyl-thiols.

As used herein, the term "heteroalkylene" refers to a heteroalkyl group, as defined above, linking at least two other groups. The two moieties linked to the heteroalkylene can be linked to the same atom or different atoms of the heteroalkylene.

"Electrophile" refers to an ion or atom or collection of atoms, which may be ionic, having an electrophilic center, i.e., a center that is electron seeking, capable of reacting with a nucleophile. An electrophile (or electrophilic reagent) is a reagent that forms a bond to its reaction partner (the nucleophile) by accepting both bonding electrons from that reaction partner.

"Nucleophile" refers to an ion or atom or collection of atoms, which may be ionic, having a nucleophilic center, i.e., a center that is seeking an electrophilic center or capable of reacting with an electrophile. A nucleophile (or nucleophilic reagent) is a reagent that forms a bond to its reaction partner (the electrophile) by donating both bonding electrons. A "nucleophilic group" refers to a nucleophile after it has reacted with a reactive group. Non limiting examples include amino, hydroxyl, alkoxy, haloalkoxy and the like.

"Maleimido" refers to a pyrrole-2,5-dione-1-yl group having the structure:

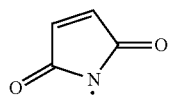

which on reaction with a sulfhydryl (e.g., a thio alkyl) forms an —S-maleimido group having the structure

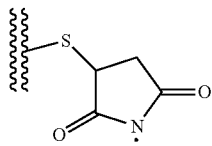

where "•" indicates the point of attachment for the maleimido group and "$" indicates the point of attachment of the sulfur atom the thiol to the remainder of the original sulfhydryl bearing group.

For the purpose of this disclosure, "naturally occurring amino acids" found in proteins and polypeptides are L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and or L-valine. "Non-naturally occurring amino acids" found in proteins are any amino acid other than those recited as naturally occurring amino acids. Non-naturally occurring amino acids include, without limitation, the D isomers of the naturally occurring amino acids (a mixture would more accurately be described as some natural and some non-natural amino acids. Other amino acids, such as 4-hydroxyproline, desmosine, isodesmosine, 5-hydroxylysine, epsilon-N-methyllysine, 3-methylhistidine, although found in naturally occurring proteins, are considered to be non-naturally occurring amino acids found in proteins for the purpose of this disclosure as they are generally introduced by means other than ribosomal translation of mRNA.

"Linear" in reference to the geometry, architecture or overall structure of a polymer, refers to polymer having a single polymer arm.

"Branched," in reference to the geometry, architecture or overall structure of a polymer, refers to a polymer having 2 or more polymer "arms" extending from an initiator. The initiator may be employed in an atom transfer radical polymerization (ATRP) reaction. A branched polymer may possess 2 polymer chains (arms), 3 polymer arms, 4 polymer arms, 5 polymer arms, 6 polymer arms, 7 polymer arms, 8 polymer arms, 9 polymer arms, 10 polymer arms, 11 polymer arms, 12 polymer arms or more. Each polymer arm extends from a polymer initiation site. Each polymer initiation site is capable of being a site for the growth of a polymer chain by the addition of monomers. For example and not by way of limitation, using ATRP, each site of polymer initiation on an initiator is typically an organic halide undergoing a reversible redox process catalyzed by a transition metal compound such as cuprous halide Preferably, the halide is a bromine.

"Pharmaceutically acceptable" composition or "pharmaceutical composition" refers to a composition comprising a compound of the invention and a pharmaceutically acceptable excipient or pharmaceutically acceptable excipients.

"Pharmaceutically acceptable excipient" and "pharmaceutically acceptable carrier" refer to an excipient that can be included in the compositions of the invention and that causes no significant adverse toxicological effect on the patient and is approved or approvable by the FDA for therapeutic use, particularly in humans. Non-limiting examples of pharmaceutically acceptable excipients include water, NaCl, normal saline solutions, lactated Ringer's, normal sucrose, normal glucose and the like.

"Patient" or "subject in need thereof" refers to a living organism suffering from or prone to a condition that can be prevented or treated by administration of a pharmaceutical composition as provided herein. Non-limiting examples include humans, other mammals and other non-mammalian animals.

Conjugates are preferably provided in isolated form. Isolated means that an object species has been at least partially separated from contaminants with which it is naturally associated or which are used in its manufacture but does not necessarily exclude the presence of other components intended to act in combination with an isolated species, such as a pharmaceutical excipient. Preferably a conjugate is the predominant macromolecular species present in a sample (i.e., on a molar basis) in a composition and typically comprises at least about 50 percent (on a molar basis) of all macromolecular species present. Generally, an isolated conjugate comprises more than 80, 90, 95 or 99 percent of all macromolecular species present in a composition. Most preferably, a conjugate is purified to essential homogeneity (i.e., contaminant species cannot be detected in a composition by conventional detection methods), such that the composition consists essentially of a single macromolecular species. Conjugates have the same heavy and light chains are considered to be the same species notwithstanding there may be variation in glycosylation on protein moieties and variation in numbers of monomers in polymer moieties linked to different molecules of the conjugate.

"Effective amount" refers to an amount of a conjugated functional agent or of a pharmaceutical composition useful for treating, ameliorating, or prophylaxis of an identified disease or condition, or for exhibiting a detectable therapeutic or inhibitory effect. The effect can be detected in an individual patient relative to a baseline measurement before treatment or by determining a statistically significant difference in outcome between treated and control populations. Likewise effective regime, means a combination of amount, frequency and route of administration of any conjugation, fusion protein or other agent described herein effective for reducing, inhibiting, or delaying at least one sign or symptom of a disease.

The "biological half-life" of a substance is a pharmacokinetic parameter which specifies the time required for one half of the substance to be removed from an organism following introduction of the substance into the organism.

Sequence identity can be determined by aligning sequences using algorithms, such as BESTFIT, FASTA, and TFASTA in the Wisconsin Genetics Software Package Release 7.0, Genetics Computer Group, 575 Science Dr., Madison, Wis., using default gap parameters, or by inspection, and the best alignment (i.e., resulting in the highest percentage of sequence similarity over a comparison window). Percentage of sequence identity is calculated by comparing two optimally aligned sequences over a window of comparison, determining the number of positions at which the identical residues occur in both sequences to yield the number of matched positions, dividing the number of matched positions by the total number of positions in the window of comparison (i.e., the window size), and multiplying the result by 100 to yield the percentage of sequence identity.

If a specific SEQ ID NO: is provided for a full-length mature protein, residues are numbered consecutively starting at 1 for the first residue of the mature protein (i.e., not taking into account residues of any signal peptide). Residues in variants or fragments of a SEQ ID NO: are numbered by maximal alignment with the SEQ ID NO: and assigning aligned residues the same number.

The term "protein" is used in its broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. A peptide of three or more amino acids is commonly called an oligopeptide if the peptide chain is short. If the peptide chain is long, the peptide is commonly called a polypeptide or a protein.

Non-limiting examples of proteins, include an enzyme, a cytokine, a neurotropic factor, an antibody, a peptide, a hormone, a DNA-binding protein, an aptamer, vaccines, toxins, Interleukin-1. (IL-1 α), IL-1 β, IL-2, IL-3, IL-4, IL-5, IL-6, IL-11, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-31, IL-32, IL-33, colony stimulating factor-1 (CSF-1), macrophage colony stimulating factor, glucocerobrosidase, thyrotropin, stem cell factor, granulocyte macrophage colony stimulating factor, granulocyte colony stimulating factor (G-CSF), EPO, interferon-.alpha. (IFN-α), consensus interferon-.beta. (IFN-β), interferon- (IFN-), interferon-Ω (IFN-Ω), thrombopoietin (TPO), Angiopoietin-1 (Ang-1), Ang-2, Ang-4, Ang-Y, angiopoietin-like polypeptide 1 (ANGPTL1), angiopoietin-like polypeptide 2 (ANGPTL2), angiopoietin-like polypeptide 3 (ANGPTL3), angiopoietin-like polypeptide 4 (ANGPTL4), angiopoietin-like polypeptide 5 (ANGPTL5), angiopoietin-like polypeptide 6 (ANGPTL6), angiopoietin-like polypeptide 7 (ANGPTL7), vitronectin, vascular endothelial growth factor (VEGF), angiogenin, activin A, activin B, activin C, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, bone morphogenic protein receptor II, brain derived neurotrophic factor, cardiotrophin-1, ciliary neutrophic factor, ciliary neutrophic factor receptor, cripto, cryptic, cytokine-induced neutrophil chemotactic factor 1, cytokine-induced neutrophil, chemotactic factor 2α, hepatitis B vaccine, hepatitis C vaccine, drotrecogin .alpha., cytokine-induced neutrophil chemotactic factor 2β, endothelial cell growth factor, endothelin 1, epidermal growth factor (EGF), epigen, epiregulin, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor 11, fibroblast growth factor 12, fibroblast growth factor 13, fibroblast growth factor 16, fibroblast growth factor 17, fibroblast growth factor 19, fibroblast growth factor 20, fibroblast growth factor 21, fibroblast growth factor acidic, fibroblast growth factor basic, glial cell line-derived neutrophic factor receptor .alpha.1, glial cell line-derived neutrophic factor receptor, growth related protein, growth related protein a, IgG, IgE, IgM, IgA, and IgD, α-galactosidase, β-galactosidase, DNAse, fetuin, leutinizing hormone, alteplase, estrogen, insulin, albumin, lipoproteins, fetoprotein, transferrin, thrombopoietin, urokinase, integrin, thrombin, Factor IX (FIX), Factor VIII (FVIII), Factor VIla (FVIIa), Von Willebrand Factor (VWF), Factor FV (FV), Factor X (FX), Factor XI (FXI), Factor XII (FXII), Factor XIII (FXIII), thrombin (FII), protein C, protein S, tPA, PAI-1, tissue factor (TF), ADAMTS 13 protease, growth related protein .beta., growth related protein, heparin binding epidermal growth factor, hepatocyte growth factor, hepatocyte growth factor receptor, hepatoma-derived growth factor, insulin-like growth factor I, insulin-like growth factor receptor, insulin-like growth factor II, insulin-like growth factor binding protein, keratinocyte growth factor, leukemia inhibitory factor, somatropin, antihemophiliac factor, pegaspargase, orthoclone OKT 3, adenosine deaminase, alglucerase, imiglucerase, leukemia inhibitory factor receptor .alpha., nerve growth factor nerve growth factor receptor, neuropoietin, neurotrophin-3, neurotrophin-4, oncostatin M (OSM), placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor .alpha., platelet derived growth factor receptor .beta., pre-B cell growth stimulating factor, stem cell factor (SCF), stem cell factor receptor, TNF, TNF0, TNF1, TNF2, transforming growth factor α, hymic stromal lymphopoietin (TSLP), tumor necrosis factor receptor type I, tumor necrosis factor receptor type II, urokinase-type plasminogen activator receptor, phospholipase-activating protein (PUP), insulin, lectin ricin, prolactin, chorionic gonadotropin, follicle-stimulating hormone, thyroid-stimulating hormone, tissue plasminogen activator (tPA), leptin, Enbrel (etanercept).

In some embodiments, the protein is an antibody. As used herein, an "antibody" includes, without limitation, whole antibodies and any antigen binding fragment, including without limitation a Fab, or a single chain thereof. Thus the term "antibody" includes, without limitation, any protein or peptide containing molecule that comprises at least a portion of an immunoglobulin molecule having biological activity of binding to the antigen. Examples of such may comprise a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein. "Antibody" also includes both monoclonal antibodies and polyclonal antibodies.

Examples of antibodies include, without limitation, Infliximab, Bevacizumab, Ranibizumab, Cetuximab, Ranibizumab, Palivizumab, Abagovomab, Abciximab, Actoxumab, Adalimumab, Afelimomab, Afutuzumab, Alacizumab, Alacizumab pegol, ALD518, Alemtuzumab, Alirocumab, Alemtuzumab, Altumomab, Amatuximab, Anatumomab mafenatox, Anrukinzumab, Apolizumab, Arcitumomab, Aselizumab, Altinumab, Atlizumab, Atorolimiumab, tocilizumab, Bapineuzumab, Basiliximab, Bavituximab, Bectumomab, Belimumab, Benralizumab, Bertilimumab, Besilesomab, Bevacizumab, Bezlotoxumab, Biciromab, Bivatuzumab, Bivatuzumab mertansine, Blinatumomab, Blosozumab, Brentuximab vedotin, Briakinumab, Brodalumab, Canakinumab, Cantuzumab mertansine, Cantuzumab mertansine, Caplacizumab, Capromab pendetide, Carlumab, Catumaxomab, CC49, Cedelizumab, Certolizumab pegol, Cetuximab, Citatuzumab bogatox, Cixutumumab, Clazakizumab, Clenoliximab, Clivatuzumab tetraxetan, Conatumumab, Crenezumab, CR6261, Dacetuzumab, Daclizumab, Dalotuzumab, Daratumumab, Demcizumab, Denosumab, Detumomab, Dorlimomab aritox, Drozitumab, Duligotumab, Dupilumab, Ecromeximab, Eculizumab, Edobacomab, Edrecolomab, Efalizumab, Efungumab, Elotuzumab, Elsilimomab, Enavatuzumab, Enlimomab pegol, Enokizumab, Enokizumab, Enoticumab, Enoticumab, Ensituximab, Epitumomab cituxetan, Epratuzumab, Erlizumab, Ertumaxomab, Etaracizumab, Etrolizumab, Exbivirumab, Exbivirumab, Fanolesomab, Faralimomab, Farletuzumab, Fasinumab, FBTA05, Felvizumab, Fezakinumab, Ficlatuzumab, Figitumumab, Flanvotumab, Fontolizumab, Foralumab, Foravirumab, Fresolimumab, Fulranumab, Futuximab, Galiximab, Ganitumab, Gantenerumab, Gavilimomab, Gemtuzumab ozogamicin, Gevokizumab, Girentuximab, Glembatumumab vedotin, Golimumab, Gomiliximab, GS6624, Ibalizumab, Ibritumomab tiuxetan, Icrucumab, Igovomab, Imciromab, Imgatuzumab, Inclacumab, Indatuximab ravtansine, Infliximab, Intetumumab, Inolimomab, Inotuzumab ozogamicin, Ipilimumab, Iratumumab, Itolizumab, Ixekizumab, Keliximab, Labetuzumab, Lebrikizumab, Lemalesomab, Lerdelimumab, Lexatumumab, Libivirumab, Ligelizumab, Lintuzumab, Lirilumab, Lorvotuzumab mertansine, Lucatumumab, Lumiliximab, Mapatumumab, Maslimomab, Mavrilimumab, Matuzumab, Mepolizumab, Metelimumab, Milatuzumab, Minretumomab, Mitumomab, Mogamulizumab, Morolimumab, Motavizumab, Moxetumomab pasudotox, Muromonab-CD3, Nacolomab tafenatox, Namilumab, Naptumomab estafenatox, Narnatumab, Natalizumab, Nebacumab, Necitumumab, Nerelimomab, Nesvacumab, Nimotuzumab, Nivolumab, Nofetumomab merpentan, Ocaratuzumab, Ocrelizumab, Odulimomab, Ofatumumab, Olaratumab, Olokizumab, Omalizumab, Onartuzumab, Oportuzumab monatox, Oregovomab, Orticumab, Otelixizumab, Oxelumab, Ozanezumab, Ozoralizumab, Pagibaximab, Palivizumab, Panitumumab, Panobacumab, Parsatuzumab, Pascolizumab, Pateclizumab, Patritumab, Pemtumomab, Perakizumab, Pertuzumab, Pexelizumab, Pidilizumab, Pintumomab, Placulumab, Ponezumab, Priliximab, Pritumumab, PRO140, Quilizumab, Racotumomab, Radretumab, Rafivirumab, Ramucirumab, Ranibizumab, Raxibacumab, Regavirumab, Reslizumab, Rilotumumab, Rituximab, Robatumumab, Roledumab, Romosozumab, Rontalizumab, Rovelizumab, Ruplizumab, Samalizumab, Sarilumab, Satumomab pendetide, Secukinumab, Sevirumab, Sibrotuzumab, Sifalimumab, Siltuximab, Simtuzumab, Siplizumab, Sirukumab, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tefibazumab, Telimomab aritox, Tenatumomab, Tefibazumab, Telimomab aritox, Tenatumomab, Teneliximab, Teplizumab, Teprotumumab, TGN1412, tremelimumab, Ticilimumab, Tildrakizumab, Tigatuzumab, TNX-650, Tocilizumab, Toralizumab, Tositumomab, Tralokinumab, Trastuzumab, TRBS07, Tregalizumab, Tremelimumab, Tucotuzumab celmoleukin, Tuvirumab, Ublituximab, Urelumab, Urtoxazumab, Ustekinumab, Vapaliximab, Vatelizumab, Vedolizumab, Veltuzumab, Vepalimomab, Vesencumab, Visilizumab, Volociximab, Vorsetuzumab mafodotin, Votumumab, Zalutumumab, Zanolimumab, Zatuximab, Ziralimumab and Zolimomab aritox. For each of the above, the present invention contemplates use of a Fab as well as the full antibody.

III. Bioscavenger Conjugates and Constructs

BuChE isolated from human serum is a globular, tetrameric molecule with a molecular weight of 340 kDa. Haupt H, Heide K, Zwisler O and Schwick H G. 1966. Isolierun and Physikalischchemiscle Charakterisierung der Cholinesterase aus Humanserum. Blut. 14:65-75. Each of the four subunits of the enzyme are 574 amino acids in length. Each chain has nine Asn-linked carbohydrate chains. Lockridge O, Bartels C F, Vaughan T A, Wong C K, Norton S E, Johnson L L. 1987. Complete amino acid sequence of human serum cholinesterase. J Biol Chem. 262:549-557.

Various attempts have been made to produce a recombinant version of BuChE. However, the dominant tetramer form observed in plasma turns out to be just a minor component of the protein produced by recombinant DNA technology. For example, expression of rhBuChE in Chinese hamster ovary (CHO) cells produces a mixture of proteins: dimers (not stable) (50-55%), monomers (15-40%) and a relatively small percentage of tetramers (10-30%). Blong R M, Bedows E, Lockridge O. 1997. Tetramerization domain of human butyrylcholinesterase is at the C-terminus Biochem J. 327:747-757.

The C-terminus of hBuChE has been identified as being responsible for tetramerization. Expression of C-terminally deleted proteins results in exclusive production of monomers. In addition, Blong et al. reported that up to 50 amino acids of the C-terminus can be removed without loss of enzyme activity (as noted above only the monomeric form is detectable). However deletion of 51 amino from the C-terminus results in an inactive version of the protein which is retained in the cell (i.e. not secreted).

The 602 amino acid sequence of human butyryleholinesterase (P06276.1) is shown in SEQ ID NO: 1, The first 28 amino acids (MHSKVTIICIRFLFWFLLLCMLIGKSHT (SEQ ID NO: 27)) constitute the natural leader sequence of hBuChE. The mature enzyme, thus, begins with the sequence EDDIII (SEQ ID NO: 28).

In accordance with an aspect of the present invention, butyrylcholinesterase (BuChE) enzymes are presented. Preferably, the butyrylcholinesterase enzymes are human enzymes (hBuChE). More preferably, the enzymes are recombinant human enzymes (rhBuChE).

In preferred embodiments of the present invention, the butyrylcholinesterase enzymes have one or more deletions and or amino acid substitutions. Preferably, the cysteine residue at position 66 (starting from the N-terminus of the mature is changed to some other natural or unnatural amino acid. More preferably, C66 is converted to tyrosine or isoleucine. Most preferably, C66 is converted to tyrosine (C66Y).

In accordance with an aspect of the present invention, C-terminal deletions of rhBuChE are presented. It is preferred that nor more than 50 amino acids are deleted from the C-terminus of rhBuChE. More preferably, 50 amino acids are deleted from the C-terminus of rhBuChE resulting in the construct rhBuChE524 (referring to the 524 N-terminal retained amino acids). More preferably, 40 amino acids are deleted from the C-terminus of rhBuChE resulting in the construct rhBuChE534. Preferably, the deletion mutations have one of more of the C66 mutations described above. More preferably, the deletion mutations have the C66Y mutation. In a most preferred aspect of the present invention, the protein sequence of the 524 deletion with the C66Y mutation (rhBChE524 (C66Y)) is set forth in SEQ ID NO: 11. In another most preferred aspect of the present invention, the protein sequence of the 534 deletion with the C66Y mutation (rhBChE534 (C66Y)) is set forth in SEQ ID NO: 10.

In accordance with an aspect of the instant invention, a polymer may be conjugated to a BuChE, Preferably, polymers are conjugated using maleimide to a Cys residue. The Cys residue may be a maturally courring cysteine. In other preferred embodiments of the present invention, a cysteine residue can be added to one of the rhBuChE C-terminal deletions so that the protein can be conjugated to a polymer. Preferably, the cysteine is added to the C-terminus of the deleted rhBuChE. In still more preferred embodiments, the cysteine is added via a GGC or a GGGC (SEQ ID NO:20) peptide to the C-terminus. In one of the more preferred embodiments, the peptide GGGC (SEQ ID NO: 20) is added to the C-terminal end of the rhBuChE524 (C66Y) enzyme (see SEQ ID NO: 12), In another more preferred embodiment, the peptide GGC is added to the C-terminus of the rhBuChE534 (C66Y) (see SEQ ID NO: 13).

In accordance with an aspect of the present invention, a butyrylcholinesterase fusion protein having a butyrylcholinesterase enzyme segment and a non-butyrylcholinesterase protein segment is presented. In preferred aspects of the present invention, the butyrylcholinesterase protein segment is N-terminal to the non-butyrylcholinesterase segment. Preferably, the non-butyrylcholinesterase protein is an immunoglobulin (Ig) domain. More preferably the Ig domain is selected from the group consisting of IgG-Fc, IgG-CH and IgG-CL. Still more preferably, the Ig domain is from IgG1 (SEQ ID NO. 8).

In other preferred embodiments of the present invention, the IgG1 Fc sequence can be modified in various ways, for example, to modulate complement binding and effector function. Optionally, the IgG1 Fc domain has one or more mutations to reduce effector function. Optionally the mutations are to one or more of the following amino acid positions (EU numbering): E233, L234, L235, G236, G237, A327, A330, and P331, These amino acid positions correspond to amino acid positions E13, L14, L15, G16, G17, Ala107, Ala110, and Pro111 in SEC) ID NO: 8. Preferably in this regard, the IgG1 Fc has the following substitutions: L234A, L235E, G237A, A330S and P331S, A lysine residue at the C-terminus of an Fc domain can sometimes be deleted by posttranslation processing. Therefore, when a SEQ ID of an Fc domain terminates in lysine, the lysine may or may not be omitted.

In accordance with an aspect of the present invention, modifications of the Fe region may be introduced to allow for a site of polymer conjugation. For example, a cysteine residue may be added which can be the site of polymer conjugation. Preferably, the Fc domain has a mutation selected from the group consisting of Q347C and L443C. These amino acid positions correspond to amino acid positions Q127 and L223 in SEES ID NO: 8. More preferably, the mutation is Q347C.

In accordance with an aspect of the present invention, the fusion protein preferably contains a polypeptide linker between the butyrylcholinesterase enzyme and the non-butyrylcholinesterase protein. Preferably, the linker is G, GG, GGGGS (SEQ ID NO: 22), GGGS (SEQ ID NO: 23), and GGGES (SEQ ID NO: 24), and oligomers of the foregoing. More preferably, the linker is selected from the group consisting of GGGSGGGSGGGS (SEQ ID NO: 21) and GGSGGGSGGGS (SEQ ID NO: 25).

In preferred embodiments of the present invention, the butyrylcholinesterase enzyme of the fusion protein is one of the C-terminal truncates described above having the preferred C66Y mutation (rhBuChE524 (C66Y) or rhBuChE534 (C66Y)) at the N-terminus of the fusion followed by a linker and a non-butyrylcholinesterase protein sequence at the C-terminus. In more preferred aspects of the present invention, the fusion protein is composed, starting at the N-terminus, of the 524 or 534 C-terminal truncate described above, having the C66Y mutation, fused to the linker GGGSGGGSGGGS (SEQ ID NO: 21) followed by an IgG1 Fc sequence with the mutations: L234A, L235E, G237A, A330S and P331S (EU numbering). In the most preferred embodiments of the invention, the butyrylcholinesterase truncate of the fusion protein is rhBuChE534 (C66Y). The protein sequence of this construct is set forth in SEQ ID NO: 15. In another highly preferred embodiment of the instant invention, the Fc region of the fusion has either the Q347C or L443C (EU numbering) mutations. Most preferably, the Fe region of the fusion has the Q347C mutation and L234A, L235E, G237A, A330S and P331S. The protein sequence of this preferred embodiment is shown in SEQ ID NO: 2.

In accordance with an another aspect of the present invention, protein-polymer conjugates are presented having an OP bioscavenger, either a catalytic OP bioscavenger or a stoichiometric OP bioscavenger, covalently bound to a polymer. Preferably, the polymer is a zwitterionic polymer, the polymer having one or more monomer units where at least one of the monomer units has a zwitterion. Catalytic OP bioscavengers are typically enzymes selected from the group consisting of aryldialkylphosphatases, organophosphate hydrolases (OPH), carboxylesterases, triesterases, phosphotriesterases, arylesterases, paraoxonases (PON), organophosphate acid anhydrases, and diisopropylfluorophosphatases (DFPases).

In an aspect of the present invention, the OP bioscavenger is a stoichiometric OP bioscavenger. Preferably, the stoichiometric OP scavenger is a cholinesterase selected from the group consisting of acetylcholinesterase (AChE) and butyrylcholinesterase. Preferably, the cholinesterase is a BuChE.

In accordance with an aspect of the present invention, cholinesterases, including butyrylcholinesterases, can be purified from blood serum according to known techniques. Thus, if it is desired to prepare a conjugate in accordance with an aspect of the present invention for administration to humans, human blood serum can be used as a source of the cholinesterase. Alternatively, in accordance with another aspect of the present invention, cholinesterases, and the various enzymes associated with catalytic OP bioscavengers, are produced using recombinant DNA technology.

In accordance with certain aspects of the present invention, production of cholinesterases (or the enzymes associated with catalytic OP bioscavengers) includes any method known in the art for (i) the production of recombinant DNA by genetic engineering, (ii) introducing recombinant DNA into prokaryotic or eukaryotic cells by, for example and without limitation, transfection, electroporation or microinjection, (iii) cultivating said transformed cells, (iv) expressing protein, e.g. constitutively or on induction, and (v) isolating the protein, e.g. from the culture medium or by harvesting the transformed cells, in order to (vi) obtain purified protein.

In preferred aspects of the present invention, protein is produced by expression in a suitable prokaryotic or eukaryotic host system characterized by producing a pharmacologically acceptable protein molecule. Examples of eukaryotic cells are mammalian cells, such as CHO, COS, HEK 293, BHK, SK-Hip, and HepG2.

In still other aspects, a wide variety of vectors are used for the preparation of proteins and are selected from eukaryotic and prokaryotic expression vectors. Examples of vectors for prokaryotic expression include plasmids such as, and without limitation, preset, pet, and pad, wherein the promoters used in prokaryotic expression vectors include one or more of, and without limitation, lac, trc, tip, recA, or araBAD. Examples of vectors for eukaryotic expression include: (i) for expression in yeast, vectors such as, and without limitation, pAO, pPIC, pYES, or pMET, using promoters such as, and without limitation, AOX1, GAP, GAL1, or AUG1; (ii) for expression in insect cells, vectors such as and without limitation, pMT, pAc5, pIB, pMIB, or pBAC, using promoters such as and without limitation PH, p10, MT, Ac5, OpIE2, gp64, or polh, and (iii) for expression in mammalian cells, vectors such as, and without limitation, pSVL, pCMV, pRc/RSV, pcDNA3, or pBPV, and vectors derived from, in one aspect, viral systems such as and without limitation vaccinia virus, adeno-associated viruses, herpes viruses, or retroviruses, using promoters such as and without limitation CMV, SV40, EF-1, UbC, RSV, ADV, BPV, and beta-actin.

Assays for BuChE are know in the art BuChE efficiently catalyzes the hydrolysis of acetylthiocholine (ATCh)—a sulfur analog of the natural substrate of the enzyme. Other thiocholine substrates can be used, including S-butyrylthiocholine (BTCH) iodide. On hydrolysis, this substrate analog produces acetate and thiocholine. Thiocholine, in the presence of the highly reactive dithiobisnitro-benzoate (DTNB) ion, generates a yellow color, which is visible and can be quantitatively monitored by spectrophotometric absorption at 405 nm. Such techniques are described in the following, all of which are incorporated by reference: G. L. Ellman, K. D. Courtney, V. Andres, and R. M. Featherstone, "A new and rapid colorimetric determination of acetylcholinesterase activity," Biochemical Pharmacology, vol. 7, no. 2, pp. 88-95, 1961; M. A. Gordon, D. E. Carpenter, H. W. Barrett, and I. B. Wilson, "Determination of the normality of cholinesterase solutions," Analytical Biochemistry, vol. 85, no. 2, pp. 519-527, 1978; and V. Gorun, I. Proinov, V. Baltescu, G. Balaban, and O. Barzu, "Modified Ellman procedure for assay of cholinesterases in crude enzymatic preparations," Analytical Biochemistry, vol. 86, no. 1, pp. 324-326, 1978.

In accordance with an aspect of the present invention, the endogenous leader peptide of hBuChE can be used for recombinant expression of the protein. More preferably, however, a leader peptide should be chosen to maximize the levels of protein expression. In preferred embodiments, a CTLA4 leader is used. Most preferably, the leader peptide set forth in SEQ ID NO: 18 is preferred.

In accordance with preferred aspects of the present invention, the zwitterionic polymer is formed of monomers having a phosphorylcholine group. Preferably the monomer is 2-(acryloyloxyethyl)-2'-(trimethylammoniumethyl) phosphate. More preferably, the monomer is 2-(methacryloyloxyethyl)-2'-(trimethylammoniumethyl) phosphate (HEMA-PC).

A polymer conjugated to a bioscavenger preferably has at least 2 polymer arms more preferably 3 or more arms. Some polymers have 2, 3, 4, 5, 6, 7, 8, 9, 10, 11 or 12 arms. Still more preferably the polymer has 3, 6 or 9 arms. Most preferably, the polymer has 9 arms. Preferably, the polymer peak molecular weight is between 300,000 and 1,750,000 Da. More preferably, the polymer has a peak molecular weight between 500,000 and 1,000,000 Da. Still more preferably, the polymer has a peak molecular weight between 600,000 to 800,000 Da. Unless otherwise specified, molecular weights of a branched polymer refer to the aggregate molecular weight of all arms.

Nucleophilic groups on proteins, including antibodies, which can be used to conjugate polymer in accordance with an aspect of the present invention include, but are not limited to: (i) N-terminal amine groups, (ii) side chain amine groups, e.g. lysine, (iii) side chain thiol groups, e.g. cysteine, and (iv) sugar hydroxyl or amino groups where the protein is glycosylated Amine, thiol, and hydroxyl groups are nucleophilic and capable of reacting to form covalent bonds with electrophilic groups on linker moieties and linker reagents attached to the polymer including: (i) active esters such as NHS esters, HOBt esters, haloformates, and acid halides; (ii) alkyl and benzyl halides such as haloacetamides; (iii) aldehydes, ketones, carboxyl, and maleimide groups. Many proteins, including antibodies, have cysteine thiol groups which can potentially be used for conjugation. Preferably, cysteine residues are added for conjugation by recombinant DNA technology. Many cysteine residues are in the form of reducible interchain disulfides, i.e. cysteine bridges. Cysteine residues in the form of disulfides are generally not available to react with reagents such as maleimide. Cysteine residues may also be free or unpaired. However, free cysteine residues are frequently found to be "capped" by one or more reagents in various media and are also not available for conjugation. Cysteine residues may be made reactive for conjugation with linker reagents such as maleimide by treatment with a reducing agent such as DTT (dithiothreitol) or tricarbonylethylphosphine (TCEP), such that the protein is fully or partially reduced. Each cysteine bridge will thus form, theoretically, two reactive thiol nucleophiles. In the case of free cysteine, one thiol nucleophile is formed by reduction.

Depending on the conditions employed, reduction by TCEP or DTT can result in the loss of proper protein folding with concomitant loss of activity. However, activity may be recovered by allowing protein refolding under the appropriate conditions.

Additional nucleophilic groups can be introduced into antibodies through modification of lysine residues, e.g., by reacting lysine residues with 2-iminothiolane (Traut's reagent), resulting in conversion of an amine into a thiol. Reactive thiol groups may be introduced into a protein by introducing one, two, three, four, or more cysteine residues (e.g., by preparing variant comprising one or more non-native cysteine amino acid residues).

In accordance with preferred aspects of the invention, the butyrylcholinesterase fusion corresponding to that of SEQ ID NO: 2 and the Cys residue for conjugation to polymer is that at amino acid 672.

In accordance with an aspect of the present invention, a method for treatment or prophylaxis of OP poisoning is presented in which of the present invention conjugates or fusion proteins are administered to a patient in need thereof in an effective regime. With respect to prophylaxis, a subject who will or may be exposed to OP compounds (either OP pesticides or OP nerve agents) at a statistically significantly higher frequency than a control population of randomly selected individuals from the general public would be in need of the instant invention. For example, a soldier or law enforcement office who might be exposed to OP nerve agents in a battlefield or criminal context may be in need of the instant invention. Similarly, a worker involved in applying OP pesticides to crops may be in need of the instant inventions as would a worker responsible for dealing with accidental leakage of pesticides or nerve agents. Although protective clothing and gas masks might be available to prevent exposure, such protective measures can fail to provide protection. In case of such failure, the instant prophylactic methods can be applied.

In preferred aspects of the instant invention, the conjugate or fusion protein is administered by intravenous administration, subcutaneous administration, intramuscular administration, intralesional administration or intradermal administration. Preferably, administered is by intramuscular administration.

In another aspect of the present invention, a method for effecting a long term prophylaxis against OP poisoning is presented in which a conjugate having an OP bioscavenger selected from the group consisting of a stoichiometric OP bioscavenger and a catalytic OP bioscavenger covalently bound to a zwitterionic polymer wherein the polymer has one or more monomer units and wherein at least one monomer has a zwitterionic group is administered at least 7 days prior to expected exposure to an OP compound. In other words, such a conjugate administered prophylactically is effective for at least seven days against possible exposure to OP poisoning.

In preferred aspects of the present invention, the conjugate is administered at least 14 days prior to expected exposure to the OP nerve agent. More preferably, the conjugate is administered at least 21 days prior to expected exposure to the OP nerve agent. Still more preferably, the conjugate is administered at least 30 days prior to expected exposure to the OP nerve agent. Or put another way, the conjugate is effective in providing protecting for at least 14, 21 or 30 days against possible exposure to an OP.

In another aspect of the present invention, a method for effecting rapid prophylaxis against OP poisoning is presented in which a conjugate having an OP bioscavenger selected from the group consisting of a stoichiometric OP bioscavenger and a catalytic OP bioscavenger covalently bound to a zwitterionic polymer wherein the polymer has one or more monomer units and wherein at least one monomer has a zwitterionic group is administered to a subject in need thereof at least 12 hours prior to expected exposure to an OP compound. More preferably, the conjugate is administered at least 24 hours prior to expected exposure to the OP compound. In other words, the conjugate remains effective in providing protection for at least 12 or 24 hr.

The pharmaceutical composition of the invention may further comprise a pharmaceutically acceptable diluent, adjuvant or carrier.

Pharmaceutical compositions adapted for oral administration may be presented as discrete units such as capsules, as solutions, syrups or suspensions (in aqueous or non-aqueous liquids; as edible foams or whips; or as emulsions). Suitable excipients for tablets or hard gelatin capsules include lactose, maize starch or derivatives thereof, stearic acid or salts thereof. Suitable excipients for use with soft gelatin capsules include for example vegetable oils, waxes, fats, semi-solid, or liquid polyols, etc. For the preparation of solutions and syrups, excipients which may be used include for example water, polyols and sugars. For the preparation of suspensions oils (e.g. vegetable oils) may be used to provide oil-in-water or water in oil suspensions.

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient. Pharmaceutical compositions adapted for administration by inhalation include fine particle dusts or mists which may be generated by means of various types of metered dose pressurized aerosols, nebulizers or insufflators.

Pharmaceutical compositions adapted for parenteral administration include aqueous and non-aqueous sterile injection solutions which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerin and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets. Pharmaceutical compositions can be substantially isotonic, implying an osmolality of about 250-350 mOsm/kg water.

In general, the pharmaceutical compositions may contain preserving agents, solubilizing agents, stabilizing agents, wetting agents, emulsifiers, sweeteners, colorants, odorants, salts (substances of the present invention may themselves be provided in the form of a pharmaceutically acceptable salt), buffers, coating agents or antioxidants. They may also contain therapeutically active agents in addition to the substance of the present invention. The pharmaceutical compositions of the invention may be employed in combination with pharmaceutically acceptable diluents, adjuvants, or carriers. Such excipients may include, but are not limited to, saline, buffered saline (such as phosphate buffered saline), dextrose, liposomes, water, glycerol, ethanol and combinations thereof.

The pharmaceutical compositions may be administered in any effective, convenient manner effective for treating a patient's disease including, for instance, administration by oral, intravenous, subcutaneous, intramuscular, intraosseous, intranasal routes, among others. In therapy or as a prophylactic, the active agent may be administered to an individual as an injectable composition, for example as a sterile aqueous dispersion, preferably isotonic.

For administration to mammals, and particularly humans, it is expected that the daily dosage of the active agent will be from 0.01 mg/kg body weight, typically around 1 mg/kg. The physician in any event will determine the actual dosage which will be most suitable for an individual which will be dependent on factors including the age, weight, sex and response of the individual. The above dosages are exemplary of the average case. There can, of course, be instances where higher or lower dosages are merited, and such are within the scope of this invention.

Dosages of the substance of the present invention can vary between wide limits, depending on the disease or disorder to be treated, the age and condition of the individual to be treated, and so forth, and a physician will ultimately determine appropriate dosages.

This dosage may be repeated as often as appropriate. If side effects develop, the amount and/or frequency of the dosage can be reduced, in accordance with normal clinical practice. In one embodiment, the pharmaceutical composition may be administered once every one to thirty days.

The pharmaceutical compositions of the invention may be employed alone or in conjunction with other compounds, such as therapeutic compounds or molecules, e.g. carbamates, anti-muscarinics, cholinesterase reactivators and anti-convulsives. Such administration with other compounds may be simultaneous, separate or sequential. The components may be prepared in the form of a kit which may comprise instructions as appropriate.

Preferably, the pharmaceutical compositions of the invention and the other therapeutic compounds are directly (as opposed to what?) administered to a patient in need thereof.

The invention also provides a kit of parts comprising a pharmaceutical composition of invention, and an administration vehicle including, but not limited to, capsules for oral administration, inhalers for lung administration, and injectable solutions for parenteral administration.

As used herein, the term "treatment" includes any regime that can benefit a human or a non-human animal. The treatment of "non-human animals" extends to the treatment of domestic animals, including horses and companion animals (e.g. cats and dogs) and farm/agricultural animals including members of the ovine, canine, porcine, bovine and equine families. The treatment may be in respect of any existing condition or disorder, or may be prophylactic (preventive treatment). The treatment may be of an inherited or an acquired disease. The treatment may be of an acute or chronic condition.

In accordance with an aspect of the present invention, a method is presented of preparing a conjugate having the step of contacting a polymeric reagent with a biologically active agent comprising a free sulfhydryl residue under suitable conditions to thereby provide the conjugate, wherein the polymeric reagent has the following structure:

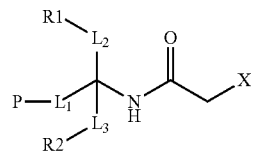

wherein P is a branched or unbranched water soluble polymer; L1 is a first linker, L2 is a second linker and L3 is a third linker, wherein L1, L2 and L3 are the same or different and are each selected from the group consisting of —C1-C12 alkyl-, —C3-C12 cycloalkyl-, (—(CH2)1-6-O—(CH2)1-6-)1-12-, (—(CH2)1-4-NH—(CH2)1-4(1-12-, —(CH2)1-12O—, (—(CH2)1-4-O—(CH2)1-4)1-12-O—, —(CH2)1-12-(CO)—O—, —(CH2)1-12-(CO)—NH—, —(CH2)1-12-O—(CO)—, —(CH2)1-12-NH—(CO)—, (—(CH2)1-4-O—(CH2)1-4)1-12-O—(CH2)1-12-, —(CH2)1-12-(CO)—O—(CH2)1-12-, —(CH2)1-12-(CO)—NH—(CH2)1-12-, —(CH2)1-12-O—(CO)—(CH2)1-12-, —(CH2)1-12-NH—(CO)—(CH2)1-12-, —(C3-C12 cycloalkyl)-, —(C1-C8alkyl)-(C3-C12 cycloalkyl)-, —(C3-C12 cycloalkyl)-(C1-8alkyl)-, —(C1-8alkyl)-(C3-C12 cycloalkyl)-(C1-8alkyl)-, —NH—(CH2CH2-O-)0-20-NH—(CH2CH2-O-)0-20- and —(CH2)0-3-aryl-(CH2)0-3-, a bond and any combination of the above; X is selected from the group consisting of F, Cl, Br and I; R1 and R2 are the same or different and are selected from the group consisting of H, provided that not both R1 and R2 are H, and one or more basic groups wherein a basic group is selected from the group consisting of

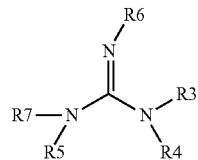

wherein R3, R4, R5, R6 and R7 are the same or different and are selected from the group consisting of a bond, H, amino, aryl6-12 and alkyl1-6;

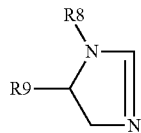

wherein R8 and R9 are the same or different and are selected from the group consisting of a bond, H, aryl6-12, and alkyl1-6;

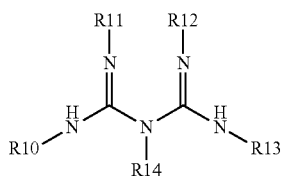

wherein R10, R11, R12, R13 and R14 are the same or different and are selected from the group consisting of a bond, H, amino, aryl6-12 and alkyl1-6 and one or more arginine residues.

Preferably, the biologically active agent is selected from the group consisting of a therapeutic protein and an aptamer. More preferably, the biologically active agent is a therapeutic protein. The therapeutic protein is preferably a cytokine, an enzyme, an antibody and an antibody fragment. Still more preferably, the therapeutic protein is a Fab. Most preferably, the Fab is IgG1.

Where the biologically active agent is a therapeutic protein, the free sulfhydryl group is preferably contributed by a cysteine residue of the protein. In some aspects of the present invention, the cysteine residue is a naturally occurring cysteine residue. Alternatively, the cysteine residue is introduced via recombinant DNA technology.

P is preferably poly(alkylene oxide), poly(MPC), poly(vinyl pyrrolidone), poly(vinyl alcohol), polyoxazoline or poly(N-acryloylmorpholine). More preferably, P is poly(alkylene oxide). Still more preferably, P is poly(ethylene oxide) more commonly known as polyethylene glycol or PEG. Where P is PEG, the PEG is preferably branched. Preferably, the branched PEG has two arms. Each arm is preferably between about 5 to about 40 kDa. More preferably, each arm has a molecular weight of PEG of about 20 kDa.

With respect to the water-soluble polymer, the polymeric reagents of the invention also comprise at least one water-soluble polymer segment. Water-soluble polymers that are nonpeptidic and water-soluble, with from 2 to about 2000 monomer units, are particularly useful in the invention. Examples of suitable water-soluble polymers include, but are not limited to, poly(alkylene glycols), such as poly(ethylene glycol) ("PEG"), copolymers of ethylene glycol and propylene glycol having water-solubility, poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(MPC) and poly(N-acryloylmorpholine), such as described in U.S. Pat. No. 5,629,384, incorporated herein by reference. In some applications where relatively high water solubility is desired, the water-soluble polymer is not poly(propylene oxide).

In another aspect of the present invention, P is poly(MPC). Poly(MPC) preferably has 2, 3, 4, 5, 6, 7, 8, 9, 10, 11 or 12 arms. More preferably, polyMPC has 3, 6 or 9 arms. Most preferably, the poly(MPC) has 9 arms.

According to an aspect of the present invention, poly(MPC) preferably has a peak molecular weight of between 300,000 and 1,750,000 daltons, more preferably between 500,000 and 1,000,000 daltons and still more preferably between 600,000 to 800,000 daltons.

According to a preferred aspect of the present invention, L3 is a bond, R2 is H and R1 is

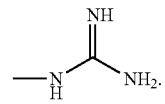

Preferably, L2 is —(CH2)1-6-. More preferably, L2 is —(CH2)3-.

In another aspect of the present invention, an initiator for polymer synthesis is presented having the following structure:

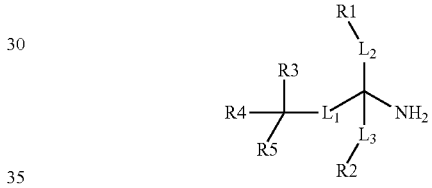

wherein L1 is a first linker, L2 is a second linker and L3 is a third linker, wherein L1, L2 and L3 are the same or different and are each selected from the group consisting of —C1-C12 alkyl-, —C3-C12 cycloalkyl-, (—(CH2)1-6-O—(CH2)1-6-)1-12-, (—(CH2)1-4-NH—(CH2)1-4(1-12-, —(CH2)1-12O—, (—(CH2)1-4-O—(CH2)1-4)1-12-O—, —(CH2)1-12-(CO)—O—, —(CH2)1-12-(CO)—NH—, —(CH2)1-12-O—(CO)—, —(CH2)1-12-NH—(CO)—, (—(CH2)1-4-O—(CH2)1-4)1-12-O—(CH2)1-12-, —(CH2)1-12-(CO)—O—(CH2)1-12-, —(CH2)1-12-(CO)—NH—(CH2)1-12-, —(CH2)1-12-O—(CO)—(CH2)1-12-, —(CH2)1-12-NH—(CO)—(CH2)1-12-, —(C3-C12 cycloalkyl)-, —(C1-C8alkyl)-(C3-C12 cycloalkyl)-, —(C3-C12 cycloalkyl)-(C1-8alkyl)-, —(C1-8alkyl)-(C3-C12 cycloalkyl)-(C1-8alkyl)-, —NH—(CH2CH2-O-)1-20-NH—(CH2CH2-O-)1-20- and —(CH2)0-3-aryl-(CH2)0-3-, a bond and any combination of the above; R1 and R2 are the same or different and are selected from the group consisting of H, provided that not both R1 and R2 are H, and one or more basic groups wherein a basic group is selected from the group consisting of

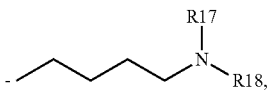

wherein R17 and R18 are C1-6 alkyl, preferably wherein R17 and R18 are both methyl,

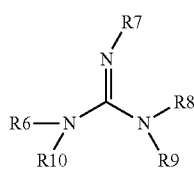

wherein R6, R7, R8, R9 and R10 are the same or different and are selected from the group consisting of a bond, H, amino, aryl6-12 and alkyl1-6;

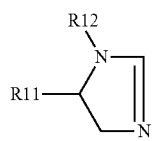

wherein R11 and R12 are the same or different and are selected from the group consisting of
a bond, H, aryl6-12 and alkyl1-6;

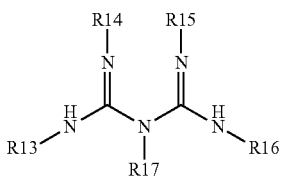

wherein R13, R14, R15, R16 and R17 are the same or different and are selected from the group consisting of a bond, H, amino, aryl6-12 and alkyl1-6 and one or more arginine residues; and R3, R4 and R5 are the same or different and are selected from the group consisting of

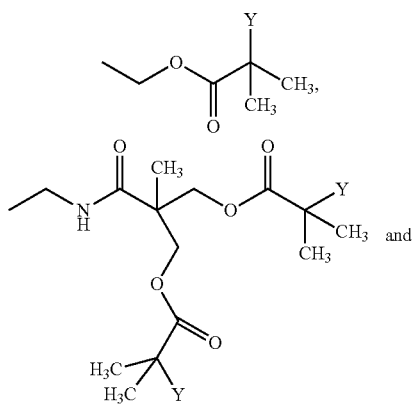

wherein Y is NCS, F, Cl, Br or I.

Preferably, Y is Br. R3, R4 and R5 are preferably each

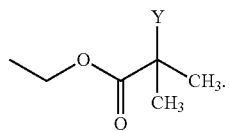

More preferably, R3, R4 and R5 are each

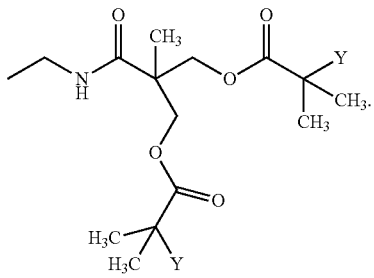

Still more preferably, R4, R5 and R6 are each

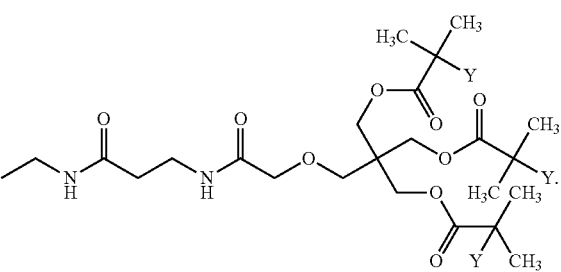

In an aspect of the present invention, preferably L3 is a bond, R2 is H and R1 is

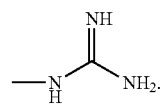

L2 is preferably —(CH2)1-6-. More preferably, L2 is —(CH2)3-.

IV. Examples

Example 1 rBuChE Truncations

An OP bioscavenger was made by truncating the hBuChE enzyme at position 524 (referring to the mature protein) (rhBuChE524). In addition, the mutation C66Y was introduced. The protein sequence of rhBuChE524 (C66Y) is shown in SEQ ID NO: 10. If it is desirable to conjugate a polymer to the rhBuChE524 (C66Y) a GGC or GGGC sequence (SEQ ID NO: 20) can be added on to the end. The protein sequence of rhBuChE524GGGC (C66Y) is shown in SEQ ID NO: 12 ("GGGC" disclosed as SEQ ID NO: 20).

Another bioscavenger was made by truncating hBuChE at position 534 (referring to the mature protein). The sequence of rhBuChE534 (C66Y) is shown in SEQ ID NO: 10. For conjugation to a polymer using cysteine, GGC is optionally added to the end. The protein sequence of rhBuChE534GGC (C66Y) is SEQ ID NO: 13.

Example 2 rBuChE Fusion Proteins

A rhBuChE-Fc fusion protein was made by recombinant genetic engineering by using the 534 truncate described above and fusing it to the Fc region of IgG1 with a GS linker (GGGSGGGSGGGS) (SEQ ID NO:21) in between the two protein segments. The sequence rhBuChE534-Fc is shown in SEQ ID NO: SEQ ID NO, 16. The fusion construct with the C66Y mutation (rhBuChE534 (C66Y)-Fc) is shown in SEQ ID NO: 17. In another version, various effector function mutations are introduced: L234A, L235E, G237A, A330S and P331S. The hBuChE534 (C66Y)-Fc(L234A, L235E, G237A, A330S and P331S, EU numbering) fusion is shown in SEQ ID NO: 15. Another mutation which can be engineered into the Fc portion of the protein is Q347C which can be used to conjugate polymers such as POLY(MPC) to the protein. The protein sequence of rhBuChE534 (C66Y)-Fc(L234A, L235E, G237A, A330S, P331S and Q347C, EU numbering) is shown in SEQ ID NO: 2.

The various protein constructs were expressed in CHO-K1 cells using appropriate DNA constructs for eukaryotic gene expression. While the endogenous hBuChE leader sequence can be used for recombinant expression of the constructs (see SEQ ID NO: 1), a CTLA4 leader was preferred the sequence of which is shown in SEQ ID NO: 18. The DNA sequence used to express rhBuChE534 (C66Y)-Fc(L234A, L235E, G237A, A330S, P331S and Q347C, EU numbering) is set forth in SEQ ID NO: 9.

Example 3 Transient Expression of Constructs

A transient expression analysis was performed in Expi293 Expression System (Gibco). The expression of a number of rhBuChE524 truncates was examined. In general, the rhBuChE524 constructs either were not expressed or were not expressed as well as the corresponding rhBuChE534 constructs. With regard to the rhBuChE534 constructs, it was found that the C66Y constructs were in generally better expressed than constructs without this change A summary of transient expression data for the 534 constructs is shown in the table below:

TABLE 1

| Construct | Ellman's Assay test (units/mL) |
|---|---|
| rhBuChE534 | 15 |
| rhBuChE534GGC | 7.5 |
| rhBuChE534GGC (C66Y) | 32 |
| rhBuChE534 (C66Y) - Fc (L234A, L235E, G237A, A330S, P331S and Q347C) | 27 |

Example 4 Stable Transfectants

Based on the results of the transient expression analysis, stable transformants were made of the rhBuChE534GGC (C66Y) and rhBuChE534 (C66Y)-Fc (L234A, L235E, G237A, A330S, P331S and Q347C, EU numbering). The stable transfectant for the Fc fusion employs the CTLA4 leader which is shown in SEQ ID NO: 18 fused at the N-terminus of the protein shown in SEQ ID NO: 2. The DNA sequence for this construct is set forth in SEQ ID NO: 9.

Example 5 Conjugation of BuChE-Fc Fusion Protein to MPC Polymer

Human BuChE-Fc fusion protein according to SEQ ID NO: 2 was denatured (as set forth in Example 6 below) with TCEP to provide a free cysteine thiol at position 347 of the Fc chain, followed by limited renaturation. TCEP treated BuChE-Fc was then conjugated to a 750 kDa polymer using a 15 to 50 fold excess of polymer to protein to produce a conjugate as shown below.

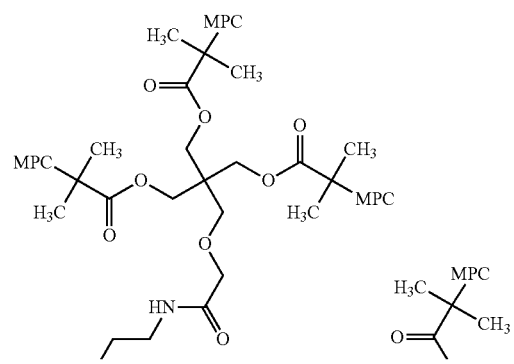

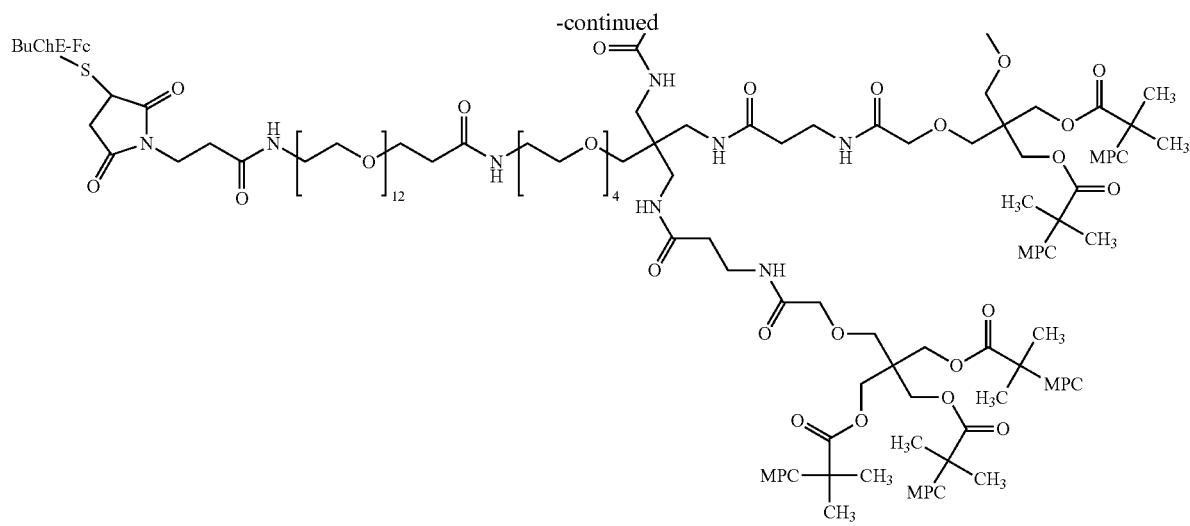

Example 6 Decapping and Refolding of BuChE-Fc

The BuChE-Fc fusion was reduced at room temperature with 30 fold molar excess of TCEP for several hours at room temperature in the presence of EDTA. Following this reduction, the protein was subjected to a step of TCEP washing in UF/DF to reduce the TCEP concentration to about an 8 fold molar excess. Further UF/DF and dilution was performed to reduce TCEP to less than 1 μM. Reduced BuChE-Fc was then allowed to renature and the progress of renaturation (seen by disappearance of monomeric BuChE-Fc and the appearance of dimeric BuChE-Fc) was followed by SDS-PAGE. Following renaturation, conjugation of the protein to polymer was performed as described above.

Example 7 Synthesis of Polymer R5743

Polymer R5743, shown below, was synthesized as follows:

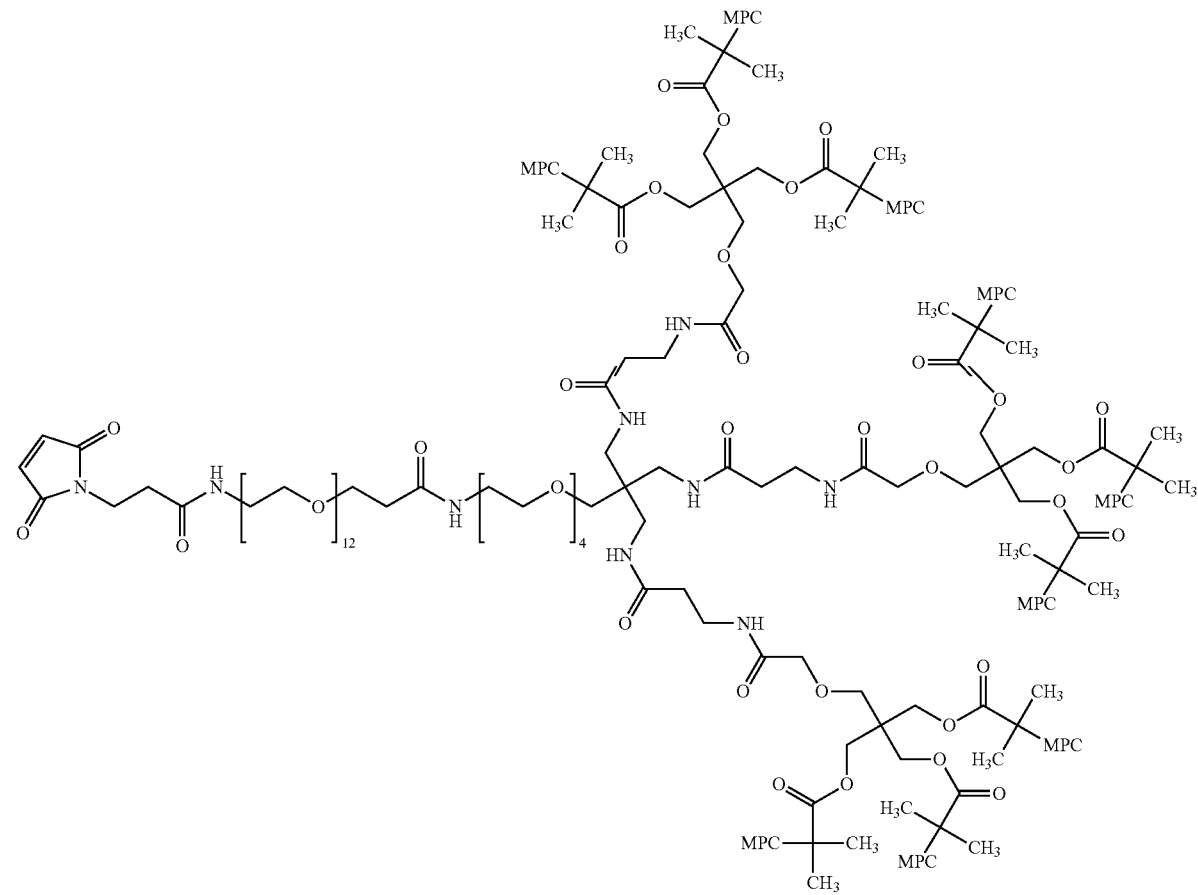

A TFA/amine salt initiator (Compound L) having the structure below was synthesized as follows.
Compound L
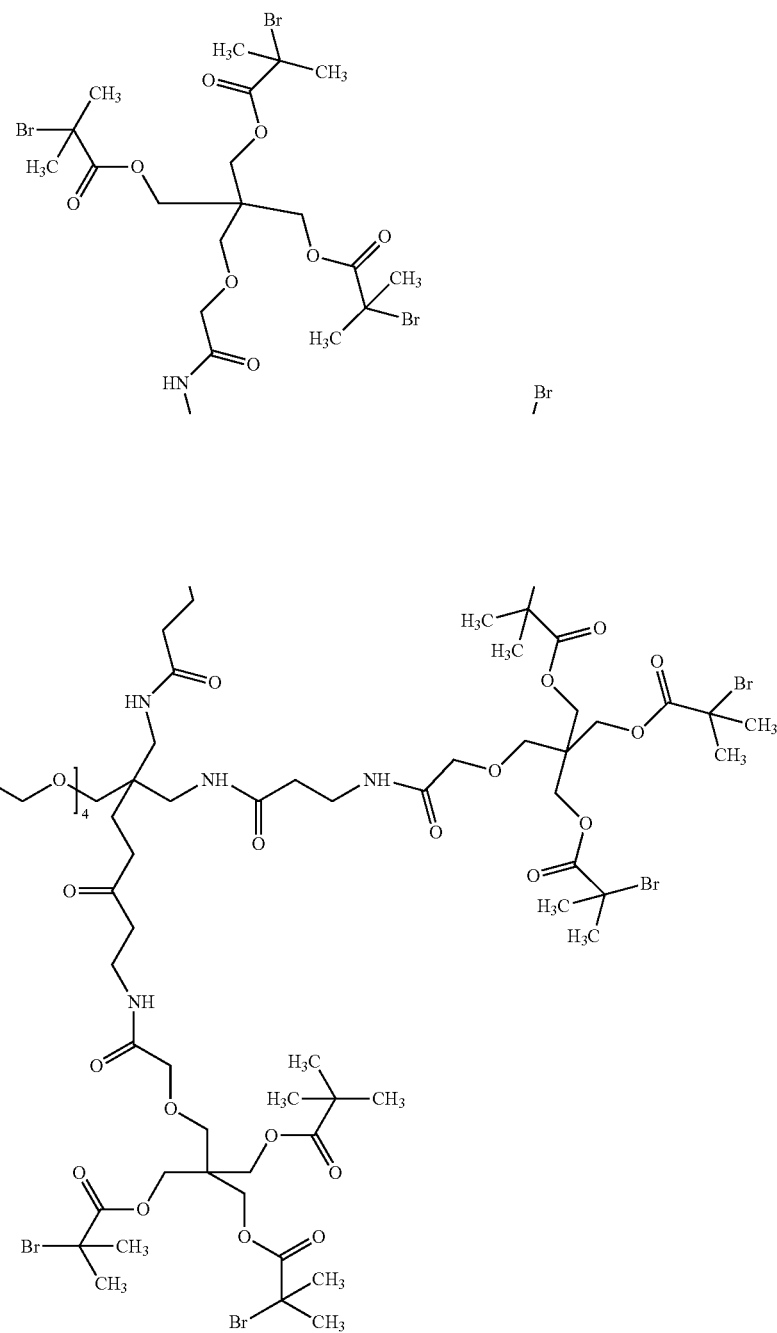

First, Compound K, having the following structure, was synthesized:
Compound K
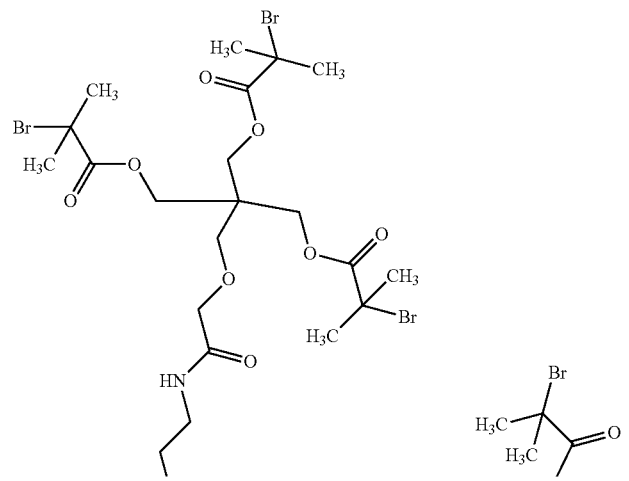
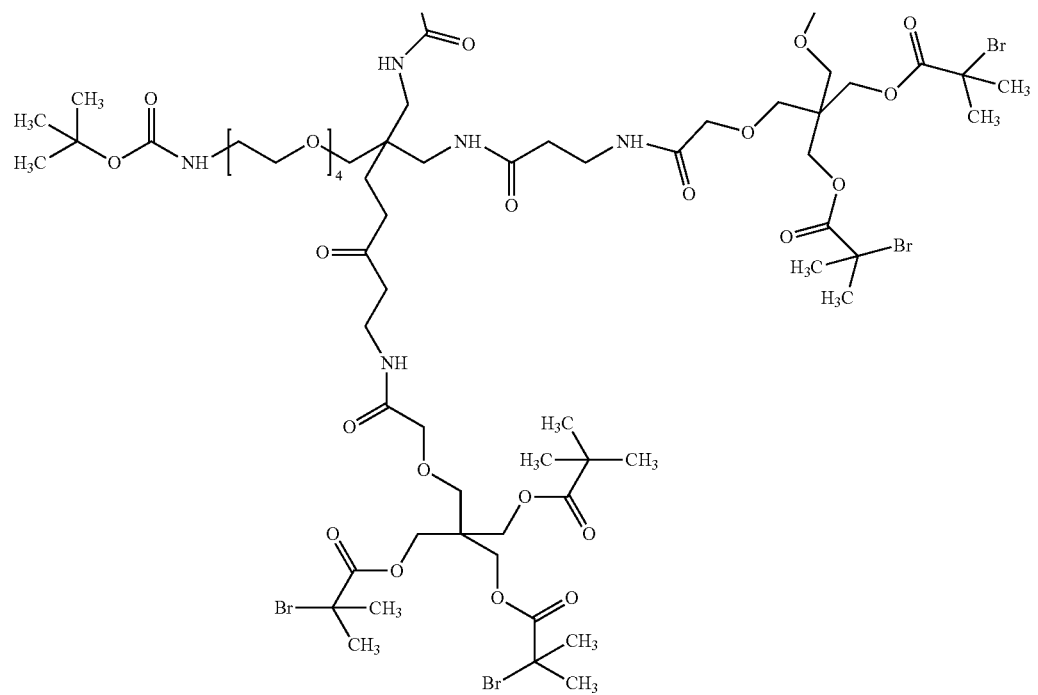

Into a 200 mL round bottom flask under nitrogen was placed Compound J (1.9 g, 2.67 mmol, 3.3 equiv)

Compound J

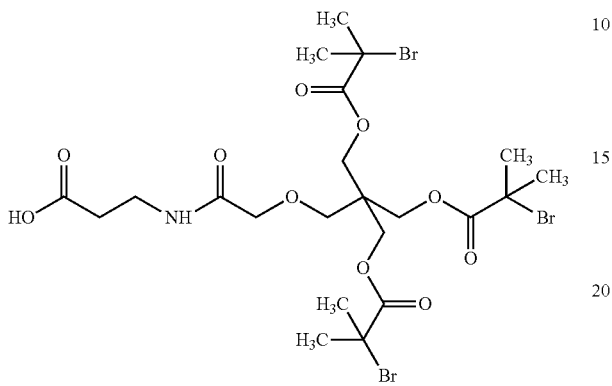

and Compound E (0.525 g, 0.81 mmol, 1.0 equiv) (see below)

Compound E

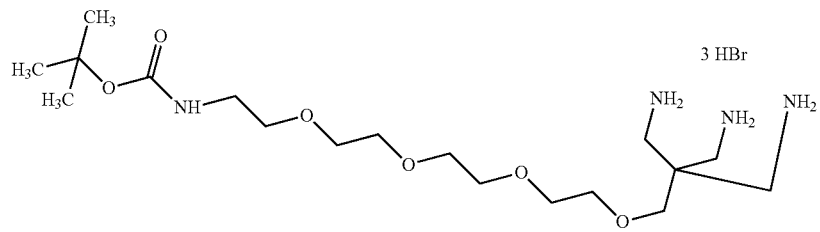

followed by dimethylformamide (10 mL) then diisopropylethylamine (2.5 mL, 14.6 mmol, 18 equiv). The flask was cooled to 0° C. using an ice bath. To this was added propylphosphonic anhydride solution (50 wt. % in ethyl acetate, 2.5 mL, 4.04 mmol, 5 equiv) over ~6 minutes.

The reaction was warmed to room temperature and stirred for 15 minutes. The reaction was quenched by adding water (20 mL), saturated aqueous sodium bicarbonate (20 mL), and ethyl acetate (100 mL). The organic layer was separated and the aqueous layer extracted with ethyl acetate (75 mL). The combined organic layers were washed with saturated aqueous sodium bicarbonate (30 mL), 0.5 M aqueous citric acid (40 mL), water (25 mL), and saturated aqueous sodium chloride (40 mL), then dried (sodium sulfate), filtered and concentrated under vacuum. The residue which was used without further purification resulted in 2.0 g (0.80 mmol, 99%) of Compound K.

1H NMR (400 MHz DMSO-d6): δ=1.36 (s, 9H, OCCH3), 1.90 (s, 54H, CC(CH3)2Br), 2.31 (t, J=7.2 Hz, 6H, CCH2CH2NH), 2.98 (d, J=5.6 Hz, 6H, CCH2NH), 3.04 (q, J=6.0 Hz, 2H, OCH2CH2NH), 3.18 (s, 2H, OCH2C), 3.3-3.37 (m, 8H, CH2), 3.47-3.55 (m, 12H, CH2), 3.58 (s, 6H, OCH2C), 3.87 (s, 6H, d at room temperature for 30 minutes. The reaction was concentrated under a vacuum. The reaction was diluted using dichloromethane (10 mL) and concentrated under a vacuum. The residue was dissolved using acetonitrile (10 mL), filtered through a syringe filter (Acrodisc CR25, PN 4225T) and loaded onto a preparatory HPLC column and eluted with 60% acetonitrile in water (with 0.1% trifluoroacetic acid) up to 98% acetonitrile (with 0.1% trifluoroacetic acid). The tubes containing product were pooled, concentrated under vacuum, frozen and placed on a lyophilizer. This resulted in 990 mgs (0.4 mmol, 50% over 2 steps) Compound L as a white powder.

1H NMR (400 MHz DMSO-d6): δ=1.90 (s, 54H, CC(CH3)2Br), 2.31 (t, J=7.2 Hz, 6H, CCH2CH2NH), 2.97-3.0 (m, 8H, CCH2NH and OCH2CH2NH), 3.17 (s, 2H, OCH2C), 3.3 (q, 6H, CH2CH2NHC=O), 3.4-3.59 (m, 20H, CH2), 3.87 (s, 6H, O=CCH2O), 4.27 (s, 18H, CCH2OC=O), 7.69-7.84 (m, 9H, both CH2NHC=O and NH3+).

LC-MS (ES, m/z): [(M+2H)/2]+ Calcd for (C84H136Br9N7O33+2H)/2=1196.6. Found 1197.4.

A TFA/amine salt initiator (Compound P) having the structure below was synthesized as follows:

Compound P

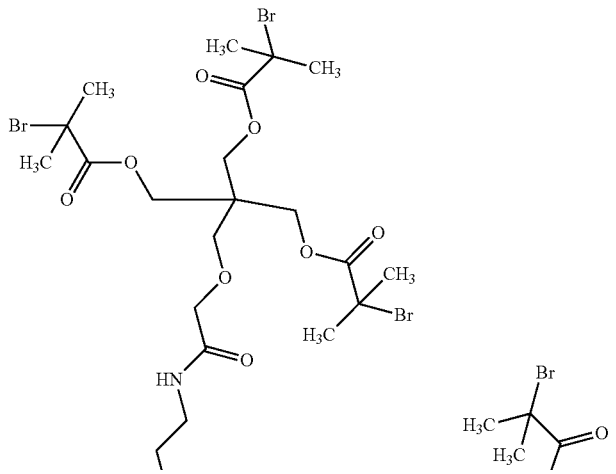

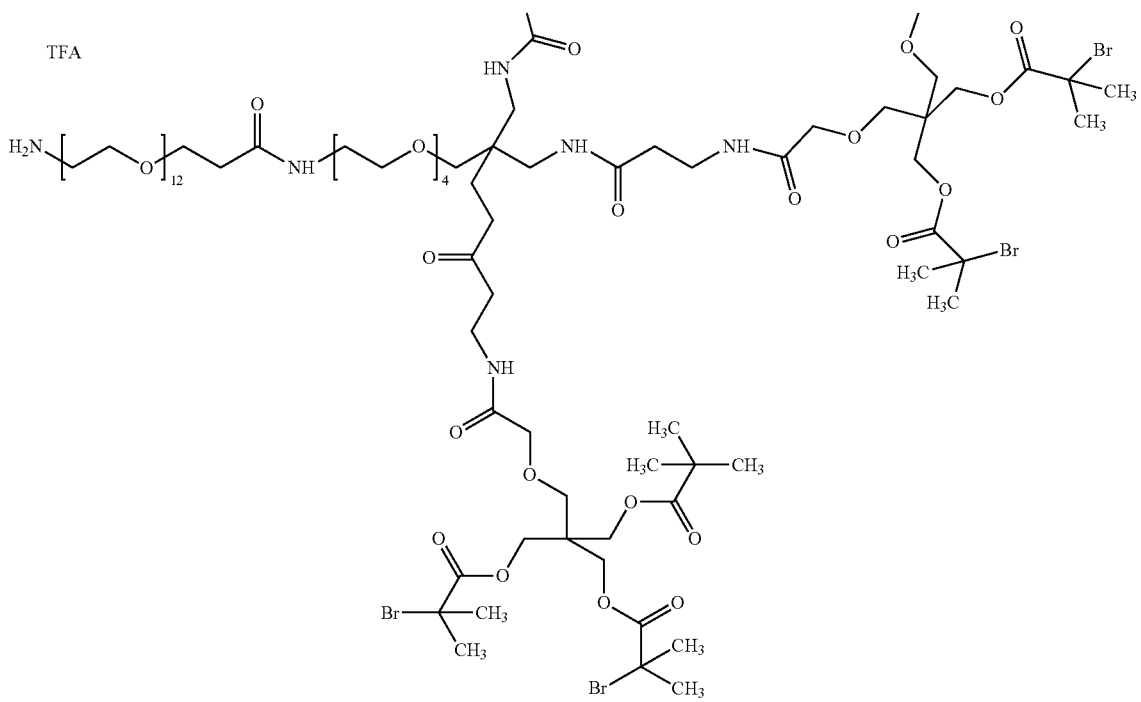

Into a 20 mL vial was placed Compound L (430 mg, 0.172 mmol, 1.0 equiv) (see above) and alpha-t-Butyloxycarbonylamino-omega-carboxy dodeca(ethylene glycol) (154 mg, 0.215 mmol, 1.25 equiv) followed by N,N-dimethylformamide (2 mL) then N,N-diisopropylethylamine (0.18 mL, 1.03 mmol, 6 equiv). The flask was cooled to 0° C. using an ice bath. To this was added propylphosphonic anhydride solution (50 wt. % in ethyl acetate, 0.215 mL, 0.343 mmol, 2 equiv) over 1 minute. The reaction was warmed to room temperature and stirred for 30 minutes. The reaction was quenched by adding water, saturated aqueous sodium bicarbonate and ethyl acetate. The organic layer was separated and the aqueous layer extracted with ethyl acetate. The combined organic layers were washed with saturated aqueous sodium bicarbonate, 0.5 M aqueous citric acid, water, and saturated aqueous sodium chloride, then dried (sodium sulfate), filtered and concentrated under vacuum. The residue which was used without further purification resulted in 0.6 g (0.194 mmol) of Compound N, shown below.

LC-MS (ES, m/z): [(M+2H-boc)/2]+ Calcd for (C111H189Br9N8O46+2H-Boc)/2=1496.3. Found 1497.2.

Compound N

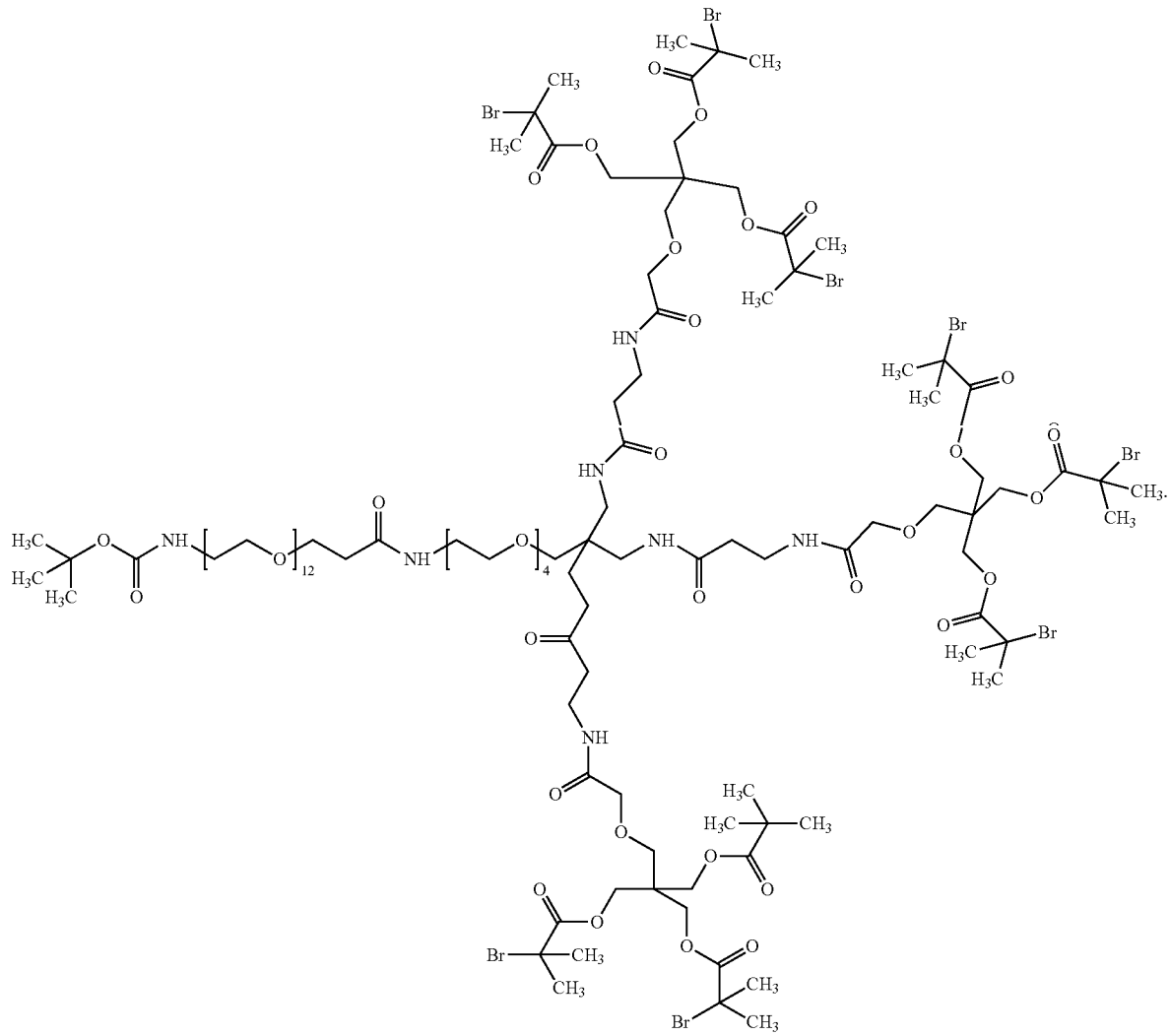

Into a 100 mL round bottom under nitrogen was added Compound N (0.6 g), dichloromethane (4 mL) followed by trifluoroacetic acid (3 mL). The reaction stirred at room temperature for 15 minutes. The reaction was concentrated under a vacuum. The residue was dissolved using acetonitrile (3 mL), filtered through a syringe filter (Acrodisc CR25, PN 4225T) and loaded onto a preparatory HPLC column and eluted with 50% acetonitrile (with 0.1% trifluoroacetic acid) in 50% water (with 0.1% trifluoroacetic acid) up to 90% acetonitrile (with 0.1% trifluoroacetic acid). The tubes containing product were pooled, concentrated under vacuum, frozen and placed on a lyophilizer. This resulted in 200 mgs (0.064 mmol, 37% over 2 steps) Compound P.

1H NMR (400 MHz DMSO-d6): δ=1.90 (s, 54H, CC(CH3)2Br), 2.3 (br t, 8H, CCH2CH2NH and CH2CH2C=O), 3.0 (m, 8H, CCH2NH and OCH2CH2NH), 3.1-3.6 (m, 84H, OCH2C), 3.87 (s, 6H, O=CCH2O), 4.27 (s, 18H, CCH2OC=O), 7.6-7.8 (m, 10H, both CH2NHC=O and NH3+).

LC-MS (ES, m/z): [(M+2H)/2]+ Calcd for (C106H181Br9N8O44+2H)/2=1496.3. Found 1496.6.

Example 8 Preparation of Zwitterionic Polymers

Initiator is typically prepared as a stock solution in DMF of about 100 mg/mL. The initiator and the ligand (2,2'-bipyridyl) were introduced into a Schlenk tube. The resultant solution was cooled to −78° C. using a dry ice/acetone mixture, and was degassed under vacuum for 10 min. The tube was refilled under Argon and the catalyst (CuBr unless otherwise indicated), kept under Argon, was introduced into the Schlenck tube (the Molar ratio of atom bromine on the initiator/catalyst (CuBr)/ligand was kept at 1/1/2). The solution became dark brown immediately. The Schlenk tube was sealed and immediately purged by applying a short cycle vacuum/Argon. A solution of HEMA-PC was prepared by mixing a defined quantity of monomer, prepared in a glove box kept under nitrogen, with 200 proof degassed ethanol. The monomer solution was added drop wise into the Schlenk tube (via canula). The temperature was maintained at −78° C. A thorough vacuum was applied to the reaction mixture for at least 10 to 15 min until bubbling from the solution ceased. The tube was then refilled with Argon and warmed to room temperature. The solution was stirred, and as the polymerization proceeded, the solution became viscous. After 3 to 8 hours or overnight, the reaction was quenched by direct exposure to air in order to oxidize Cu (I) to Cu (II), the mixture became blue-green in color, and was passed through a silica column in order to remove the copper catalyst. The collected solution was concentrated by rotary evaporation and the resulting mixture was either precipitated with tetrahydrofuran or dialyzed against water followed by freeze drying to yield a free-flowing white powder. Table 2 sets forth exemplary polymers made in accordance with the present invention.

TABLE 2

| Theor. MW (kDa) | Polymer ID No. | Initiator (see Table 3) | Mn (kDa) | Mp (kDa) | PDI |
|---|---|---|---|---|---|
| 150 [w2199] [d2191] | 60 | B5 | 150 | 158 | 1.05 |
| 250 [wR2765] [dR2731] | 70 | B4 | 205 | 230 | 1.05 |
| 250 [wR3350] [dR3324] | 80 | B5 | 117 | 137 | 1.1 |
| 250 [wR3373] [dR3372] | 90 | B6 | 235 | 258 | 1.1 |
| 250 [wR3460I] [wR3461M] [dR3418] | 100 | B | 242 | 259 | 1.1 |
| 250 [wR3482I] [wR3483M] [dR3463] | 110 | F1 | 245 | 270 | 1.1 |
| 500 [wR3763] [dR3662] | 120 | F1 | 490 | 557 | 1.1 |
| 500 [wR3758] [dR3706] | 130 | L | 490 | 530 | 1.1 |
| 750 [wR3764] [dR3667] | 140 | F1 | 586 | 695 | 1.1 |
| 750 [wR3759] [dR3707] | 150 | L | 645 | 750 | 1.1 |
| 750 [wR3836] [dR3804] | 160 | O | 656 | 740 | 1.1 |
| 750 [wR3835] [dR3808] | 170 | P | 785 | 900 | 1.1 |

TABLE 3

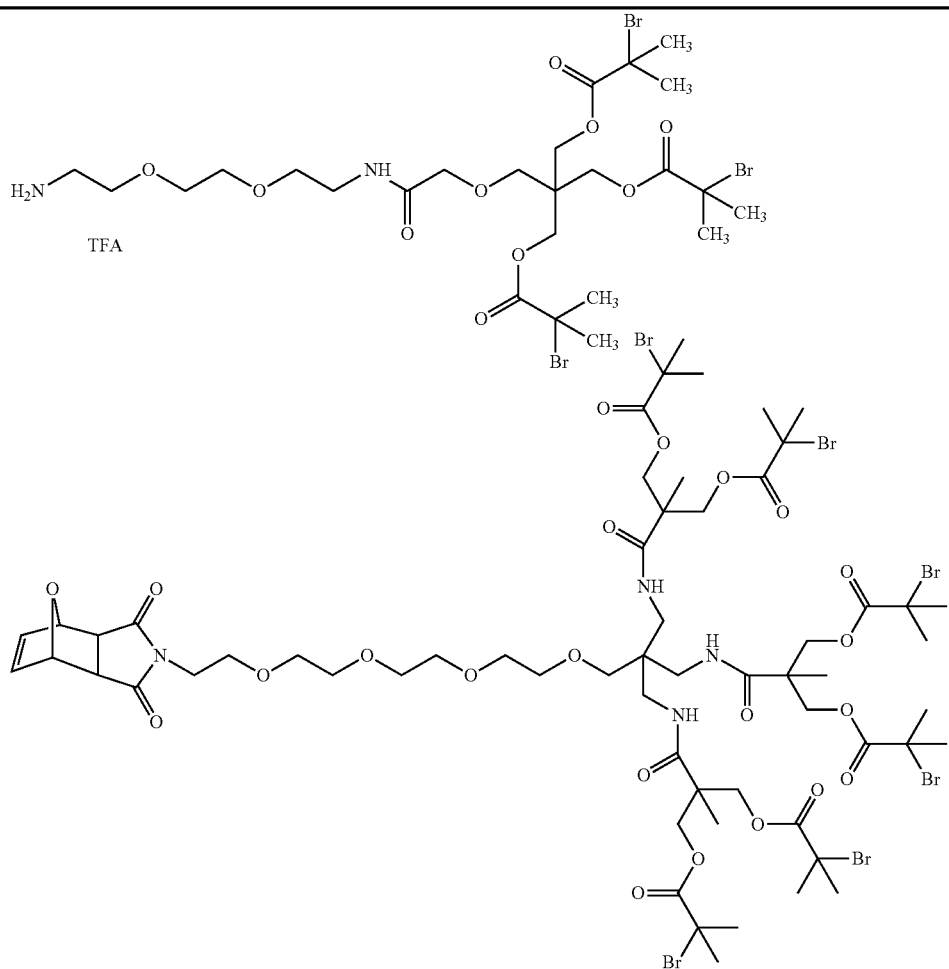

TABLE 3-continued
B5
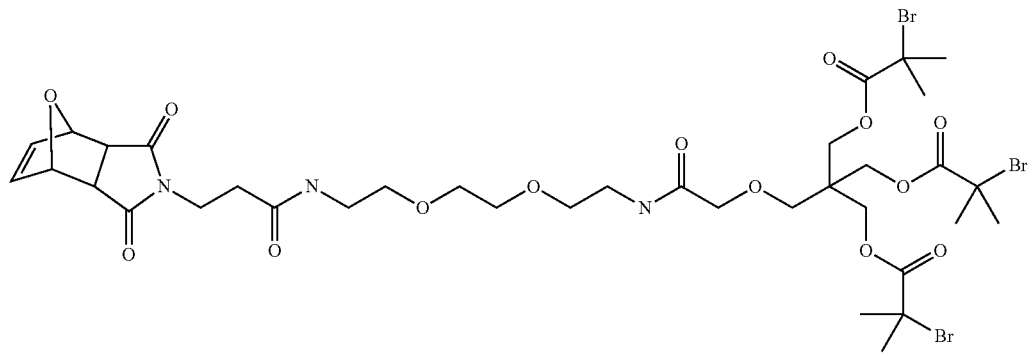 [SMILES: CC(C)(Br)C(=O)OCC(COCC(=O)NCCOCCOCCNC(=O)CCN1C(=O)C2C3C=CC(O3)C2C1=O)(COC(=O)C(C)(C)Br)COC(=O)C(C)(C)Br]
B6
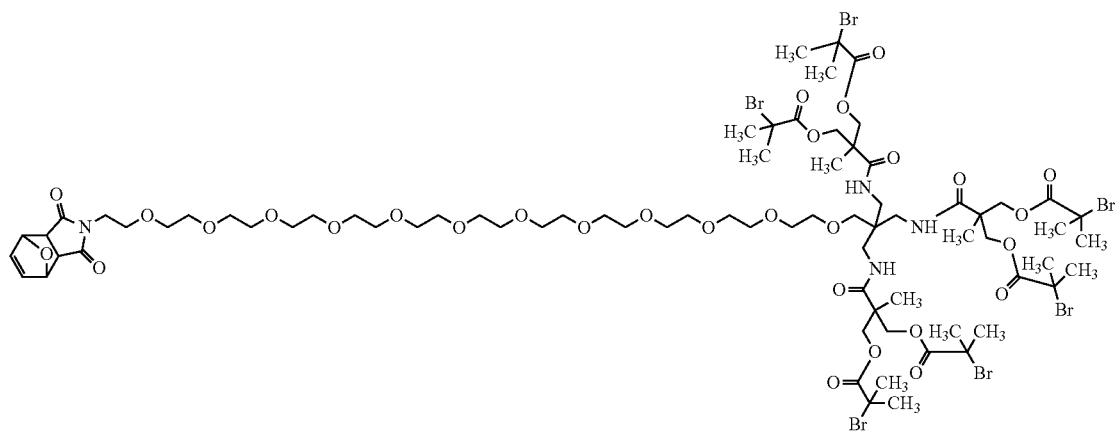 [SMILES: CC(C)(Br)C(=O)OCC(C)(COC(=O)C(C)(C)Br)C(=O)NCC(CNC(=O)C(C)(COC(=O)C(C)(C)Br)COC(=O)C(C)(C)Br)(CNC(=O)C(C)(COC(=O)C(C)(C)Br)COC(=O)C(C)(C)Br)COCCOCCOCCOCCOCCOCCOCCOCCOCCOCCOCCOCCN1C(=O)C2C3C=CC(O3)C2C1=O]
F1
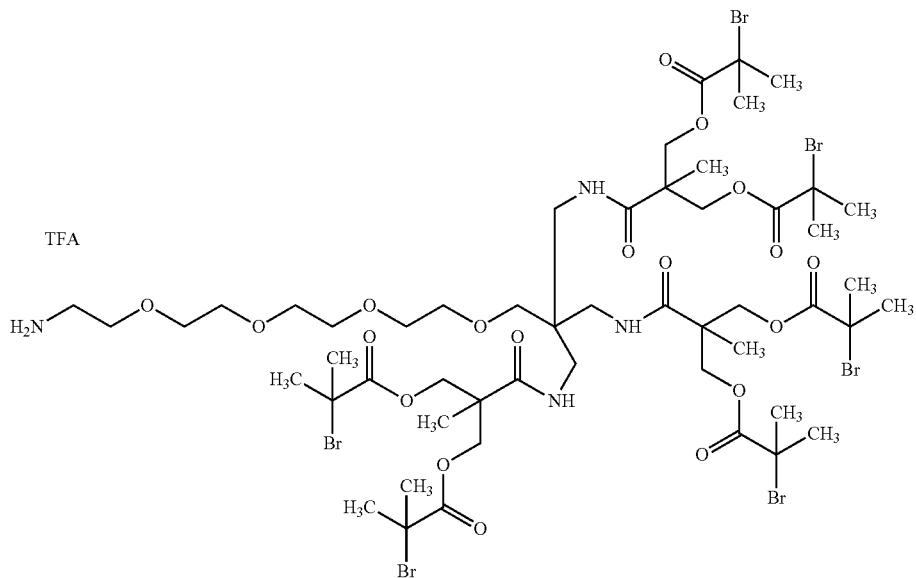

TABLE 3-continued
L
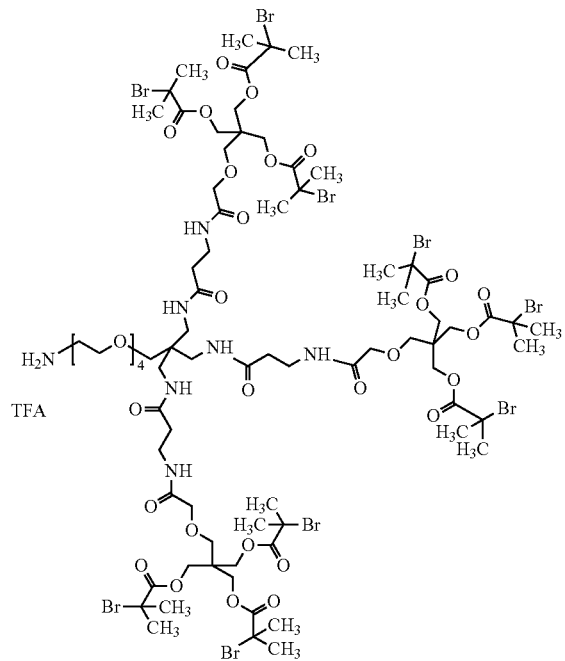
O
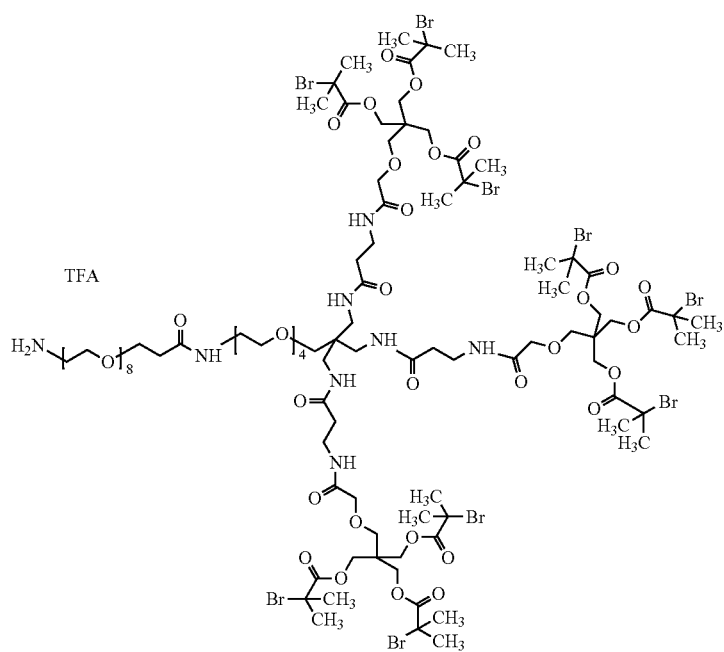

P
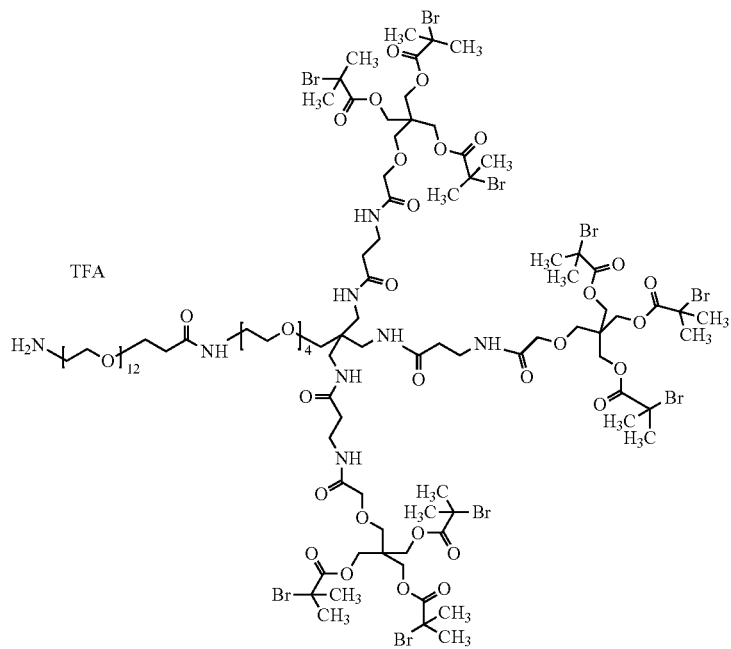
Example 9 Preparation of Maleimide 9-Arm Conjugatable Polymer
A maleimide conjugatable 9-arm polymer (Q) having the following structure was synthesized as follows:
Polymer Q
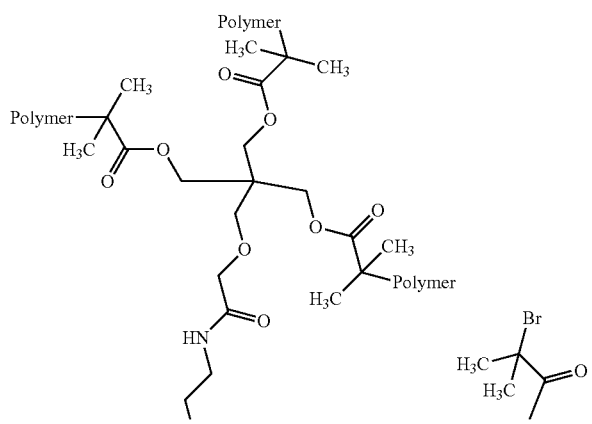

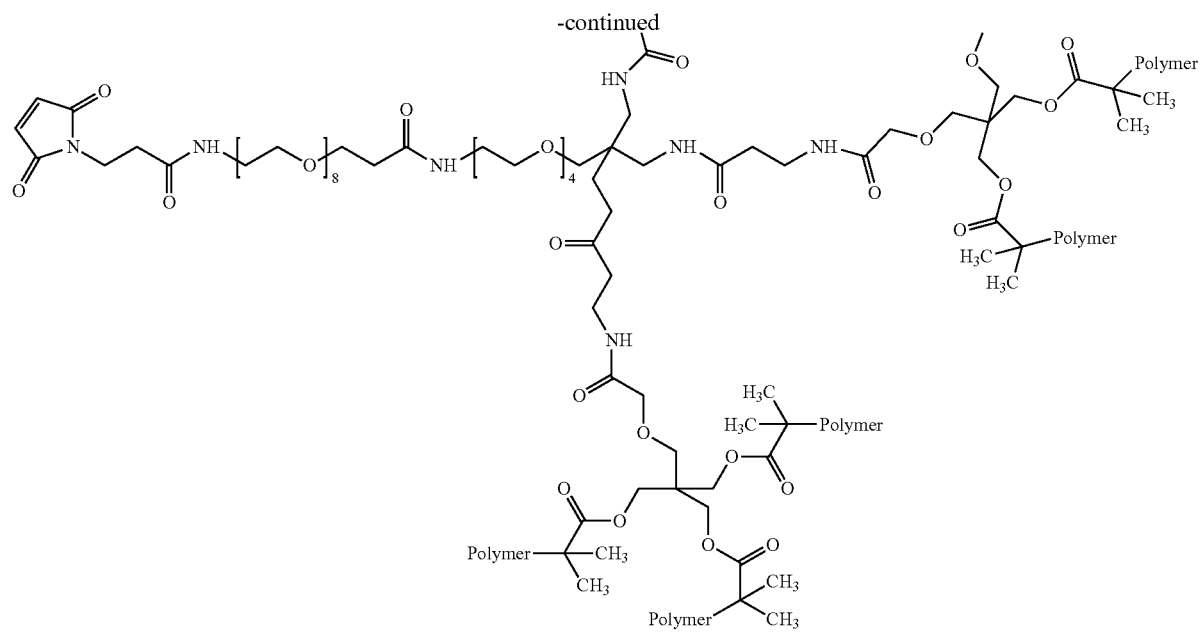

Conjugatable polymer Q was prepared as follows: into a 20 mL vial was placed Polymer ID No. 160 (Table 2) (540 mg, 0.0007 mmol, 1.0 equiv) and dissolved using water (4 mL). To this was added 0.5 M aqueous sodium phosphate dibasic (0.4 mL). In a separate vial was dissolved 3-maleimidopropionic acid, NHS ester (0.93 mg, 0.0035 mmol, 5 equiv) in tetrahydrofuran (1 mL). The NHS ester solution was added to the polymer solution over ~2 minutes at room temperature and the resulting solution was stirred for 30 minutes. The reaction was diluted with water (~15 mL), filtered through a syringe filter (Acrodisc Supor, PN 4612) and placed evenly into 3 Amicon centrifuge membrane dialysis tubes (30,000 mwco). The tubes were diluted and mixed with water (~5 mL each), placed into centrifuge (rpm 3000) for 30 minutes. The filtrate was removed for analysis while the retentate was diluted and mixed with water (~10 mL/tube). The centrifuge procedure was repeated 5 more times, after which the retentate was removed and placed into a vial. The Amicon membrane tubes were rinsed with water (2x~2 mL each tube) and this combined with the retentate. The retentate solution was filtered through a syringe filter (Acrodisc Supor, PN 4612), frozen and placed on a lyophilizer. This resulted in 508 mgs (94%) Polymer Q as a white powder.

Example 10 Preparation of Maleimide 9-Arm Conjugatable Polymer

A maleimide conjugatable 9-arm polymer (R) having the following structure was synthesized using the same techniques as describe for Conjugatable polymer Q:

Polymer R

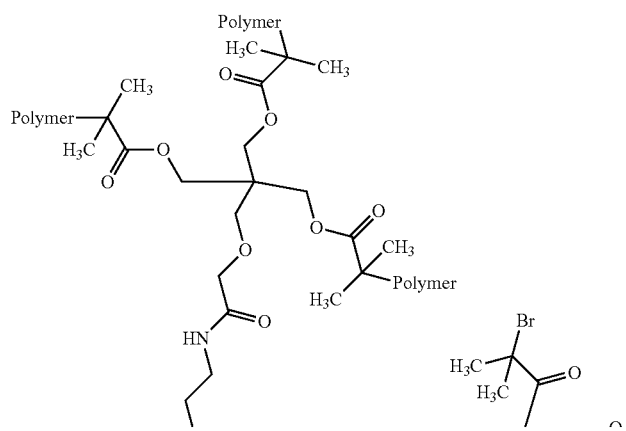

-continued

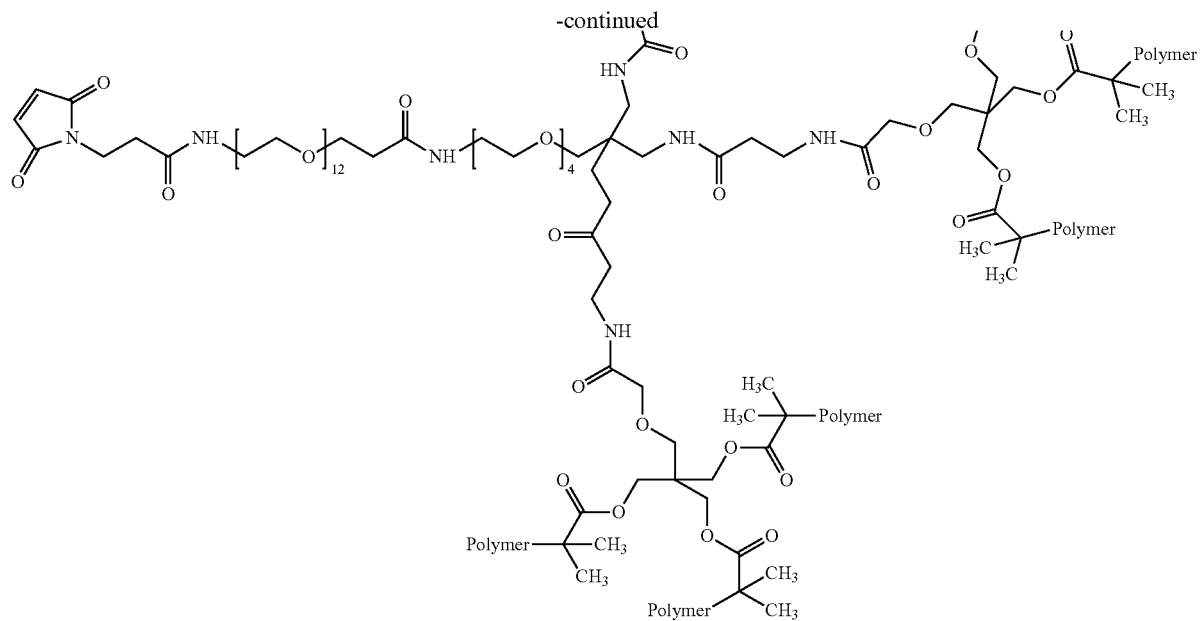

Example 11 Activity of Conjugates

BuChE enzyme activity was measured for conjugated and unconjugated protein as set forth in Table 1 below. In Table 1, rBuChE534 (C66Y) is rhBuChE534GGC and rBuChE534Fc is rhBuChE534 (C66Y)-Fc (L234A, L235E, G237A, A330S, P331S and Q347C, EU numbering):

TABLE 4

| Sample | Enzyme Activity (EU/mg) | S.D. (%) | Δ Activity |
|---|---|---|---|
| rBuChE534 (CHO-K1) | 724 | 4 | — |
| rBuChE534Fc (CHO-K1) | 788 | 5 | — |
| rBuChE534-9A750K HEMA-PC | 620 | 4 | 14% |
| rBuChE534Fc-9A750K HEMA-PC | 748 | 3 | 5% |
| BuChE (human plasma) (control) | 640 | 4 | — |
| rBuChE (goat milk) (control) | 423 | 5 | — | rBuChE (goat milk) refers to rhBuChE produced in transgenic goats. In summary, the BuChE-Fc fusion protein maintained good activity. Moreover, activity was well maintained after conjugation to polymers. For the Fc construct, activity loss after conjugation to MPC polymer was only 5%.

Example 12 Plasma Stability of BuChE

To determine if the rBuChE534GGC (C66Y) (SEQ ID NO: 13) and rhBuChE534 (C66Y)-Fc (L234A, L235E, G237A, A330S, P3318 and Q347C, EU numbering (SEQ ID NO: 2) had overcome the stability problems associated with transgenic goat rBuChE, we tested the stability of these constructs versus human plasma derived BuChE, and transgenic goat rhBuChE (full length) in cynomolgus monkey (cyno) plasma. Samples were introduced into commercially available cyno plasma and aliquots were withdrawn over time and enzyme activity determined via Ellman's assay. FIG. 1 shows the activity of both the rBuChE534GGC (C66Y)) and rhBuChE534 (C66Y)-Fc (L234A, L235E, G237A, A330S, P331S and Q347C) were well maintained over nearly 35 days storage at 37.degree. C. in cyno plasma. Both of these constructs performed better than the gold standard human plasma purified BuChE. In contrast, the activity of the transgenic goat enzyme dropped off rapidly over time, approaching less than 5% towards the end of the study.

It was also determined whether conjugation to polymer affected enzyme stability. FIG. 2 shows a plot of activity vs. time for protein rhBuChE534 (C66Y)-Fc (L234A, L235E, G237A, A330S, P331S and Q347C, EU numbering conjugated to a 9 arm 750 kDa HEMA-PC polymer compared with human plasma derived BuChE at 4° C. and 37° C. Although the activity of polymer conjugated protein declines somewhat over time, the decline is no more than that seen with human plasma derived enzyme.

Example 13 In Vitro Inhibition of BuChE by Nerve Agents

To determine whether the rBuChEs of the instant invention were active against nerve agents, various BuChE batches, conjugated and unconjugated, were assayed using the Ellman's assay described above in the presence of OP agents: GA (Tabun (Ethyl dimethylamidocyanophosphate)), GB (Sarin (Propan-2-yl methylphosphonofluoridate)), GD (Soman (3,3-Dimethylbutan-2-ylmethylphosphonofluoridate)), GF (Cyclosarin (Cyclohexyl methylphoshonofluoridate)), VX (V Series nerve agent (Ethyl ({2-[bis(propan-2-yl)amino]ethyl}sulfanyl)(methyl)phosphinate), and VR (V series nerve agent (N,N-diethyl-2-(methyl-(2-methylpropoxy)phosphoryl)sulfanylethanamine)). Table 2 shows the inhibition constant Ki for human plasma rBuChE, rBuChE534=rBuChE534GGC (C66Y), rBuChE534-Fc=rhBuChE534 (C66Y)-Fc (L234A, L235E, G237A, A330S, P331S and Q347C, EU numbering), and rBuChE534-Fc-polymer=rhBuChE534 (C66Y)-Fc (L234A, L235E, G237A, A330S, P331S and Q347C)-9 arm 750 kDa HEMA-PC polymer with the various nerve agents.

TABLE 5 ki ($M^{-1}min^{-1}$) of Nerve Agents

| Agent | Plasma BuChE | rBuChE534 | rBuChE534-Fc | rBuChE534-Fc-polymer |
|---|---|---|---|---|
| GA | $4.93 \times 10^6$ | $4.75 \times 10^6$ | $3.25 \times 10^6$ | $8.89 \times 10^6$ |
| GB | $8.62 \times 10^6$ | $8.48 \times 10^6$ | $7.19 \times 10^6$ | $6.87 \times 10^6$ |
| GD | $8.52 \times 10^7$ | $4.76 \times 10^7$ | $3.74 \times 10^7$ | $5.61 \times 10^7$ |
| GF | $1.61 \times 10^8$ | $9.43 \times 10^7$ | $6.81 \times 10^7$ | $1.27 \times 10^8$ |
| VX | $6.92 \times 10^6$ | $3.12 \times 10^6$ | $2.93 \times 10^6$ | $9.06 \times 10^6$ |
| VR | $1.08 \times 10^8$ | $4.34 \times 10^7$ | $4.53 \times 10^7$ | $4.53 \times 10^7$ |

As can be seen from the table, each of the constructs, including the conjugate, is very close to the standard human plasma BuChE.

Example 14 In Vivo Pharmacokinetics of BuChE Constructs

To determine the in vivo pharmacokinetic properties of the rhBuChE534 (C66Y)-Fc (L234A, L235E, G237A, A330S, P331S and Q347C, EU numbering) (and corresponding conjugates) of the present invention, constructs were injected administered to homozygous carboxylesterase ES1 knockout mice (−/−) on a C57BL/6 background. Duysen, E. G., et al. Production of ES1 Plasma Carboxylesterase Knockout Mice for Toxicity Studies (2011) Chem. Res. Toxicol. 24(11) 1891-1898. These ES1 KO mice are completely deficient in plasma carboxylesterase activity which has been reported as boosting the LD50 of nerve agents in mice relative to humans. Duysen et al.

Serum stability of the various constructs and conjugates described below was tested in mouse serum (C57BL/6) as described above for monkey serum. The results were similar (data not shown). The various constructs and conjugates were injected intravenously into groups of 4-6 mice at time 0 (zero). Aliquots of blood were then withdrawn from the animals at various times after injection and the activity of BuChE measured as described above. Below is a summary of test articles injected into KO mice.

TABLE 6

Design of In Vivo pK Study in KO Mice

| Test Article | Specific Activity (U/mg) | Concentration (protein) | Delivered Dose (mg/Kg) |
|---|---|---|---|
| BuChE (Plasma-derived) | 641 ± 22 | 5 | 60.6 |
| rhBuChE534 (C66Y) - Fc (L234A, L235E, G237A, A330S, P331S and Q347C) | 534 ± 14 | 5.58 | 17 |
| 3A500K-conjugate | 503 ± 9 | 5.17 | 17.2 |

Figure 3:
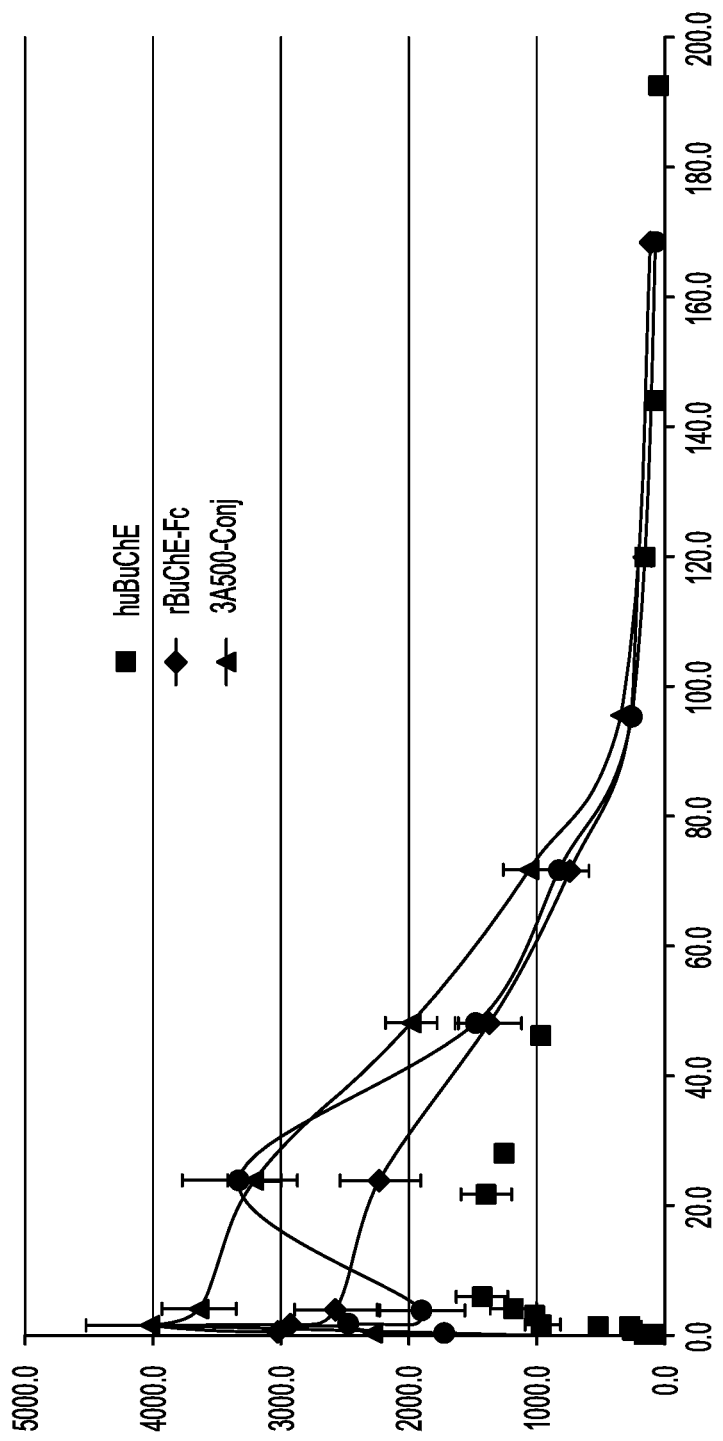
FIG. 3 Activity of unconjugated rhBuChE534 (C66Y)-Fc (L234A, L235E, G237A, A330S, P331S and Q347C, EU numbering), conjugated to 3 arm 500 kDa MPC polymer, conjugated to 9 arm 750 kDa MPC polymer and plasma derived hBuChE, normalized activity (units×106) after injection into mice over time (hours).

BuChE enzyme activity was monitored in the withdrawn blood samples and normalized based on the above activity data. pK data for the various constructs set forth in Table 1 is shown below in FIG. 3.

Example 15 Buffer Stability Comparison or BuChE Conjugates at 37° C.

Figure 4:
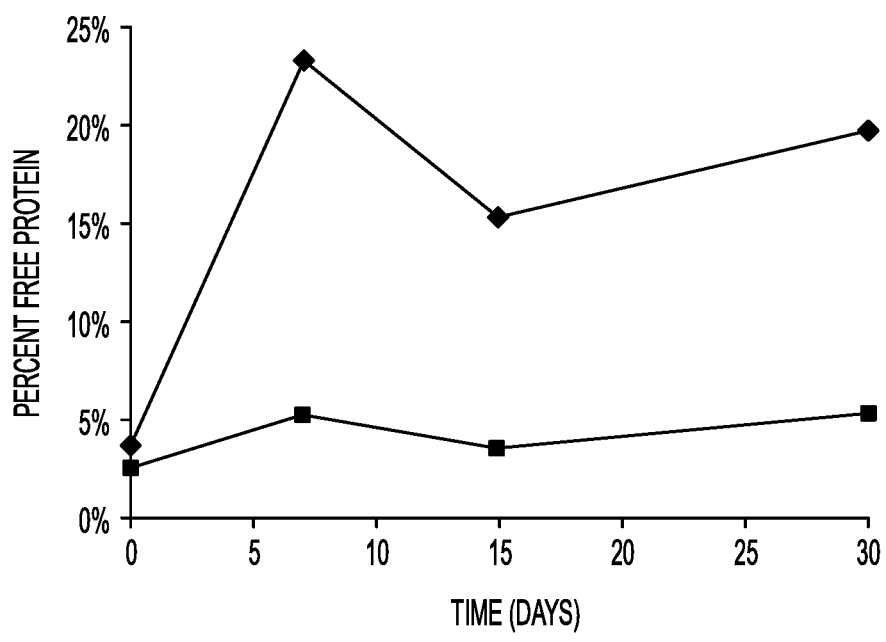
FIG. 4 shows the stability profile for full length rhBuChE from the milk of transgenic goats conjugated via iodoacetamide and maleimide to MPC polymers.

Full length rhBuChe purified from the milk of transgenic goats was conjugated via a native cysteine to a polymer using malemide or iodoacetamide. The stability of these two different conjugates was compared below in FIG. 4. To assess conjugate stability, the maleimide and iodoacetamide based conjugates were incubated in phosphate buffered saline at 37° C., pH 7.0 for 30 days. Aliquots were withdrawn and free protein assessed by SDS PAGE. The results can be seen in FIG. 4. Iodoacetamide conjugates were very stable over the 30 days with the line remaining near the base line set at time 0. In contrast, the maleimide based conjugates rapidly jumped off the base line set at time 0. Hence, in accordance with the present invention, it can be seen that iodoacetamide based conjugates are substantially more stable for some proteins than maleimide conjugates. The instability of maleimite conjugates is protein dependent. Many malemide conjugates are quite stable.

Example 16 Maleimide 750 kDa MPC Polymer Conjugated to Goat Derived rhBuChE

Compound AA

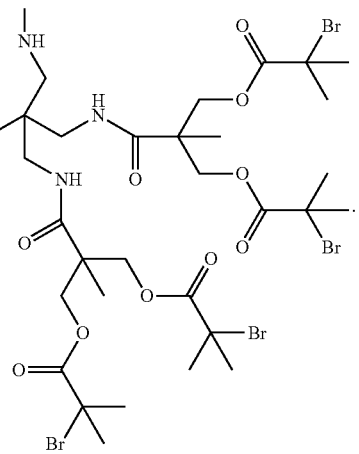

For maleimide conjugation, a heat deportectable maleimide initiator was employed to conjugate MPC polymer to BuChE. An initiator, Compound AA, having the structure above was synthesized as set out in PCT/US2012/060301 (see Example 6):

Synthesis of MPC polymer was carried out as described in Example 11 of PCT/US2012/060301) to produce an approximately 750 kDa 6-arm MPC polymer. The polymer was prepared for conjugation by heat deprotection as described in U.S. provisional app. no. U.S. 61/875,099. The resulting heat deprotected polymer was conjugated to TCEP treated BuChE in Tris buffered saline, pH 7.5 at 4° C. overnight. Conjugation was assayed by SDS PAGE. Conjugates were purified from free protein and polymer via DEAE chromatography.

Example 17 Iodoacetamide 3 Arm, 250 kDa MPC Polymer Conjugated to Goat Derived rhBuChE A TFA/amine salt initiator (Compound B) having the structure below was synthesized as follows.

Compound B

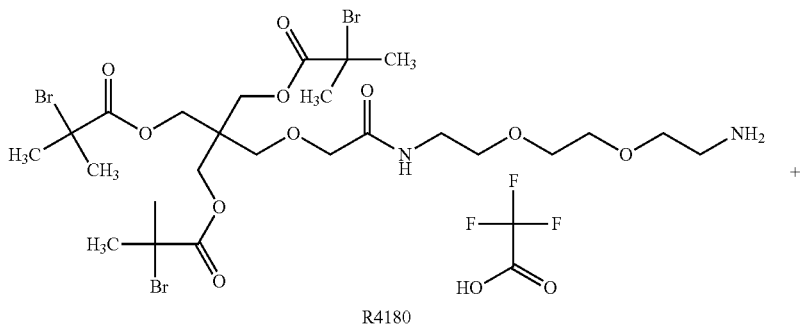

R4180

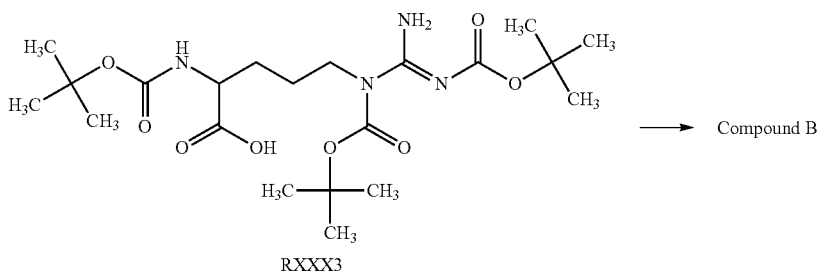

RXXX3

⟶ Compound B

First, a BOC protected 3-arm initiator, Compound A, having the following structure:

Compound A

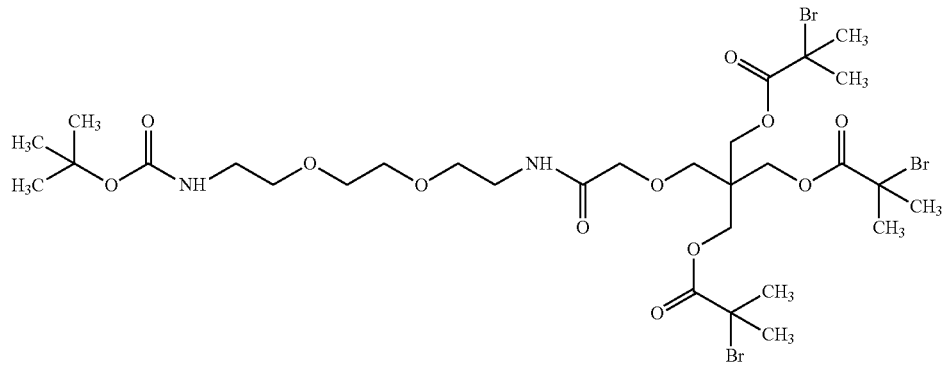

was prepared as follows: into a 25 mL round bottom flask under nitrogen was placed tert-butyl 2-[2-(2-aminoethoxy)ethoxy]ethylcarbamate (66 mg, 0.26 mmol, 1.2 equiv) and (2,2,2-Tri(2-bromo-2-methyl-propionyloxymethyl)-ethoxy)-acetic acid (prepared as described in PCT/US2012/060301 for Product 4.5, which is incorporated herein by reference) (142 mg, 0.22 mmol, 1.0 equiv) followed by N,N-dimethylformamide (2 mL) and then N,N-diisopropylethylamine (0.19 mL, 1.1 mmol, 5.0 equiv). The flask was cooled to 0° C. using an ice bath. To this was added propylphosphonic anhydride solution (50 wt. % in ethyl acetate, 0.16 mL, 0.26 mmol, 1.2 equiv) over 1 minute. The reaction was warmed to room temperature and stirred for 1.5 hours. The reaction was quenched by adding water, then partitioned using water and ethyl acetate. The organic layer was separated and the aqueous layer extracted with ethyl acetate. The combined organic layers were washed with water, saturated aqueous sodium bicarbonate, water, 0.5 M aqueous citric acid, water, then dried (sodium sulfate), filtered and concentrated under vacuum. The residue was applied onto a silica gel column (60 mL) and eluted with 70% ethyl acetate with 30% hexanes. The tubes containing product was pooled and concentrated under vacuum, which resulted in 150 mg (0.17 mmol, 77%) of Compound A.

Compound A was de-protected to yield Compound B as follows: into a 20 mL round bottom under nitrogen was added Compound A (120 mg, 0.14 mmol, 1 equiv), dichloromethane (2 mL) followed by trifluoroacetic acid (2 mL, 26.9 mmol, 192 equiv). The reaction stirred at room temperature for 30 minutes. The reaction was diluted using hexanes dichloromethane (20 mL) and concentrated under a vacuum. The reaction was diluted using hexanes (50 mL) and concentrated under vacuum (twice), which resulted in 2.2 g (2.73 mmol, (with residual dichloromethane)) of compound B.

Polymer B2, having the following structure, was prepared as follows.

Polymer B2

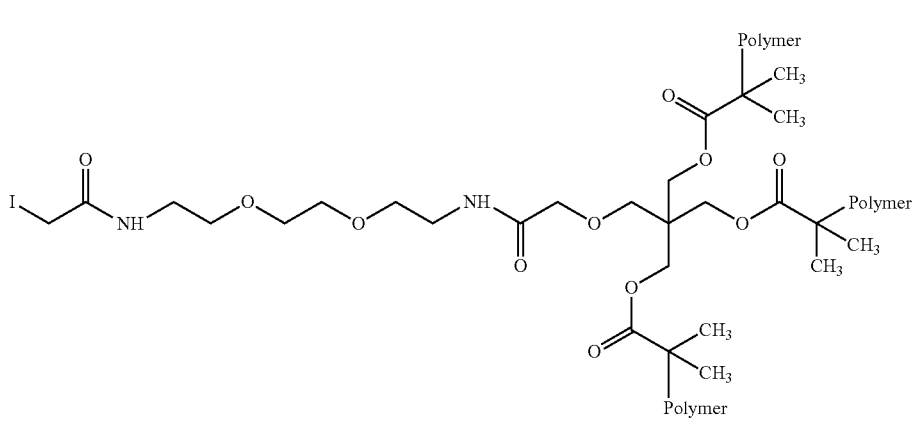

Into a 20 mL vial was placed Polymer 103 (280 mg, 0.00123 mmol, 1.0 equiv) and dissolved using water (2 mL). To this was added 0.5 M aqueous sodium phosphate dibasic (0.2 mL). In a separate vial was dissolved iodoacetic acid N-hydroxysuccinimide ester (1.6 mg, 0.00548 mmol, 4.5 equiv) in tetrahydrofuran (0.5 mL). The NHS ester solution was added to the polymer solution over ~2 minutes at room temperature and the resulting solution was stirred for 75 minutes. The reaction was diluted with 4:1 water:tertahydrofuran (4 mL) and placed into a Amicon centrifuge membrane dialysis tube (30,000 mwco) and the tube placed into centrifuge (rpm 3000) for 30 minutes. The filtrate is removed for analysis while the retentate is diluted and mixed with 4:1 water:tertahydrofuran (6 mL) and the tube placed into centrifuge (rpm 3000) for 30 minutes. The filtrate is removed for analysis while the retentate is diluted and mixed with water (8 mL), placed into centrifuge (rpm 3000) for 30 minutes. The filtrate is removed for analysis while the retentate is diluted and mixed with water (8 mL). The centrifuge procedure repeated 3 more times, after which the retentate is removed and placed into a vial. The Amicon membrane tube was rinsed with water (2x~2 mL) and this combined with the retentate, which was frozen and placed on a lyophilizer. This resulted in 270 mgs (96%) Polymer B2 as a white powder.

Polymer B2 was conjugated to TCEP treated rhBuChE, prepared as described above. Approximately 5× molar excess ration of Polymer B2 to rhBuChE was used in approximately pH 8.5 sodium carbonate buffer at room temperature overnight. Conjugate was purified from free polymer and protein via DEAE chromatography.

Example 18 Enhanced Conjugation of 3A—250 kDa Iodoacetamide MPC Polymer Via Basic Groups Various basic groups were positioned near the iodoacetamide functionality and their ability to enhance conjugation to rBuChE was assayed.

TABLE 7

Figure 5:
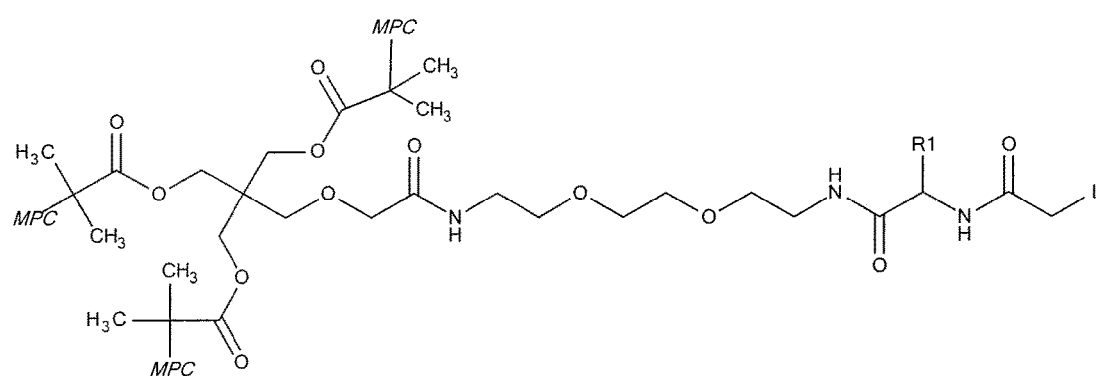
FIG. 5 shows 3-arm, 250 kDa, MPC polymers with modified (R1) iodoacetamide moiety.

| Conjugation to rhBuChE from goat milk | | | |
|---|---|---|---|
| Iodoacetamide Functionality (see FIG. 5) for structure re R1 | Polymer molar excess | pH | Conjugation Efficiency |
| [R4341] R1 = CH3 | 10 x | 7.5 | 11% |
| [R4118] R1 = (CH2)3-guanidine | 10 x | 7.5 | 24% |
| [R4440] R1 = CH2-guanidine | 10 x | 7.5 | 17% |
| [R4442] R1 = (CH2)2-guanidine | 10 x | 7.5 | 32% |

TABLE 7-continued

| Conjugation to rhBuChE from goat milk | | | |
|---|---|---|---|
| Iodoacetamide Functionality (see FIG. 5) for structure re R1 | Polymer molar excess | pH | Conjugation Efficiency |
| [R4341] R1 = CH3 | 10 x | 8.5 | 23% |
| [R4118] R1 = (CH2)3-guanidine | 10 x | 8.5 | 57% |
| [R4440] R1 = CH2-guanidine | 10 x | 8.5 | 40% |
| [R4442] R1 = (CH2)2-guanidine | 10 x | 8.5 | 64% |
| [R4341] R1 = CH3 | 10 x | 9.5 | 74% |
| [R4342] R1 = 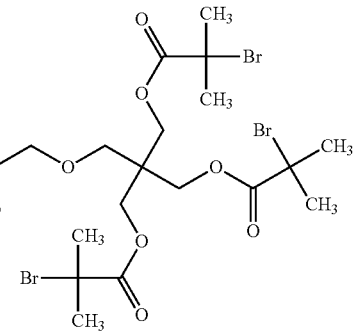 | 10 x | 8.5 | 22% |
| [R4439] R1 = (CH2)3—N(CH3)2 | 10 x | 8.5 | 43% |
| [R4441] R1 = (CH2)2—N(CH3)2 | 10 x | 8.5 | 6% |
| [R4320] R1 = (CH2)4—N(CH3)2 | 10 x | 8.5 | 42% |
| [R4438] R1 = CH2—N(CH3)2 | 10 x | 8.5 | 4% |
| [R4451] R1 = (CH2)4-guanidine | 10 x | 8.5 | 51% |
| [R4118] R1 = (CH2)3-guanidine | 20 x | 8.5 | 70% |
| [R4451] R1 = (CH2)4-guanidine | 20 x | 8.5 | 75% |

Example 19 Synthesis of Polymer R4341

First, R4163, having the following structure was synthesized:

Compound R4163

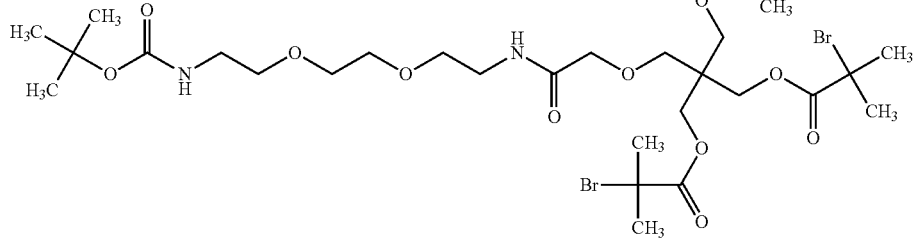

Compound R3329, structure shown below, was purchased from JStar Research.

Compound R3329

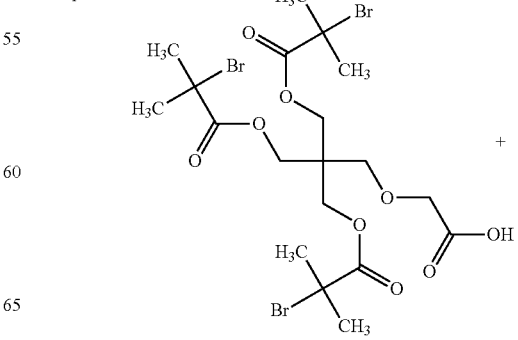

6 g of R3329 was mixed with 2.8 g of N—BOC-2,2'-(ethylenedioxy)diethylamine in THF at room temperature. To this was added 8.2 ml of diisopropylethylamine, followed by 7.7 ml of propylphosphonic anhydride solution (1.6 M). Following incubation at room temperature for 30 minutes, the reaction mixture was partitioned by EtOAcMTBE and water. This was followed by washing with 0.5 M citric acid ×1, saturated sodium bicarbonate and saturated NaCl. The product was dried over magnesium sulfate. R4163 was confirmed by LCMS.

Next the BOC group was removed from R4613. 9.4 g of R4163 was dissolved in 60 ml of dichloromethane. To this was added 60 ml of trifluoro acetic acid. After 10 minutes incubation at room temperature. The solution was dried down. The solid material was dissolved in water/acetonitrile and R4180, shown below, was purified by RP-HPLC.

200 mg of R4180 was mixed with 43 mg of BOC-L-Ala-OH in 2 ml of acetonitrile. To this was added 200 µl of diisopropylethylamine, followed by 175 µl of propylphosphonic anhydride solution (1.6 M). Following incubation at room temperature for 20 minutes, water was added and the solution stirred for 5 minutes. The solution was then acidified by acetic acid and diluted in methanol. R4203 was purified by RV-HPLC.

The initiator was prepared for polymer synthesis by removing the BOC functionality via trifluoro acetic acid to produce a TFA salt. 171 mg of R4203 was dissolved in 500 µl of trifluoroacetic acid and incubated at room temperature Compound R4180

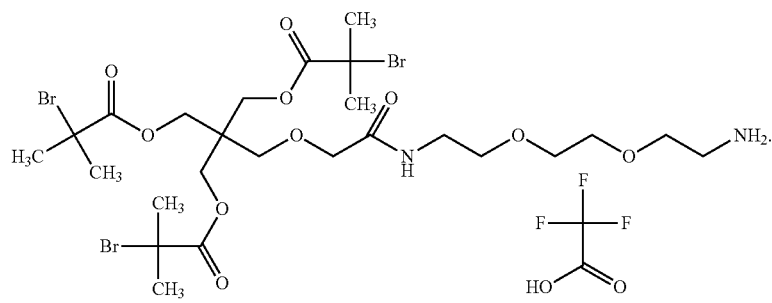

Next, compound R4203, having the following structure, was produced:

for a few minutes. R4235, shown below, was purified by RV-HPLC and confirmed by LCMS and NMR.

Compound R4203

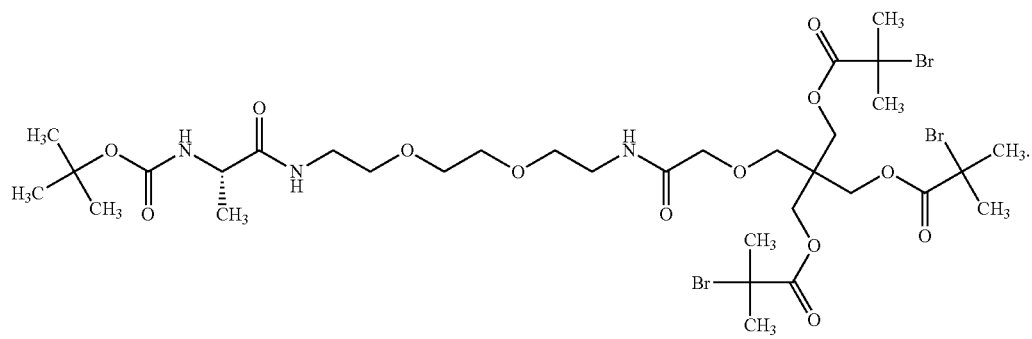

Compound R4235

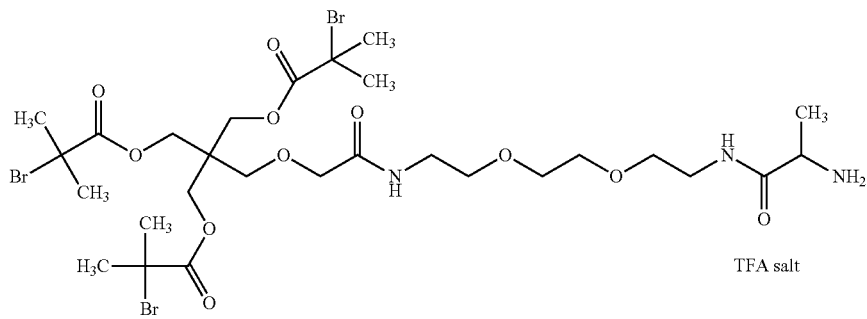

R4235 was then used to initiate MPC polymer synthesis to produce compound R4258, shown below:

Compound R4258

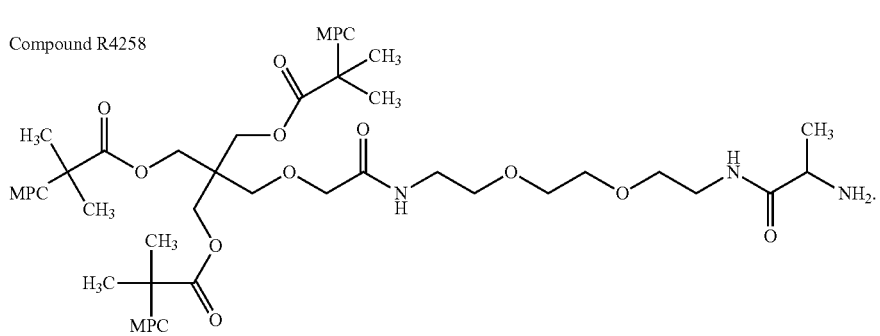

In a 25 mL Schlenk tube was loaded 4.8 mg of 2,2'-bipyridyl, then 47.7 uL of a stock solution of initiator (R4235) in DMF (6.3 mg of initiator in 63 uL of DMF). De-gas the stock solution then add 2.8 mg of CuBr, de-gas, then add the stock solution of monomer (2-hydroxyethyl methacrylate (HEMA) phosphorylcholine (PC)) in ethanol (1 g in 4 mL of ethanol) dropwise. Degas the reaction mixture for one hour at least and seal under 3 psi of Ar. Allow the reaction to proceed for 20 h at RT. Brown coloration: quenching, sampling for conversion and MW analysis. Purification by dialysis (MWCO is 1 kDa) 4 washings before freeze-drying.

Finally, R4341 was synthesized by putting an iodoacetate group on the lone primary amine. Polymer R4258 (100 mg) was dissolved in water to which phosphate buffer was added. To this was added 100 μl of a 6.5 mg/ml solution of iodoacetic acid N-hydroxysuccinimide ester in THF. After 5 minutes another 100 μl of the ester was added and the reaction mixture incubated at room temperature for 30 minutes. Dilute to ~10 mL with water. Filter. Centrifuge dialyze (30 kDa cut-off). Re-dialyze ×4. Dilute to ~10 mL with water, filter and lyophilize: Product: Mp: 221.9 kDa, PDI 1.10.

Example 20 Synthesis of Polymer R4118

Polymer R4118 is shown below:

Compound R4118

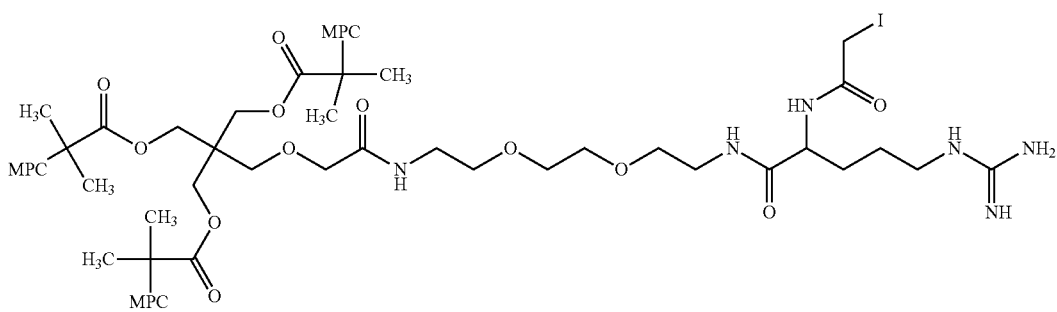

First, R4180 was synthesized as described above. R4180 was then used in the following reaction to produce RXXX1:

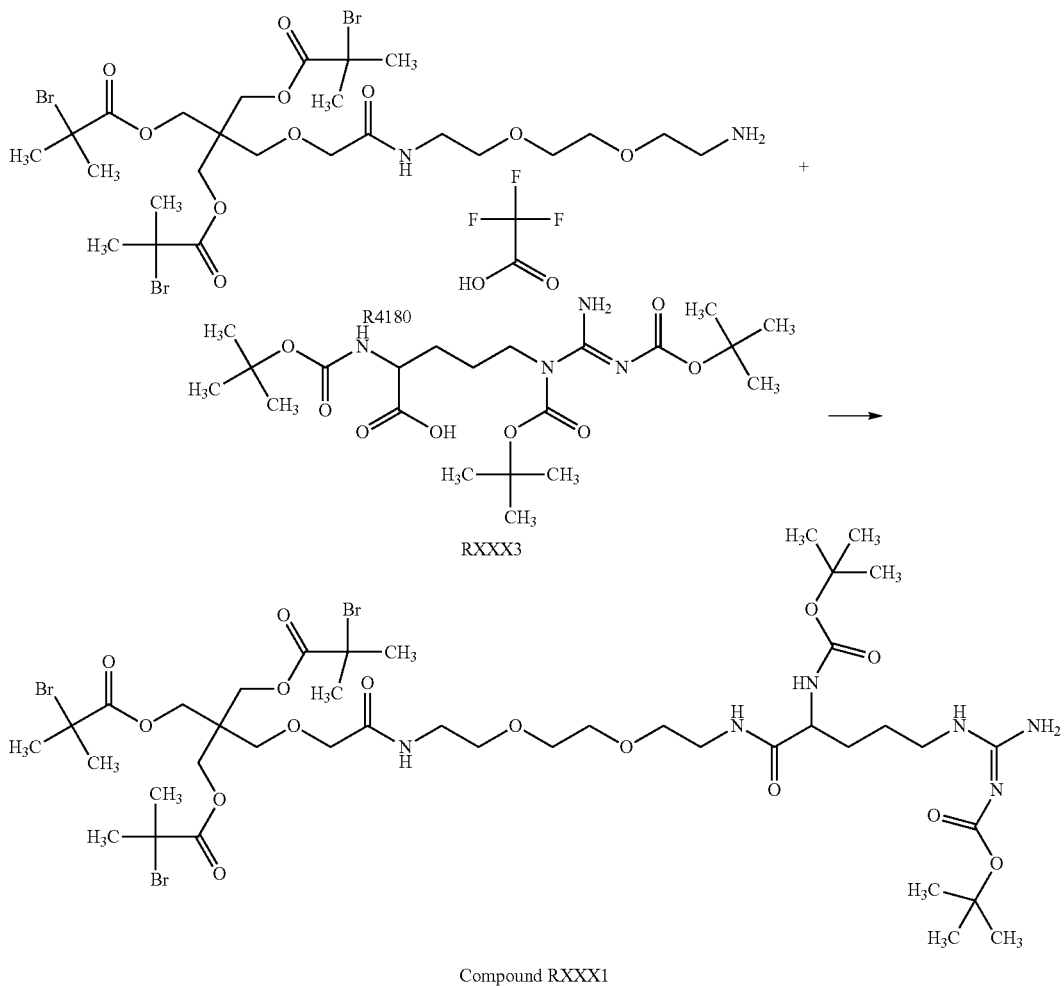

RXXX3

Compound RXXX1

200 mg of R4180 and 107 mg of RXXX1 were dissolved in acetonitrile (2 ml). To this was added 200 microL of N,N'-Diisopropylethylamine and 175 microL of propylphosphonic anhydride (50% in ethylacetate). This reaction mixture was incubated for about 3 hours at room temperature. 3 ml of water was added and the solution stirred for 5 minutes. The solution was acidified with acetic acid and diluted with 1 ml of methanol. RXXX1 was purified by RV-HPLC.

The BOC protective groups were removed with TFA to produce a TFA salt. 140 mg of RXXX1 was dissolved in 1.5 ml of dichloromethane. To this 1.5 ml of TFA was added. This solution was incubated at room temperature for about 2 hours and 45 minutes. The TFA and dichloromethane were vacuumed off and the solid material was dissolved in water/acetonitrile. Compound R4037, shown below, was purified by RV-HPLC and confirmed by LCMS.

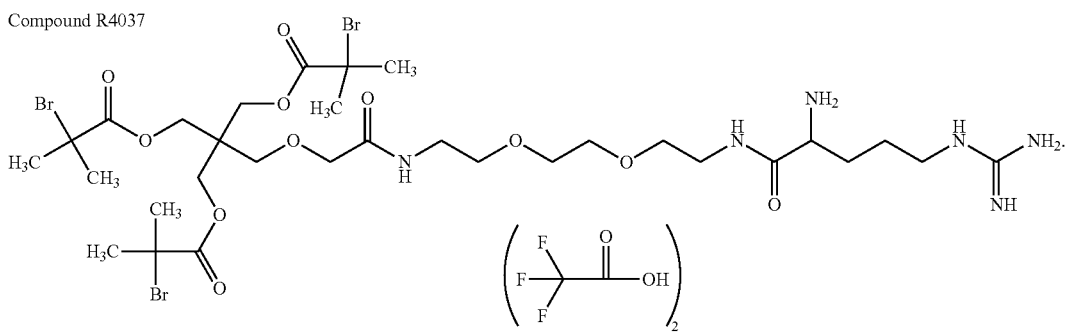

Compound R4037

Next, an MPC polymer was produced using R4037 as an initiator. In a 10 mL Schlenk tube was loaded 4.8 mg of 2,2'-bipyridyl, then 57.7 uL of a stock solution of initiator (R4037) in DMF (6.2 mg of initiator in 62 uL of DMF). Degas the stock solution then add 2.9 mg of Cu(I)Br, degas, then add the stock solution of monomer (2-hydroxyethyl methacrylate (HEMA) phosphorylcholine (PC)) in ethanol (1 g in 4 mL of ethanol) dropwise.

Degas the reaction mixture for one hour at least and seal under 3 psi of Ar. Allow the reaction to proceed overnight at RT (20 hours). Polymer R4053, shown below, was then subjected to SEC/MALS and was found to have a PDI of 1.073 and an Mp of 213.7 kDa.

Compound R4053

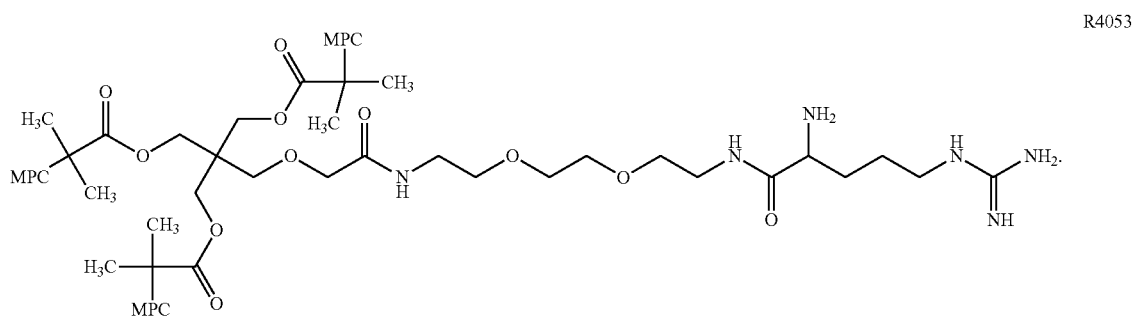

R4053

Compound R4118 was then produced by reacting R4053 with Iodoacetic acid N-hydroxysuccinimide ester. 150 mg of the polymer was stirred in water until it dissolved and phosphate buffer was added. 3 mg of Iodoacetic acid N-hydroxysuccinimide ester was dissolved in 450 μl of THF. Add two 150 μL aliquots of NHS ester solution 5 minutes apart. Stir at room temperature for 30 minutes. Dilute to ~10 mL with water and centrifuge and dialyze (30K cut off). Redialyze 5× with ~10 mL water.

Dissolve supernatant in ~10 mL water, filter and lyophilize: SEC/MALS: Mp 215.3 kDa, PDI 1.1.

Example 21 Synthesis of Polymer R4440

First, R4180, see above, was reacted as shown below to produce a BOC protected initiator:

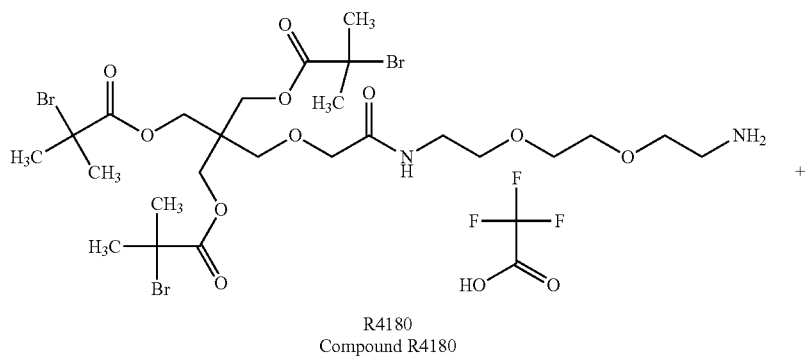

R4180
Compound R4180

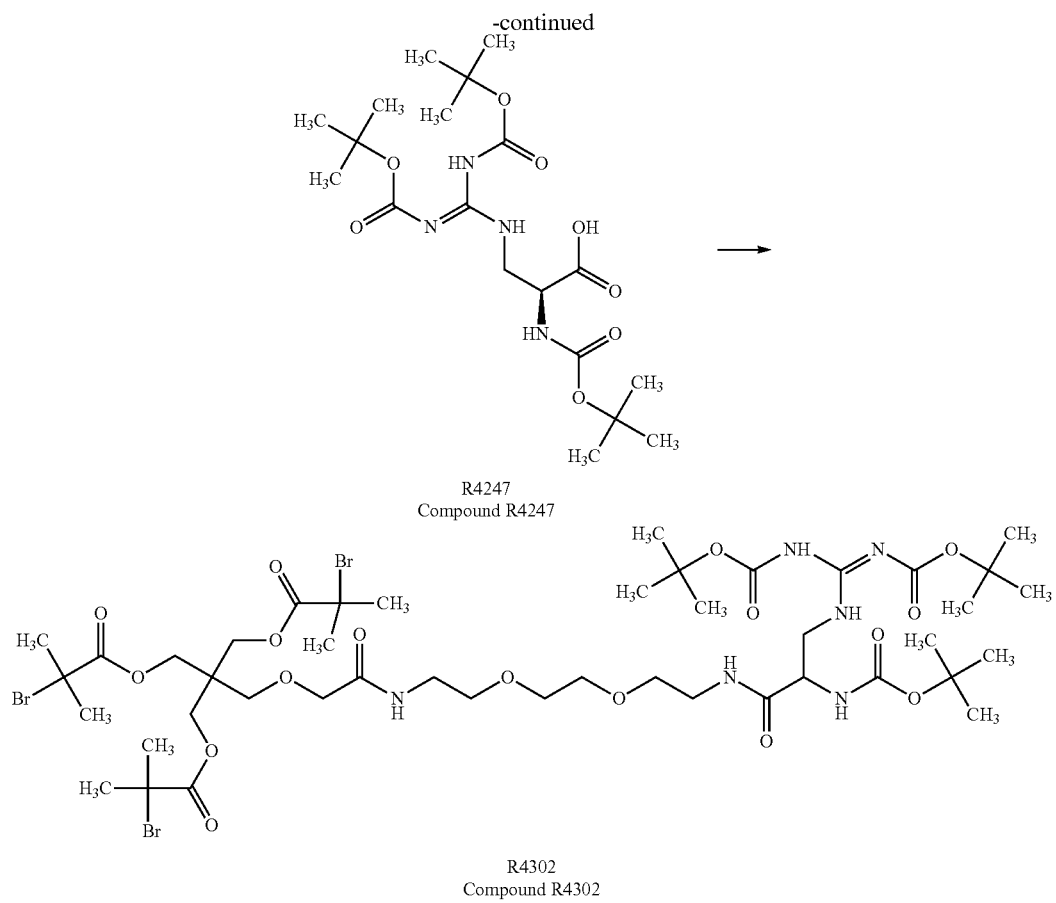

R4247
Compound R4247

R4302
Compound R4302

R4180 (200 mg) and R4247 (111 mg) were dissolved in 2 ml of acetonitrile. 200 µl of N,N'-Disopropylethylamine was added followed by 175 µl of propylphosphonic anhydride. This solution was incubated at room temperature for 25 minutes. Add water, followed by acetic acid then methanol. R4302 was purified by RP-HPLC. Identity was confirmed by LCMS.

Next, BOC groups were removed from R4302 via TFA to produce R4315, shown below.

Compound 4315

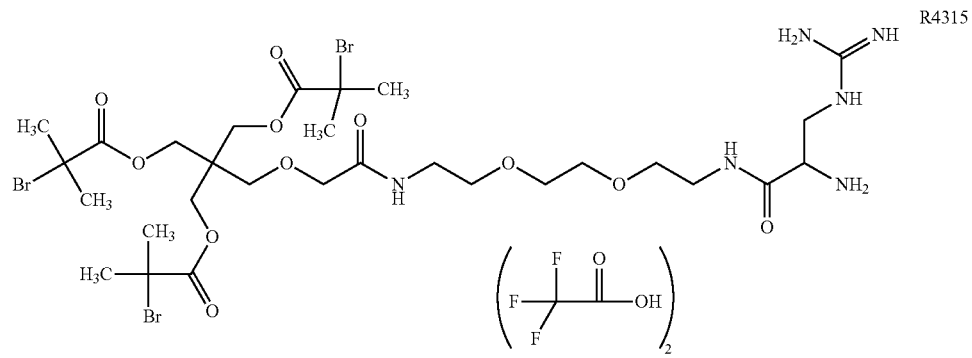

R4315

173 mg of R4302 was dissolved in 500 µl of TFA and incubated at room temperature for 80 minutes. The solution was diluted with water/acetonitrile and the product purified by RP-HPLC. Identity of the product was confirmed with LCMS and NMR.

Compound 4315 was used as an initiator for polymer synthesis to produce MPC polymer (R4367, shown below). In a 25 mL Schlenk tube was loaded 4.8 mg of 2,2'-bipyridyl, then 56.2 uL of a stock solution of initiator (R4315) in DMF (6.8 mg of initiator in 68 uL of DMF). Degas the stock solution then add 2.8 mg of Cu(I)Br, degas, then add the stock solution of monomer ({2-[(2-methylprop-2-enoyl)oxy]ethoxy}[2-(trimethylamino)ethoxy]phosphinic acid) in ethanol (1 g in 4 mL of ethanol) dropwise. Degas the reaction mixture for one hour at least and seal under 3 psi of Ar. Allow the reaction to proceed for 20 h at RT. Brown coloration: quenching, sampling for conversion and MW analysis. Purification by dialysis (MWCO is 1 kDa) 4 washings before freeze-drying. The resulting polymer was analyzed by SEC/MALS: PDI 1.1 and Mp 200.7 kDa.

Compound R4367

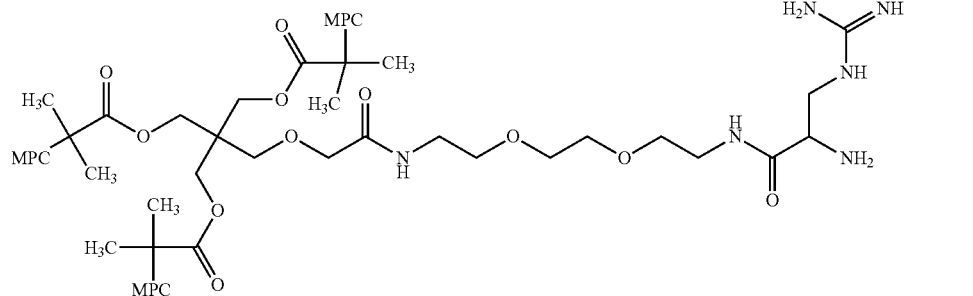

R4367

Finally, compound R4440, shown below, was produced by coupling Iodoacetic acid N-hydroxysuccinimide ester to R4367. 100 mg of R4367 was dissolved in 800 µl of water. To this was added 80 µl of 0.5 M pH 7.4 sodium phosphate buffer. To the buffered solution was added 100 µL of a 6.5 mg/mL solution of Iodoacetic acid N-hydroxysuccinimide ester. Incubate at room temperature for 5 minutes, then add a further 100 µL and incubated a further 30 minutes at room temperature. Dilute with water to ~10 mL, filter, centrifuge dialyze (30 kDa cut-off). Re-dialyze from water ×4. Dilute to ~10 mL, filter and lyophilize. SEC/MALS analysis: Mp 206 kDa, PDI 1.1.

Compound R4440

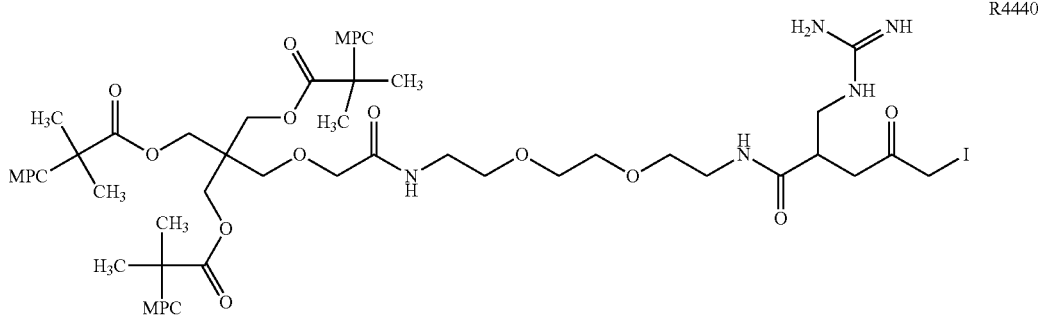

R4440

Example 22 Synthesis of Polymer R4342

First, R4180 (see above) was reacted with BOC-His(3-Me)-OH to produce R4176 as shown in the reaction scheme below:

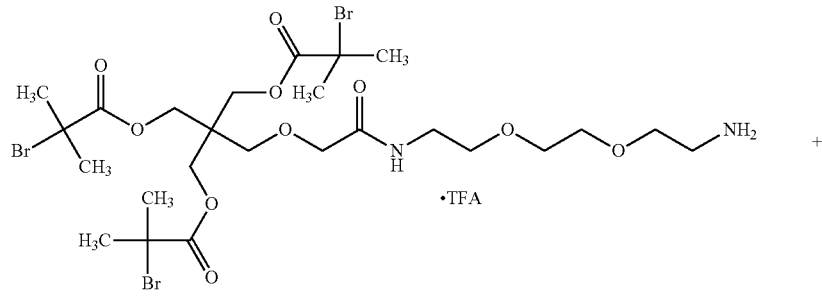

R4180 (actually R4167)

Compound R4180BOC-His(3-Me)—OH

-continued

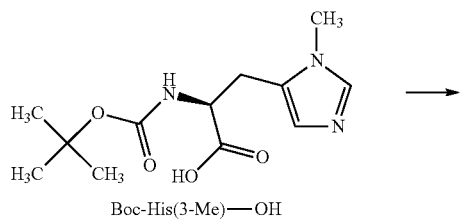

Boc-His(3-Me)—OH

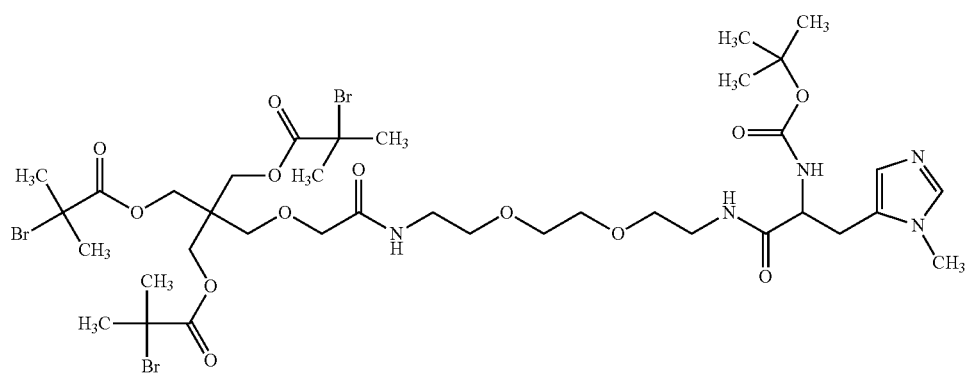

R4176

Compound R4176

165 mg of R4180 and 50 mg of BOC-His(3-Me)-OH were suspended in acetonitrile. The R4180 dissolved but the BOC-His(3-Me)-OH did not. 165 μl of N,N-Diisopropylethylamine was added and the acid dissolved. Following, 144 μl of polyphosphonic acid anhydride solution was added and the reaction mixture incubated for about an hour. Another 80 μl of polyphosphonic anhydride solution was added and the reaction mixture allowed to stand for another 45 minutes. The reaction mixture was then acidified with acetic acid and diluted with methanol. R4176 was purified by RP-HPLC.

Next, the BOC group of R4176 was removed via TFA to produce compound R4182, shown below. 117 mg of R4176 was dissolved in 500 μl TFA and incubated for 10 minutes at room temperature. The reaction mixture was then diluted with water/acetonitrile and R4182 purified by RV-HPLC.

Compound R4182

Compound R4182

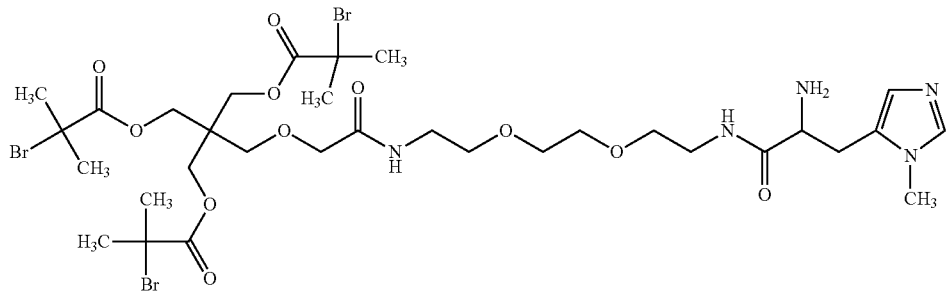

Compound R4182 was used as a substrate for MPC polymer synthesis to produce compound R4259. In a 25 mL Schlenk tube was loaded 4.8 mg of 2,2'-Bipyridyl, then 57.1 uL of a stock solution of initiator (R4182) in DMF (6.8 mg of initiator in 68 uL of DMF). Degas the stock solution then add 2.8 mg of CuBr, degas, then add the stock solution of monomer 2-hydroxyethyl methacrylate phosphorylcholine in ethanol (1 g in 4 mL of ethanol) dropwise. Degas the reaction mixture for one hour at least and seal under 3 psi of Ar. Allow the reaction to proceed for 20 h at RT. Brown coloration: quenching, sampling for conversion and MW analysis. Purification by dialysis (MWCO is 1 kDa) 4 washings before freeze-drying. SEC/MALS: PDI=1.1 and Mp=225.7 kDa.

Finally, compound R4259 was reacted with Iodoacetic acid N-hyroxysuccinimide ester to produce compound R4342, shown below. 100 mg of polymer R4259 was dissolved 800 µl of water. To this 50 µl of 0.5 M pH 7.4 sodium phosphate buffer was added. Add 100 µL of a 6.5 mg/mL solution of Iodoacetic acid N-hydroxysuccinimide ester in THF was added. This solution was incubated in room temperature for 5 minutes. Add an additional 100 µL of the 6.5 mg/mL NHS ester/THF solution. Incubate for 30 more minutes at room temperature. Dilute to ~10 mL with water. Filter. Centrifuge dialyze (30 kDa cut-off). Re-dialyze ×4. Dilute to ~10 mL with water, filter and lyophilize SEC/MALS: Mp 227.7 kDa, PDI 1.1.

Polymer R4342

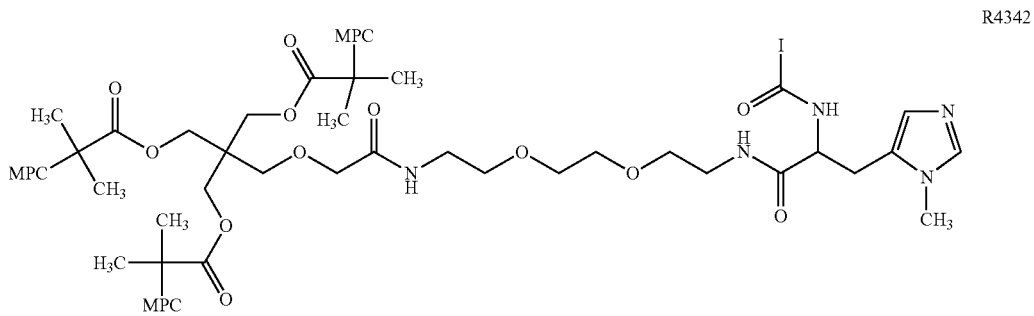

Example 23 Synthesis of Polymer R4439

First, R4180, see above, was reacted with 2-{[(tert-butoxy)carbonyl]amino}-5-(dimethylamino)pentanoic acid trifluoroacetic acid salt, as shown below, to produce compound R4301.

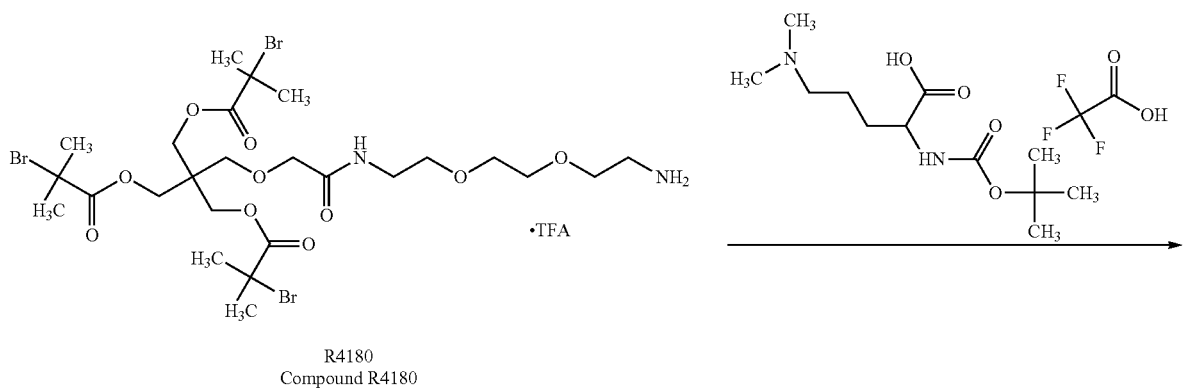

R4180
Compound R4180

-continued

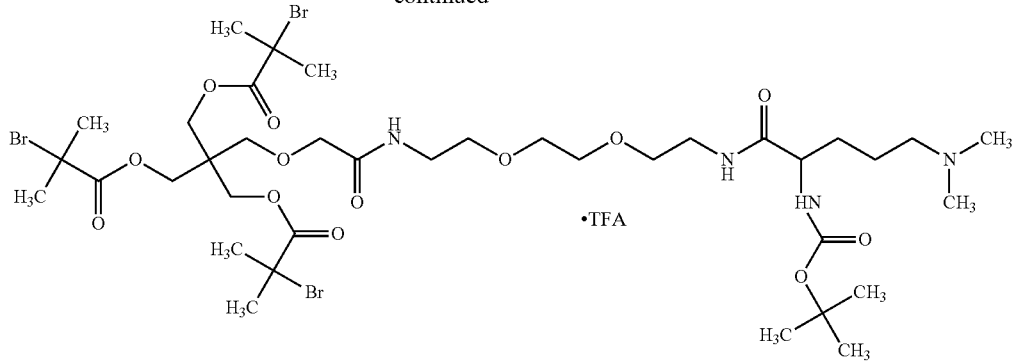

R4301
Compound R4301

200 mg of R4180 was dissolved in 2 ml of acetonitrile. This solution was added to 130 mg of 2-{[(tert-butoxy)carbonyl]amino}-5-(dimethylamino)pentanoic acid trifluoroacetic acid salt which was dissolved. 300 μl of N,N-Diisopropylethylamine (DIPEA) was added as was 175 μl of propylphosphonic acid anhydride (T3P solution). The reaction mixture was allowed to stand at room temperature for about 30 minutes. An additional 200 μl of DIPEA and 100 μl of T3P were added and the reaction mixture allowed to stand for another 15 minutes. The mixture was diluted with water, acetic acid and methanol. R4301 was purified by RP-HPLC and confirmed by LCMS.

Next the BOC protective moiety was removed from R4301 via TFA to produce compound R4314. 93 mg of R4301 was dissolved in 500 μl of TFA. The reaction mixture was allowed to stand for 20 minutes at room temperature. Thereafter the reaction mixture was diluted with water/acetonitrile and R4314 was purified by RV-HPLC.

R4314 was then used a substrate for MPC polymer production to produce R4366. In a 25 mL Schlenk tube was loaded 4.8 mg of 2,2'-Bipyridyl, then 56.9 uL of a stock solution of initiator (R4314) in DMF (9.2 mg of initiator in 92 uL of DMF). Degas the stock solution then add 2.8 mg of CuBr, degas, then add the stock solution of monomer in ethanol (1 g in 4 mL of ethanol) dropwise. Degas the reaction mixture for one hour at least and seal under 3 psi of Ar. Allow the reaction to proceed for 20 h at RT. Brown coloration: quenching, sampling for conversion and MW analysis. Purification by dialysis (MWCO is 1 kDa) 4 washings before freeze-drying. SEC/MALS: PDI=1.1, Mp=233.4 kDa.

Finally, R4366 was reacted with Iodoacetic acid N-hydroxysuccinimide ester to produce R4439 (shown below). 100 mg of polymer R4366 was dissolved in 800 μl of water. To this was added 80 μl of 0.5 M pH 7.4 sodium phosphate buffer. To this 100 μl of 6.5 mg/ml solution of Iodoacetic acid N-hydroxysuccinimide ester in THF. The reaction mixture was allowed to stand at room temperature for 5 minutes at which point another 100 μl of the ester was added. The reaction mixture was allowed to stand at room temperature for another 30 minutes. Dilute with water to ~10 mL, filter, centrifuge dialyze (30 kDa cut-off). Re-dialyze from water ×4. Dilute to ~10 mL, filter and lyophilize: SEC/MALS: Mp 233.4 kDa, PDI 1.1.

Polymer R4439

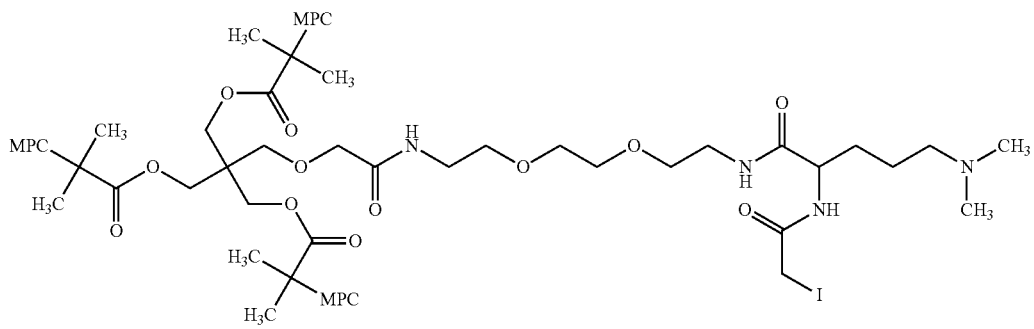

R4439

Example 24 Synthesis of R4441

First, R4108 (see above) was reacted with BOC-Dab (Me2)-OH, TFA salt to produce R4308 as shown in the scheme below:

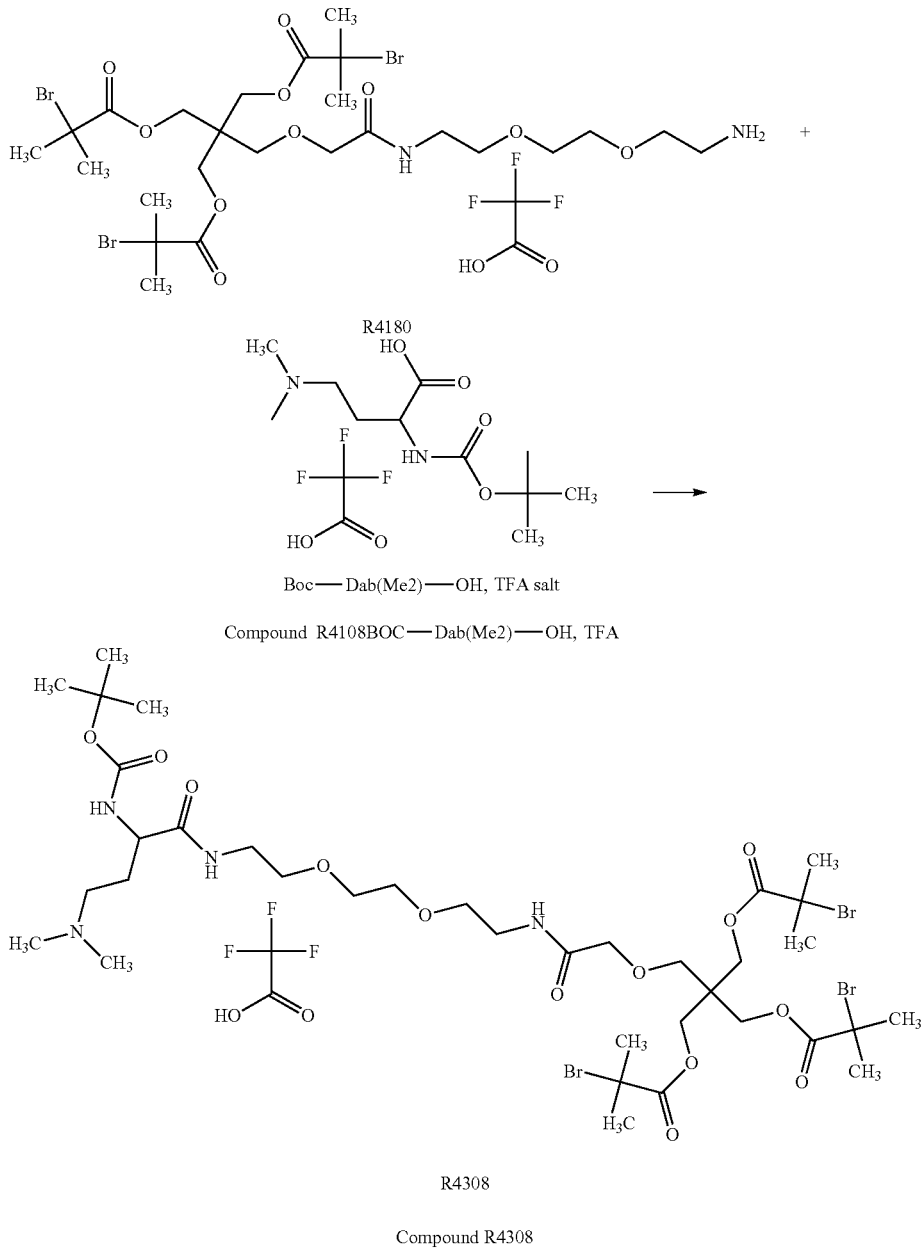

Compound R4308

200 mg of 4180 was dissolved in 2 ml of acetonitrile. The solution was then used to dissolve 106 mg of BOC-Dab (Me2)-OH, TFA salt. 200 µl of N,N-Diisopropylethylamine (DIPEA) and 265 µl of propylphosphonic anhydride (T3P) was added. Incubate at room temperature for 15 minutes. Add 200µ more of DIPEA and 175 µl T3P and incubate for 15 minutes more. Add water, then acetic acid. Dilute with methanol. Purify R4308 via RV-HPLC. Confirm by LCMS.

Next, the BOC protective group was removed to provide R4331 via TFA. 135 mg of R4308 was dissolved in 500 µl of TFA. The reaction mixture was allowed to stand for 15 minutes. R4331 was purified by RV-HPLC.

R4331 was then used as an initiator for polymer synthesis to provide polymer R4368. In a 25 mL Schlenk tube was loaded 4.8 mg of 2,2'-Bipyridyl, then 56.2 uL of a stock solution of initiator in DMF (7.1 mg of initiator in 71 uL of DMF). Degas the stock solution then add 2.8 mg of CuBr, degas, then add the stock solution of monomer in ethanol (1 g in 4 mL of ethanol) dropwise. Degas the reaction mixture for one hour at least and seal under 3 psi of Ar and allow the reaction to proceed for 20 h at RT when a brown coloration. The reaction was then quenched for sampling, conversion and MW analysis. Purification by dialysis (MWCO is 1 kDa) 4 washings before freeze-drying. SEC/MALS analysis: PDI 1.1, Mp 256.6 kDa.

Finally, R4368 was reacted with Iodoacetic acid N-Hydroxysuccinimide ester to provide R4441, shown below. 100 mg of R4368 was dissolved in 800 µl of water. 80 nl of 0.5 M pH 7.4 sodium phosphate buffer was added. Add 100 µL of a 6.5 mg/mL solution of NHS ester. Leave at room temperature for 5 minutes, then add a further 100 µL. Allow to sit for 30 minutes. Dilute with water to ~10 mL, filter, centrifuge dialyze (30 kDa cut-off). Re-dialyze from water ×4. Dilute to ~10 mL, filter and lyophilize SEC/MALS R4441 Mp 256.6 kDa, PDI 1.1.

200 mg of R4180 and 74 mg of BOC-L-Lys(Me2)-OH were dissolved in 2 ml of acetonitrile. To this was added 200 µl of N,N-Diisopropylethylamine (DIPEA) and 204 µl of Propylphosphonic acid anhydride (T3P). The reaction mixture was allowed to stand for 15 minutes at room temperature. The reaction mixture was then diluted with water and stirred for 5 minutes. Finally, the reaction mixture was acidified with acetic acid and diluted with methanol. R4196 was purified by RV-HPLC and the product confirmed by LCMS.

Next the BOC group on R4196 was removed via TFA to produce R4211, compound shown below. 153 mg of R4196 was dissolved in 500 µl of TFA. Solution allowed to sit at room temperature for 15 minutes. Dilute by water/acetonitrile. Purify by RV-HPLC. Structure confirmed by LCMS and NMR.

Compound R4441

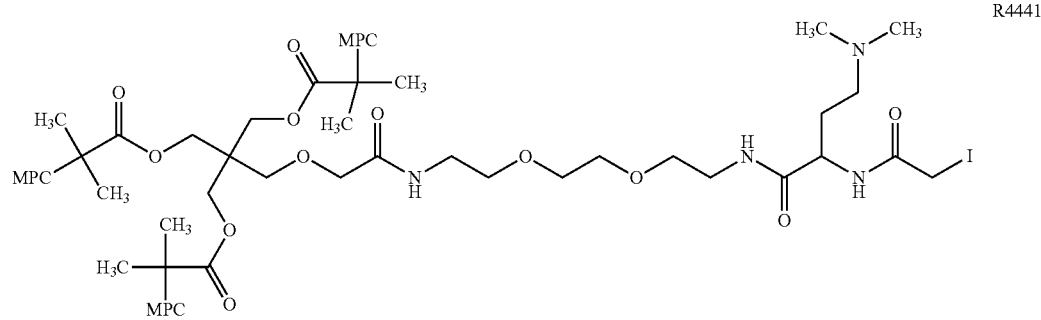

Example 25 Synthesis of Polymer R4320

First, R4180, see above, was reacted with BOC-Lys(Me2)-OH to produce R4196.

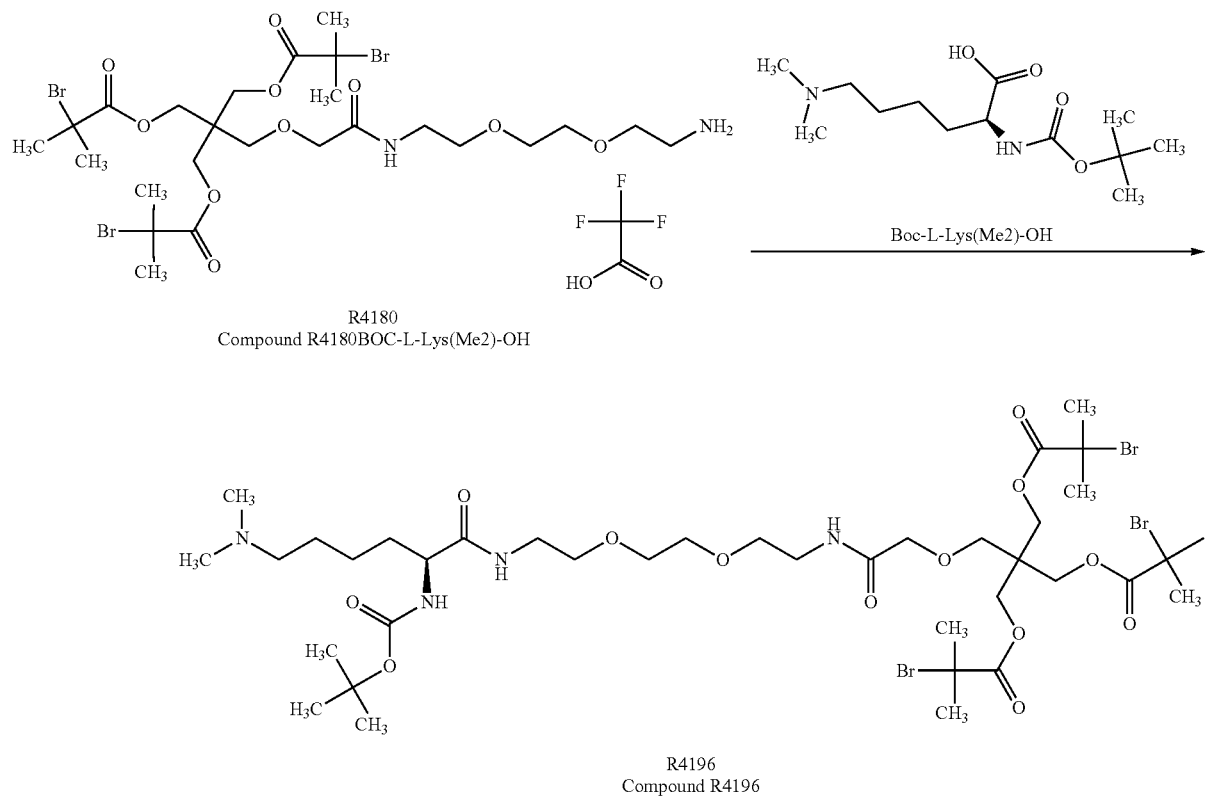

R4180
Compound R4180 BOC-L-Lys(Me2)-OH

R4196
Compound R4196

Compound R4211

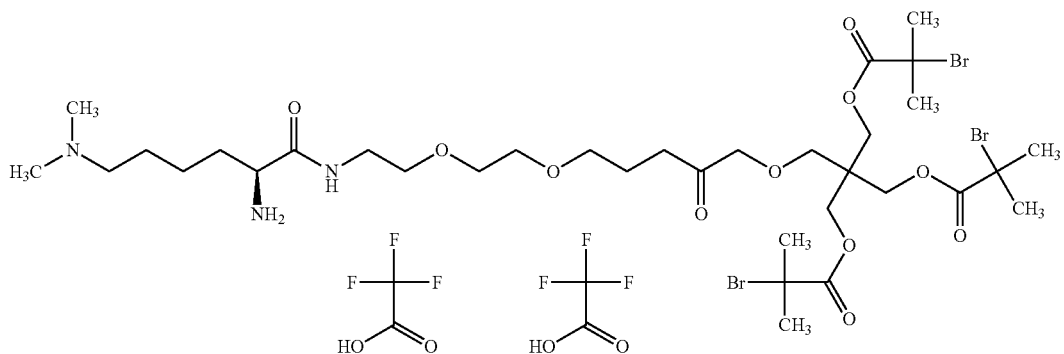

Next, R4211 was used as a substrate for MPC polymer production to produce polymer R4255. In a 25 mL Schlenk tube was loaded 4.8 mg of 2,2'-Bipyridyl, then 57.7 uL of a stock solution of initiator in DMF (8 mg of initiator in 80 uL of DMF). Degas the stock solution then add 2.8 mg of CuBr, degas, then add the stock solution of monomer in ethanol (1 g in 4 mL of ethanol) dropwise. Degas the reaction mixture for one hour at least and seal under 3 psi of Ar. Allow the reaction to proceed for 20 h at RT. Brown coloration: quenching, sampling for conversion and MW analysis. Purification by dialysis (molecular weight cutoff is 1 kDa) 4 washings before freeze-drying. SEC/MALS: PDI 1.076, Mp 205.3.

Finally, polymer R4320 (shown below) was produced by coupling polymer R4255 to Iodoacetic acid N-Hydroxysuccinimide ester. 100 mg of R4255 was dissolved in 800 µl of water. To this was added 80 µl of 0.5 M pH 7.4 sodium phosphate buffer. Add 100 µL of a 6.5 mg/mL solution of NHS ester in THF. Stir 5 minutes, then add a further 100 µL of NHS ester solution. Let stand at room temperature for 30 minutes. Dilute with water to ~10 mL volume, filter, centrifuge and dialyze (30 kDa MW cutoff).

Dilute to ~10 mL and re-dialyze 4 times. Dilute to ~10 mL, filter and lyophilize. SEC/MALS: Mp: 225.7 kDa, PDI: 1.1.

Polymer R4320

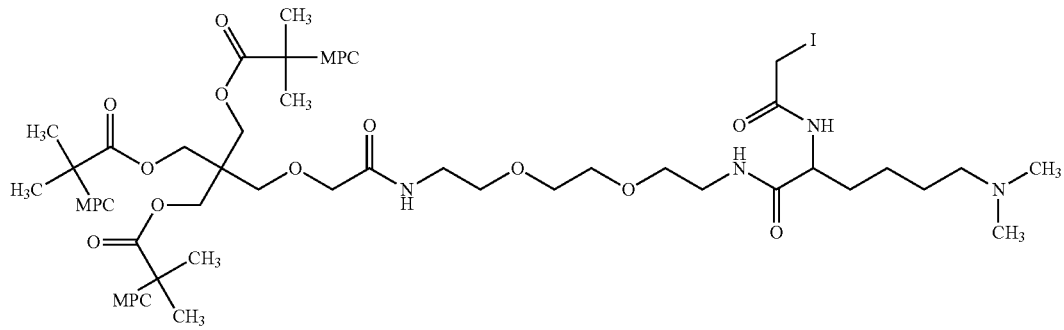

Example 26 Synthesis of Polymer R4438

First, R4180 (see above) was reacted with BOC-Dap (Me2)-OH TFA salt to produce compound R4300 as shown below.

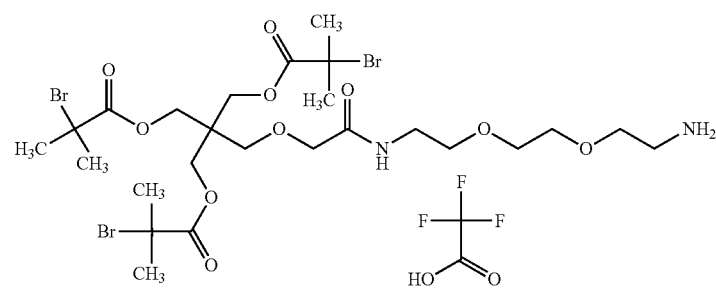

R4180
Compound R4180BOC-Dap(Me2)-OH, TFA

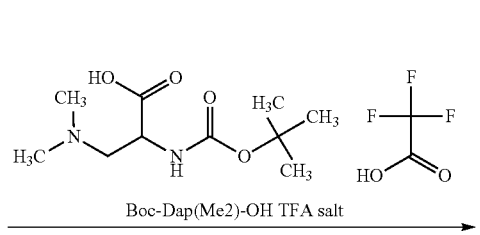

Boc-Dap(Me2)-OH TFA salt

-continued

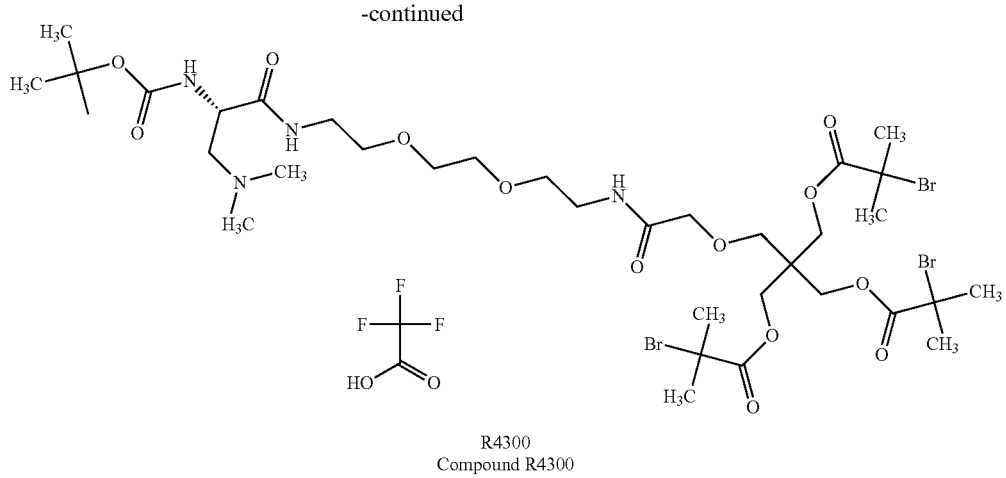

R4300
Compound R4300

200 mg of R4180 and 86 mg of BOC-Dap(Me2)-OH TFA salt were dissolved in 2 ml of acetonitrile. 200 µl of N,N-Diisopropylethylamine (DIPEA) and 175 µl of propylphosphonic anhydride solution (T3P) were added and the solution incubated at room temperature for about 15 minutes. 40 mg more of the BOC-Dap(Me2)-OH TFA salt, 200 µl more of DIPEA and 100 µl more of T3P were added, followed by another 10 minutes incubation at room temperature. Dilute with water, acidify with acetic acid then dilute with methanol. R4300 purified by RV-HPLC and confirmed by LCMS.

Next, the BOC group on R4300 was removed via TFA to produce R4307 as shown below:

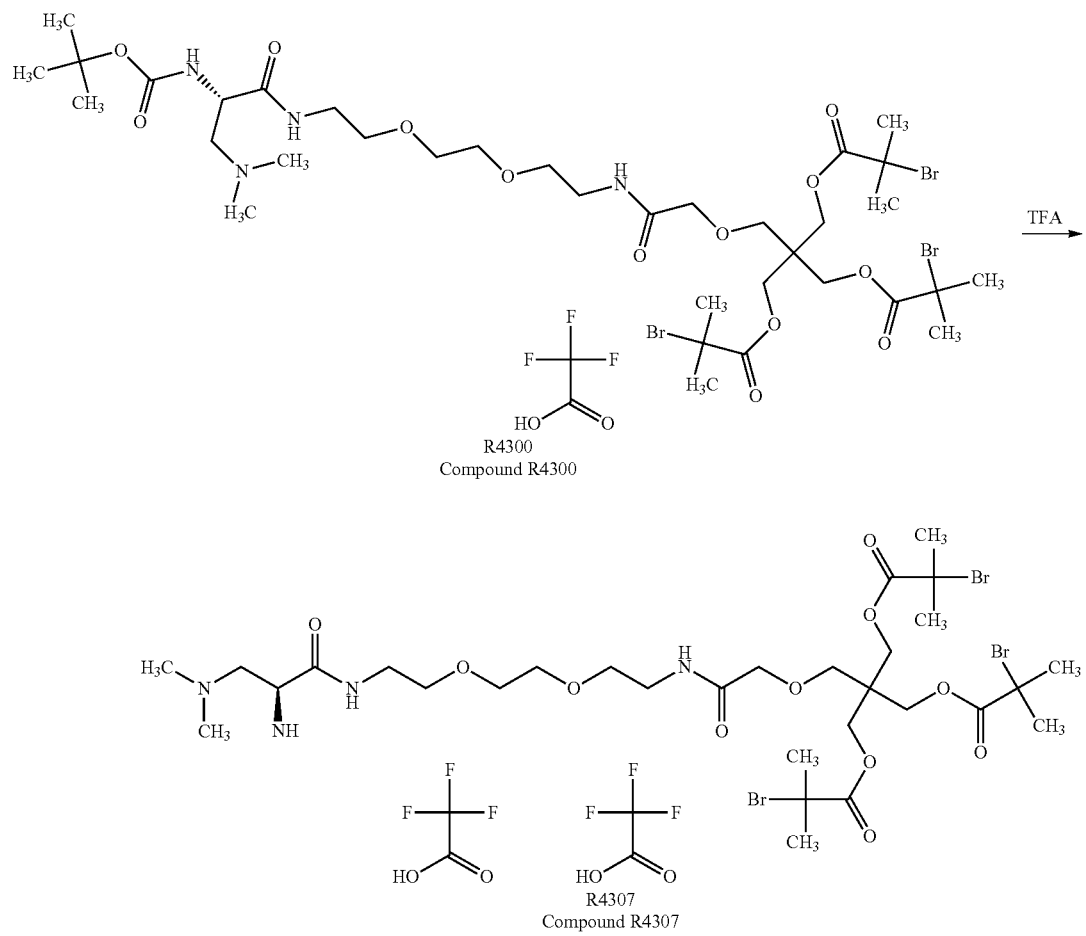

118 mg of R4300 was dissolved in 500 µl of TFA and the reaction mixture allowed to stand for 20 minutes. Water/acetonitrile were added and compound 4307 was purified by RF-HPLC and confirmed by LCMS.

Next, R4307 was used as an initiator for MPC polymer synthesis. In a 25 mL Schlenk tube was loaded 4.8 mg of 2,2' Bipyridiyl, then 55.5 uL of a stock solution of initiator in DMF (6.8 mg of initiator in 68 uL of DMF). Degas the stock solution then add 2.8 mg of CuBr, degas, then add the stock solution of monomer in ethanol (1 g in 4 mL of ethanol) dropwise. Degas the reaction mixture for one hour at least and seal under 3 psi of Ar. Allow the reaction to proceed for 20 h at RT. Brown coloration: quenching, sampling for conversion and MW analysis. Purification by dialysis (MWCO is 1 kDa) and washing before freeze-drying procedure. SEC/MALS: Mp 230.8 kDa, PDI 1.1.

Finally, iodoacetamide functionality was added to R4307 to produce compound R4438 (shown below). 100 mg of R4307 was dissolved in 800 µl of water. To this was added 80 µl of 0.5 M pH 7.4 sodium phosphate buffer. Then add 100 µl of a 6.5 mg/ml solution of the NHS ester was added, followed by incubation at room temperature for 5 minutes. Add a further 100 µL of a 6.5 mg/mL solution of NHS ester and incubate for about 40 minutes at room temperature. Dilute with water to ~10 mL, filter, centrifuge dialyze (30 kDa cut-off). Re-dialyze from water ×4. Dilute to ~10 mL, filter and lyophilize. SEC/MALS: Mp 230.8 kDa, PDI 1.1.

Polymer R4438

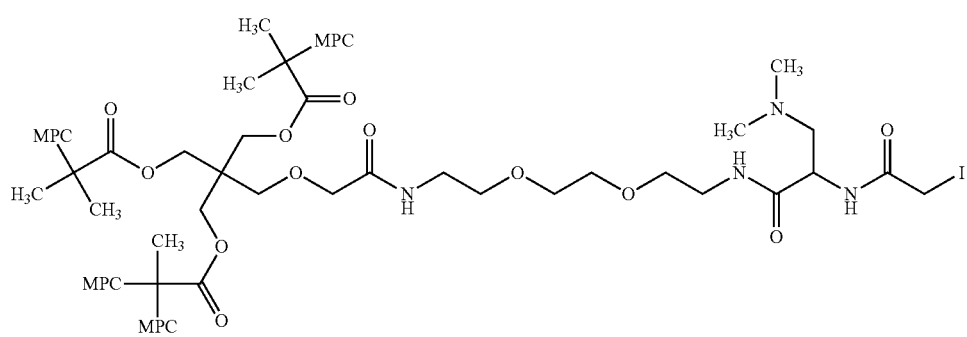

Example 27 Synthesis of Polymer R4451

First, R4180 (see above) was reacted with BOC-homoarg-OH.HCl to produce R4366 as shown below:

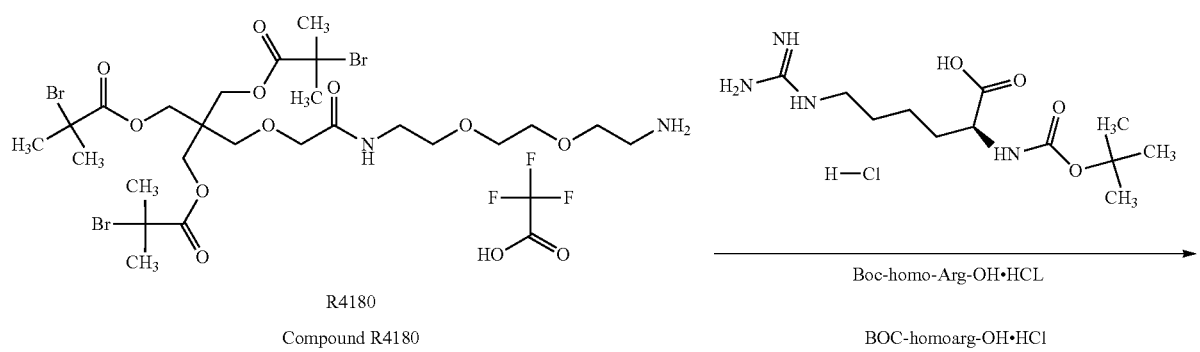

Compound R4180  BOC-homoarg-OH·HCl

-continued

R4366
Compound R4366

200 mg of R4180 was dissolved in 2 ml of acetonitrile. This solution was added to 80 mg of BOC-homoarg-OH.HCl, which was partially soluble. 175 µl of Diisopropylethylamine (DIPEA) was added and the BOC-homoarg-OH.HCl all appeared to precipitate out. However, when 200 µl of propylphosphonic anhydride solution (T3P) was added all solids dissolved. This reaction mixture was incubated for 40 minutes at room temperature. Another 81 mg of BOC-homoarg-OH.HCL was added followed by 200 µl more of DIPEA and 175 µl more of T3P. The reaction mixture was incubated for another 50 minutes. The reaction mixture was diluted with water and R4366 was purified by RV-HPLC and confirmed by LCMS.

Next, the BOC group was removed to produce compound R4354 as shown:

Compound R4366

TFA →

R4354
Compound R4354

90 mg of R4366 was dissolved in 500 μl of TFA. 30 minutes at room temperature. Add water/acetonitrile. Purify by RV-HPLC and confirm by LCMS and NMR.

Next, R4354 was used as a substrate for MPC polymer synthesis to produce R4386. In a 25 mL Schlenk tube was loaded 4.8 mg of 2,2 Bipyridyl, then 58.3 uL of a stock solution of initiator (R4354) in DMF (7.4 mg of initiator in 74 uL of DMF). Degas the stock solution then add 2.8 mg of CuBr, degas, then add the stock solution of monomer in ethanol (1 g in 4 mL of ethanol) dropwise. Degas the reaction mixture for one hour at least and seal under 3 psi of Ar. Allow the reaction to proceed for 20 h at RT. Brown coloration: quenching, sampling for conversion and MW analysis. Purification by dialysis (MWCO is 3.5 kDa) before the freeze-drying procedure. SEC/MALS PDI 1.1 Mp 258.4 kDa.

Finally, an iodoacetamide functionality was added to R4386 to produce R4551 (shown below). 100 mg of R4386 was dissolved in 800 μl of water. To this was added 80 μl of 0.5 M pH 7.4 sodium phosphate buffer. 100 μl of a 6.5 mg/ml solution of Iodoacetic acid N-Hydroxysuccinimide ester was added. Incubate at room temperature for 5 minutes and add another 100 μl of the NHS ester.

Incubate at room temperature for 30 minutes. Dilute with water to ~10 mL, filter, centrifuge dialyze (30 kDa cut-off). Re-dialyze from water x 4. Dilute to ~10 mL, filter and lyophilize. SEC/MALS: Mp 258.4 kDa, PDI 1.1.

where n is the number of PEG units. PEG Reagent R500 is conveniently synthesized by the following reaction:

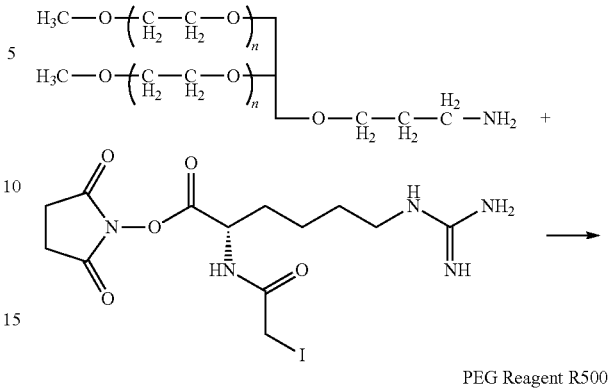

PEG Reagent R500

Example 29

Mammalian expression vector, cell line and expression optimization for rhBuChE534 (C66Y)-Fc (L234A, L235E, G237A, A330S, P331S, Q347C, EU numbering)

A DNA fragment containing the rhBuChE534 (C66Y)-Fc (L234A, L235E, G237A, A330S, P331S, Q347C, EU numbering) construct was cloned into a mammalian expression Compound R4451

R4451

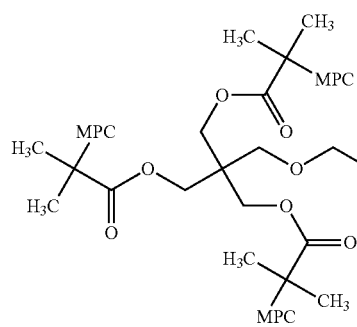

Example 28 Synthesis of PEG Reagents

PEG reagents are conveniently made via coupling of NHS esters to amines. Branched PEGs ending in amine functionalities are commercially available. For example, the following PEG iodoacetamine reagent may be used in accordance with the instant invention:

PEG Reagent R500

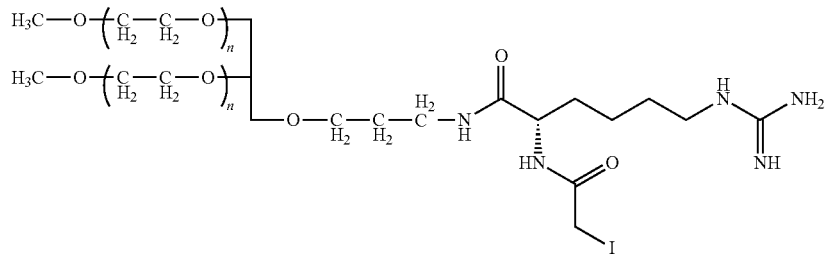

vector encoding a puromycin resistance gene. The sequence that was inserted is shown in SEQ ID NO: 9. The expression vector with the inserted BuChE-Fc fusion is called Construct 14. Construct 14 was transfected into CHO cells and a stable transfected pool was constructed. The stable pool was subjected to cell line development and a stably transfected clone was isolated called C98. A shake flask study was performed to determine which media and conditions to use to maximize the amount of protein produced. Seeding density for each flask was 0.4.times.106 cells/ml. The results are set forth in Table 2 below:

TABLE 8

Shake Flask Experiment

| Flask # | Medium | Feed Condition | Feed Amount | Feed Days | Temp Shift? | Peak Titer (mg/L) |
|---|---|---|---|---|---|---|
| 1 | CD OptiCHO | Glucose Only | Up to 4 g/L | As needed | No | 60 |
| 2 | CD OptiCHO | CD Efficient Feed C | 10% | 3, 6 | No | 40 |
| 3 | CD OptiCHO | CD Efficient Feed C | 10% | 3, 6 | Yes | 35 |
| 4 | CD FortiCHO | Glucose only | Up to 4 g/L | As needed | No | 145 |
| 5 | CD FortiCHO | CD Efficient Feed C (2x) | 5% | 3, 6 | No | 475 |
| 6 | CD FortiCHO | CD Efficient Feed C (2x) | 5% | 3, 6 | Yes | 265 |
| 7 | ActiCHO P | Glucose only | Up to 4 g/l | As needed | No | 150 |
| 8 | ActiCHO P | ActiCHO Feed A + B | 3% + 0.3% | 3 | No | 100 |
| 9 | ActiCHO P | ActiCHO Feed A + B | 3% + 0.3% | 3 | Yes | 80 |
| 10 | BalanCD CHO A | Glucose only | Up to 4 g/L | As needed | No | 35 |
| 11 | BalanCD CHO A | BalanCD Feed 3 | 15% | 3, 6 | No | 40 |
| 12 | BalanCD CHO A | BalanCD Feed 3 | 15% | 3, 6 | Yes | 40 |

Example 30 Unimolecular Initiators

The introduction of a basic group (e.g., guanidine or tertiary amines) covalently attached to the previous ATRP initiators resulted in potential interference during the polymerization process by ATRP due to potential complexing of the copper halide species (CuBr) with such basic groups when the ligand was added (2,2'-Bipyridine noted bpy). This example tests whether if such basic group claimed in the invention could also act as ligands in an ATRP process and to be able to skip the use of such compounds when aiming to obtain tailor-made polymers with such initiators.

Unimolecular ATRP initiators containing tertiary amine group covalently attached were already reported in the polymerization of styrene (polym. Preprint 2012 43(2), p 245). The goal of using such initiators in an ATRP system for vinylic monomers (styrene, methyl methacrylate) was only to suppress the use of external agent by covalently attach the amine onto the initiator but not for conjugation purpose where a bioactive compound is involved. Studies on unimolecular initiator were only performed on styrene and MMA in organic solvent (toluene) requiring heating. According to the authors, moderate control of the molecular weights were obtained. High molecular weights were achieved with a broader range distribution.

The use of guanidine molecules as ligand in ATRP process was reported as guanidine-pyridine derivatives (dimethylethyleneguanidine)methylenepyridine (DMEGpy) or (tetramethylguanidine)methylenepyridine (TMGpy). These structures were not used as ligands in an ATRP process for the control polymerization of styrene and methyl methacrylate. Low molecular weight polymers were obtained only (below 10,000 Da).

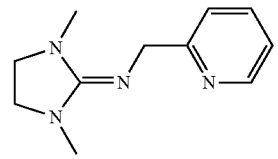

TMGpy

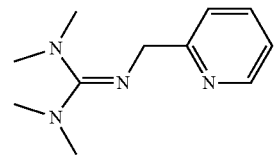

DMEGPy

This example tests whether groups newly introduced on the initiator do not interfere with the traditional ATRP process described above and check on their capability to be used as a ligand in an ATRP polymerization process.

A first block Poly (HEMA-PC) was synthesized (step 1) without any bpy introduced to check on the polymer formation and the control of the molecular weight. This step was followed by the introduction of bpy and an incremental addition of monomer (step 2) to check on a chain extension and the livingness of the system according to the scheme below.

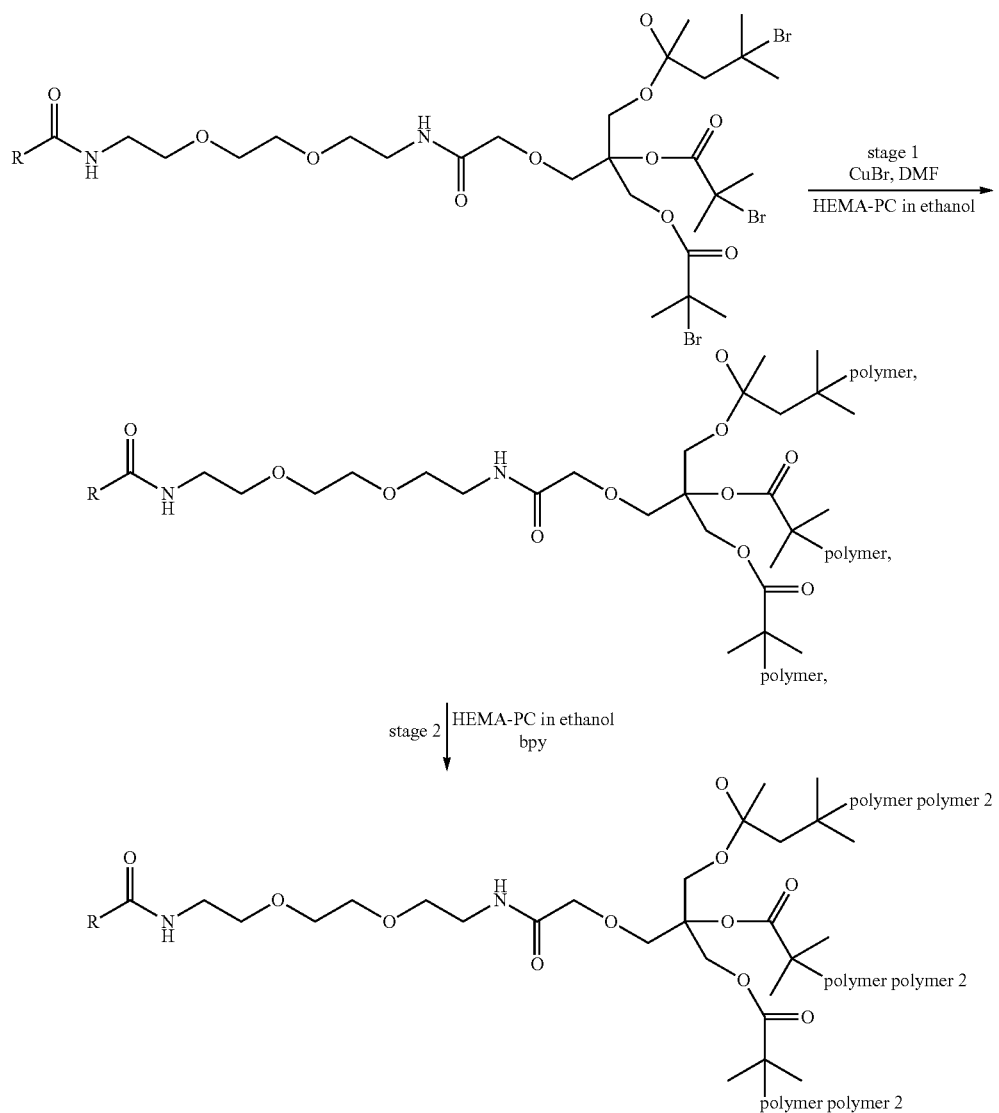
Compounds R4235 was used as a reference. The structure of all the other compounds used are described below:
Compound R4235
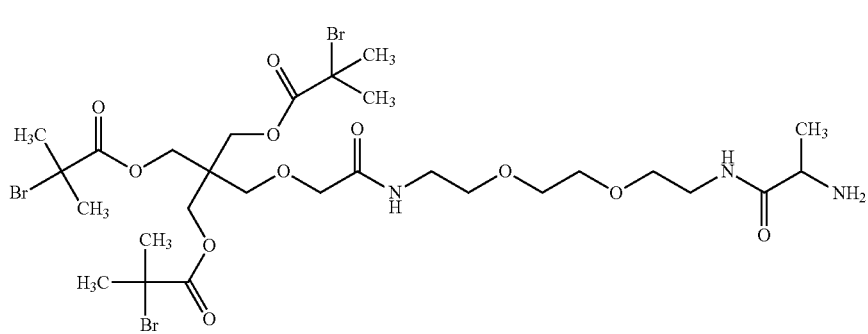
TFA salt Compound R4315
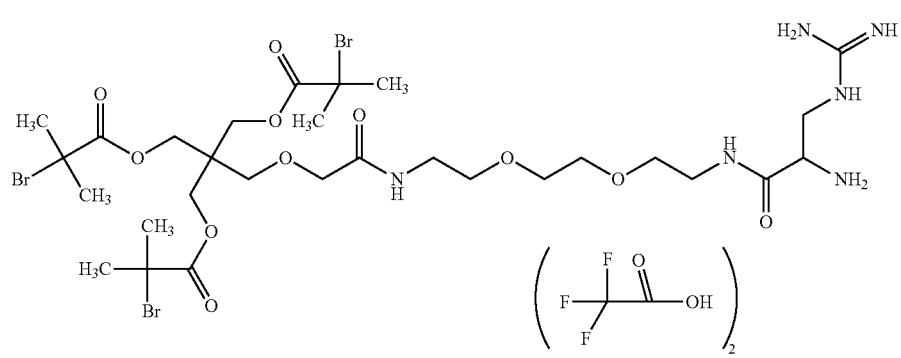
Compound R4334
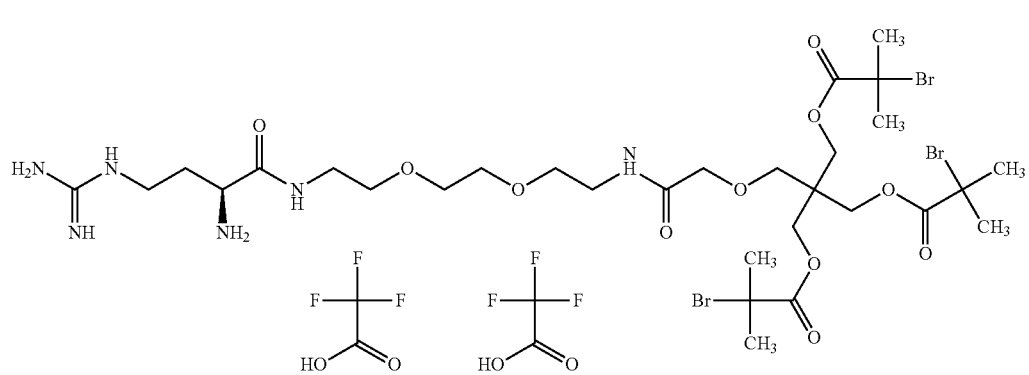
Compound R4037
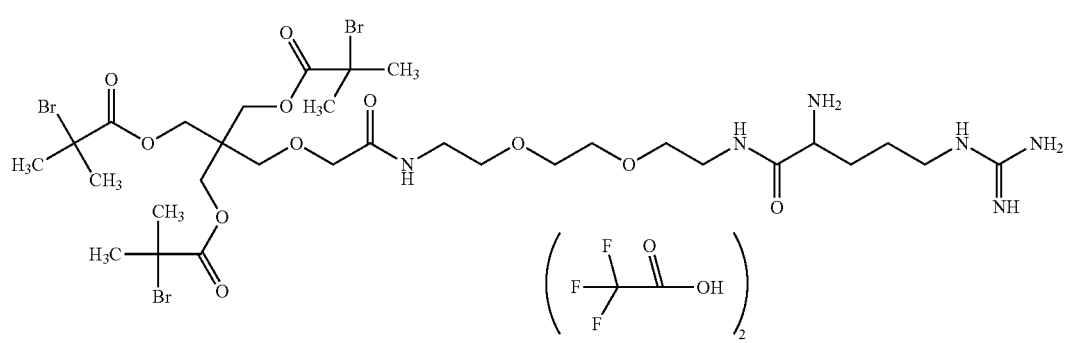
Compound R4314
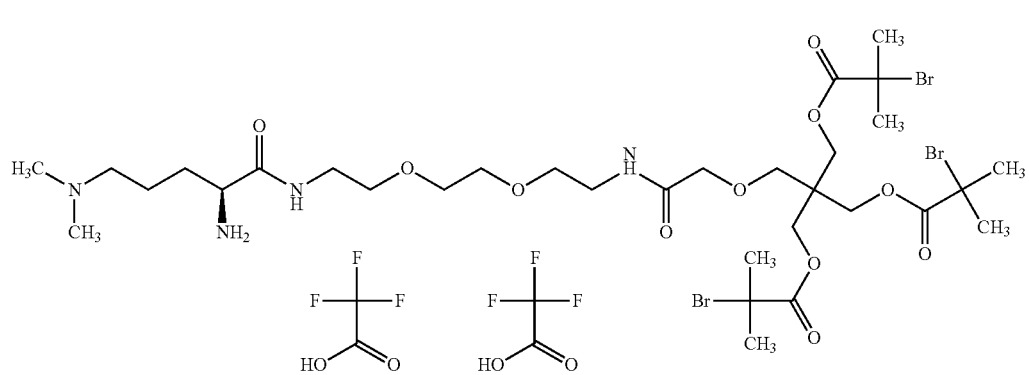

Compound R4211

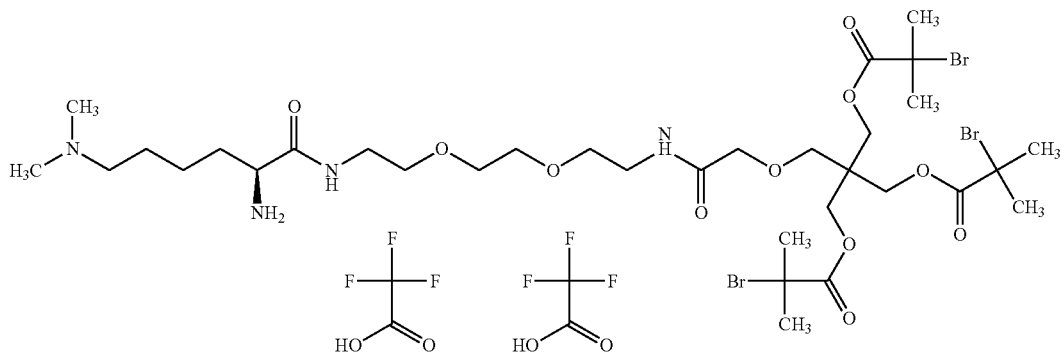

Compound R4182

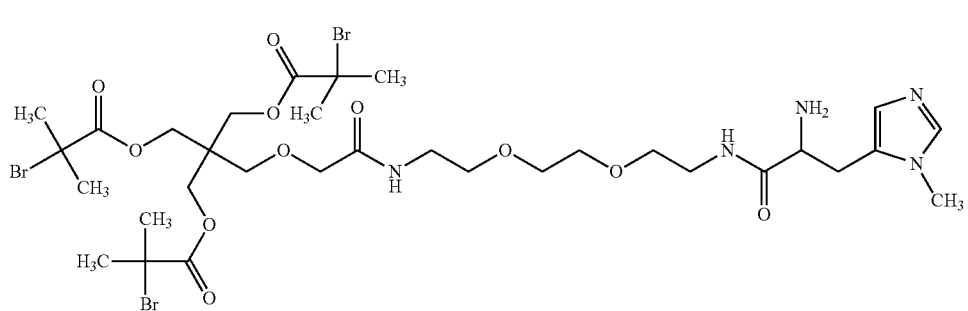

The protocol used was the same for all the initators:

Polymerization protocol without bpy as ligand. A stock solution of initiator as a 100 mg/mL in DMF was freshly prepared. The solution was dispensed to introduce 5×10-6 mol of initiator in the Schlenk tube. The solution was degassed before the addition of 2.48 mg of CuBr (1.7×10-5 mol) (no change of coloration). A stock solution of HEMA-PC in ethanol (1 g in 4 mL) was added dropwise. Reaction mixture was seated under 3 psi and polymerization and allowed to proceed at RT for 20 hours at RT Reaction stayed colorless and a aliquots was taken to analyze the conversion and molecular weights in each case (see table below on step 1).

In step 2, bpy was added to the crude mixture of step 1 immediately followed by an incremental addition of monomer (HEMA-PC) in solution (1 g in 2 mL of ethanol) and 4.8 mg of bpy (3.1×10−5 mol) inside the reaction mixture (a brown coloration immediately appears). Reaction was sealed, thoroughly degassed, homogenized and allowed to proceed at room temperature until viscous before final quenching.

Results are shown in table 9 below:

TABLE 9

| | | 1st block (no bpy introduced) Step1 | | | | 2nd block (polymerization continuation afte introduction of bpy as external ligand) Step 2 | | | |
|---|---|---|---|---|---|---|---|---|---|
| | Initiator | Mn | Mp | PDI | conversion | Mn | Mp | PDI | conversion |
| Reference | R4235 | N/A | N/A | N/A | N/A | 335 | 406 | 1.15 | 92 |
| Guanidine series | R4315 | 220 | 245 | 1.15 | 81 | 350 | 415 | 1.15 | 95 |
| | R4334 | 255 | 318 | 1.2 | 96 | 368 | 436 | 1.2 | 95 |
| | R4037 | 210 | 255 | 1.2 | 91 | 354 | 410 | 1.15 | 95 |
| | R4354 | 260 | 330 | 1.2 | 94 | 360 | 420 | 1.2 | 95 |
| Tertiary amine series | R4314 | 215 | 283 | 1.2 | 94 | 323 | 410 | 1.2 | 91 |
| | R4211 | 218 | 280 | 1.2 | 90 | 354 | 425 | 1.15 | 90 |
| Histidine series | R4182 | 205 | 260 | 1.2 | 95 | 335 | 415 | 1.2 | 97 |

In the absence of bpy for the reference (compound R4235) no polymer formation was obtained with in the presence of bpy. Polymerization proceeded only when bipyridyl as ligand was introduced inside the reaction mixture to reach the desired molecular weight and high conversion.

For all the other initiators listed in the table (compounds R4315, R4334, R4037, R4354, R4314, R4211 and R4182) polymerization proceeded in all cases without any bpy ligand introduced in the reaction for step one. Controlled molecular weights were obtained with low PDIs (1.2 and below). When adding bpy with an incremental addition of HEMA-PC monomer for step 2, a brown coloration a brown coloration immediately appeared suggesting a recomplexation of the copper species with bpy. Polymerizations were resumed in all case by a chain extensions of the polymers obtained in step 1 with the desired molecular weights and narrow polydispersities.

The newly introduced group not only participates at the conjugation at neutral pH but can also act as efficient ligand in an ATRP. For such polymerizations, the use of an external ligand (such as bpy) is unnecessary.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

```
                        SEQUENCE LISTING

SEQ ID NO: 1 (human butyrylcholinesterase P06276.1)
MHSKVTIICI RFLFWFLLLC MLIGKSHTED DIIIATKNGK VRGMNLTVFG
GTVTAFLGIP YAQPPLGRLR FKKPQSLTKW SDIWNATKYA NSCCQNIDQS
FPGFHGSEMW NPNTDLSEDC LYLNVWIPAP KPKNATVLIW IYGGGFQTGT
SSLHVYDGKF LARVERVIVV SMNYRVGALG FLALPGNPEA PGNMGLFDQQ
LALQWVQKNI AAFGGNPKSV TLFGESAGAA SVSLHLLSPG SHSLFTRAIL
QSGSFNAPWA VTSLYEARNR TLNLAKLTGC SRENETEIIK CLRNKDPQEI
LLNEAFVVPY GTPLSVNFGP TVDGDFLTDM PDILLELGQF KKTQILVGVN
KDEGTAFLVY GAPGFSKDNN SIITRKEFQE GLKIFFPGVS EFGKESILFH
YTDWVDDQRP ENYREALGDV VGDYNFICPA LEFTKKFSEW GNNAFFYYFE
HRSSKLPWPE WMGVMHGYEI EFVFGLPLER RDNYTKAEEI LSRSIVKRWA
NFAKYGNPNE TQNNSTSWPV FKSTEQKYLT LNTESTRIMT KLRAQQCRFW
TSFFPKVLEM TGNIDEAEWE WKAGPHRWNN YMMDWKNQFN DYTSKKESCV GL
Natural Leader, C66Y mutation and C-terminal removed domain underlined.

SEQ ID NO: 2 (preferred rBuChE534(C66Y)-GS10-Fc(w/mutations) fusion)
EDDIIIATKN GKVRGMNLTV FGGTVTAFLG IPYAQPPLGR LRFKKPQSLT
KWSDIWNATK YANSCYQNID QSFPGFHGSE MWNPNTDLSE DCLYLNVWIP
APKPKNATVL IWIYGGGFQT GTSSLHVYDG KFLARVERVI VVSMNYRVGA
LGFLALPGNP EAPGNMGLFD QQLALQWVQK NIAAFGGNPK SVTLFGESAG
AASVSLHLLS PGSHSLFTRA ILQSGSFNAP WAVTSLYEAR NRTLNLAKLT
GCSRENETEI IKCLRNKDPQ EILLNEAFVV PYGTPLSVNF GPTVDGDFLT
DMPDILLELG QFKKTQILVG VNKDEGTAFL VYGAPGFSKD NNSIITRKEF
QEGLKIFFPG VSEFGKESIL FHYTDWVDDQ RPENYREALG DVVGDYNFIC
PALEFTKKFS EWGNNAFFYY FEHRSSKLPW PEWMGVMHGY EIEFVFGLPL
ERRDNYTKAE EILSRSIVKR WANFAKYGNP NETQNNSTSW PVFKSTEQKY
LTLNTESTRI MTKLRAQQCR FWTSFFPKVL EMTGGGSGGG SGGGSDKTHT
CPPCPAPEAE GAPSVFLFPP KPKDTLMISR TPEVTCVVVD VSHEDPEVKF
NWYVDGVEVH NAKTKPREEQ YNSTYRVVSV LTVLHQDWLN GKEYKCKVSN
KALPSSIEKT ISKAKGQPRE PCVYTLPPSR DELTKNQVSL TCLVKGFYPS
DIAVEWESNG QPENNYKTTP PVLDSDGSFF LYSKLTVDKS RWQQGNVFSC
SVMHEALHNH YTQKSLSLSP GK
BuChE joined via linked (underlined) to IgG1-Fc with GS linker and amino
acid changes from wildtype underlined.

SEQ ID NO: 3 (human AChE AAA68151.1)
MRPPQCLLHT PSLASPLLLL LLWLLGGGVG AEGREDAELL VTVRGGRLRG
IRLKTPGGPV SAFLGIPFAE PPMGPRRFLP PEPKQPWSGV VDATTFQSVC
YQYVDTLYPG FEGTEMWNPN RELSEDCLYL NVWTPYPRPT SPTPVLVWIY
GGGFYSGASS LDVYDGRFLV QAERTVLVSM NYRVGAFGFL ALPGSREAPG
NVGLLDQRLA LQWVQENVAA FGGDPTSVTL FGESAGAASV GMHLLSPPSR
GLFHRAVLQS GAPNGPWATV GMGEARRRAT QLAHLVGCPP GGTGGNDTEL
VACLRTRPAQ VLVNHEWHVL PQESVFRFSF VPVVDGDFLS DTPEALINAG
DFHGLQVLVG VVKDEGSYFL VYGAPGFSKD NESLISRAEF LAGVRVGVPQ
VSDLAAEAVV LHYTDWLHPE DPARLREALS DVVGDHNVVC PVAQLAGRLA
AQGARVYAYV FEHRASTLSW PLWMGVPHGY EIEFIFGIPL DPSRNYTAEE
KIFAQRLMRY WANFARTGDP NEPRDPKAPQ WPPYTAGAQQ YVSLDLRPLE
VRRGLRAQAC AFWNRFLPKL LSATDTLDEA ERQWKAEFHR WSSYMVHWKN
QFDHYSKQDR CSDL
Leader peptide underlined SEQ ID NO: 5 (aryldialkylphosphatase [Desulfarculus baarsii DSM 2075;
ADK83762.1])
MAAKMVNTVA GPVSADELGL TLMHEHIVFG YPGWNGDVTL GAFDRPAAVK
QAVETLSALK QAFGLGTLVD ATPNETGRDP LLLKEVSEKS GVNIVCSTGY
YSQAEGGAAY FAFRASLGDA VAEIREMFLT ELTKGVADTG VRPGVIKLAS
SQGQITDYEK MFFTAAVAAQ KETGAPIITH TEHGTMGPEQ AKFLLELGAD
```

SEQUENCE LISTING

```
PKRTMIGHMC DNLDLDYQEA VLRQGVYVSW DRMGLQGLAG CPMEATRYPV
LNELIQRGWA KQLMLSHDSI NTWLGRPLSI PEAALPMVID WRPDHIFNKV
APALLAGGAT QADLDVILKD NPRRLFAGV

SEQ ID NO: 6 (human PON 1, P27169.3)
MAKLIALTLL GMGLALFRNH QSSYQTRLNA LREVQPVELP NCNLVKGIET
GSEDLEILPN GLAFISSGLK YPGIKSFNPN SPGKILLMDL NEEDPTVLEL
GITGSKFDVS SFNPHGISTF TDEDNAMYLL VVNHPDAKST VELFKFQEEE
KSLLHLKTIR HKLLPNLNDI VAVGPEHFYG TNDHYFLDPY LQSWEMYLGL
AWSYVVYYSP SEVRVVAEGF DFANGINISP DGKYVYIAEL LAHKIHVYEK
HANWTLTPLK SLDFNTLVDN ISVDPETGDL WVGCHPNGMK IFFYDSENPP
ASEVLRIQNI LTEEPKVTQV YAENGTVLQG STVASVYKGK LLIGTVFHKA LYCEL SEQ ID NO: 7 (diisopropylfluorophosphatase from Loligo vulgaris Q7SIG4.1)
MEIPVIEPLF TKVTEDIPGA EGPVFDKNGD FYIVAPEVEV NGKPAGEILR
IDLKTGKKTV ICKPEVNGYG GIPAGCQCDR DANQLFVADM RLGLLVVQTD
GTFEEIAKKD SEGRRMQGCN DCAFDYEGNL WITAPAGEVA PADYTRSMQE
KFGSIYCFTT DGQMIQVDTA FQFPNGIAVR HMNDGRPYQL IVAETPTKKL
WSYDIKGPAK IENKKVWGHI PGTHEGGADG MDFDEDNNLL VANWGSSHIE
VFGPDGGQPK MRIRCPFEKP SNLHFKPQTK TIFVTEHENN AVWKFEWQRN
GKKQYCETLK FGIF SEQ ID NO: 8 (human IgG1)
DKTHTCPPCP APELLGGPSV FLFPPKPKDT LMISRTPEVT CVVVDVSHED
PEVKFNWYVD GVEVHNAKTK PREEQYNSTY RVVSVLTVLH QDWLNGKEYK
CKVSNKALPA PIEKTISKAK GQPREPQVYT LPPSRDELTK NQVSLTCLVK
GFYPSDIAVE WESNGQPENN YKTTPPVLDS DGSFFLYSKL TVDKSRWQQG
NVFSCSVMHE ALHNHYTQKS LSLSPGK SEQ ID NO: 9 (DNA sequence preferred BuChE-GS10-Fc (w/mutations) fusion)
GCTAGCGCCG CCACCATGGC ATGCCTCGGA TTTCAAAGAC ATAAAGCCCA GTTGAACCTC
GCCACTAGAA CCTGGCCTTG CACCCTGCTG TTCTTCCTCC TGTTCATTCC GGTGTTCTGC
AAGGCTGAGG ACGACATCAT CATCGCTACC AAGAATGGAA AGGTCCGCGG TATGAACCTT
ACGGTGTTCG GCGGAACTGT CACTGCCTTC TTGGGGATCC CATACGCACA ACCCCCACTT
GGCAGACTGC GCTTTAAGAA ACCTCAATCG CTCACGAAGT GGAGCGATAT CTGGAACGCG
ACCAAGTACG CAAATAGCTG CTACCAGAAT ATCGATCAGA GCTTCCCCGG ATTCCACGGC
TCGGAAATGT GGAACCCGAA CACCGATCTG TCGGAGGATT GCCTGTACCT GAACGTCTGG
ATCCCGGCCC CTAAGCCGAA AAATGCTACC GTGTTGATCT GGATCTACGG GGGAGGATTC
CAAACCGGAA CTTCCAGCCT GCACGTCTAC GACGGAAAGT TTTTGGCGCG CGTGGAGCGG
GTCATTGTGG TGTCCATGAA TTACAGAGTG GGGGCTCTCG GATTCCTGGC ACTGCCAGGT
AACCCAGAGG CCCCGGGAAA CATGGGCCTG TTCGACCAGC AGCTCGCGCT TCAGTGGGTG
CAGAAGAATA TCGCCGCCTT TGGCGGTAAC CCGAAGTCGG TGACTCTCTT TGGCGAATCA
GCCGGAGCTG CATCAGTCTC CCTTCATCTG TTGTCCCCCG AAGCCACTC GCTGTTCACC
AGGGCGATCC TGCAATCCGG ATCCTTCAAC GCCCCATGGG CGGTTACTTC ACTTTACGAG
GCCCGTAACC GGACCCTTAA CCTGGCAAAG CTCACCGGAT GTAGCCGCGA GAACGAAACC
GAAATCATAA AGTGCCTGCG AAACAAAGAC CCACAAGAAA TCCTCCTGAA TGAGGCATTC
GTGGTCCCAT ACGGTACCCC GCTCTCAGTG AACTTCGGCC CCACTGTGGA CGGAGACTTC
CTGACCGACA TGCCGGACAT TTTGCTGGAG CTGGGCCAGT TCAAGAAAAC GCAGATCCTG
GTGGGCGTCA ACAAAGATGA AGGAACTGCG TTCCTCGTGT ACGGCGCCCC GGGCTTCTCA
AAGGACAACA ATTCCATCAT TACGCGGAAG GAGTTCCAAG AAGGGCTGAA AATCTTCTTC
CCTGGAGTGT CGGAATTTGG AAAGGAAAGC ATCCTGTTCC ACTACACCGA CTGGGTGGAC
GATCAGCGGC CGGAAAACTA CCGGGAGGCG CTGGGTGATG TGGTCGGAGA CTATAACTTC
ATCTGCCCGG CCCTGGAGTT TACCAAAAAG TTTTCCGAAT GGGGGAATAA TGCTTTCTTT
TACTACTTCG AACATAGAAG CTCGAAGCTC CCTTGGCCGG AATGGATGGG AGTTATGCAC
GGGTATGAAA TCGAGTTTGT CTTTGGGCTC CCTCTGGAGC GCAGGGATAA CTACACTAAA
GCCGAAGAGA TCCTGTCACG CTCGATCGTG AAGCGGTGGG CGAATTTCGC GAAGTACGGA
AATCCAAACG AAACTCAGAA CAACTCGACC TCGTGGCCGG TGTTCAAGTC TACCGAGCAG
AAATACCTCA CTCTGAATAC TGAATCAACC CGCATTATGA CTAAGCTCAG GGCCCAGCAA
TGTCGGTTCT GGACTTCCTT CTTCCCGAAA GTGCTCGAAA TGACTGGCGG TGGATCCGGA
GGCGGATCGG GTGGAGGCTC CGACAAGACG CACACCTGTC CGCCCTGCCC TGCCCCTGAA
GCCGAGGGAG CACCGTCGGT GTTTCTCTTC CCGCCAAAGC CAAAGGACAC TCTGATGATC
TCGCGCACTC CAGAGGTGAC TTGCGTCGTC GTGGATGTCA GCCACGAGGA CCCCGAAGTG
AAGTTTAACT GGTACGTGGA TGGGGTGGAA GTCCACAACG CTAAGACCAA GCCAAGGGAA
GAACAATACA ATTCAACCTA CCGCGTCGTG TCCGTCCTGA CCGTGCTGCA CCAAGATTGG
CTGAACGGAA AGGAGTACAA GTGTAAAGTG TCAAACAAAG CCCTCCCGTC ATCCATTGAA
AAGACTATCT CGAAGGCGAA AGGTCAGCCT AGAGAGCCGT GCGTGTATAC TCTCCCACCG
TCGCGCGATG AACTGACCAA AAACCAGGTG TCCCTTACGT GTCTCGTGAA GGGGTTCTAC
CCGTCCGACA TCGCAGTGGA GTGGGAGTCA AATGGCCAAC CGGAAAACAA TTACAAGACT
ACCCCGCCTG TGCTGGACAG CGATGGATCC TTTTTCTTGT ACAGCAAGCT GACCGTCGAC
AAGAGCCGGT GGCAGCAGGG GAACGTGTTT AGCTGCAGCG TGATGCATGA AGCTCTGCAT
AATCATTACA CTCAGAAAAG CCTGTCGCTC TCGCCCGGAA GTAATAATA CGTAGAATTC SEQ ID NO: 10 (rBuChE534)
EDDIIIATKN GKVRGMNLTV FGGTVTAFLG IPYAQPPLGR LRFKKPQSLT
KWSDIWNATK YANSCYQNID QSFPGFHGSE MWNPNTDLSE DCLYLNVWIP
APKPKNATVL IWIYGGGFQT GTSSLHVYDG KFLARVERVI VVSMNYRVGA
LGFLALPGNP EAPGNMGLFD QQLALQWVQK NIAAFGGNPK SVTLFGESAG
```

```
                           SEQUENCE LISTING

AASVSLHLLS PGSHSLFTRA ILQSGSFNAP WAVTSLYEAR NRTLNLAKLT
GCSRENETEI IKCLRNKDPQ EILLNEAFVV PYGTPLSVNF GPTVDGDFLT
DMPDILLELG QFKKTQILVG VNKDEGTAFL VYGAPGFSKD NNSIITRKEF
QEGLKIFFPG VSEFGKESIL FHYTDWVDDQ RPENYREALG DVVGDYNFIC
PALEFTKKFS EWGNNAFFYY FEHRSSKLPW PEWMGVMHGY EIEFVFGLPL
ERRDNYTKAE EILSRSIVKR WANFAKYGNP NETQNNSTSW PVFKSTEQKY
LTLNTESTRI MTKLRAQQCR FWTSFFPKVL EMTG

SEQ ID NO: 11 (rBuChE524 truncate w/C66Y)
EDDIIIATKN GKVRGMNLTV FGGTVTAFLG IPYAQPPLGR LRFKKPQSLT
KWSDIWNATK YANSCYQNID QSFPGFHGSE MWNPNTDLSE DCLYLNVWIP
APKPKNATVL IWIYGGGFQT GTSSLHVYDG KFLARVERVI VVSMNYRVGA
LGFLALPGNP EAPGNMGLFD QQLALQWVQK NIAAFGGNPK SVTLFGESAG
AASVSLHLLS PGSHSLFTRA ILQSGSFNAP WAVTSLYEAR NRTLNLAKLT
GCSRENETEI IKCLRNKDPQ EILLNEAFVV PYGTPLSVNF GPTVDGDFLT
DMPDILLELG QFKKTQILVG VNKDEGTAFL VYGAPGFSKD NNSIITRKEF
QEGLKIFFPG VSEFGKESIL FHYTDWVDDQ RPENYREALG DVVGDYNFIC
PALEFTKKFS EWGNNAFFYY FEHRSSKLPW PEWMGVMHGY EIEFVFGLPL
ERRDNYTKAE EILSRSIVKR WANFAKYGNP NETQNNSTSW PVFKSTEQKY
LTLNTESTRI MTKLRAQQCR FWTS SEQ ID NO: 12 (rBuChE524GGGC truncate w/C66Y)
EDDIIIATKN GKVRGMNLTV FGGTVTAFLG IPYAQPPLGR LRFKKPQSLT
KWSDIWNATK YANSCYQNID QSFPGFHGSE MWNPNTDLSE DCLYLNVWIP
APKPKNATVL IWIYGGGFQT GTSSLHVYDG KFLARVERVI VVSMNYRVGA
LGFLALPGNP EAPGNMGLFD QQLALQWVQK NIAAFGGNPK SVTLFGESAG
AASVSLHLLS PGSHSLFTRA ILQSGSFNAP WAVTSLYEAR NRTLNLAKLT
GCSRENETEI IKCLRNKDPQ EILLNEAFVV PYGTPLSVNF GPTVDGDFLT
DMPDILLELG QFKKTQILVG VNKDEGTAFL VYGAPGFSKD NNSIITRKEF
QEGLKIFFPG VSEFGKESIL FHYTDWVDDQ RPENYREALG DVVGDYNFIC
PALEFTKKFS EWGNNAFFYY FEHRSSKLPW PEWMGVMHGY EIEFVFGLPL
ERRDNYTKAE EILSRSIVKR WANFAKYGNP NETQNNSTSW PVFKSTEQKY
LTLNTESTRI MTKLRAQQCR FWTSGGGC SEQ ID NO: 13 (rBuChE534GGC truncate w/C66Y)
EDDIIIATKN GKVRGMNLTV FGGTVTAFLG IPYAQPPLGR LRFKKPQSLT
KWSDIWNATK YANSCQNID QSFPGFHGSE MWNPNTDLSE DCLYLNVWIP
APKPKNATVL IWIYGGGFQT GTSSLHVYDG KFLARVERVI VVSMNYRVGA
LGFLALPGNP EAPGNMGLFD QQLALQWVQK NIAAFGGNPK SVTLFGESAG
AASVSLHLLS PGSHSLFTRA ILQSGSFNAP WAVTSLYEAR NRTLNLAKLT
GCSRENETEI IKCLRNKDPQ EILLNEAFVV PYGTPLSVNF GPTVDGDFLT
DMPDILLELG QFKKTQILVG VNKDEGTAFL VYGAPGFSKD NNSIITRKEF
QEGLKIFFPG VSEFGKESIL FHYTDWVDDQ RPENYREALG DVVGDYNFIC
PALEFTKKFS EWGNNAFFYY FEHRSSKLPW PEWMGVMHGY EIEFVFGLPL
ERRDNYTKAE EILSRSIVKR WANFAKYGNP NETQNNSTSW PVFKSTEQKY
LTLNTESTRI MTKLRAQQCR FWTSFFPKVL EMTGGGC SEQ ID NO: 14 (rBuChE534(C66Y)-GS10-Fc(wt) fusion)
EDDIIIATKN GKVRGMNLTV FGGTVTAFLG IPYAQPPLGR LRFKKPQSLT
KWSDIWNATK YANSCQNID QSFPGFHGSE MWNPNTDLSE DCLYLNVWIP
APKPKNATVL IWIYGGGFQT GTSSLHVYDG KFLARVERVI VVSMNYRVGA
LGFLALPGNP EAPGNMGLFD QQLALQWVQK NIAAFGGNPK SVTLFGESAG
AASVSLHLLS PGSHSLFTRA ILQSGSFNAP WAVTSLYEAR NRTLNLAKLT
GCSRENETEI IKCLRNKDPQ EILLNEAFVV PYGTPLSVNF GPTVDGDFLT
DMPDILLELG QFKKTQILVG VNKDEGTAFL VYGAPGFSKD NNSIITRKEF
QEGLKIFFPG VSEFGKESIL FHYTDWVDDQ RPENYREALG DVVGDYNFIC
PALEFTKKFS EWGNNAFFYY FEHRSSKLPW PEWMGVMHGY EIEFVFGLPL
ERRDNYTKAE EILSRSIVKR WANFAKYGNP NETQNNSTSW PVFKSTEQKY
LTLNTESTRI MTKLRAQQCR FWTSFFPKVL EMTGGGSGGG SGGGSDKTHT
CPPCPAPELL GGPSVFLFPP KPKDTLMISR TPEVTCVVVD VSHEDPEVKF
NWYVDGVEVH NAKTKPREEQ YNSTYRVVSV LTVLHQDWLN GKEYKCKVSN
KALPAPIEKT ISKAKGQPRE PQVYTLPPSR DELTKNQVSL TCLVKGFYPS
DIAVEWESNG QPENNYKTTP PVLDSDGSFF LYSKLTVDKS RWQQGNVFSC
SVMHEALHNH YTQKSLSLSP GK
GS linker underlined.

SEQ ID NO: 15 (rBuChE534(C66Y)-GS10-Fc(no Q347C w/ effector function
mutations) fusion)
EDDIIIATKN GKVRGMNLTV FGGTVTAFLG IPYAQPPLGR LRFKKPQSLT
KWSDIWNATK YANSCYQNID QSFPGFHGSE MWNPNTDLSE DCLYLNVWIP
APKPKNATVL IWIYGGGFQT GTSSLHVYDG KFLARVERVI VVSMNYRVGA
LGFLALPGNP EAPGNMGLFD QQLALQWVQK NIAAFGGNPK SVTLFGESAG
AASVSLHLLS PGSHSLFTRA ILQSGSFNAP WAVTSLYEAR NRTLNLAKLT
GCSRENETEI IKCLRNKDPQ EILLNEAFVV PYGTPLSVNF GPTVDGDFLT
DMPDILLELG QFKKTQILVG VNKDEGTAFL VYGAPGFSKD NNSIITRKEF
QEGLKIFFPG VSEFGKESIL FHYTDWVDDQ RPENYREALG DVVGDYNFIC
PALEFTKKFS EWGNNAFFYY FEHRSSKLPW PEWMGVMHGY EIEFVFGLPL
```

-continued

SEQUENCE LISTING

ERRDNYTKAE EILSRSIVKR WANFAKYGNP NETQNNSTSW PVFKSTEQKY
LTLNTESTRI MTKLRAQQCR FWTSFFPKVL EMTGGGSGGG SGGGSDKTHT
CPPCPAPEAE GAPSVFLFPP KPKDTLMISR TPEVTCVVVD VSHEDPEVKF
NWYVDGVEVH NAKTKPREEQ YNSTYRVVSV LTVLHQDWLN GKEYKCKVSN
KALPSSIEKT ISKAKGQPRE PQVYTLPPSR DELTKNQVSL TCLVKGFYPS
DIAVEWESNG QPENNYKTTP PVLDSDGSFF LYSKLTVDKS RWQQGNVFSC
SVMHEALHNH YTQKSLSLSP GK
GS linker and effector function mutations underline.

SEQ ID NO: 16 (rBuChE534-GS10-Fc(wt) fusion)
EDDIIIATKN GKVRGMNLTV FGGTVTAFLG IPYAQPPLGR LRFKKPQSLT
KWSDIWNATK YANSCCQNID QSFPGFHGSE MWNPNTDLSE DCLYLNVWIP
APKPKNATVL IWIYGGGFQT GTSSLHVYDG KFLARVERVI VVSMNYRVGA
LGFLALPGNP EAPGNMGLFD QQLALQWVQK NIAAFGGNPK SVTLFGESAG
AASVSLHLLS PGSHSLFTRA ILQSGSFNAP WAVTSLYEAR NRTLNLAKLT
GCSRENETEI IKCLRNKDPQ EILLNEAFVV PYGTPLSVNF GPTVDGDFLT
DMPDILLELG QFKKTQILVG VNKDEGTAFL VYGAPGFSKD NNSIITRKEF
QEGLKIFFPG VSEFGKESIL FHYTDWVDDQ RPENYREALG DVVGDYNFIC
PALEFTKKFS EWGNNAFFYY FEHRSSKLPW PEWMGVMHGY EIEFVFGLPL
ERRDNYTKAE EILSRSIVKR WANFAKYGNP NETQNNSTSW PVFKSTEQKY
LTLNTESTRI MTKLRAQQCR FWTSFFPKVL EMTGGGSGGG SGGGSDKTHT
CPPCPAPELL GGPSVFLFPP KPKDTLMISR TPEVTCVVVD VSHEDPEVKF
NWYVDGVEVH NAKTKPREEQ YNSTYRVVSV LTVLHQDWLN GKEYKCKVSN
KALPAPIEKT ISKAKGQPRE PQVYTLPPSR DELTKNQVSL TCLVKGFYPS
DIAVEWESNG QPENNYKTTP PVLDSDGSFF LYSKLTVDKS RWQQGNVFSC
SVMHEALHNH YTQKSLSLSP GK
GS linker underlined.

SEQ ID NO: 17 (rBuChE534 (C66Y)-GS10-Fc(wt) fusion)
EDDIIIATKN GKVRGMNLTV FGGTVTAFLG IPYAQPPLGR LRFKKPQSLT
KWSDIWNATK YANSCYQNID QSFPGFHGSE MWNPNTDLSE DCLYLNVWIP
APKPKNATVL IWIYGGGFQT GTSSLHVYDG KFLARVERVI VVSMNYRVGA
LGFLALPGNP EAPGNMGLFD QQLALQWVQK NIAAFGGNPK SVTLFGESAG
AASVSLHLLS PGSHSLFTRA ILQSGSFNAP WAVTSLYEAR NRTLNLAKLT
GCSRENETEI IKCLRNKDPQ EILLNEAFVV PYGTPLSVNF GPTVDGDFLT
DMPDILLELG QFKKTQILVG VNKDEGTAFL VYGAPGFSKD NNSIITRKEF
QEGLKIFFPG VSEFGKESIL FHYTDWVDDQ RPENYREALG DVVGDYNFIC
PALEFTKKFS EWGNNAFFYY FEHRSSKLPW PEWMGVMHGY EIEFVFGLPL
ERRDNYTKAE EILSRSIVKR WANFAKYGNP NETQNNSTSW PVFKSTEQKY
LTLNTESTRI MTKLRAQQCR FWTSFFPKVL EMTGGGSGGG SGGGSDKTHT
CPPCPAPELL GGPSVFLFPP KPKDTLMISR TPEVTCVVVD VSHEDPEVKF
NWYVDGVEVH NAKTKPREEQ YNSTYRVVSV LTVLHQDWLN GKEYKCKVSN
KALPAPIEKT ISKAKGQPRE PQVYTLPPSR DELTKNQVSL TCLVKGFYPS
DIAVEWESNG QPENNYKTTP PVLDSDGSFF LYSKLTVDKS RWQQGNVFSC
SVMHEALHNH YTQKSLSLSP GK
GS linker underlined.

SEQ ID NO: 18 (leader peptide)
MACLGFQRHK AQLNLATRTW PCTLLFFLLF IPVFCKA

SEQ ID NO: 19 (hBuChE mature protein sequence)
EDDIIIATKN GKVRGMNLTV FGGTVTAFLG IPYAQPPLGR LRFKKPQSLT
KWSDIWNATK YANSCCQNID QSFPGFHGSE MWNPNTDLSE DCLYLNVWIP
APKPKNATVL IWIYGGGFQT GTSSLHVYDG KFLARVERVI VVSMNYRVGA
LGFLALPGNP EAPGNMGLFD QQLALQWVQK NIAAFGGNPK SVTLFGESAG
AASVSLHLLS PGSHSLFTRA ILQSGSFNAP WAVTSLYEAR NRTLNLAKLT
GCSRENETEI IKCLRNKDPQ EILLNEAFVV PYGTPLSVNF GPTVDGDFLT
DMPDILLELG QFKKTQILVG VNKDEGTAFL VYGAPGFSKD NNSIITRKEF
QEGLKIFFPG VSEFGKESIL FHYTDWVDDQ RPENYREALG DVVGDYNFIC
PALEFTKKFS EWGNNAFFYY FEHRSSKLPW PEWMGVMHGY EIEFVFGLPL
ERRDNYTKAE EILSRSIVKR WANFAKYGNP NETQNNSTSW PVFKSTEQKY
LTLNTESTRI MTKLRAQQCR FWTSFFPKVL EMTGNIDEAE WEWKAGFHRW
NNYMMDWKNQ FNDYTSKKES CVGL

What is claimed is:

1. A fusion protein comprising: a butyrylcholinesterase enzyme or carboxy terminal truncation fragment thereof and an immunoglobulin (Ig) domain or fragment thereof, wherein a linker is positioned between and connecting the butyrylcholinesterase enzyme or fragment thereof and the Ig domain of fragment, wherein the Ig domain or fragment thereof comprises substitutions L234A, L235E, and G237A per EU numbering which corresponds to substitutions L14A, L15E, and G17A as numbered within SEQ ID NO: 8, wherein the linker is selected from the group consisting of at least one of Q, GQG, GGGGS (SEQ ID NO: 22), GGGS (SEQ ID NO: 23), GGGES (SEQ II) NO: 24), GGGSGGGSGGGS (SEQ ID NO: 21), and GGSGGGSGGGS (SEQ ID NO: 25).

2. The fusion protein according to claim 1, wherein the butyrylcholinesterase enzyme or fragment thereof comprises amino acids 29-561 of SEQ ID NO: 1.

3. The fusion protein according to claim 1, wherein the butyrylcholinesterase enzyme or fragment thereof comprises amino acids 29-562 of SEQ ID NO: I.

4. The fusion protein according to claim 1, wherein the butyrylcholinesterase enzyme fragment thereof comprises amino acids 29-561 of SEQ ID NO: I, except that residue C94 of SEQ ID NO: I is a Y.

5. The fusion protein according to claim 1, wherein the butyrylcholinesterase enzyme or fragment thereof comprises amino acids 29-562 of SEQ ID NO: 1, except that residue C94 of SEQ ID NO: I is a Y.

6. The fusion protein according to claim 1, wherein the fusion protein comprises SEQ ID NO: 2.

7. The fusion protein according to claim 1, wherein the fusion protein comprises SEQ ID NO: 2 except that residue C672 of SEQ ID NO: 2 is a Q.

8. A fusion protein that shares at least 85% sequence identity to a protein comprising residues 29-561 of SEQ ID NO: I linked to residues 546-772 of SEQ ID NO: 2, wherein the protein comprises amino acid substitution C672Q in SEQ ID NO: 2, wherein a linker is positioned between and connecting the residues of SEQ ID NO: 1 and the residues of SEQ ID NO: 2, wherein the protein comprises an Ig domain or fragment that comprises substitutions L234A, L235E, and G237A per EU numbering which corresponds to substitutions L14A, L15E, and G17A as numbered within SEQ ID NO: 8, wherein the linker is selected from the group consisting of at least one of G, GG, GGGGS (SEQ ID NO: 22), GGGS (SEQ ID NO: 23), GGGES (SEQ ID NO: 24), GGGSGGGSGGGS (SEQ ID NO: 21), and GGSGGGSGGGS (SEQ I1) NO: 25).

9. The fusion protein of claim 8, wherein the protein shares at least 98% sequence identify to a protein comprising residues 29-561 of SEQ ID NO: 1 linked to residues 546-772 of SEQ ID NO: 2, wherein the protein comprises amino acid substitution C672Q in SEQ ID NO: 2.

10. The fusion protein of claim 8, wherein the protein shares at least 99% sequence identity to a protein comprising residues 29-561 of SEQ ID NO: 1 linked to residues 546-772 of SEQ ID NO: 2, wherein the protein comprises a amino acid substitution C672Q in SEQ ID NO: 2.

11. The fusion protein of claim 8 comprising residues 29-561 of SEQ ID NO: 1 linked to residues 546-772 of SEQ ID NO: 2, wherein the protein comprises amino acid substitution C672Q in SEQ ID NO: 2.

12. A protein that shares at least 98% sequence identity to the amino acids in SEQ ID NO: 2, wherein the protein comprises A559, E560, and A562.

13. A protein comprising the amino acids in SEQ ID NO: 2, wherein there is one or more amino acid substitutions within SEQ ID NO: 2 at position E560, S655, S656, and C672.

14. The protein of claim 13, wherein the one or more amino acid substitutions includes: S655A.

15. The protein of claim 14, wherein the one or amino acid substitutions includes E560, S655, and S656 of SEQ ID NO: 2.

16. A fusion protein comprising: a butyrylcholinesterase truncation; and an immunoglobulin (Ig) domain or fragment thereof; and a linker, wherein the linker is selected from the group consisting of at least one of G, GG, GGGGS (SEQ ID NO: 22), GGGS (SEQ ID NO: 23), GGGES (SEQ ID NO: 24), GGGSGGGSGGGS (SEQ ID NO: 21), and GGSGGGSGGGS (SEQ ID NO: 25), wherein the Ig domain or fragment comprises substitutions L234A, L235E, and G237A per EU numbering which corresponds to substitutions L14A, L15E, and G17A as numbered within SEQ ID NO: 8.

17. A fusion protein comprising: a butyrylcholinesterase enzyme carboxy terminal truncation fragment and an immunoglobulin (Ig) domain or fragment thereof that comprises substitutions L234A, L235E, and G237A per EU numbering which corresponds to substitutions L14A, L15E, and G17A as numbered within SEQ ID NO: 8, wherein the butyrylcholinesterase fragment consists of amino acids 29-561 of SEQ ID NO.1.

18. A fusion protein comprising: a butyrylcholinesterase enzyme carboxy terminal truncation fragment and an immunoglobulin (Ig) domain or fragment thereof, wherein a linker is positioned between and connecting the butyrylcholinesterase enzyme or truncation and the Ig domain of fragment, wherein the linker is selected from the group consisting of at least one of G, GG, GGGS (SEQ ID NO: 23), GGGES (SEQ ID NO: 24), GGGSGGGSGGGS (SEQ ID NO: 21), and GGSGGGSGGGS (SEQ ID NO: 25), and wherein the butyrylcholinesterase enzyme or truncation is a carboxyl truncate, wherein the fusion protein shares at least 85% sequence identity to a protein comprising residues 29-561 of SEQ ID NO: 1 linked to residues 546-772 of SEQ ID NO: 2, wherein the protein comprises C672Q in SEQ ID NO: 2.

19. A fusion protein comprising: a butyrylcholinesterase enzyme or carboxy terminal truncation fragment thereof and an immunoglobulin (Ig) domain or fragment thereof, wherein a linker is positioned between and connecting the butyrylcholinesterase enzyme or truncation and the Ig domain of fragment, wherein the Ig domain or fragment comprises substitutions L14A, L15E, and G17A of SEQ ID NO: 8, wherein the linker is selected from the group consisting of at least one of G, G, GGGS (SEQ ID NO: 23), CGOES (SEQ ID NO: 24), GGGSGGGSGGGS (SEQ ID NO: 21), and GGSGGGSG(GS (SEQ ID NO: 25).

* * * * *